(12) United States Patent
Yao et al.

(10) Patent No.: US 10,438,686 B2
(45) Date of Patent: Oct. 8, 2019

(54) METHODS AND SYSTEMS FOR ASSESSMENT OF CLINICAL INFERTILITY

(71) Applicant: The Board of Trustees of the Leland Stanford Junior University, Stanford, CA (US)

(72) Inventors: Mylene W. M. Yao, Stanford, CA (US); Wing H. Wong, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 270 days.

(21) Appl. No.: 15/242,215

(22) Filed: Aug. 19, 2016

(65) Prior Publication Data

US 2016/0357917 A1 Dec. 8, 2016

Related U.S. Application Data

(62) Division of application No. 12/496,493, filed on Jul. 1, 2009, now Pat. No. 9,458,495.
(Continued)

(51) Int. Cl.
*G16B 5/00* (2019.01)
*A61B 17/425* (2006.01)
(Continued)

(52) U.S. Cl.
CPC .............. *G16B 5/00* (2019.02); *A61B 17/425* (2013.01); *C12Q 1/6809* (2013.01);
(Continued)

(58) Field of Classification Search
CPC .. G06F 19/24; G06F 19/3431; G06F 19/3437; G06F 19/3443; G06F 19/345; A61B 17/425–17/435; G16H 50/70
See application file for complete search history.

(56) References Cited

U.S. PATENT DOCUMENTS

| 4,816,257 A | 3/1989 | Buster et al. |
| 5,612,869 A | 3/1997 | Letz et al. |

(Continued)

FOREIGN PATENT DOCUMENTS

| WO | 2007130673 | 11/2007 |
| WO | WO2010045463 | 4/2010 |

OTHER PUBLICATIONS

American Society for Reproductive Medicine (ASRM), Guidelines on Number of Embryos Transferred, Fertility and Sterility 90:S163-S164 (2008).

(Continued)

*Primary Examiner* — Catherine B Kuhlman
(74) *Attorney, Agent, or Firm* — Edward J. Baba; Bozicevic, Field & Francis LLP

(57) ABSTRACT

Methods and computer-based systems for facilitating assessment of clinical infertility are provided. The methods and systems can be implemented to, for example, facilitate assessment of a subject for an in vitro fertilization treatment cycle, including determining probability of a live birth event. The methods and systems can be implemented to, for example, facilitate a determination of success implantation of embryos, selection of an optimal number of embryos to transfer, and determination of success in subsequent in vitro fertilization treatment cycles following an unsuccessful treatment cycle.

42 Claims, 34 Drawing Sheets

Specification includes a Sequence Listing.

Related U.S. Application Data

(60) Provisional application No. 61/077,439, filed on Jul. 1, 2008, provisional application No. 61/081,596, filed on Jul. 17, 2008.

(51) Int. Cl.
  G16B 25/00 (2019.01)
  G16B 40/00 (2019.01)
  C12Q 1/6809 (2018.01)
  C12Q 1/6883 (2018.01)
  G06F 19/00 (2018.01)
  G16H 10/60 (2018.01)
  G16B 20/00 (2019.01)

(52) U.S. Cl.
  CPC ......... *C12Q 1/6883* (2013.01); *G06F 19/325* (2013.01); *G16B 25/00* (2019.02); *G16B 40/00* (2019.02); *G16H 10/60* (2018.01); *C12Q 2600/158* (2013.01); *G16B 20/00* (2019.02); *Y02A 90/22* (2018.01); *Y02A 90/26* (2018.01)

(56) References Cited

U.S. PATENT DOCUMENTS

| | | |
|---|---|---|
| 5,619,991 A | 4/1997 | Sloane |
| 5,809,997 A | 7/1998 | Wolf |
| 5,812,984 A | 7/1998 | Goltra |
| 5,816,246 A | 10/1998 | Mirza |
| 5,832,450 A | 11/1998 | Myers et al. |
| 5,866,354 A | 2/1999 | Froman |
| 5,924,074 A | 7/1999 | Evans |
| 6,278,999 B1 | 8/2001 | Knapp |
| 6,347,329 B1 | 2/2002 | Evans |
| 6,523,009 B1 | 2/2003 | Wilkins |
| 6,529,876 B1 | 3/2003 | Dart et al. |
| 6,597,946 B2 | 7/2003 | Avrahami et al. |
| 6,600,696 B1 | 7/2003 | Lynn |
| 7,076,437 B1 | 7/2006 | Levy |
| 7,188,073 B1 | 3/2007 | Tam et al. |
| 7,188,082 B2 | 3/2007 | Keane et al. |
| 7,263,493 B1 | 8/2007 | Provost |
| 7,275,220 B2 | 9/2007 | Brummel et al. |
| 7,295,988 B1 | 11/2007 | Reeves |
| 7,311,666 B2 | 12/2007 | Stupp et al. |
| 7,361,142 B2 | 4/2008 | Suda |
| 7,392,199 B2 | 6/2008 | Karlov et al. |
| 7,438,228 B2 | 10/2008 | Robertson et al. |
| 7,461,079 B2 | 12/2008 | Walker et al. |
| 7,487,102 B2 | 2/2009 | Castille |
| 7,643,969 B2 | 1/2010 | Soto et al. |
| 7,685,000 B1 | 3/2010 | Petit |
| 7,703,042 B2 | 4/2010 | Brummel et al. |
| 7,730,024 B2 | 6/2010 | Harinth |
| 7,853,456 B2 | 12/2010 | Soto et al. |
| 8,160,977 B2 | 4/2012 | Poulin |
| 2003/0017481 A1 | 1/2003 | Golub et al. |
| 2004/0097460 A1 | 5/2004 | Ivey et al. |
| 2004/0193019 A1 | 9/2004 | Wei |
| 2005/0118563 A1 | 6/2005 | Sher et al. |
| 2005/0202426 A1 | 9/2005 | Short et al. |
| 2005/0203892 A1 | 9/2005 | Wesley et al. |
| 2006/0052945 A1 | 3/2006 | Rabinowitz et al. |
| 2006/0147900 A1 | 7/2006 | Zhang et al. |
| 2006/0173663 A1 | 8/2006 | Lagheier et al. |
| 2006/0246495 A1 | 11/2006 | Garrett et al. |
| 2007/0027636 A1 | 2/2007 | Rabinowitz et al. |
| 2007/0053563 A1 | 3/2007 | Tu et al. |
| 2007/0054289 A1 | 3/2007 | Cibelli et al. |
| 2007/0055552 A1 | 3/2007 | St Clair et al. |
| 2007/0082329 A1 | 4/2007 | Williams et al. |
| 2007/0130206 A1 | 6/2007 | Zhou et al. |
| 2007/0162992 A1 | 7/2007 | Burns |
| 2007/0178501 A1 | 8/2007 | Rabinowitz et al. |
| 2007/0192134 A1 | 8/2007 | Littenberg et al. |
| 2007/0238111 A1 | 10/2007 | Cibelli et al. |
| 2008/0133275 A1 | 6/2008 | Haug et al. |
| 2008/0163824 A1 | 7/2008 | Moser et al. |
| 2009/0029375 A1 | 1/2009 | Jupe et al. |
| 2009/0259491 A1 | 1/2009 | Jupe et al. |
| 2010/0021898 A1 | 1/2010 | Sirard et al. |
| 2010/0036192 A1 | 2/2010 | Yao et al. |
| 2010/0049689 A1 | 2/2010 | Jorg et al. |
| 2010/0112605 A1 | 5/2010 | Paul et al. |
| 2010/0138199 A1 | 6/2010 | Soto et al. |
| 2011/0173018 A1 | 7/2011 | Hoffner et al. |
| 2011/0288789 A1 | 11/2011 | Rabinowitz et al. |
| 2011/0313790 A1 | 12/2011 | Yao |
| 2012/0016184 A1 | 1/2012 | Yao |

OTHER PUBLICATIONS

Banerjee et al., Deep Phenotyping to Predict Live Birth Outcomes in In Vitro Fertilization, PNAS 107(31):13570-13575 (2010).

Bonduelle et al., A Multi-Centre Cohort Study of the Physical Health of 5-Year-Old Children Conceived After Intracytoplasmic Sperm Injection, In Vitro Fertilization and Natural Conception, Human Reproduction 20(2):413-419 (2005).

Friedman, Greedy Function Approximation: A Gradient Boosting Machine, IMS 1999 Reitz Lecture, Feb. 24, 1999 (modified Mar. 15, 2000 and Apr. 15, 2001).

Friedman, Stochastic Gradient Boosting, Stanford University Technical Paper, Mar. 26, 1999.

Friedman, Tutorial: Getting Started in MART with R, Stanford University Technical Paper, May 13, 2002.

Friedman et al., Multiple Additive Regression Trees with Application in Epidemiology, Statistics in Medicine 22:1365-1381 (2003).

Horvitz, From Data to Predictions and Decisions: Enabling Evidence-Based Healthcare, Computing Community Consortium, Version 6: Sep. 16, 2010.

Hsieh et al., Decreased Expression of Mitochondrial Genes in Human Unfertilized Oocytes and Arrested Embryos, Fertility and Sterility 81 Supp. 1, pp. 912-918, Mar. 2004.

Hunault et al., Two new prediction rules for spontaneous pregnancy leading to live birth among subfertilie couples, based on the synthesis of three previous models, Human Reproduction 19(9):2019-2026 (2004).

Kalu et al., Reducing Multiple Pregnancy in Assisted Reproduction Technology: Towards a Policy of Single Blastocyst Transfer in Younger Women, British Journal of Obstetrics and Gynecology (BJOG) 115:1143-1150 (2008).

Khalaf et al., Selective Single Blastocyst Transfer Reduces the Multiple Pregnancy Rate and Increases Pregnancy Rates: A Pre- and Postintervention Study, British Journal of Obstetrics and Gynecology (BJOG) 115:385-390 (2008).

Li et al., Analysis of Gene Expression in Single Human Oocytes and Preimplantation Embryos, Biochem. and Biophys. Res. Comm. 340(1):48-53 (2006).

Minaretzis et al., Multivariate Analysis of Factors Predictive of Successful Live Births in In Vitro Fertilization (IVF) Suggests Strategies to Improve IVF Outcome, Journal of Assisted Reproduction and Genetics, 15(6):365-371 (1998).

Martin et al., Births: Final Data for 2006, National Vital Statistics Reports (NVSR) 57(7):1-102 (2009).

Osterman et al., Expanded Health Data From the New Birth Certificate, 2006, National Vital Statistics Reports (NVSR) 58(5):1-24 (2009).

Passmore et al., Assessing Decision Tree Models for Clinical In-Vitro Fertilization Data, Technical Report TR03-296, Department of Computer Science and Statistics, University of Rhode Island, Mar. 2004.

Pinborg et al., Neonatal Outcome in a Danish National Cohort of 8602 Children Born After In Vitro Fertilization or Intracytoplasmic Sperm Injection: The Role of Twin Pregnancy, Acta Obstet Gynecol Scand 83:1071-1078 (2004).

(56) References Cited

OTHER PUBLICATIONS

Styer et al., Single-Blastocyst Transfer Decreases Twin Gestation Without Affecting Pregnancy Outcome, Fertility and Sterility 89(6):1702-1708 (2008).
Sunderam et al., Assisted Reproductive Technology Surveillance—United States, 2006, Morbidity and Mortality Weekly Report (MMWR) 58(SS05):1-25 (2009).
Sutcliffe et al., Outcome of Assisted Reproduction (Review), Lancet 370:351-59 (2007).
Templeton et al., Factors that affect outcome of in-vitro fertilisation treatment The Lancet 348(9039):1402-1406 (1996).
Van Voorhis, In Vitro Fertilization, The New England Journal of Medicine 356:379-86 (2007).

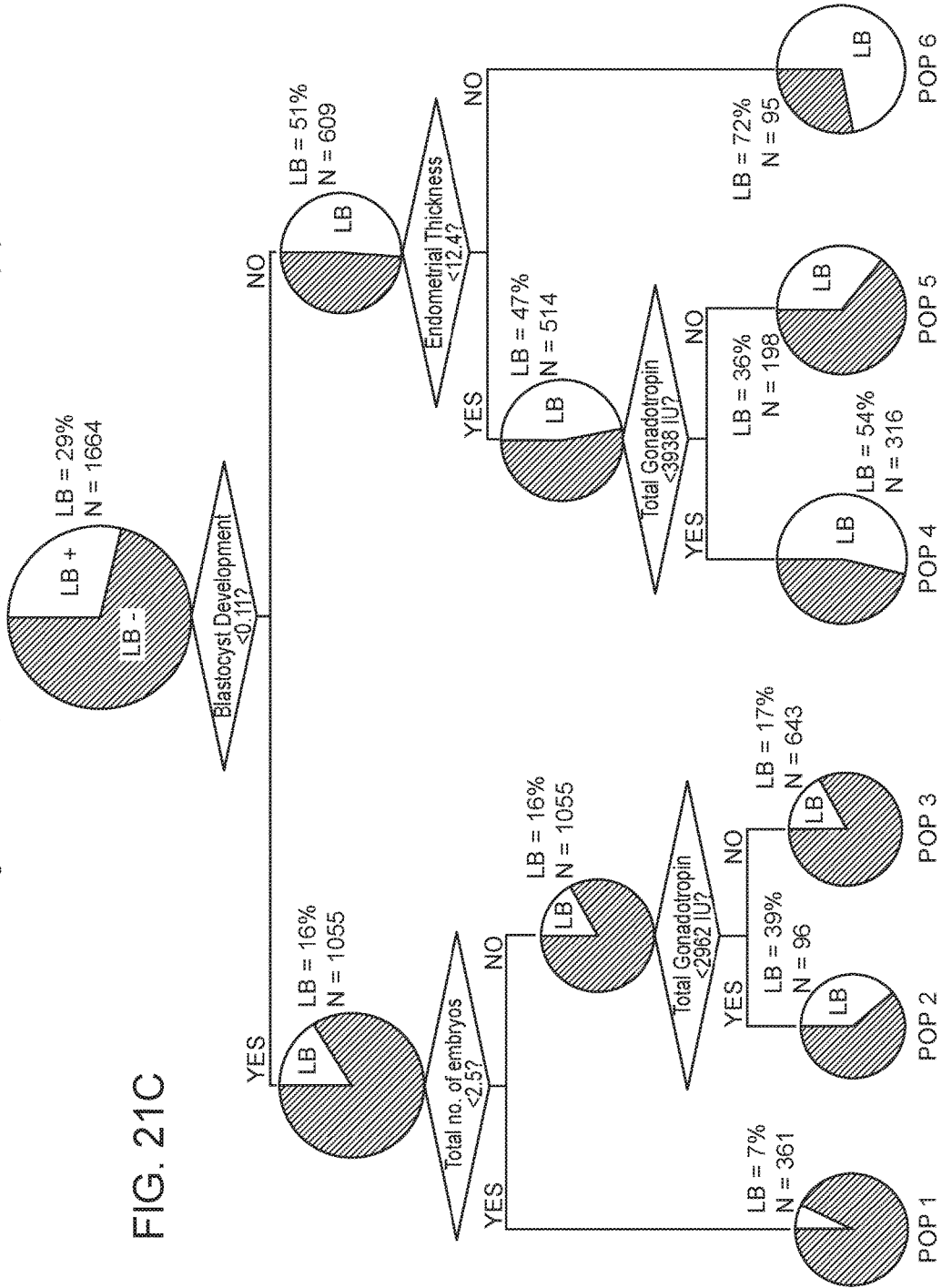

Total no. of cycles (2003-06):

No. of cycles eligible
(fresh, non-donor oocytes)

No. of cycles analyzed

| Cycle 1 (C1) | 1879 | → Model generation |
| Cycle 2 (C2) | 778 | |
| Cycle 3 (C3) | 312 | → Validate models |

} Linked outcomes

METHODS AND SYSTEMS FOR ASSESSMENT OF CLINICAL INFERTILITY

CROSS-REFERENCE

This application is a divisional of U.S. patent application Ser. No. 12/496,493, filed Jul. 1, 2009, which application claims the benefit of U.S. Provisional Application Nos. 61/077,439, filed Jul. 1, 2008, and 61/081,596, filed Jul. 17, 2008, which applications are incorporated by reference herein in their entirety.

GOVERNMENT RIGHTS

This invention was made with government support under federal grant nos. R01 GM067250 and R01 HD057970 awarded by the National Institutes of Health. The United States Government has certain rights in this invention.

BACKGROUND OF THE INVENTION

Reproductive failure is a serious problem that has been addressed clinically by various assisted reproductive technologies, including in vitro fertilization (IVF) and embryo transfer (ET). These procedures might be expected to yield exceptionally high conception rates as in vitro fertilization provides embryos that appear normal at a morphological level for transfer into a fully primed recipient. Despite these efforts the success rate of IVF/ET is less than ideal. In the published data for IVF/ET in the United States and Canada in 1994, there were 26,961 initiated cycles of standard IVF. Of these, 86.2% led to retrieval and of these 90.2% led to a transfer. However, the overall success rate in terms of clinical pregnancies was 22.7% per initiated cycle and a 29.1% pregnancy rate per transfer.

Additionally, there appears to be a high incidence of early pregnancy loss after in vitro fertilization with a biochemical pregnancy rate of 18% and a spontaneous abortion rate of 27%. Thus, it appears that the IVF technique has been well optimized but implantation failure may be the cause for a large number of losses with ET and this peri-implantational loss is an area of potential improvement. A major factor in the success rate of various assisted reproductive technologies is endometrial receptivity, a transient state that must be coordinated with embryo development to implantation-competent blastocysts.

IVF is an expensive procedure and can be psychologically traumatic for a patient. Surgical procedures are required to collect eggs from a female for IVF and, following fertilization, further surgery is required to implant the fertilized eggs in the womb. The recipient must then wait for a period of time before it can be determined whether or not pregnancy has been established. In some cases, pregnancy may never be achieved despite repeated attempts, and these cases can represent a considerable expense to the patient and society, both in financial and human terms.

Therefore, until success rates of IVF can be improved, it would be desirable to be able to identify recipients for whom IVF is unlikely to be successful prior to treatment, so that such patients may avoid the above mentioned costs and trauma of the IVF procedure.

The present invention addresses these needs.

SUMMARY OF THE INVENTION

Methods and computer-based systems for facilitating assessment of clinical infertility are provided. The methods and systems can be implemented to, for example, facilitate assessment of a subject for an in vitro fertilization treatment cycle, including determining probability of a live birth event. The methods and systems can be implemented to, for example, facilitate a determination of success of implantation of embryos, selection of an optimal number of embryos to transfer, and determination of success in subsequent in vitro fertilization treatment cycles following an unsuccessful treatment cycle.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 14, Panel A shows unsupervised clustering of 3 Oct4 knockdown, 3 Ccna2 knockdown, and 6 uninjected (NI) pooled embryo samples, and increased (red) and decreased (blue) gene expression. Scale is standard deviation FIG. 14, Panel B shows intersection of differentially expressed genes in Oct4 and Ccna2 knockdown embryos. FIG. 14, Panel C and FIG. 15 show relative expression of Oct4 knockdown by single-embryo q-PCR for FIG. 14, Panel C overexpressed genes ($p<0.05$ for Hes5) and FIG. 15 downregulated genes (*$p<<0.001$, $p<0.05$, *$p<0.1$). TR translational repression. Error bars indicate s.e.m.

FIGS. 21A, 21B, and 21C show tree models for three analysis groups: Pre-IVF (21A), Pre-OR (21B) and Post-IVF (21C). The pie-charts show the percentage of live births (LB) among the total number (N) of cycles analyzed. Terminal populations are labeled as population 1 (Pop 1), etc., with its live birth rate indicated.

Figure 1:
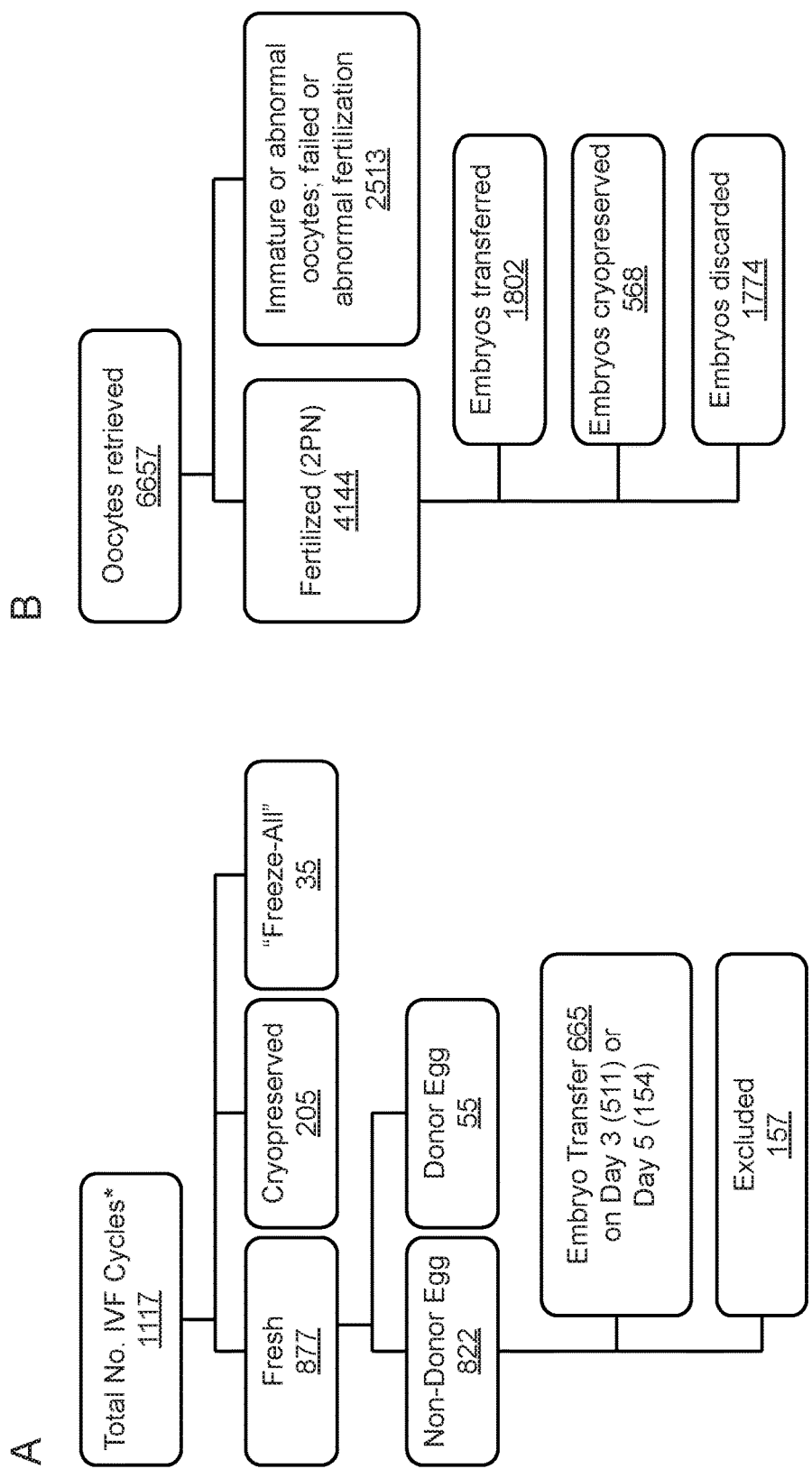
FIG. 1 shows the source of the data. Panel A shows the IVF cycles performed in 2005. Panel B shows the utilization of oocytes and embryos in 665 fresh, non-donor IVF cycles. All numbers in Panel A indicate the number of cycles and numbers in Panel B indicate the number of oocytes or embryos. Fresh cycles are defined by ovarian stimulation of gonadotropins and embryo transfer performed within the same cycle; cryopreserved cycles utilize embryos that were obtained and cryopreserved from a previous cycle; "freeze-all" are cycles in which ovarian stimulation was performed, but embryos were cryopreserved instead of being transferred back within the same cycle for medical or non-medical reasons. 157 cycles were removed from analysis for a variety of medical and non-medical reasons that did not result in fresh embryo transfer.

Before the present embodiments are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the compound" includes reference to one or more compounds and equivalents thereof known to those skilled in the art, and so forth.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "subject," "individual," and "patient" are used interchangeably herein to refer to a mammal being assessed for treatment and/or being treated. In an embodiment, the mammal is a human, such as a female human. The terms "subject," "individual," and "patient" thus encompass individuals in need of assessment of clinical infertility, including those who have undergone or are candidates for an in vitro fertilization cycle.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

A "biological sample" encompasses a variety of sample types obtained from an individual. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's uterus, including embryo cultures.

The terms "gene product" and "expression product" are used interchangeably herein in reference to a gene, to refer to the RNA transcription products (transcripts) of the gene, including mRNA and the polypeptide translation products of such RNA transcripts, whether such product is modified post-translationally or not. The terms "gene product" and "expression product" are used interchangeably herein, in reference to an RNA, particularly an mRNA, to refer to the polypeptide translation products of such RNA, whether such product is modified post-translationally or not. A gene product can be, for example, an unspliced RNA, an mRNA, a splice variant mRNA, a polypeptide, a post-translationally modified polypeptide, a splice variant polypeptide, etc.

As used herein, the term "normalized expression level" refers to an expression level of a response indicator gene relative to the level of an expression product of a reference gene(s).

As used herein, the terms "label" and "detectable label" refer to a molecule capable of being detected, where such molecules include, but are not limited to, radioactive isotopes, fluorescers (fluorophores), chemiluminescers, chromophores, enzymes, enzyme substrates, enzyme cofactors, enzyme inhibitors, chromophores, dyes, metal ions, metal sols, ligands (e.g., biotin, avidin, strepavidin or haptens), intercalating dyes and the like. The term "fluorescer" or "fluorophore" refers to a substance or a portion thereof which is capable of exhibiting fluorescence in a detectable range.

As used herein, the term "target nucleic acid region" or "target nucleic acid" refers to a nucleic acid with a "target sequence" to be detected (e.g., in a method involving nucleic acid hybridization and/or amplification). The target nucleic acid may be either single-stranded or double-stranded and may or may not include other sequences besides the target sequence (e.g., the target nucleic acid may or may not include nucleic acid sequences upstream or 5' flanking sequence, and may or may not include downstream or 3' flanking sequence. Where detection is by amplification, these other sequences in addition to the target sequence may or may not be amplified with the target sequence.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal ion concentration, and salt concentration. Primers are generally of a length compatible with their use in synthesis of primer extension products, and can be in the range of between about 8 nucleotides and about 100 nucleotides (nt) in length, such as about 10 nt to about 75 nt, about 15 nt to about 60 nt, about 15 nt to about 40 nt, about 18 nt to about 30 nt, about 20 nt to about 40 nt, about 21 nt to about 50 nt, about 22 nt to about 45 nt, about 25 nt to about 40 nt, and so on, e.g., in the range of between about 18 nt and about 40 nt, between about 20 nt and about 35 nt, between about 21 and about 30 nt in length, inclusive, and any length between the stated ranges. Primers can be in the range of between about 10-50 nucleotides long, such as about 15-45, about 18-40, about 20-30, about 21-25 nt and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length. In this context, the term "about" may be construed to mean 1, 2, 3, 4, 5, 6, 7, 8, 9, 10, 11, 12, 13, 14, 15, 16, 17, 18, 19 or 20 more nucleotides either 5' or 3' from either termini or from both termini.

Primers are in many embodiments single-stranded for maximum efficiency in amplification, but may alternatively be double-stranded. If double-stranded, the primer is in many embodiments first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the covalent addition of bases at its 3' end.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

As used herein, the term "probe" or "oligonucleotide probe", used interchangeable herein, refers to a structure comprised of a polynucleotide, as defined above, which contains a nucleic acid sequence complementary to a nucleic acid sequence present in the target nucleic acid analyte (e.g., a nucleic acid amplification product). The polynucleotide regions of probes may be composed of DNA, and/or RNA, and/or synthetic nucleotide analogs. Probes are generally of a length compatible with their use in specific detection of all or a portion of a target sequence of a target nucleic acid, and are in many embodiments in the range of between about 8 nt and about 100 nt in length, such as about 8 to about 75 nt, about 10 to about 74 nt, about 12 to about 72 nt, about 15 to about 60 nt, about 15 to about 40 nt, about 18 to about 30 nt, about 20 to about 40 nt, about 21 to about 50 nt, about 22 to about 45 nt, about 25 to about 40 nt in length, and so on, e.g., in the range of between about 18-40 nt, about 20-35 nt, or about 21-30 nt in length, and any length between the stated ranges. In some embodiments, a probe is in the range of between about 10-50 nucleotides long, such as about 15-45, about 18-40, about 20-30, about 21-28, about 22-25 and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length. In this context, the term "about" may be construed to mean 1, 2, 3, 4, 5, 6, 7, 8, 9, 10, 11, 12, 13, 14, 15, 16, 17, 18, 19 or 20 more nucleotides either 5' or 3' from either termini or from both termini.

Where a nucleic acid is said to hybridize to a recited nucleic acid sequence, hybridization is under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 μg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, e.g., at least about 90% as stringent as the above specific stringent conditions.

DETAILED DESCRIPTION OF THE INVENTION

As noted above, methods and computer-based systems for facilitating assessment of clinical infertility are provided. The methods and systems can be implemented to, for example, facilitate assessment of a subject for an in vitro fertilization treatment cycle. The methods and systems can be implemented to, for example, facilitate a determination of success for implantation of embryos, selection of an optimal number of embryos to transfer, and determination of success in subsequent in vitro fertilization treatment cycles following an unsuccessful treatment cycle.

In certain embodiments, the method includes obtaining items of information from a female subject to provide a profile for the female subject, wherein each item of information relate to preselected patient variables, comparing the profile for the female subject to a library of known profile patterns known to be indicative of responsiveness to an in vitro fertilization procedure using an algorithm based upon the preselected patient variables, wherein the comparing provides an evaluation of the female subject for an in vitro fertilization procedure. In certain embodiments, the in vitro fertilization procedure is at least a second vitro fertilization procedure for said female subject.

The items of information may be provided by the female subject based on a written or electronic questionnaire or may be requested, transcribed, or otherwise logged, by a health care practitioner, such as a doctor, nurse, technician, or the like, during or concurrent with a medical evaluation that may optionally be associated with a determination to undergo a first or subsequent in vitro fertilization cycle.

Exemplary items of information relating to preselected patient variables include, but are not limited to: patient characteristics, such as age, previous infertility history, clinical diagnosis; clinical treatment information, such as type of medication, number of days of stimulation, number of oocytes, etc.; conventional embryo morphology data, such as number of embryos, developmental stage, grade, and the like. In some embodiments, the information includes age, total number of embryos, rate of cleavage arrest, number of 8-cell embryos, day 3 follicle stimulating hormone (FSH) level, and number of 8-cell embryos transferred.

In certain embodiments, the in vitro fertilization procedure provides for a live birth event following the in vitro fertilization procedure. In such embodiments, the method provides a probability of a live birth event occurring resulting from the first or subsequent in vitro fertilization cycle based at least in part on items of information from the female subjects.

In some embodiments, the female subject is a pre-in vitro fertilization (pre-IVF) procedure patient. In certain embodiments, the items of information relating to preselected patient variables for determining the probability of a live birth event for a pre-IVF procedure patient may include age, diminished ovarian reserve, 3 follicle stimulating hormone (FSH) level, body mass index, polycystic ovarian disease, season, unexplained female infertility, number of spontaneous miscarriages, year, other causes of female infertility, number of previous pregnancies, number of previous term deliveries, endometriosis, tubal disease, tubal ligation, male infertility, uterine fibroids, hydrosalpinx, and male infertility causes.

In some embodiments, the female subject is a pre-surgical (pre-OR) procedure patient (pre-OR is also referred to herein as pre-oocyte retrieval). In certain embodiments, the items of information relating to preselected patient variables for determining the probability of a live birth event for a pre-OR procedure patient may include age, endometrial thickness, total number of oocytes, total amount of gonatropins administered, number of total motile sperm after wash, number of total motile sperm before wash, day 3 follicle stimulating hormone (FSH) level, body mass index, sperm collection, age of spouse, season number of spontaneous miscarriages, unexplained female infertility, number of previous term deliveries, year, number of previous pregnancies, other causes of female infertility, endometriosis, male infertility, tubal ligation, polycystic ovarian disease, tubal disease, sperm from donor, hydrosalpinx, uterine fibroids, and male infertility causes.

In some embodiments, the female subject is a post-in vitro fertilization (post-IVF) procedure patient. In certain embodiments, the items of information relating to preselected patient variables for determining the probability of a live birth event for a post-IVF procedure patient may include blastocyst development rate, total number of embryos, total amount of gonatropins administered, endometrial thickness, flare protocol, average number of cells per embryo, type of catheter used, percentage of 8-cell embryos transferred, day 3 follicle stimulating hormone (FSH) level, body mass index, number of motile sperm before wash, number of motile sperm after wash, average grade of embryos, day of embryo transfer, season, number of spontaneous miscarriages, number of previous term deliveries, oral contraceptive pills, sperm collection, percent of unfertilized eggs, number of embryos arrested at 4-cell stage, compaction on day 3 after transfer, percent of normal fertilization, percent of abnormally fertilized eggs, percent of normal and mature oocytes, number of previous pregnancies, year, polycystic ovarian disease, unexplained female infertility, tubal disease, male infertility only, male infertility causes, endometriosis, other causes of female infertility, uterine fibroids, tubal ligation, sperm from donor, hydrosalpinx, performance of ICSI, or assisted hatching.

Additional examples of parameters are provided in the examples section, including, for example, Tables 13 and 15.

In certain embodiments, the method includes obtaining items of information relating to at least two preselected patient variables, or more. As such, in other embodiments, the method includes obtaining items of information relating to at 3 or more preselected patient variables, including 4 or more, 5 or more, 6 or more, 7 or more, 8 or more, 9 or more, 10 or more, 12 or more, 15 or more, 17 or more, 20 or more, and the like.

In certain embodiments, the method includes assigning a weighted relative importance to each preselected patient variable in relation to other preselected patient variables. For example, in an analysis of a Pre-IVF model subject, the preselected patient variables of age and diminished ovarian reserve are given a higher relative importance value over other preselected patient variables, such as, for example, body mass index, tubular disease, and endometriosis. In such embodiments, the sum of the relative importance of each preselected patient variables will equal 100.

In another embodiment, in an analysis of a Pre-OR model subject, the preselected patient variables of total amount of gonoatropins, endometrial thickness and age are given a higher relative importance value over other preselected patient variables, such as, for example, number of previous pregnancies, tubal ligation and number of spontaneous miscarriages. In such embodiments, the sum of the relative importance of each preselected patient variables will equal 100.

In yet another embodiment, in an analysis of a Post-IVF model subject, the preselected patient variables of blastocyst development rate, total number of embryos, total amount of gonatropins administered, and endometrial thickness are given a higher relative importance value over other preselected patient variables, such as, for example, body mass index, number of motile sperm before wash, number of motile sperm after wash, average grade of embryos, and day of embryo transfer. In such embodiments, the sum of the relative importance of each preselected patient variables will equal 100.

In some embodiments, the comparing includes applying a decision rule. In some embodiments, the data analysis algorithm comprises the use of a classification tree. In other embodiments, the data analysis algorithm is nonparametric, such as using a Wilcoxon Signed Rank Test. In certain embodiments, the data analysis algorithm detects differences in a distribution of feature values. In some embodiments, the data analysis algorithm includes using a multiple additive regression tree. In some embodiments, the data analysis algorithm is a logistic regression.

In further embodiments, the method includes assessment of a gene expression profile of an arrested embryo from the female subject. For example, embryos that have arrested, for example embryos that have fewer than about 5 cells on day 3 following in vitro fertilization, are tested for a relative expression level of a panel of genes that are critical to embryo development. The gene expression profile is then compared to a control gene expression profile.

Any gene that for which normalized expression level is correlated (either positively or negatively) with infertility or likelihood of success or failure of an in vitro fertilization cycle is suitable for use with the methods of the invention. Exemplary genes include, but are not limited to, Oct4, Eif3c, Papola, Piwil2, Eif3b, Eif4b, Rbm3, Cpsf4 and other genes found to be down- or upregulated upon Oct4 knockdown, or the knockdown of another gene encoding a pluripotency regulator (e.g. Sal14). Other exemplary genes include those listed in Tables 8A, 8B, 9A, and 9B in attached Appendixes A-D, as well as Table 12. These gene products are referred to herein as "infertility indicator gene products"; and genes encoding the response indicator gene products are referred to as "infertility indicator genes." Normalized expression levels of one or more of these infertility indicator genes can be determined to assess a female patient for an in vitro fertilization treatment cycle. Infertility indicator genes were identified as described in detail below in the Examples. Other genes that are suitable for use in the analysis can be identified using the methods described here in the Examples section.

In carrying out a subject assessment, a sample comprising an infertility indicator gene is assayed for a level of an infertility indicator gene product(s). Where the gene product being assayed is a nucleic acid, a nucleic acid sample (e.g., a sample comprising nucleic acid) is obtained from an embryo cell. Where the gene product being assayed is a protein, a polypeptide sample (e.g., a sample comprising polypeptides) is obtained from an embryo.

Nucleic acid (including mRNA) and/or polypeptide infertility indicator gene products can be obtained from an embryo, including an oocyte, such as an arrested embryo or oocyte (e.g., an embryo or oocyte having less than about 8 cells on about day 3 following fertilization, including about 7 cells, about 6 cells, about 5 cells, about 4 cells, about 3 cells, etc.), using standard methods. Levels of nucleic acid and/or polypeptide gene products can be measured using any of a variety of well-known methods, including those described in the Examples below.

An expression level of a response indicator gene is normalized relative to the level of an expression product of a reference gene(s). Assessing the infertility likelihood is conducted by comparing the normalized expression level to a range of values of normalized expression levels of the gene product in an embryo cell.

Normalized expression level of one or more infertility indicator genes can be carried out to assess the likelihood that a patient will respond positively or negatively to an in vitro fertilization treatment cycle. Normalized expression level of a single infertility indicator gene can be carried out to assess the likelihood that a patient will respond positively or negatively to an in vitro fertilization treatment cycle. In addition, normalized expression level of two or more infertility indicator genes can be carried out to assess the likelihood that a patient will respond positively or negatively to an in vitro fertilization treatment cycle. The analysis can be more stringent, e.g., the optimal number of embryos to transfer to the female patient to maximize the likelihood of a live birth outcome while minimizing the likelihood of multiple gestations. The analysis can be less stringent, e.g., the likelihood that a patient will exhibit a beneficial response to an in vitro fertilization treatment cycle.

In some embodiments, the analysis includes determining the optimal number of embryos to transfer in order to minimize the probability of multiple gestation events in a subject. In such embodiments, the subject is first identified as a subject having a high probability of having multiple gestation events. The subject is then analyzed to determine the optimal number of embryos to transfer in order to provide for a single live birth event following the in vitro fertilization cycle.

It will be appreciated that assessment of likelihood that a patient will respond positively or negatively in vitro fertilization treatment cycle can be conducted by determining normalized expression levels of two or more infertility indicator genes (e.g., 1, 2, 3, 4, 5, 6, 7, 8, 9, 10, or more infertility indicator genes), or any combination of one or more sets of infertility indicator genes. The assessment can involve analyzing expression levels of a combination of infertility indicator genes, and determining normalized expression levels of the combination of infertility indicator genes, where the infertility indicator gene products can include gene products that are positively correlated with an in vitro fertilization treatment cycle and gene products that are negatively correlated with an in vitro fertilization treatment cycle. For example, a normalized level of a first gene that positively correlates with an in vitro fertilization treatment cycle, and a normalized level of a second gene that negatively correlates with an in vitro fertilization treatment cycle, can be determined.

Determining a Normalized Level of a Gene Product

As discussed above, the expression level of an infertility indicator gene is normalized, thereby providing a normalized value. The expression level of an infertility indicator gene is normalized relative to the level of an expression product of a reference gene(s).

For example, the expression level of an infertility indicator gene can be normalized relative to the mean level of gene products of two or more reference genes. As an example, the expression level of an infertility indicator gene can be normalized relative to the mean level of gene products of all assayed genes, or a subset of the assayed genes, where a subset of the assayed genes can include 3, 4, 5, 6, 7, 8, 9, or more assayed genes.

Suitable reference genes include, but are not limited to, glyceraldehyde-3-phosphate dehydrogenase (GAPDH) (see, e.g., GenBank Accession No. NM_002046; phosphoglycerate kinase 1 (see, e.g., GenBank Accession No. NM_000291); lactate dehydrogenase A (see, e.g., GenBank Accession No. NM_005566); ribosomal protein L32 (see, e.g., GenBank Accession No. NM_000994); ribosomal protein S18 (see, e.g., GenBank Accession No. NM_022551); tubulin, beta polypeptide (TUBB) (see, e.g., GenBank Accession No. NM_001069); and beta actin (see, e.g., GenBank Accession No. NM_001101). See, e.g., Eisenberg and Levanon (2003) *Trends in Genetics* 19:362, for a list of additional suitable reference genes.

The level of an RNA transcript as measured by TaqMan® RT-PCR refers to the cycle threshold (Ct) value. The lower the Ct, the greater the amount of mRNA present in the sample. The expression value of a RNA transcript in a sample is normalized, e.g., by first determining the mean expression value in Ct of designated reference genes in a sample ($Ct_{Ref}$). The normalized expression value for a gene ($Ct_{Gene}$) is then calculated as $Ct_{Gene}$–Ct $Ct_{Ref}$. Optionally, the normalized expression values for all genes can be adjusted, e.g., so that all adjusted normalized Ct have a value >0.

Determining a Probability of Beneficial Response

A normalized level of an infertility indicator gene product determined for an individual patient can be compared to normalized expression level values for the infertility indication gene determined in a population of patients for which the clinical outcome is already known in order to determine an individual patient's probability of beneficial response to an in vitro fertilization treatment cycle. Normalized expression level values (e.g., expressed as Ct) correlated with a probability can be used. For example, a normalized level of a response indicator gene product can be compared graphically, to determine the probability of beneficial response to an in vitro fertilization treatment cycle.

The analyses and determinations described herein in connection with a subject method for assessing likelihood of response can be made without the need for assessing any change in the level of a response indicator gene over time.

Classification Tree Analysis

One approach to analyze this data is to use a classification tree algorithm that searches for patterns and relationships in large datasets. A "classification tree" is a recursive partition to evaluate a female subject for an in vitro fertilization procedure using a series of questions that are designed to accurately place the patient into one of the classes. Each question asks whether a patient's condition satisfies a given predictor, with each answer being used to guide the user down the classification tree until a class into which the patient falls can be determined. As used herein, a "predictor" is the range of values of the features—such as, for example, age, total number of embryos, rate of cleavage arrest, number of 8-cell embryos, day 3 follicle stimulating hormone (FSH) level, and number of 8-cell embryos transferred.

Multiple Additive Regression Trees

An automated, flexible modeling technique that uses multiple additive regression trees (MART) may also be used to classify sets of features as belonging to one of two populations. A MART model uses an initial offset, which specifies a constant that applies to all predictions, followed by a series of regression trees. Its fitting is specified by the number of decision points in each tree, the number of trees to fit, and a "granularity constant" that specifies how radically a particular tree can influence the MART model. For each iteration, a regression tree is fitted to estimate the direction of steepest descent of the fitting criterion. A step having a length specified by the granularity constant is taken in that direction. The MART model then consists of the initial offset plus the step provided by the regression tree. The differences between the observed and predicted values are recalculated, and the cycle proceeds again, leading to a progressive refinement of the prediction. The process continues either for a predetermined number of cycles or until some stopping rule is triggered.

The number of splits in each tree is a particularly meaningful fitting parameter. If each tree has only one split, the model looks only at one feature and has no capability for combining two predictors. If each tree has two splits, the model can accommodate two-way interactions among features. With three trees, the model can accommodate three-way interactions, and so forth.

The value of sets of features in predicting class status was determined for data sets with features and known class status. MART provides a measure of the contribution or importance of individual features to the classification decision rule. Specifically, the degree to which a single feature contributes to the decision rule upon its selection at a given tree split can be measured to provide a ranking of features by their importance in determining the final decision rule. Repeating the MART analysis on the same data set may yield a slightly different ranking of features, especially with respect to those features that are less important in establishing the decision rule. Sets of predictive features and their corresponding biomarkers that are useful for the present invention, therefore, may vary slightly from those set forth herein.

One exemplary implementation of the MART technology is found in a module, or "package," for the R statistical programming environment (see Venables et al., in Modern Applied Statistics with S, 4th ed. (Springer, 2002); www.r-project.org). Results reported in this document were calculated using R versions 1.7.0 and 1.7.1. The module implementing MART, written by Dr. Greg Ridgeway, is called "gbm" and is also available for download (see www.r-project.org). The MART algorithm is amenable to ten-fold cross-validation. The granularity parameter was set to 0.05, and the gbm package's internal stopping rule was based on leaving out 20% of the data cases at each marked iteration. The degree of interaction was set to one, so no interactions among features were considered. The gbm package estimates the relative importance of each feature on a percentage basis, which cumulatively equals 100% for all the features of the biomarker profile. The features with highest importance, which together account for at least 90% of total importance, are reported as potentially having predictive value. Note that the stopping rule in the fitting of every MART model contributes a stochastic component to model fitting and feature selection. Consequently, multiple MART modeling runs based on the same data may choose slightly, or possibly even completely, different sets of features. Such different sets convey the same predictive information; therefore, all the sets are useful in the present invention. Fitting MART models a sufficient number of times is expected to produce all the possible sets of predictive features within a profile. Accordingly, the disclosed sets of predictors are merely representative of those sets of features that can be used to classify individuals into populations.

Wilcoxon Signed Rank Test Analysis

In yet another method, a nonparametric test such as a Wilcoxon Signed Rank Test can be used to identify individual biomarkers of interest. The features in a biomarker profile are assigned a "p-value," which indicates the degree of certainty with which the biomarker can be used to classify individuals as belonging to a particular reference population. Generally, a p-value having predictive value is lower than about 0.05. Biomarkers having a low p-value can be used by themselves to classify individuals. Alternatively, combinations of two or more biomarkers can be used to classify individuals, where the combinations are chosen on the basis of the relative p-value of a biomarker. In general, those biomarkers with lower p-values are preferred for a given combination of items of information. Combinations of at least three, four, five, six, 10, 20 or 30 or more biomarkers also can be used to classify individuals in this manner. The artisan will understand that the relative p-value of any given biomarker may vary, depending on the size of the reference population.

Analysis Results Reporting

As discussed above, evaluation of a female subject for an in vitro fertilization procedure, including determining probability of a live birth event, is done by obtaining and comparing items of information from the female subject to a library of known profile patterns known to be indicative of responsiveness to an in vitro fertilization procedure using an algorithm based upon said preselected patient variables and optionally evaluating the normalized expression level of one or more fertility response genes. In some embodiments, a patient's evaluation is provided in a report. Thus, in some embodiments, the method further includes a step of preparing or generating a report that includes information regarding the patient's likelihood of successes for an in vitro fertilization procedure. For example, a subject method can further include a step of generating or outputting a report providing the results of a patient's evaluation, which report can be provided in the form of an electronic medium (e.g., an electronic display on a computer monitor), or in the form of a tangible medium (e.g., a report printed on paper or other tangible medium).

A report that includes information regarding the patient's evaluation is provided to a user. The evaluation may include, for example, a determination of success for implantation of embryos, selection of an optimal number of embryos to transfer, and determination of success in subsequent in vitro fertilization treatment cycles following an unsuccessful treatment cycle.

The report generator may also perform one or more of sample gathering, sample processing, and data generation, e.g., the report generator may also perform one or more of: a) sample gathering; b) sample processing; c) measuring a level of an infertility indicator gene product(s); d) measuring a level of a reference gene product(s); and e) determining a normalized level of a infertility indicator gene product(s). Alternatively, an entity other than the report generator can perform one or more sample gathering, sample processing, and data generation.

For clarity, it should be noted that the term "user," which is used interchangeably with "client," is meant to refer to a person or entity to whom a report is transmitted, and may be the same person or entity who does one or more of the following: a) collects a sample; b) processes a sample; c) provides a sample or a processed sample; and d) generates data (e.g., level of a response indicator gene product(s); level of a reference gene product(s); normalized level of a response indicator gene product(s)) for use in the likelihood assessment. In some cases, the person(s) or entity(ies) who provides sample collection and/or sample processing and/or data generation, and the person who receives the results and/or report may be different persons, but are both referred to as "users" or "clients" herein to avoid confusion. In certain embodiments, e.g., where the methods are completely executed on a single computer, the user or client provides for data input and review of data output. A "user" can be a health professional (e.g., a clinician, a laboratory technician, a physician (e.g., a Reproductive Endocrinologist), etc.).

In embodiments where the user only executes a portion of the method, the individual who, after computerized data processing according to the methods of the invention, reviews data output (e.g., results prior to release to provide a complete report, a complete, or reviews an "incomplete" report and provides for manual intervention and completion of an interpretive report) is referred to herein as a "reviewer." The reviewer may be located at a location remote to the user (e.g., at a service provided separate from a healthcare facility where a user may be located).

Report

A "report," as described herein, is an electronic or tangible document which includes report elements that provide information of interest relating to a subject likelihood assessment and its results. A subject report includes at least an evaluation for an in vitro fertilization treatment cycle, e.g., facilitate a determination of success for implantation of embryos, selection of an optimal number of embryos to transfer, and determination of success in subsequent in vitro fertilization treatment cycles following an unsuccessful treatment cycle. A subject report can be completely or partially electronically generated. A subject report can further include one or more of: 1) information regarding the testing facility; 2) service provider information; 3) patient data; 4) sample data; 5) an interpretive report, which can include various information including: a) indication; b) test data, where test data can optionally include normalized level of one or more infertility indicator gene products; and 6) other features.

Where government regulations or other restrictions apply (e.g., requirements by health, malpractice, or liability insurance), all results, whether generated wholly or partially electronically, are subjected to a quality control routine prior to release to the user.

Testing Facility Information

The report can include information about the testing facility, which information is relevant to the hospital, clinic, or laboratory in which sample gathering and/or data generation was conducted. Data generation can include one or more of: a) measuring a level of a gene product(s) (e.g., an infertility indicator gene product(s), a reference gene product(s)); b) determination of a normalized level of an infertility indicator gene product. This information can include one or more details relating to, for example, the name and location of the testing facility, the identity of the lab technician who conducted the assay and/or who entered the input data, the date and time the assay was conducted and/or analyzed, the location where the sample and/or result data is stored, the lot number of the reagents (e.g., kit, etc.) used in the assay, and the like. Report fields with this information can generally be populated using information provided by the user.

Service Provider Information

The report can include information about the service provider, which may be located outside the healthcare facility at which the user is located, or within the healthcare facility. Examples of such information can include the name and location of the service provider, the name of the reviewer, and where necessary or desired the name of the individual who conducted sample gathering and/or data generation. Report fields with this information can generally be populated using data entered by the user, which can be selected from among pre-scripted selections (e.g., using a drop-down menu). Other service provider information in the report can include contact information for technical information about the result and/or about the interpretive report.

Patient Data

The patient data can include patient medical history (which can include, e.g., data about prior or current in vitro fertilization treatment cycles), personal history; administrative patient data (that is, data that are not essential to the likelihood assessment), such as information to identify the patient (e.g., name, patient date of birth (DOB), gender, mailing and/or residence address, medical record number (MRN), room and/or bed number in a healthcare facility), insurance information, and the like), the name of the patient's physician or other health professional who ordered the response likelihood assessment and, if different from the ordering physician, the name of a staff physician who is responsible for the patient's care (e.g., primary care physician). Report fields with this information can generally be populated using data entered by the user.

Exemplary items of information include, but are not limited to: patient characteristics, such as age, previous infertility history, clinical diagnosis; clinical treatment information, such as type of medication, number of days of stimulation, number of oocytes, etc.; conventional embryo morphology data, such as number of embryos, developmental stage, grade, and the like. In some embodiments, the information includes age, total number of embryos, rate of cleavage arrest, number of 8-cell embryos, day 3 follicle stimulating hormone (FSH) level, number of 8-cell embryos transferred, age, diminished ovarian reserve, endometrial thickness, blastocyst rate, total number of embryos, total number of oocytes, total amount of gonatropins administered, and number of total motile sperm.

Sample Data

The sample data can provide information about the embryo analyzed in the likelihood assessment, such as the number of days following fertilization resulting in arrest, and the date and time collected. Report fields with this information can generally be populated using data entered by the user, some of which may be provided as pre-scripted selections (e.g., using a drop-down menu).

Interpretive Report

The interpretive report portion of the report includes information generated after processing of the data as described herein. The interpretive report can include an evaluation of a female subject for an in vitro fertilization procedure. The interpretive report can include, for example, Result of analysis comparing the profile for the female subject to a library of known profile patterns known to be indicative of responsiveness to an in vitro fertilization procedure using an algorithm based upon said preselected patient variables, and optionally Result of normalized level of infertility indicator gene(s) (e.g., "normalized level of infertility indicator gene(s)"); Interpretation; and, optionally, Recommendation(s).

The Interpretation portion of the report can include a Recommendation(s). Where the results indicate a determination of success for implantation of embryos, selection of an optimal number of embryos to transfer, and determination of success in subsequent in vitro fertilization treatment cycles following an unsuccessful treatment cycle.

It will be readily appreciated that the report can include all or some of the elements above, with the proviso that the report generally includes at least the elements sufficient to provide the analysis requested by the user (e.g., likelihood assessment).

Additional Features

It will also be readily appreciated that the reports can include additional elements or modified elements. For example, where electronic, the report can contain hyperlinks which point to internal or external databases which provide more detailed information about selected elements of the report. For example, the patient data element of the report can include a hyperlink to an electronic patient record, or a site for accessing such a patient record, which patient record is maintained in a confidential database. This latter embodiment may be of interest in an in-hospital system or in-clinic setting.

Computer-Based Systems and Methods

The methods and systems described herein can be implemented in numerous ways. In one embodiment of particular interest, the methods involve use of a communications infrastructure, for example the internet. Several embodiments of the invention are discussed below. It is also to be understood that the present invention may be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site associated (e.g., at a service provider's facility).

The various elements of the computing device, such as a the input device, may be associated with other elements of the system via a wired connection or a wireless connection, including, for example, a wireless LAN connection, Bluetooth connection protocol, ZigBee connection protocol, radio-frequency connection protocol, or a cellular phone connection protocol, including code derived multiple access (CDMA) or via a global system for mobile communication (GSM).

For example, during or after data input by the user, portions of the data processing can be performed in the user-side computing environment. For example, the user-side computing environment can be programmed to provide for defined test codes to denote a likelihood "score," where the score is transmitted as processed or partially processed responses to the reviewer's computing environment in the form of test code for subsequent execution of one or more algorithms to provide a results and/or generate a report in the reviewer's computing environment.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which generally includes subject information data, such as age, total number of embryos, rate of cleavage arrest, number of 8-cell embryos, day 3 follicle stimulating hormone (FSH) level, number of 8-cell embryos transferred, age, diminished ovarian reserve, endometrial thickness, blastocyst rate, total number of embryos, total number of oocytes, total amount of gonatropins administered, and number of total motile sperm. This information received can be stored at least temporarily in a database, and data analyzed to generate a report as described above.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In an embodiment of particular interest, all or a portion of the input data and/or all or a portion of the output data (e.g., usually at least the final report) are maintained on a web server for access, preferably confidential access, with typical browsers. The data may be accessed or sent to health professionals as desired. The input and output data, including all or a portion of the final report, can be used to populate a patient's medical record which may exist in a confidential database at the healthcare facility.

A system for use in the methods described herein generally includes at least one computer processor (e.g., where the method is carried out in its entirety at a single site) or at least two networked computer processors (e.g., where data is to be input by a user (also referred to herein as a "client") and transmitted to a remote site to a second computer processor for analysis, where the first and second computer processors are connected by a network, e.g., via an intranet or internet).

The system can also include a user component(s) for input; and a reviewer component(s) for review of data, generated reports, and manual intervention. Additional components of the system can include a server component(s); and a database(s) for storing data (e.g., as in a database of report elements, e.g., interpretive report elements, or a relational database (RDB) which can include data input by the user and data output. The computer processors can be processors that are typically found in personal desktop computers (e.g., IBM, Dell, Macintosh), portable computers, mainframes, minicomputers, or other computing devices, such as Smartphone devices, including, for example, an Apple® iPhone® device.

The networked client/server architecture can be selected as desired, and can be, for example, a classic two or three tier client server model. A relational database management system (RDMS), either as part of an application server component or as a separate component (RDB machine) provides the interface to the database.

In one embodiment, the architecture is provided as a database-centric client/server architecture, in which the client application generally requests services from the application server which makes requests to the database (or the database server) to populate the report with the various report elements as required, particularly the interpretive report elements, especially the interpretation text and alerts. The server(s) (e.g., either as part of the application server machine or a separate RDB/relational database machine) responds to the client's requests.

The input client components can be complete, stand-alone personal computers offering a full range of power and features to run applications. The client component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the client and server(s), including processing on a single machine such as a mainframe, a collection of machines, or other suitable configuration are contemplated. In general, the client and server machines work together to accomplish the processing of the present invention.

Where used, the database(s) is usually connected to the database server component and can be any device which will hold data. For example, the database can be a any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

Computer-Readable Storage Media

The invention also contemplates a computer-readable storage medium (e.g. CD-ROM, memory key, flash memory card, diskette, etc.) having stored thereon a program which, when executed in a computing environment, provides for implementation of algorithms to carry out all or a portion of the methods of analysis of evaluating a subject for an in vitro fertilization procedure as described herein. Where the computer-readable medium contains a complete program for carrying out the methods described herein, the program includes program instructions for collecting, analyzing and generating output, and generally includes computer readable code devices for interacting with a user as described herein, processing that data in conjunction with analytical information, and generating unique printed or electronic media for that user.

Where the storage medium provides a program which provides for implementation of a portion of the methods described herein (e.g., the user-side aspect of the methods (e.g., data input, report receipt capabilities, etc.)), the program provides for transmission of data input by the user (e.g., via the internet, via an intranet, etc.) to a computing environment at a remote site. Processing or completion of processing of the data is carried out at the remote site to generate a report. After review of the report, and completion of any needed manual intervention, to provide a complete report, the complete report is then transmitted back to the user as an electronic document or printed document (e.g., fax or mailed paper report). The storage medium containing a program according to the invention can be packaged with instructions (e.g., for program installation, use, etc.) recorded on a suitable substrate or a web address where such instructions may be obtained. The computer-readable storage medium can also be provided in combination with one or more reagents for carrying determining subject information data, e.g., material for determining rate of cleavage arrest, number of 8-cell embryos, day 3 follicle stimulating hormone (FSH) level, and number of 8-cell embryos transferred, and the like.

Kits

The materials for use in the methods of the present invention are suited for preparation of kits produced in accordance with well known procedures. The invention thus provides kits comprising reagents, which may include gene-specific or gene-selective probes and/or primers useful for assaying the expression of genes disclosed herein and for assessing the likelihood of response to an in vitro treatment cycle.

For example, a subject kit can include one or more nucleic acid probes that hybridize specifically to nucleic acid infertility indicator gene products. A subject kit can include, e.g., one or more nucleic acid probes, where each of the one or more probes hybridizes specifically to a different response indicator gene product. For example, a subject kit can include probes that hybridize specifically to nucleic acid products of infertility indicator genes including, but are not limited to, Oct4, Eif3c, Papola, Piwil2, Eif3b, Eif4b, Rbm3, and Cpsf4. As another example, a subject kit can include a set of two or more nucleic acid probes, where each probe of the set hybridizes to a nucleic acid product of a different infertility indicator gene. For example, a subject kit can include a set of two, three, four, five, six, seven, or more, nucleic acid probes, where each probe of the set hybridizes to a nucleic acid product of a different member of a set of infertility indicator genes.

In some cases, a subject kit will include, in addition to a probe that hybridizes specifically to a nucleic acid product of an infertility indicator gene, one or more probes that hybridize specifically to a reference gene product. Such probes can be used in determining normalized expression levels of an infertility indicator gene.

A subject kit can include one or more nucleic acid primer pairs, where the primer pairs, when used as primers in a polymerase chain reaction, amplify a target nucleic acid response indicator gene product, or a target region of a nucleic acid response indicator gene product. A subject kit can include primer pairs for multiple infertility indicator genes.

Exemplary sequences of nucleic acid primers and probes are provided in the Examples described herein. Those skilled in the art will readily appreciate that other probe and primer sequences are also possible, and are readily obtained based on known nucleotide sequences of infertility indicator genes, and/or based on known nucleotide sequences of reference genes.

In addition to the above-mentioned probes and primers, a subject kit can comprise reagents for the extraction and/or isolation of RNA from single cell embryos, in particular fixed paraffin-embedded tissue samples and/or reagents for preparing a cDNA copy of an mRNA, and/or reagents for nucleic acid amplification. Exemplary reagents include those required for use of a FLUIDIGM® BIOMARK® 48.48 Dynamic array system, comparable single-cell gene expression analysis platform (RT-PCR), or emerging technology such as next-generation, whole-transcriptome sequencing at the single-cell level.

Primers and probes can be designed based on known sequences of infertility indicator genes, and are readily synthesized by standard techniques, e.g., solid phase synthesis via phosphoramidite chemistry, as disclosed in U.S. Pat. Nos. 4,458,066 and 4,415,732, incorporated herein by reference; Beaucage et al. (1992) Tetrahedron 48:2223-2311; and Applied Biosystems User Bulletin No. 13 (1 Apr. 1987). Other chemical synthesis methods include, for example, the phosphotriester method described by Narang et al., Meth. Enzymol. (1979) 68:90 and the phosphodiester method disclosed by Brown et al., Meth. Enzymol. (1979) 68:109. Poly(A) or poly(C), or other non-complementary nucleotide extensions may be incorporated into probes using these same methods. Hexaethylene oxide extensions may be coupled to probes by methods known in the art. Cload et al. (1991) J. Am. Chem. Soc. 113:6324-6326; U.S. Pat. No. 4,914,210 to Levenson et al.; Durand et al. (1990) Nucleic Acids Res. 18:6353-6359; and Horn et al. (1986) Tet. Lett. 27:4705-4708.

A probe or a primer can include a detectable label. Exemplary labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM), N,N,N',N'-tetramethyl-6-carboxyrhodamine (TAMRA), Cy5, Cy3, and the like; and radioactive labels (e.g., $^{32}$P, etc.).

Probes and primers for inclusion in a subject kit include those useful in various amplification and/or detection systems. Exemplary amplification and/or detection systems include Sunrise primer-based systems, Molecular Beacons, the Taqman™ system, an Amplifluor™ hairpin primer-based system, a Scorpions technology (e.g., bi-functional molecules containing a PCR primer element covalently linked to a probe element), a Light Upon Extension or LUX™-based system, and a FLUIDIGM® BIOMARK® 48.48 Dynamic array system. Further exemplary detection systems include those based on a melt-curve analysis, and using intercalating dyes such as the fluorescent dye SYBR Green.

The kits may optionally comprise reagent(s) with an identifying description or label or instructions relating to their use in the methods of the present invention. The kits may comprise containers (including microtiter plates suitable for use in an automated implementation of the method), each with one or more of the various reagents (typically in concentrated form) utilized in the methods of the invention, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more probes and primers of the present invention (e.g., appropriate length poly(T) or random primers linked to a promoter reactive with the RNA polymerase).

Instructions for the use of mathematical algorithms used to evaluate a female subject for an in vitro fertilization treatment cycle, including determining a probability of a live birth event, can also be included in a subject kit. In such embodiments, the kits will further include a written or electronic medium, or instructions to access a remote database, as described above, to provide and/or receive information, which generally includes subject information data, such as age, total number of embryos, rate of cleavage arrest, number of 8-cell embryos, day 3 follicle stimulating hormone (FSH) level, number of 8-cell embryos transferred, age, diminished ovarian reserve, endometrial thickness, blastocyst rate, total number of embryos, total number of oocytes, total amount of gonatropins administered, and number of total motile sperm, in order to carry out the methods as described above.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods

The following methods and materials were used in the examples below.

Data Collection, Inclusion and Exclusion Criteria

Data related to clinical diagnoses, IVF treatment protocol and monitoring, embryology data and treatment outcomes for all IVF cycles performed between Jan. 1, 2003 and Dec. 31, 2006 at Stanford University Medical Center were retrieved from BabySentryPro (BabySentry Ltd, Limassol, Cyprus), a widely used fertility database management system, or obtained from medical and embryology records as necessary. Retrospective data collection, de-identification, and analysis were performed according to a Stanford University Institutional Review Board-approved protocol. The inclusion criteria for data analysis were fresh, stimulated, non-donor oocyte IVF cycles.

In certain experiments, cycles that did not result in embryo transfer for any reason, cycles performed for women aged over 45, and those performed for preimplantation genetic screening were excluded.

In other experiments, we did not exclude cycles that were canceled at any point due to medical or non-medical reasons after the IVF treatment had started. We excluded cryopreserved embryo transfer cycles which used embryos that had been conceived in a different IVF clinic.

Defining Cycle Numbers

We renumbered all IVF cycles according to the following method. For each patient, the first fresh IVF cycle appearing in this four-year data set is called "Cycle 1". The final outcome of all embryo transfer treatments that utilize fresh or cryopreserved embryos conceived from Cycle 1 is defined as the outcome for Cycle 1. The second fresh IVF cycle that appears is defined "Cycle 2", and so on. Our database could not accommodate data on IVF cycles that were performed elsewhere.

Assessment of Embryo Development

The standard clinical protocols for IVF treatment, fertilization, embryo culture, embryo assessment, cryopreservation criteria, and clinical outcomes are described below. The normal progression of human embryo development in vitro is characterized by the appearance of 2 pronuclei at 16-20 hours after insemination as evidence of fertilization on Day 1, with Day 0 as the day of oocyte retrieval. By late Day 1, embryo development has reached the 2-cell stage, followed by the 4-cell and 8-cell stages on Days 2 and 3, respectively. On Days 4 and 5, embryo development is characterized by the establishment of the morula and blastocyst stages, respectively. All embryos were available for evaluation on Day 3. The day of embryo transfer was determined by the number of blastomeres on Day 3. In general, if 4 or more 8-cell embryos were present, we would recommend extended embryo culture until Day 5, when blastocyst transfer, which has been associated with higher pregnancy rates, would be performed. If fewer than four 8-cell embryos were present, embryo transfer would be performed on Day 3.

Patient, IVF Cycle, and Embryo Parameters 30 variables for association with IVF treatment outcomes were analyzed, as listed in Table 1, under four main categories: patient characteristics and clinical diagnoses, IVF cycle characteristics, embryo cohort parameters, and parameters of transferred embryos. The cleavage arrest rate was defined as the percentage of embryos within a cohort with 4 or fewer cells on Day 3 of in vitro culture. All other variables were self-explanatory.

Definition of Outcomes

Statistical analyses were performed based on the dichotomous outcomes of live birth versus no live birth. No live birth encompassed all other outcomes such as negative serum β-hCG, or positive serum β-hCG followed by biochemical pregnancy, spontaneous abortion, and ectopic pregnancy.

Statistical Analysis

Since some patients underwent more than one IVF cycle during the study period, the analyses were performed based on treatment cycles rather than patients. Statistical analyses were performed based on the dichotomous outcomes of no pregnancy, as defined by negative serum β-hCG, and pregnancy, as defined by positive serum β-hCG, and included biochemical pregnancy, clinical pregnancy, spontaneous abortion, and ectopic pregnancy. We performed pair-wise logistic regression of each variable to the outcome and determined the Pearson correlation coefficient between each pair of continuous variables.

For the main analyses, boosted classification trees were constructed by MART® to identify non-redundant prognostic variables, which were then further analyzed by CART to identify thresholds that would define them as categorical variables. MART® is a robust method used to identify interactive structure of variables that are predictive of outcomes. The use of cross-validation and boosting in parameter selection and model assessment in MART® also preserve parsimony and prevent over-fitting. In the MART® tree constructions, the whole data set is divided into 10 subsets to achieve 10 fold cross validation for model assessment. The same 10 fold cross validation was repeated 1000 times to perform a robust prediction rate estimation and identify tree models with the highest prediction rates in the CART. While MART® is powerful in selecting non-redundant prognostic variables from a large set of highly interactive variables, CART analysis results in simple algorithms, and more easily understood "decision trees", that are used in the medical literature (Guznick et al., N Engl J Med 345: 1388-1393. (2001)). Thus non-redundant, prognostic variables identified by MART® to confer prediction were analyzed by CART to further define prognostic thresholds.

In some experiments, if patients underwent multiple fresh IVF cycles during the study period, only the first three cycles were analyzed. We generated the models based on cycle 1 (C1) data only. Data from C2 and C3 were used to test inter-cycle validation of the pre-transfer model only.

In such experiments, we performed pair-wise logistic regression of each variable to the outcome and determined the Pearson correlation coefficient between each pair of continuous variables. We generated three models based on data that were available at three different time points prior to IVF treatment (pre-IVF), oocyte retrieval (pre-OR), and after embryo transfer (post-IVF). We generated each model by ranking variables according to their relative influence using gradient boosting machine (GBM), the R-software implementation of MART®, followed by construction of regression tree models using top-ranked variables with Rpart software. MART® is a robust method used to identify interactive structure of variables that are predictive of outcomes. The use of cross-validation and boosting in parameter selection and model assessment in MART® also preserve parsimony and prevent over-fitting. In the MART® tree constructions, the whole data set is divided into 10 subsets to achieve 10 fold cross validation for model assessment. The same 10 fold cross validation was repeated 1000 times to perform a robust prediction rate estimation and identify tree models with the highest prediction rates. While MART® is powerful in selecting non-redundant prognostic variables from a large set of highly interactive variables.

Treatment Protocols Used for Assisted Reproductive Technologies (ART)

The majority of our analyzed IVF cycles were performed in patients with poor ovarian reserve, severe male factor infertility, tubal infertility, anovulatory disorders, or unexplained etiology. In general, one of three stimulation protocols was used in each treatment cycle: luteal downregulation (long) was used for most patients, and microdose lupron (flare) and antagonist protocols were used primarily for patients with presumed diminished ovarian reserve or with a history of previously failed IVF cycles. The long protocol consisted of luteal downregulation using 0.5 mg leuprolide acetate, which was decreased to 0.25 mg with stimulation. In the flare protocol, microdose lupron (0.04 mg s.c. bid) was started after 2-4 weeks of oral contraceptive pills. In the antagonist protocol, GnRH antagonist was initiated when the lead follicle reached 14 mm in size. In all three protocols, baseline ultrasound testing was performed to document that no cysts >1.5 cm were present in the ovaries. When baseline criteria were met, gonadotropin therapy using recombinant FSH with human menopausal gonadotropin was begun. Stimulation was generally achieved using daily dosing of a total of 150-600 IU per day in order to maximize follicular recruitment. Ultrasound monitoring of follicular growth was performed starting on cycle day 7 and then every 1-3 days as indicated. Serum estradiol levels were monitored as necessary.

A dose of 10,000 IU of human chorionic gonadotropin was administered when at least two follicles reached an average diameter of >17 mm. Transvaginal ultrasound-guided oocyte retrieval was performed 34-36 hours after hCG administration in the standard fashion with monitored anesthetic care.

Oocyte Fertilization and Embryo Culture

Oocytes were cultured in groups before fertilization under mineral oil in approximately 125 µl droplets of Sage Cleavage Medium (Cooper Surgical, Inc, Trumbull, Conn.) with 10% Serum Protein Substitute (SPS, Irvine Scientific, Santa Ana, Calif.). Oocytes destined for conventional IVF were cultured in groups of 5 and oocytes destined for intracytoplasmic sperm injection (ICSI) were cultured in groups of up to 20 after stripping the cumulus cells. Oocytes were inseminated with sperm if the semen analysis was normal and fertilization was expected to be normal. Oocytes were inseminated conventionally between 4-6 hours after retrieval. If the semen analysis was abnormal or poor fertilization was expected, then the oocytes were injected with sperm using ICSI. The fertilized oocytes were cultured in groups of up to 20 under mineral oil in approximately 125 µl droplets of Sage Cleavage Medium (Cooper Surgical, Inc, Trumbull, Conn.) with 10% SPS at 37° C. in a humidified atmosphere of 5% $O_2$, 5% $CO_2$ and 90% $N_2$. Fertilization check was performed 16-18 hours after insemination or ICSI. The zygotes with clear two pronuclei were cultured for another 48 hours in Sage Cleavage Medium with 10% SPS. Oocytes with single pronucleus (1PN) or three or more pronuclei were considered abnormally fertilized. If Day 5 blastocyst transfer was indicated, extended embryo culture was be performed in Quinn's Advantage Blastocyst medium (Cooper Surgical) with 10% SPS for 48 hours before transfer. Of note, the same culture media was used during the study time period.

Cleavage and Grading of Embryos

A single team of experienced embryologists evaluated the embryos on post-retrieval day 3, 68 to 72 hours after oocyte harvest. Embryos were examined for cleavage (cell number) and grade, which includes cytoplastmic fragmentation. Embryos were graded as follows on Day 3: Grade 1, blastomeres have equal size and no cytoplasmic fragmentation; Grade 2, blastomeres have equal size and minor cytoplasmic fragmentation involving <10% of the embryo; Grade 3, blastomeres have unequal size and fragmentation involving 10-20% of the embryo; Grade 4, blastomeres have equal or unequal size, and moderate to significant cytoplasmic fragmentation covering 20-50% of the embryo; and Grade 5, few blastomeres and severe fragmentation covering ≥50% of the embryo (Veeck et al., (1999) An Atlas of Human Gametes and Conceptuses. New York: Parthenon Publishing. 47-50). Of note, cytoplasmic fragmentation in embryos was easily differentiated from cleavage based on the size of the fragments, their location within the embryo, and the absence of a nucleus. In contrast, cytoplasmic fragmentation of oocytes was not included as a variable because it was extremely rare. The presence or absence of compaction was routinely noted by our embryologists on Day 3. As compaction was observed in <10% of embryos, we did not include this variable in the analysis.

Assisted Hatching

Indications for assisted hatching (AH) in our center were advanced maternal age, elevated FSH level, and/or a history of multiple failed assisted reproduction cycles. On the day of embryo transfer, embryos for hatching were placed in phosphate-buffered saline (PBS) with 10% SPS. AH was accomplished by using the ZILOS-tk laser (Hamilton Thorne Biosciences, Beverly, Mass.) to make a hole in an area of the zona pellucida that was between blastomeres. Embryos were then rinsed and returned to the media until transfer.

Embryo Transfer and Cryopreservation

Ultrasound-guided embryo transfer was performed using a Tefcat or Echotip Softpass catheter (Cook Ob/Gyn, Spencer, Ind.). Progesterone supplementation with vaginal suppositories was performed in all patients. For patients having embryo transfer on Day 3, any remaining embryos with more than five blastomeres were placed in extended culture for another 2 or 3 days. Any expanding, expanded and hatching blastocysts with good inner cell mass and trophectoderm were frozen on day 5 or day 6. In addition, cryopreservation was performed on excess embryos, severe ovarian hyperstimulation syndrome, and fertility preservation due to medical or social reasons. Excess embryos that were not transferred were commonly discarded if they were not of sufficient quality for cryopreservation or if patients did not opt for embryo cryopreservation due to non-medical reasons. In cases of pre-implantation genetic diagnosis, embryos that tested positive for genetic diseases or aneuploidy were also discarded.

Clinical Outcomes

Serum quantitative β-hCG levels were obtained at 8-10 days after embryo transfer, and followed serially until the diagnosis of clinical pregnancy was made by the presence of a gestational sac on transvaginal ultrasound. Outcomes other than clinical pregnancy included: 1) no pregnancy if serum quantitative B-hCG was negative; 2) biochemical pregnancy as defined by decreasing serum quantitative B-hCG levels before a gestational sac could be visualized by transvaginal ultrasound; 3) spontaneous abortion as defined by pregnancy loss after a gestational sac was visualized by transvaiginal ultrasound; and 4) ectopic pregnancy; and 5) other abnormal gestations such as gestational trophoblastic disease. Live birth outcomes were obtained by follow-up contact with patients as part of routine clinical care, but they were not used in this study.

Regression Trees

Clinical IVF data, especially when considering oocyte and embryo parameters, often do not lend themselves to meaningful analysis by multivariate logistic regression. The high degree of interaction and multicollinearity of many relevant variables interfere with conventional multivariate regression. In these situations, the regression and classification tree models (CART), has been widely used in clinical research (Fonarow G C, Jama 293: 572-580 (2005); Friedman J (1999) Greedy function approximation: A stochastic boosting machine. Technical Report, Department of Statistics, Stanford University; Friedman J (1999) Stochastic gradient boosting. Technical Report, Department of Statistics, Stanford University; Friedman J (2002) Tutorial: Getting started with MART in R. Department of Statistics, Stanford University; Friedman et al., Stat Med 22: 1365-1381 (2003); Guzick et al., N Engl J Med 345: 1388-1393 (2001); Pilote et al., N Engl J Med 335: 1198-1205 (1996)). Here, we used Multiple Additive Regression Tree (MART®), a more powerful statistical method that combines "boosting" with CART to "boost" or increase accuracy in the CART method, to identify non-redundant prognostic variables.

In general, regression trees have several key advantages: 1) ability to consider all types of clinical IVF and embryology data, including numeric, ordinal, binary, and categorical variables; 2) ability to handle missing values well based on a "surrogate" splitting technique without the need for imputation; 3) ability to generate results that are invariant to monotonic data transformation and thus eliminate the need to test different methods of data transformation or metrics; 4) ability to generate trees that are immune to the effects of extreme outliers; 5) ability to generate trees that inherently explore and identify interactions of variables that would otherwise need to be explicitly stated in a multiple logistic regression. Most importantly, regression trees can consider a large number of variables, including ones that may turn out to be irrelevant, even if only a small number of variables have significant statistical impact on outcomes. This ability to consider many variables is critical for analysis of IVF outcomes, as many variables, such as percentage of 8-cell embryos, number of 8-cell embryos, percentage of 8-cell embryos transferred, and number of 8-cell embryos transferred, may be highly interactive; thus, arbitrarily selecting one of them may compromise completeness of data and introduce bias, while including all of them may cause the conventional multivariate regression to breakdown.

The results from MART® may help to identify variables that could be re-analyzed by multivariate logistic regression. Often, they may identify thresholds, or "cut-offs", that will be used to create categorical variables to segregate cases into subgroups for further inter-group comparison of characteristics by conventional methods such as t-tests, chi-square analysis, or Wilcoxon rank sum test. For example, CART analysis was used by Guzick et al. to classify men as subfertile, of indeterminate fertile status, or fertile based on threshold values for sperm concentration, motility, and morphology, exemplifies the power of this strategy in infertility research (Guzick et al., N Engl J Med 345: 1388-1393 (2001)).

Embryo Culture 3-5 week old wild type F1 (C57BL6×DBA/2) females (Charles River) were superovulated by intraperitoneal injections of 5 IU of pregnant mare's serum gonadotropin (Sigma) followed by 5 IU of human chorionic gonadotropin (Sigma) 48 hours later, and mated overnight with wild type males. Mice were sacrificed by cervical dislocation 17 hours after hCG injection, and 1-cell embryos were released from oviducts. Cumulus cells were removed by hyaluronidase (Sigma) treatment and pipetting. Pre-implantation embryos at the two pronuclei stage were recovered, pooled from 3-6 females in M2 media (Chemicon International), followed by immediate cytoplasmic microinjection and culture in Human Tubal Fluid with 10% serum supplement (In-Vitro Fertilization, Inc.) microdrops under mineral oil (Sigma) in mixed gas (90% nitrogen, 5% oxygen, 5% carbon dioxide; Praxair) at 37° C., and cultured at ten embryos per 20 μL drop.

Microinjection of Antisense Morpholino Oligonucleotides 25-nt, antisense morpholino oligonucleotides (MOs) that specifically target the 5'UTR or translational start site, or controls mismatched at 5 nts were purchased from Gene Tools, LLC. (See Table 1 for sequence details). We had determined 0.6-0.75 mM to be the maximal concentration that would allow normal rates of blastocyst development (data not shown). Hence, unless otherwise specified, 5-10 pL of 0.75 mM Ccna2-MO (0.60 mM for Oct4-MO) was injected into the cytoplasm of each embryo on an inverted microscope (Olympus IX70) equipped with hydraulic micromanipulation system (IM300 Microinjector, Narishige, Japan). 10 uninjected control embryos were used in each experiment, which was performed at least three times. The mean percentage and standard error of the mean (mean±s.e.m.) of embryos progressing to, or arresting at, each developmental stage were calculated, and statistical significance was determined by calculating the p-value using 2-tailed Student's t-test.

analyzed by electrophoresis on 10% Tris-HCl polyacrylamide gel, semi-dry transferred onto nitrocellulose membrane (Bio-Rad), blocked in 0.1% Tween-20-1% Casein TBS Blocking Solution (Bio-Rad), incubated overnight in 1:250 diluted primary rabbit polyclonal anti-cyclin A2 antibody (Santa Cruz Biotechnologies, sc-751) at 4° C. and in 1:2000 diluted secondary donkey anti-rabbit horseradish peroxidase-linked antibody (Amersham, NA934V) for one hour at room temperature, and visualized using ECL Blotting Detection Reagent (Amersham). Immunocytochemistry was performed according to standard protocol. Briefly, embryos were fixed in 4% paraformaldehyde-PBS solution, permeabilized in 0.1% Triton X-PBS and treated with ImageIT FX Signal Enhancer solution (Invitrogen) at RT, incubated in 1:100 diluted primary antibody overnight at 4° C., in 1:10,000 diluted secondary antibody for one hour, followed by 3 μM DAPI for 10 min., and were mounted in VectaShield Mounting Medium (Vector Laboratories, H-1000). Controls were performed in parallel with normal rabbit or mouse serum control. All antibodies were diluted in 1% BSA. Embryos were imaged by confocal microscopy using LSM 510 Confocal Laser Scanning Microscope or epifluorescence microscopy or the Axiovert 200 microscope equipped with an Axiocam digital camera (Zeiss) using fixed parameters and exposure times. Primary antibodies were purchased from Santa Cruz Biotechnologies (anti-cyclin A2

TABLE 1

Antisense Morpholino Oligonucleotides Target Gene-Specific Sequence in the 5' UTR and/or Start Site

| Name | Sequence | GC content, % |
|---|---|---|
| Ccna2-MO-1 | 5'-TCGAGGTGCCCGGCATCGCGGCTCC-3' (SEQ ID NO: 01) | 76 |
| Ccna2-MO-2 | 5'-CTGTCGGCGGCAGAGCGTTCACAGC-3' (SEQ ID NO: 02) | 68 |
| Ccna2-MM-1 | 5'-TCCAGGTCCCCCGCATCCCGGATCC-3' (SEQ ID NO: 03) | 72 |
| Oct4-MO | 5'-AGTCTGAAGCCAGGTGTCCAGCCAT-3' (SEQ ID NO: 04) | 56 |
| Oct4-MM | 5'-ACTCTCAAGCCACGTGTGCAGCGAT-3' (SEQ ID NO: 05) | 56 |
| Oct4E4-MO | 5'-CTCCGATTTGCATATCTGGGCAGGG-3' (SEQ ID NO: 06) | 56 |
| Oct4E4-MM | 5'-CTGCGATTTCCATATGTGCGCACGG-3' (SEQ ID NO: 07) | 56 |
| Standard control* | 5'-TCCAGGTCCCCCGCATCCCGGATCC-3' (SEQ ID NO: 08) | 72 |

*splice site of mutated human β-globin gene
Mismatched nucleotides are underlined Immunoblot and Immunocytochemistry Injected and control embryos were collected at 2-cell stage (43 hours post human chorionic gonadotropin (hCG) administration) and washed in PBS containing 3 mg/mL polyvinylpyrrolidone (PVP). For immunoblot, injected and control embryos were lysed in RIPA buffer (50 mM Tris-HCl, pH7.5, 150 mM NaCl, 1 mM EDTA, 1% Nonident P-40, 2 mg/ml aprotonin, 2 mg/ml leupeptin, 1 mg/ml pepstain, and 20 mg/ml phenylmethylsulfonyl) containing a phosphatase inhibitor cocktail (Roche), boiled in Laemli buffer, and stored at −80° C. until lysates from 75 embryos were collected for each condition. Samples were loaded and rabbit polyclonal (sc-751), normal rabbit IgG (sc-2027), mouse monoclonal anti-Oct4 (sc-5279), and normal mouse IgG (sc-2025). Secondary antibodies were purchased from Molecular Probes (Alexa Fluor 594 goat anti-rabbit IgG (A-11012) and goat-anti mouse IgG (A-11001).

mRNA Synthesis by In Vitro Transcription.

Full-length mouse cDNA clone, Oct4-pSPORT (clone ID 30019896) (Open Biosystems), and a plasmid encoding the fluorescence mitotic biosensor, a modified enhanced yellow fluorescence protein (mEYFP), were sequence-verified, linearized by restriction enzyme digest, and used as templates. 5' capped and polyadenylated mRNA transcripts were transcribed in vitro (mMessage and PolyA-Tail kits, Ambion), which were then quantitated by UV spectroscopy, and analyzed by electrophoresis to confirm size.

RNA Sample Preparation for Gene Chip Experiments

Samples containing 20 pooled injected or control mouse embryos were washed through 3 drops of PBS/PVP and collected for total RNA extraction and isolation (Picopure Total RNA Isolation Kit, Molecular Devices Corp.), to yield 10 µL of total RNA. 5 µL of total RNA, or the equivalent of 10 mouse embryos, was subjected to two rounds of amplification (WT-Ovation Pico system, Nugen) according to manufacturer's instructions. The quality of ssDNA resulting from the second round amplification was tested on the Bioanalyzer 2100 (Agilent), and a typical yield of 5-8 µg per sample was quantitated by the ND-1000 UV spectrophotometer (Nanodrop Technologies). Direct biotin labeling and fragmentation were performed (FL-Ovation cDNA Biotin Module (Nugen). Fragmented, labeled, ssDNA samples were submitted to Stanford University PAN Core Facility for hybridization to the GeneChip® Mouse Genome 430 2.0 Array (Affymetrix), and laser scanning.

Statistical Analysis for Gene Chip Experiments

Raw data from a total of 12 gene chips (3 Ccna2-MO and their uninjected controls, and 3 Oct4-MO and their uninjected controls) and were normalized by dChip (Li C & Wong W H (2003) in *The analysis of gene expression data: methods and software*. (Springer, New York), pp. 120-141). Unsupervised clustering analysis was performed for genes that have: 1) expression level greater than 500 Signal Intensity (SI) in at least 10 percent of the samples; 2) standard deviation to mean ratio >0.4 and <1000 across the samples. Subsequent analyses were not restricted to these criteria. The lists of differentially expressed genes and their ranking were generated by the method proposed by Johnson and Wong, which is based on fold change, logged fold change and unpaired t-statistic (Nicholas Johnson and W. H. W. (2007) Combining scientific and statistical significance in gene ranking. Unpublished.). Differential expression was defined by a threshold of 5 percent median false discovery rate (FDR) estimated from 300 random permutations across the samples. To find significantly enriched gene ontology (GO) terms (Ashburner M, et al. (2000) Gene ontology: tool for the unification of biology. The Gene Ontology Consortium. *Nat Genet* 25, 25-29), each gene list was mapped to Entrez gene identification numbers (NCBI) and tested by GOSTAT PACKAGE (Beissbarth T & Speed T P (2004) GOstat: find statistically overrepresented Gene Ontologies within a group of genes. *Bioinformatics* 20, 1464-1465) against a set of "universe" genes defined by "P" call in at least 2 out of 3 treated samples or 4 out of 6 control samples by (MAS, Affymetrix). To estimate the FDR, 50 tests were performed with randomly generated lists of genes from the "universe" gene set, and the average number of enriched GO terms were calculated (Ashburner et al.; Beissbarth et al.). The cut off for p-value was chosen to reflect FDR of ~10 percent. Differentially expressed genes with possible Oct4-binding sites were identified by comparison with putative Oct4-regulated genes previously identified by Zhou et. al. (Zhou Q, Chipperfield H, Melton D A, & Wong W H (2007) A gene regulatory network in mouse embryonic stem cells. *Proc Natl Acad Sci USA* 104, 16438-16443), followed by mapping of probe sets to Refseq using the BIOCONDUCTOR ANNOT PACKAGE (R. C. Gentleman VJC, D. M. Bates, B. Bolstad, M. Dettling, S. Dudoit, B. Ellis, L. Gautier, Y. Ge, J. Gentry, K. Hornik, T. Hothorn, W. Huber, S. Iacus, R. Irizarry, F. Leisch, C. Li, M. Maechler, A. J. Rossini, G. Sawitzki, C. Smith, G. Smyth, L. Tierney, J. Y. H. Yang, J. Zhang. (2004) Bioconductor: Open software development for computational biology and bioinformatics. *Genome Biology* 5, R80).

RT-PCR, q-PCR, and Single Embryo q-PCR Analysis

Lysis buffer was added to PBS/PVP washed embryos (Cells-to-cDNA kit, Ambion) and samples were treated with 1 µL of DNAse I. Reverse transcription (RT) was performed by using 1.0 µL of SuperScript III RT enzyme (200 U/µL) as per protocol (Invitrogen). Amplification of gene-specific product by TaqPolymerase High Fidelity Kit (Invitrogen) was performed on the thermocycler (Mastercycler gradient 5331, Eppendorf) as follows: 94.0° C. for 2 min., 94.0° C. for 15 sec., 60.0° C. for 30 sec., 68.0° C. for 45 sec, 68.0° C. for 7 minutes for 50 cycles. (See Table 2 for all primer sequence and TaqMan probes). Single embryo qRT-PCR was performed using the Biomark 48.48 Dynamic Array system (Fluidigm, South San Francisco, Calif.). Single embryos were treated with acid tyrode, and collected in 10 µl reaction buffer, followed by preamplification as per manufacturer's instructions (TaqMan Gene Expression Assay, Applied Biosystems; Table S8). Amplified cDNA was loaded onto a 48.48 Dynamic Array using the NanoFlex IFC controller (Fluidigm). Threshold cycle ($C_T$) as a measurement of relative fluorescence intensity was extracted from the BioMark PCR analysis software (Fluidigm). All reactions were performed in duplicates or triplicates along with negative RT, PBS, and positive controls in at least three to five independent experiments. Data for each gene assayed were tested with a linear model (ANCOVA) in which $C_T \sim \beta_0 + \beta_1 *\text{Condition} + \beta_2 *C_T[\text{Gapdh}] + \beta_3 *C_T[\text{beta-actin}]$, where "Condition" referred to no injection or Oct4 knockdown. $C_T$ values were directly used in data analysis, as gene expression at the single-cell level has been shown to follow a lognormal distribution.

TABLE 2

Taqman ® Probes and Gene-Specific Primers Used in q-PCR

| Probe Name | Applied Biosystems Assay ID/ Catalog No. |
|---|---|
| Bmpr1a | Mm01208758_m1 |
| Pou5f1 | Mm00658129_gH |
| Klf9 | Mm00495172_m1 |
| Fgf4 | Mm00438917_m1 |
| Sall4 | Mm01240680_m1 |
| Bclaf1 | Mm00464127_m1 |
| Yy1 | Mm00456392_m1 |
| Pknox1 | Mm00479320_m1 |
| Gata4 | Mm00484689_m1 |
| Mta2 | Mm00488671_m1 |
| Rest1 | Mm00803268_m1 |
| Tcf15 | Mm00626495_m1 |
| Dppa5 | Mm01171664_g1 |
| Bmpr1a | Mm00477650_m1 |
| Fgfr1l | Mm00475318_g1 |
| Il17rd | Mm00460340_m1 |
| Ubtf | Mm00456972_m1 |
| Gtf3c4 | Mm00557022_m1 |
| Gtf3c2 | Mm00510828_m1 |
| Polr3e | Mm00491765_m1 |
| Polr3a | Mm00805896_m1 |
| Eif3b | Mm00659801_m1 |
| Eif3s10 | Mm00468721_m1 |
| Piwil2 | Mm00502383_m1 |
| Eif4e | Mm00725633_s1 |
| Polr2h | Mm01344328_g1 |
| Eif2c5 | Mm01305462_m1 |
| Eif3c | Mm01278697_m1 |
| Eif5b | Mm01227234_m1 |
| Papola | Mm01334253_m1 |

TABLE 2-continued

Taqman ® Probes and Gene-Specific
Primers Used in q-PCR

| Probe Name | Applied Biosystems Assay ID/ Catalog No. |
|---|---|
| Eif3e | Mm01700222_g1 |
| Sox2 | Mm03053810_s1 |
| Mouse β-actin | 4352341E |
| Mouse β-actin | 4352933E |
| Mouse GAPDH | 4352932E |

Gene Specific Primers for Oct4 (302 bp product)

| Forward | GGCGTTCTCTTTGGAAAGGTGTT (SEQ NO: 09) |
|---|---|
| Reverse | CTCGAACCACATCCTTCTCT (SEQ NO: 10) |

Gene Specific Primers for Cena2 (212 bp product)

| Forward | GATAGATTCCTCTCCTCCATG (SEQ NO: 11) |
|---|---|
| Reverse | TCACACACTTAGTGTCTCTGG (SEQ NO: 12) |

Example 1

Clinical and Embryology Data

Of all 1117 IVF treatments performed at Stanford University in 2005, 822 were fresh IVF cycles that used the patients' own oocytes (FIG. 1, panel A). Based on our exclusion criteria, 157 cycles were excluded for a variety of medical and non-medical reasons.

The 157 cycles that were excluded consisted of: cancelled oocyte retrieval due to poor ovarian stimulation (63 cycles), cancelled embryo transfer due to complete lack of embryo development (8 cycles), cancelled embryo transfer due to unexpected medical or non-medical reasons (35 cycles), cycles that were not treated with gonadotropins (3 cycles), missing outcomes (8 cycles), and women being ≥45 years of age based on age alone (29 cycles). In our study, 160 patients underwent subsequent repeat cycles after a previously failed attempt for a total of 368 cycles. Of these, 126 patients had 2 IVF cycles performed, 25 patients had 3 cycles, 6 patients had 4 cycles, 1 patient had 5 cycles and 2 patients had 6 cycles performed in the same year at the same institution. 511 cycles (76.8%) with Day 3 embryo transfer and 154 cycles (23.2%) with Day 5 transfer, or a total of 665 IVF cycles, fulfilled the inclusion and exclusion criteria for analyses.

Figure 2:
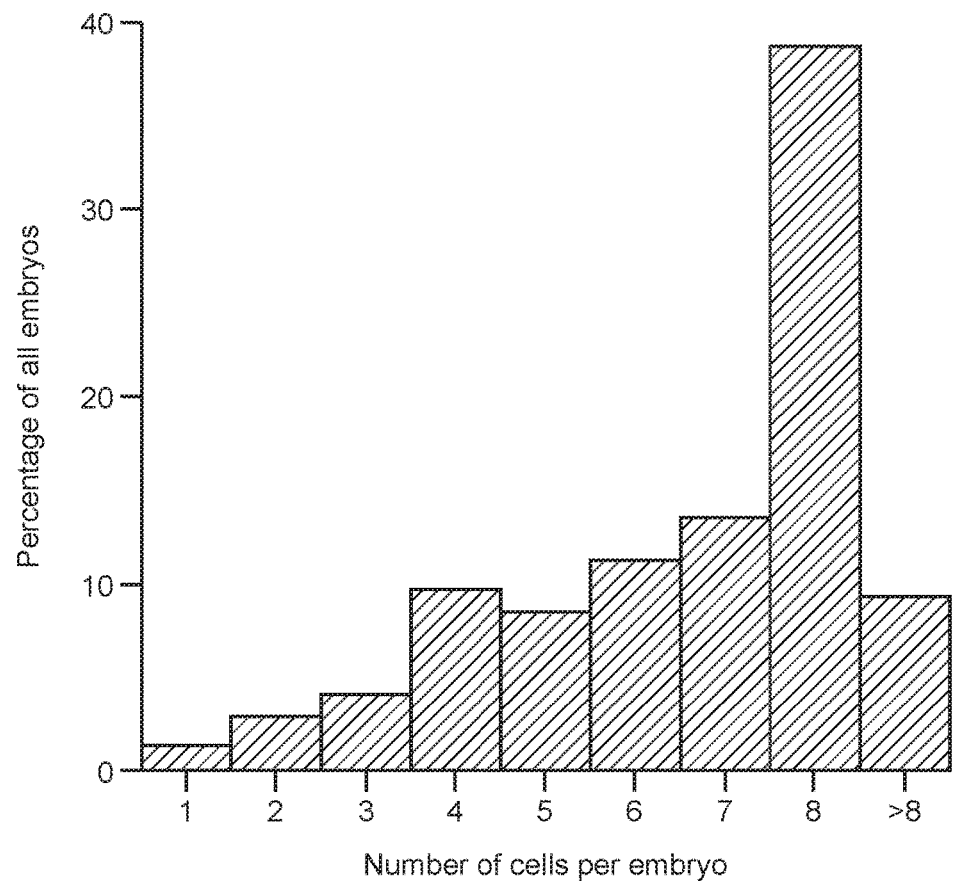
FIG. 2 shows the distribution of all embryos from 665 fresh, non-donor IVF cases according to their cell number on Day 3.

Clinical and embryology data on the remaining 665 cycles that satisfied inclusion and exclusion criteria, and their 4144 embryos, respectively, were analyzed to test the hypothesis that cohort-specific variables predict IVF cycle outcomes (FIG. 1). Of those 4144 embryos, the number of blastomeres or cells on day 3 was recorded for 4002 embryos (96.6%). Overall, 38.8% had 8 cells, the developmentally appropriate cell number, while 18.2% of embryos had <4 cells, and 33.6% had 5-7 cells (FIG. 2).

Example 2

Prognostic Significance and Correlation of Variables

We systematically examined the association of each variable with IVF outcomes, and the correlation of each pair of variables. Pair-wise logistic regression tests confirmed many known prognostic variables, including female age, day 3 FSH, and the number of 8-cell embryos. However, in addition to these known prognostic variables, we observed that cohort-specific variables such as fertilization rate and the rate of cleavage arrest were also significantly associated with IVF cycle outcome (p<0.001; Table 3). In contrast, except for male factor infertility (p<0.05), none of the conventional clinical infertility diagnoses were significantly associated with IVF outcomes. Notably, despite a high degree of correlation between many variables and age or day 3 FSH level, which estimates ovarian aging, neither age nor day 3 FSH level was correlated to cohort-specific embryo parameters (Table 4). Collectively, these results suggest that determinants other than age-related mechanisms and clinical diagnoses impact cohort-specific embryo developmental competence.

TABLE 4

Correlation between each pair of variables

| | Age | Gravidity | Maximum Day 3 FSH level | No. of oocytes | Average grade | Average grade of embryos transferred | No. of embryos | Percentage of 8-cell stage embryos | Percentage of embryos with ≤4 cells | Average cell no. of embryos |
|---|---|---|---|---|---|---|---|---|---|---|
| Age | 1.00 | 0.19 | 0.13 | −0.30 | −0.01 | 0.12 | −0.25 | 0.03 | 0.03 | 0.03 |
| Gravidity | 0.19 | 1.00 | 0.01 | −0.06 | −0.09 | −0.03 | −0.03 | 0.08 | −0.03 | 0.11 |
| Maximum Day 3 FSH level | 0.13 | 0.01 | 1.00 | −0.24 | 0.02 | 0.05 | −0.20 | −0.02 | −0.03 | 0.02 |
| No. of oocytes | −0.30 | −0.06 | −0.24 | 1.00 | −0.02 | −0.25 | 0.86 | 0.06 | −0.05 | 0.06 |
| Average grade | −0.01 | −0.08 | 0.02 | −0.02 | 1.00 | 0.84 | 0.02 | −0.35 | 0.29 | −0.39 |
| Average grade of embryos transferred | 0.12 | −0.03 | 0.05 | −0.25 | 0.84 | 1.00 | −0.28 | −0.34 | 0.28 | −0.36 |
| No. of embryos | −0.25 | −0.03 | −0.20 | 0.86 | 0.02 | −0.28 | 1.00 | 0.05 | −0.08 | 0.05 |
| Percentage of 8-cell stage embryos | 0.03 | 0.08 | −0.02 | 0.06 | −0.35 | −0.34 | 0.05 | 1.00 | −0.51 | 0.61 |
| Percentage of embryos with ≤4 cells | 0.03 | −0.03 | −0.03 | −0.05 | 0.29 | 0.28 | −0.08 | −0.51 | 1.00 | −0.83 |
| Average cell no. of embryos | 0.03 | 0.11 | 0.02 | 0.06 | −0.39 | −0.36 | 0.05 | 0.61 | −0.83 | 1.00 |
| No. of embryos transferred | 0.25 | 0.06 | −0.03 | 0.13 | 0.04 | 0.09 | 0.14 | −0.15 | 0.04 | −0.03 |
| Percentage of transferred embryos at the 8-cell stage | −0.20 | 0.03 | −0.20 | 0.35 | −0.24 | −0.42 | 0.41 | 0.77 | −0.41 | 0.45 |
| Percentage of transferred embryos at the ≤4-cell stage | 0.15 | 0.03 | 0.00 | −0.21 | 0.20 | 0.31 | −0.28 | −0.41 | 0.87 | −0.67 |
| Average cell no. of embryos | −0.13 | 0.02 | −0.05 | 0.27 | −0.28 | −0.41 | 0.35 | 0.50 | −0.70 | 0.81 |

TABLE 4-continued

Correlation between each pair of variables

| transferred | | | | | | | | | | |
|---|---|---|---|---|---|---|---|---|---|---|
| Fertilization rate | 0.03 | 0.03 | 0.04 | −0.06 | 0.04 | −0.10 | 0.35 | −0.02 | −0.12 | 0.04 |
| No. of 8-cell embryos | −0.17 | 0.06 | −0.20 | 0.68 | −0.20 | −0.39 | 0.77 | 0.51 | −0.32 | 0.35 |
| No. of 8-cell embryos transferred | −0.02 | 0.09 | −0.10 | 0.38 | −0.17 | −0.30 | 0.45 | 0.55 | −0.35 | 0.39 |

| | No. of embryos transferred | Percentage of transferred embryos at the 8-cell stage | Percentage of transferred embryos at the ≤4-cell stage | Average cell no. of embryos transferred | Fertilization rate | No. of 8-cell embryos | No. of 8-cell embryos transferred |
|---|---|---|---|---|---|---|---|
| Age | 0.25 | −0.20 | 0.15 | −0.13 | 0.03 | −0.17 | −0.02 |
| Gravidity | 0.06 | 0.03 | 0.03 | 0.02 | 0.03 | 0.06 | 0.09 |
| Maximum Day 3 FSH level | −0.03 | −0.12 | 0.00 | −0.05 | 0.04 | −0.20 | −0.10 |
| No. of oocytes | 0.13 | 0.35 | −0.21 | 0.27 | −0.06 | 0.68 | 0.38 |
| Average grade | 0.04 | −0.24 | 0.20 | −0.28 | 0.04 | −0.20 | −0.17 |
| Average grade of embryos transferred | 0.09 | −0.42 | 0.31 | −0.41 | −0.10 | −0.39 | −0.29 |
| No. of embryos | 0.14 | 0.41 | −0.28 | 0.35 | 0.35 | 0.77 | 0.45 |
| Percentage of 8-cell stage embryos | −0.15 | 0.77 | −0.41 | 0.50 | −0.02 | 0.51 | 0.55 |
| Percentage of embryos with ≤4 cells | 0.04 | −0.41 | 0.87 | −0.70 | −0.12 | −0.32 | −0.35 |
| Average cell no. of embryos | −0.03 | 0.45 | −0.67 | 0.81 | 0.04 | 0.35 | 0.39 |
| No. of embryos transferred | 1.00 | −0.22 | 0.02 | −0.06 | 0.16 | −0.03 | 0.39 |
| Percentage of transferred embryos at the 8-cell stage | −0.22 | 1.00 | −0.48 | 0.58 | 0.14 | 0.64 | 0.70 |
| Percentage of transferred embryos at the ≤4-cell stage | 0.02 | −0.48 | 1.00 | −0.80 | −0.22 | −0.34 | −0.41 |
| Average cell no. of embryos transferred | −0.06 | 0.58 | −0.80 | 1.00 | 0.20 | 0.44 | 0.48 |
| Fertilization rate | 0.16 | 0.14 | −0.22 | 0.20 | 1.00 | 0.24 | 0.19 |
| No. of 8-cell embryos | −0.03 | 0.64 | −0.34 | 0.44 | 0.24 | 1.00 | 0.59 |
| No. of 8-cell embryos transferred | 0.39 | 0.70 | −0.41 | 0.48 | 0.19 | 0.59 | 1.00 |

Example 3

Thresholds of Non-Redundant, Prognostic Variables Defining Human Embryo Cohort Phenotypes Sequential Multiple Additive Regression Tree (MART®) and Classification and Regression Tree (CART) analyses of all 30 variables (listed in Table 3 and its legend) determined that IVF cycle outcomes were most accurately predicted at ~70% by using only four non-redundant variables: total number of embryos, rate of cleavage arrest in an embryo cohort, the number of 8-cell embryos in a cohort, and day 3 FSH level. Remarkably, these four variables all describe the embryo cohort rather than individual embryos, and were more informative than age, clinical diagnoses, or any measures of the transferred embryos. Interestingly, the total number of embryos, day 3 FSH, and the number of 8-cell embryos depended on and thus captured the effects of many other variables. In contrast, the rate of cleavage arrest was independent of any of those known variables. (Details on MART® and CART analyses are reported in Table 5, and FIG. 3).

TABLE 3

Association of each variable with pregnancy outcome

| Variables | Estimate* | S.E. | P-Value |
|---|---|---|---|
| Patient Characteristics and Clinical Diagnoses[†] | | | |
| Age | −0.10 | 0.02 | 2.16E−007 |
| Maximum Day 3 FSH level | −0.08 | 0.03 | 1.70E−003 |
| Gravidity | 0.036 | 0.066 | 5.86E−001 |

TABLE 3-continued

Association of each variable with pregnancy outcome

| Variables | Estimate* | S.E. | P-Value |
|---|---|---|---|
| Male Factor (infertility diagnosis) | 0.50 | 0.24 | 3.71E−002 |
| IVF Cycle Characteristics | | | |
| Microdose lupron (flare) protocol | −1.14 | 0.24 | 2.53E−006 |
| Antagonist protocol | −0.74 | 0.19 | 9.98E−005 |
| Performance of ICSI | −0.15 | 0.16 | 3.47E−001 |
| No. of oocytes | 0.08 | 0.01 | 1.58E−009 |
| Embryo Cohort Parameters | | | |
| Fertilization rate | 1.24 | 0.36 | 5.37E−004 |
| No. of embryos | 0.14 | 0.02 | 2.67E−012 |
| Average cell no. of embryos | 0.29 | 0.06 | 6.34E−006 |
| No. of 8-cell embryos | 0.26 | 0.04 | 2.88E−012 |
| Percentage of 8-cell embryos | 0.76 | 0.28 | 5.75E−003 |
| Cleavage arrest rate[‡] | −1.28 | 0.35 | 2.76E−004 |
| Average grade of embryos | −0.091 | 0.17 | 5.88E−001 |
| Parameters of Transferred Embryos | | | |
| Day 5 embryo transfer[§] | 1.40 | 0.19 | 7.51E−013 |
| No. of embryos transferred | 0.0058 | 0.053 | 9.12E−001 |
| Average cell no. of embryos transferred | 0.47 | 0.07 | 2.19E−010 |
| Percentage of transferred embryos at the 8-cell stage | 1.33 | 0.21 | 5.35E−010 |
| No. of 8-cell embryos transferred | 0.41 | 0.08 | 4.40E−008 |

TABLE 3-continued

Association of each variable with pregnancy outcome

| Variables | Estimate* | S.E. | P-Value |
|---|---|---|---|
| No. of embryos with ≤4 cells transferred | −2.14 | 0.49 | 1.06E−005 |
| Average grade of embryos transferred | −0.52 | 0.17 | 2.61E−003 |

*Positive and negative estimates indicate association with positive and negative pregnancy outcomes, respectively.
[†]Clinical infertility diagnoses that were not significantly associated with pregnancy outcome (p-value > 0.05) were not listed: uterine factor, polycystic ovarian syndrome, endometriosis, tubal ligation, tubal disease, hydrosalpinges, unexplained infertility, and "other diagnoses". Each IVF case may have more than one clinical infertility diagnosis.
‡ of in vitro culture.
§Day 5 embryo transfer is arbitrarily listed under Parameters of Transferred Embryos. It can also be considered an Embryo Cohort Parameter, as it depends on the total number of embryos and the number of 8-cell embryos.

TABLE 5

Models generated by MART ® to identify non-redundant, prognostic variables

| Model | Degree of Interaction | Learning Rate* | Tree Number[†] | Cross-validated (CV) Prediction Error Rate[††] |
|---|---|---|---|---|
| 1 | 2 | 0.0100 | 2 | 0.300800 |
| 2 | 3 | 0.0010 | 3 | 0.300800 |
| 8 | 20 | 0.0010 | 4 | 0.308300 |
| 6 | 10 | 0.0001 | 4 | 0.315800 |
| 3 | 4 | 0.1000 | 30 | 0.323300 |
| 4 | 5 | 0.0020 | 16 | 0.323300 |
| 5 | 6 | 0.0100 | 16 | 0.330800 |
| 7 | 15 | 0.0001 | 3 | 0.330800 |

*One of the "boosting" tuning parameters in MART ® to prevent "over-fitting" of the data[2]
[†]Number of trees constructed by MART ®
[††]10-fold cross validation error Of the prognostic thresholds identified, the most robust phenotypes are A1 and A2, and B1 and B2 (Table 6). Number of embryos <6 or ≥6 is used by all 5 top CART models, defines all other phenotypes (B to F), and can be applied to all cases. Specifically, the phenotype defined by having fewer than 6 embryos, has an odds ratio of 3.9 for no pregnancy compared to cases with ≥6 embryos (95% Confidence Interval [CI], 2.8 to 5.5). Similarly, the next most robust phenotypes are defined by the number of embryos and cleavage arrest rate, such that for cases with ≥6 embryos, those with cleavage arrest rate >14.6% are 3.0 times more likely to result in no pregnancy than those with cleavage arrest rate ≤14.6% (95% CI, 1.9 to 4.9).

TABLE 6

Prognostic thresholds defining cohort-specific phenotypes

| | Embryos (No.)* | Cleavage Arrest (%)* | 8-cell embryo (No.)* | FSH (mIU/mL)* | Pregnancy- No. (%)[†] | No Pregnancy No. (%)[‡] | Applicable Cases - No. (%)[§] | No. Trees[¶] | Reference Condition[∥] | Odds Ratio | 95% Confidence Interval (C.I.) |
|---|---|---|---|---|---|---|---|---|---|---|---|
| A1** | ≥6 | | | | 177 (57.7) | 130 (42.3) | 307 (46.2) | 5 | | | |
| A2 | <6 | | | | 92 (25.7) | 266 (74.3) | 358 (53.8) | 5 | A1 | 3.9 | (2.8, 5.5) |
| B1 | ≥6 | ≤14.6 | | | 112 (70.4) | 47 (29.6) | 159 (23.9) | 4 | | | |
| B2 | ≥6 | >14.6 | | | 65 (43.9) | 83 (56.1) | 148 (22.3) | 4 | B1 | 3.0 | (1.9, 4.9) |
| B3 | ≥6 | 14.6-52.8 | | | 62 (47.3) | 69 (52.7) | 131 (19.7) | 1 | B1 | 2.6 | (1.6, 4.3) |
| B4 | ≥6 | ≤52.8 | | | 174 (60.0) | 116 (40.0) | 290 (43.6) | n/a | B1 | 10.6 | (3.2, 49.6) |
| B5 | ≥6 | >52.8 | | | 3 (17.6) | 14 (82.3) | 17 (2.6) | 1 | B4 | 6.7 | (2.1, 30.9) |
| C1 | ≥6 | | ≥2 | | 157 (63.6) | 90 (36.4) | 247 (37.1) | 1 | | | |
| C2 | ≥6 | | <2 | | 20 (33.3) | 40 (66.7) | 60 (9.2) | 1 | C1 | 3.5 | (1.9, 6.4) |
| D1 | ≥6 | >14.6 | ≥2 | | 51 (53.1) | 45 (46.9) | 96 (14.4) | 1 | | | |
| D2 | ≥6 | >14.6 | <2 | | 14 (26.9) | 38 (73.1) | 52 (7.8) | 1 | D1 | 3.0 | (1.5, 6.5) |
| E1 | ≥6 | >14.6 | ≥2 | ≤4.6 | 14 (82.4) | 3 (17.6) | 17 (2.6) | 1 | | | |
| E2 | ≥6 | >14.6 | ≥2 | >4.6 | 34 (46.9) | 37 (53.1) | 71 (12.2) | 1 | E1 | 4.8 | (1.4, 23.4) |

*Cohort phenotypes defined by thresholds of non-redundant prognostic variables. Each set of conditions (A-E) use "AND" as the operator where more than one condition is listed.

[†]No. of cases that satisfy the threshold conditions and have pregnancy outcome. This percentage is calculated by using the No. Applicable Cases as denominator. In general, conditions that discriminate between pregnancy and no pregnancy outcomes more highly are more robust and are expected to be more useful in both clinical management and translational research.

[‡]No. of cases that satisfy the threshold conditions and have no pregnancy outcome. This percentage is calculated by using the No. Applicable Cases as denominator.

[§]The No. Applicable Cases is the total number of cases that satisfy the threshold conditions. This percentage is calculated by using the total number of cycles (665) as the denominator. In general, the larger the number of applicable cases, the more useful the set of conditions are for clinical management and counseling. However, for the purpose of translational research, conditions that define a smaller number of cases may have more specific correlates on a molecular level.

[¶]No. Trees shows the number of CART trees that utilize each set of conditions. There area total of 5 trees. (See Supplemental Results.) Increased utilization indicates "usefulness" or "robustness" of that particular set of conditions.

[∥]Reference condition against which the Odds Ratio and 95% C.I. for having no pregnancy is calculated.

**Conditions A-E are listed from most robust and "useful" to least "useful" based on: the number of trees that utilize each set of conditions, the number of applicable cases, and the odds ratio and 95% CI.

In contrast, the rest of the thresholds listed in Table 6 are used by only 1 CART model each, and is applicable to fewer cases. However, as some of those phenotypes describe very specific subset of cases and have odds ratios that are highly discriminatory, they may be extremely useful depending on the clinical or translational research context. For example, for cases with ≥6 embryos, having cleavage arrest rates of 14.6-52.8% and >52.8% increase the odds of no pregnancy by 2.6 (95% CI 1.6 to 4.3) and 10.6 (95% CI 3.2 to 49.6), respectively, when compared to cases with cleavage rates of ≤14.6%.

Example 3

Analyses by MART® and Cart Models

To overcome the challenges presented by the highly interactive nature and potentially non-linear dependence amongst variables, and their multicollinearity, all 30 variables listed in Table 5 and its legend were analyzed by MART® to generate models that utilize non-redundant prognostic variables. Eight models were generated by MART® with increasing complexity of individual trees for boosting, while the learning rate was chosen to produce a minimum test error for the given complexity. Among them, the 3 top-ranking models had cross-validated (CV) prediction error rates of 0.301 to 0.308, which separated them well from the other five models, whose CV error rates ranged from 0.315 to 0.331 (Table 5). The third model, however, was based on very complex individual trees yet showed a larger CV error than the two preceding models; thus it was excluded from the analysis. The resulting two top models, consistent with characteristics of meaningful regression tree models, used very few trees and shared common features, such that the two models collectively used only 5 trees containing 5 variables, while some of the other models used up to 16 to 30 trees each.

These 5 non-redundant prognostic variables were: total number of embryos, the rate of cleavage arrest, the number of 8-cell embryos, day 3 FSH level, and the number of 8-cell embryos transferred. In each model, removal of each of the first four variables while keeping all other parameters constant, increased the error rate of the model, thus confirming their significant contribution. However, removal of the number of 8-cell embryos transferred, did not alter the error rate (data not shown), which suggested that this variable was less relevant than others.

24 models representing all possible combinations of these 5 variables were analyzed by CART to further define thresholds that have prognostic significance. The top 5 trees generated by CART had superior prediction scores (0.6828 to 0.6950) compared to the rest of the models (0.565 to 0.6700). As there were shared features, these top 5 tree models utilize mostly the same threshold conditions for 4 variables, while the variable, number of 8-cell embryos transferred, was not utilized by any of these top models. Therefore, IVF cycle outcomes could be most accurately predicted at ~70% by using only four non-redundant variables that are more informative than age, clinical diagnoses, or any measures of the transferred embryos.

Figure 3:
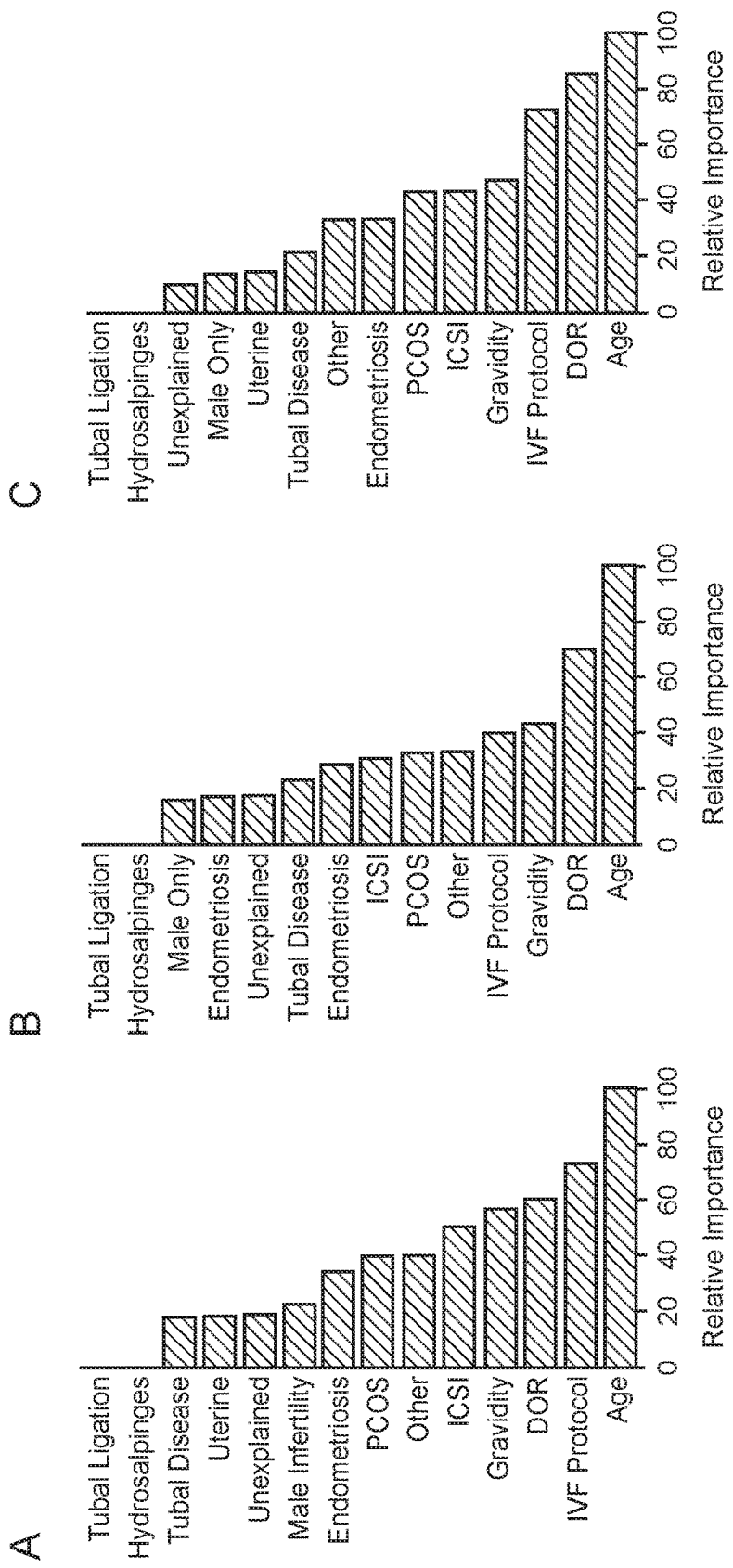
FIG. 3 shows variables and their relative importance in determining A) number of 8-cell embryos (Panel A), day 3 FSH (Panel B), and the total number of embryos (Panel C).

In order to understand which factors amongst patient characteristics, diagnoses, and IVF treatment characteristics, in turn determined these four non-redundant, cohort-specific prognostic variables, tree models were constructed by MART to represent the dependence of each of these four prognostic variables. The total number of embryos, day 3 FSH, and the number of 8-cell embryos depended on and thus captured the effects of many other variables (FIG. 3). In contrast, the rate of cleavage arrest was independent of any of those known variables.

Example 4

Morpholino Mediated Gene Knockout Study

Figure 4:
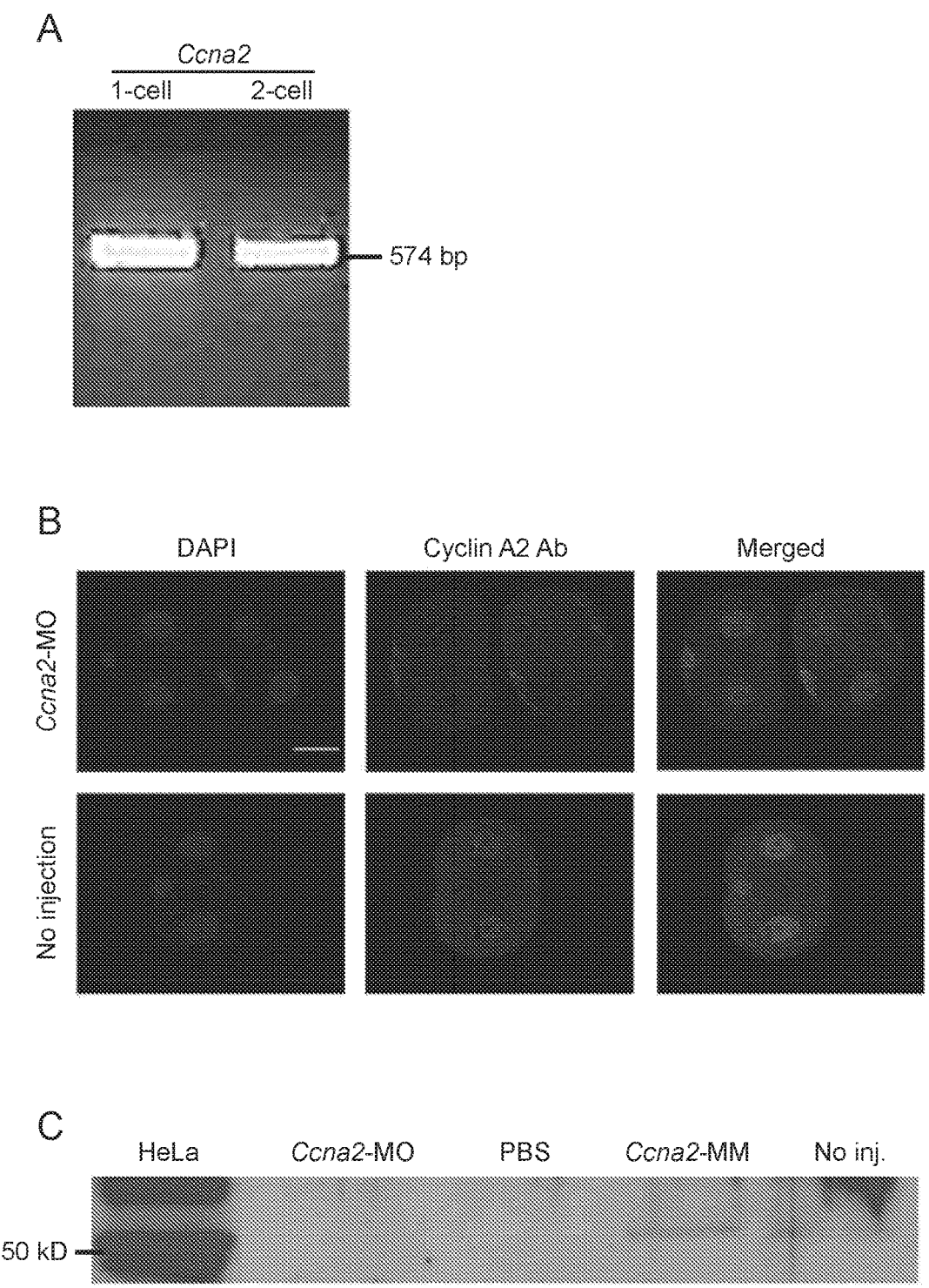
FIG. 4 shows that translational block of cyclin A2 by Ccna2-MO causes embryos to arrest at the 2-cell stage. Panel A shows Ccna2 expression in 1- to 2-cell embryos by RT-PCR. Panel B shows nuclear cyclin A2 localization was absent in 83.4±6.0% of Ccna2-MO-injected embryos but present in all uninjected embryos; p<0.01). Panel C shows that ~50 kD cyclin A2 protein was not detected in Ccna2-MO-injected embryos.
Figure 5:
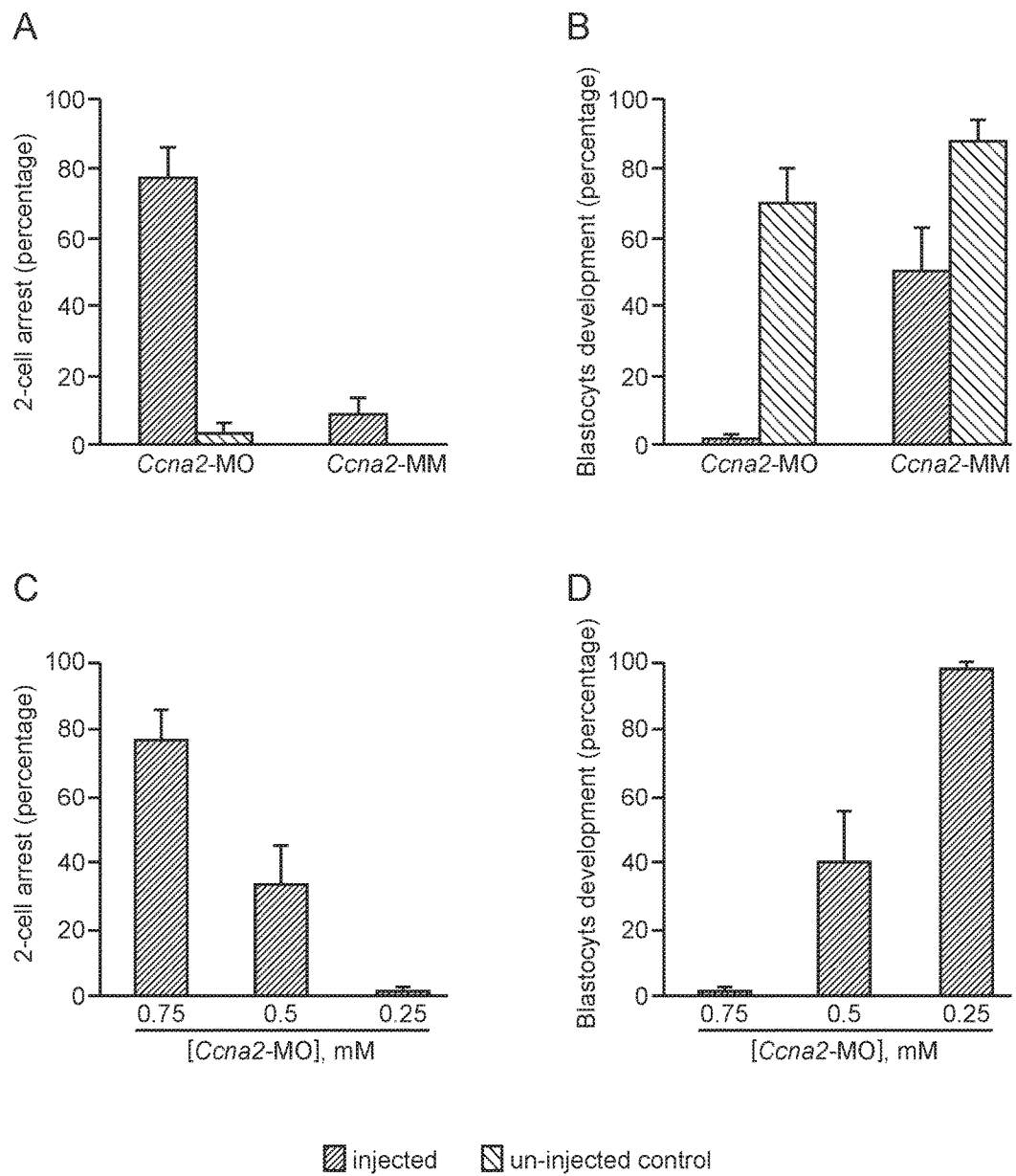
FIG. 5, panel A shows that Ccna2-MO induced higher rates of 2-cell stage arrest compared to controls (p<0.01). Panel B shows that only 1.8±1.8% of Ccna2-MO-injected embryos reached blastocyst stage (p=0.06 compared to Ccna2-MM). Panel C shows that the rates of 2-cell stage arrest decreased with the concentration of Ccna2-MO (p=0.05 for 0.5 mM; p=0.01 for 0.25 mM). Panel D shows that the rate of blastocyst development at were higher at 0.25 mM than at 0.75 mM (p<0.001). All columns and error bars represent mean±s.e.m., respectively, from at least three independent sets of experiments. Scale bar 40 μm. See Table 1 for the targeted sequence of all MOs used, and Table 7 for the total number of embryos tested in each set of experiments.

Here, we provide proof-of-concept of the efficiency and specificity of MO-mediated gene knockdown by testing the procedure on the Ccna2 gene. We then report the novel role of Oct4 that was revealed by MO-mediated gene knockdown. Ccna2, the gene encoding cell cycle regulator cyclin A2, has been suggested as an important transcriptional regulator in embryonic genome activation (Hara K T, et al. (2005) *Dev Biol* 286, 102-113), a critical developmental milestone at the 1- to 2-cell stages for which few clear mechanisms or regulators have emerged. Consistent with the literature, MO-mediated Ccna2 knockdown decreased cyclin A2 protein expression. In addition, our results showed that cyclin A2 is required for development beyond the 2-cell stage (FIG. 4, panels A-C, FIG. 5, panels A-D, Tables 1 and 7). MOs block translation of transcripts by steric hindrance in an efficient and gene-specific manner, which has been well established in zebrafish and other model organisms (Gore A V, et al. (2005) *Nature* 438, 1030-1035; Imai et al., (2006). *Science* 312, 1183-1187; Sumanas S & Larson J D (2002) *Brief Funct Genomic Proteomic* 1, 239-256; Yamada L, et al. (2003) *Development* 130, 6485-6495). Most importantly, MOs mediate rapid knockdown of transcripts regardless of their maternal or embryonic origin, before activation of downstream genes can provide partial "rescue" of the phenotype. Unlike siRNAs, MOs function independently of endogenous pathways, so the MO-mediated translational block should not limit knockdown efficiency or interfere with the endogenous mRNA degradation machinery.

Figure 6:
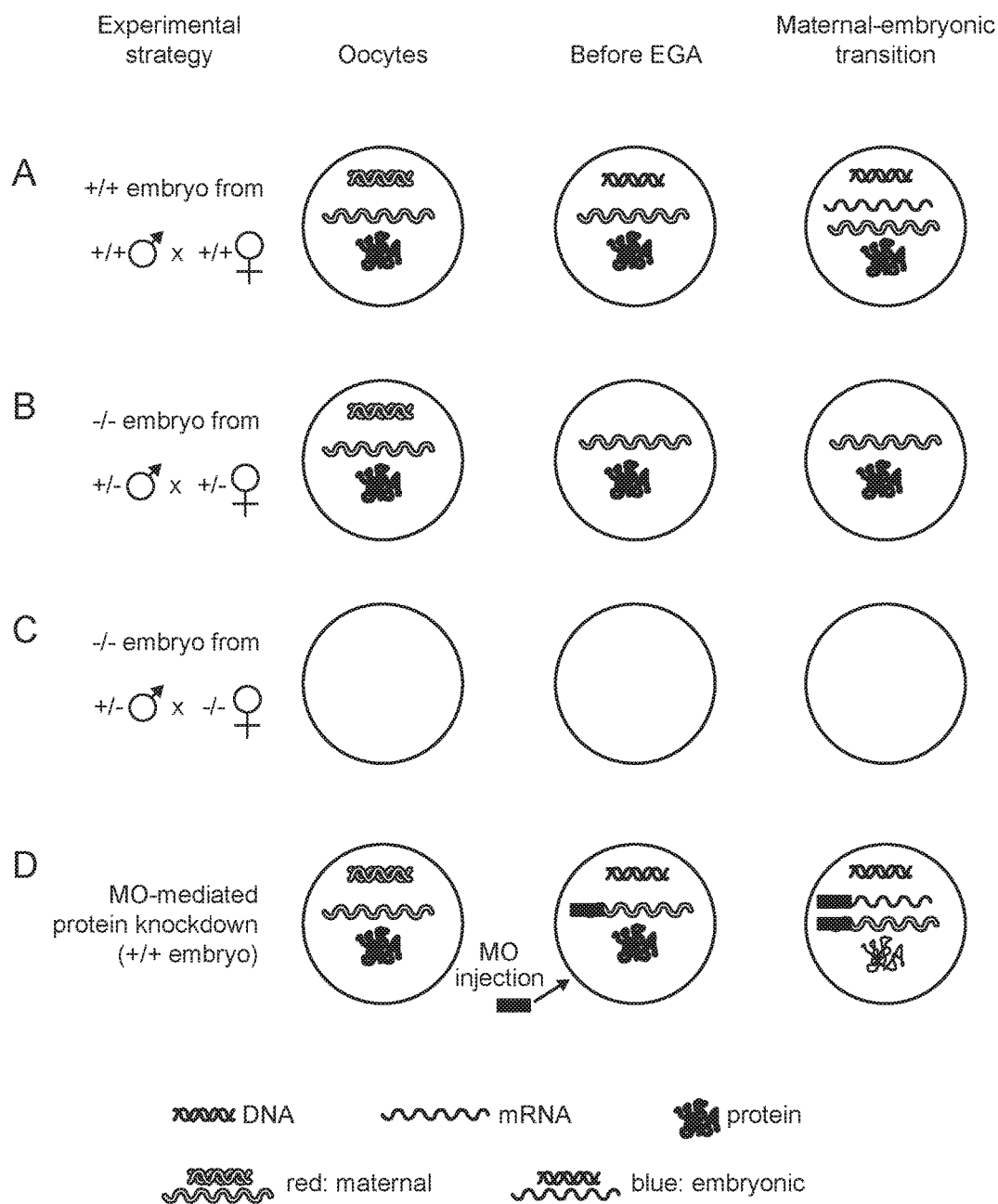
FIG. 6 shows the mechanisms that regulate mammalian embryo development at the earliest stages. In wild type (+/−) embryos, maternal transcripts are present before embryonic genome activation (EGA), while maternal and embryonic transcripts are present at maternal-embryonic transition stage, both resulting in production of a normal gene product (Panel A). In homozygous null mutant (−/−) embryos generated from a mother that is heterozygous (+/−) for the null mutation, persistent maternal transcripts and/or proteins may "rescue" or delay the phenotype onset (Panel B). In contrast, homozygous null mutant embryos generated from a homozygous mutant female, or a female with oocyte-specific gene deletion, the observed defects may reflect oocyte defects, rather than specific gene requirement in the early embryo (Panel C). Therefore, these strategies do not address the precise roles of specific genes at the cusp of EGA or during EGA, when both maternal and early embryonic transcripts may be present simultaneously. Cytoplasmic microinjection of antisense morpholino oligonucleotides (MOs) into wild type embryo just at or before EGA results in specific translational block of both maternal and embryonic gene transcripts (Panel D). Since MOs persist for at least a few cycles of cell division, gene-specific translational block is presumably effective until the morula-blastocyst stages. The absence of gene product during these developmental stages would reveal critical gene function and unmask early phenotypes that may not be detectable in conventional gene-targeting strategies by homologous recombination and transgenesis. While this model is well established in other species, it shifts the paradigm from investigating function of embryonic genes to that of gene products regardless of their maternal or embryonic origin.
Figure 7:
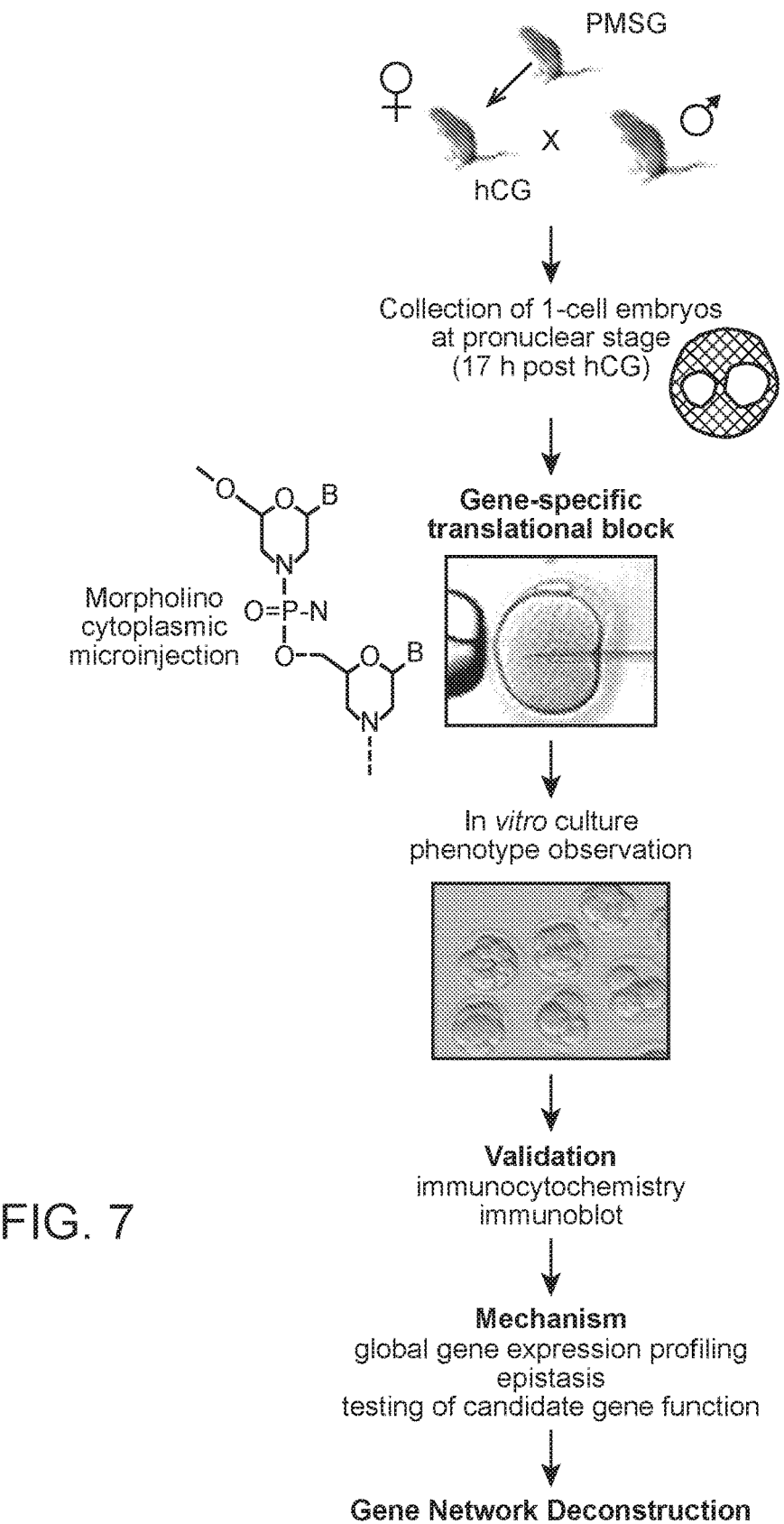
FIG. 7 shows the experimental strategy. Embryos at the 2 pronuclei (2PN) or 1-cell stage were collected from wild type matings, and injected with an antisense morpholino oligomer (MO) that was designed to target a specific gene. MO binds to 5' UTR or transcription start site and blocks translation by steric hindrance. Microinjected embryos and uninjected control embryos were cultured in vitro and observed for developmental phenotypes such as fragmentation, or arrest at the 2-cell, 4-cell, multicell, or morula stages. If a gene-specific MO produces the same phenotype consistently, while the mismatch control MO allows normal development, then knockdown of the gene of interest was validated by immunocytochemistry and/or immunoblotting. Mechanism of gene function was further investigated by obtaining global gene expression profiles from injected and control embryos at the mid-2-cell stage (43 hours post-HCG). Candidate downstream genes were tested for differential expression, and gene function in the early embryo.
Figure 8:
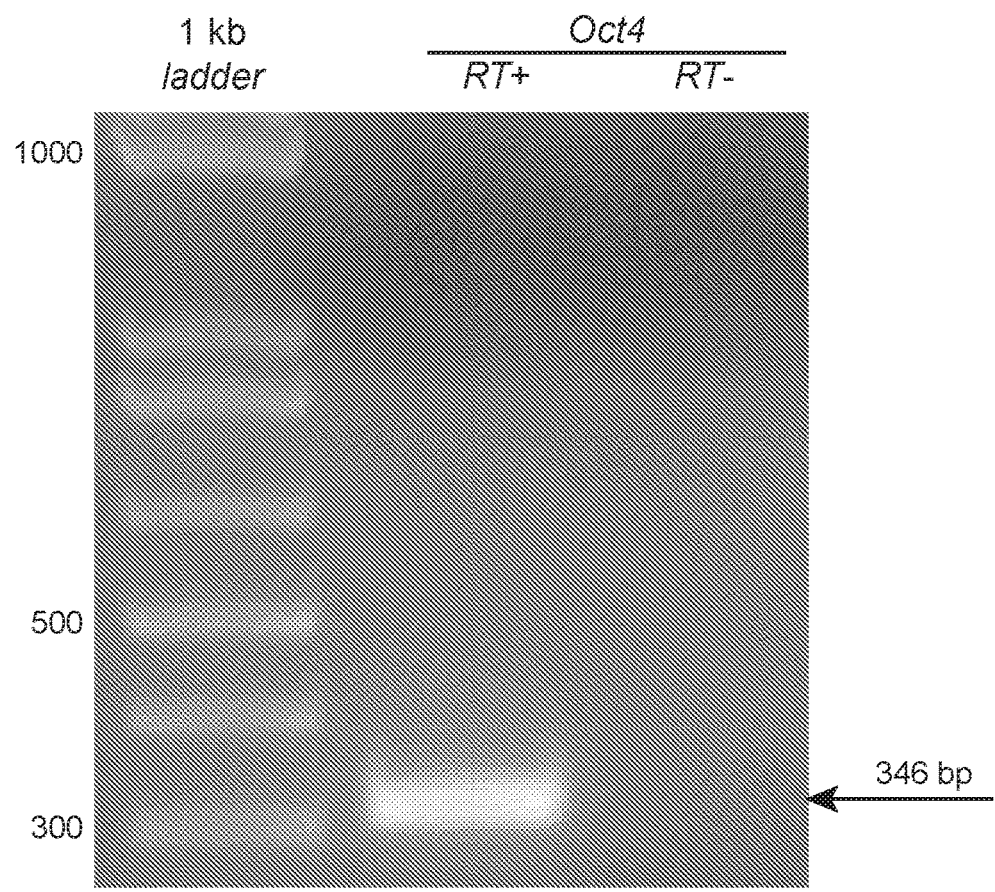
FIG. 8 shows Oct4 expression in mouse zygote by single embryo RT-PCR.
Figure 9:
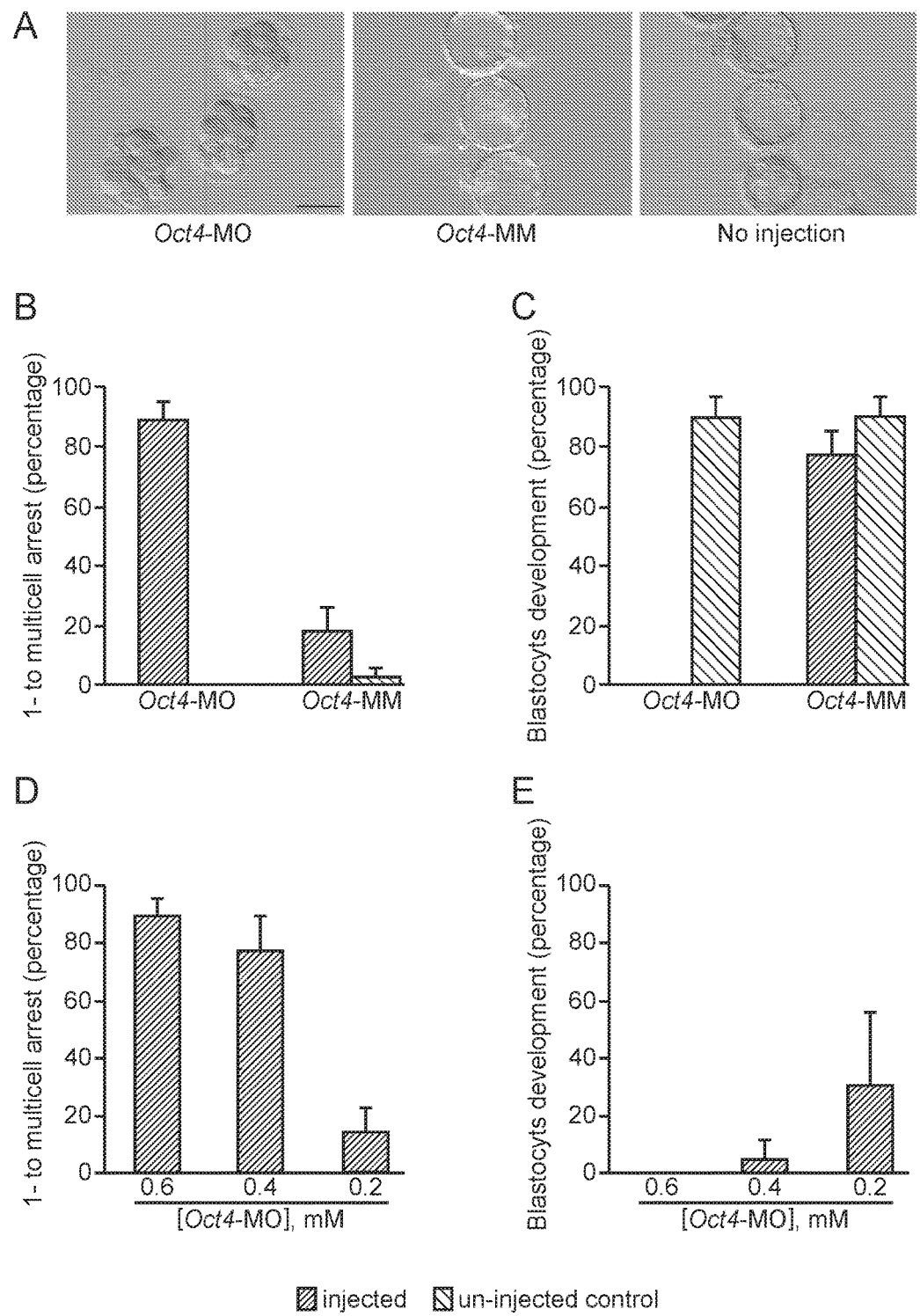
FIG. 9 shows that Oct4 is required for early embryo development prior to formation of the blastocyst. Panel A shows that Oct4-MO-injected embryos arrested at multicell stage, while controls reached blastocyst stage. Panel B shows that Oct4 knockdown induced higher arrest rates at the 1- to multicell stages; $p<0.01$. Panel C shows that None of the Oct4-MO-injected embryos developed to blastocysts. Panel D shows that the rates of arrest at the 1- to multicell stages decreased with concentration of Oct4-MO ($p<0.01$). Panel E shows that there was a non-significant trend for higher rates of blastocyst development with decreasing concentrations of Oct4-MO.
Figure 10:
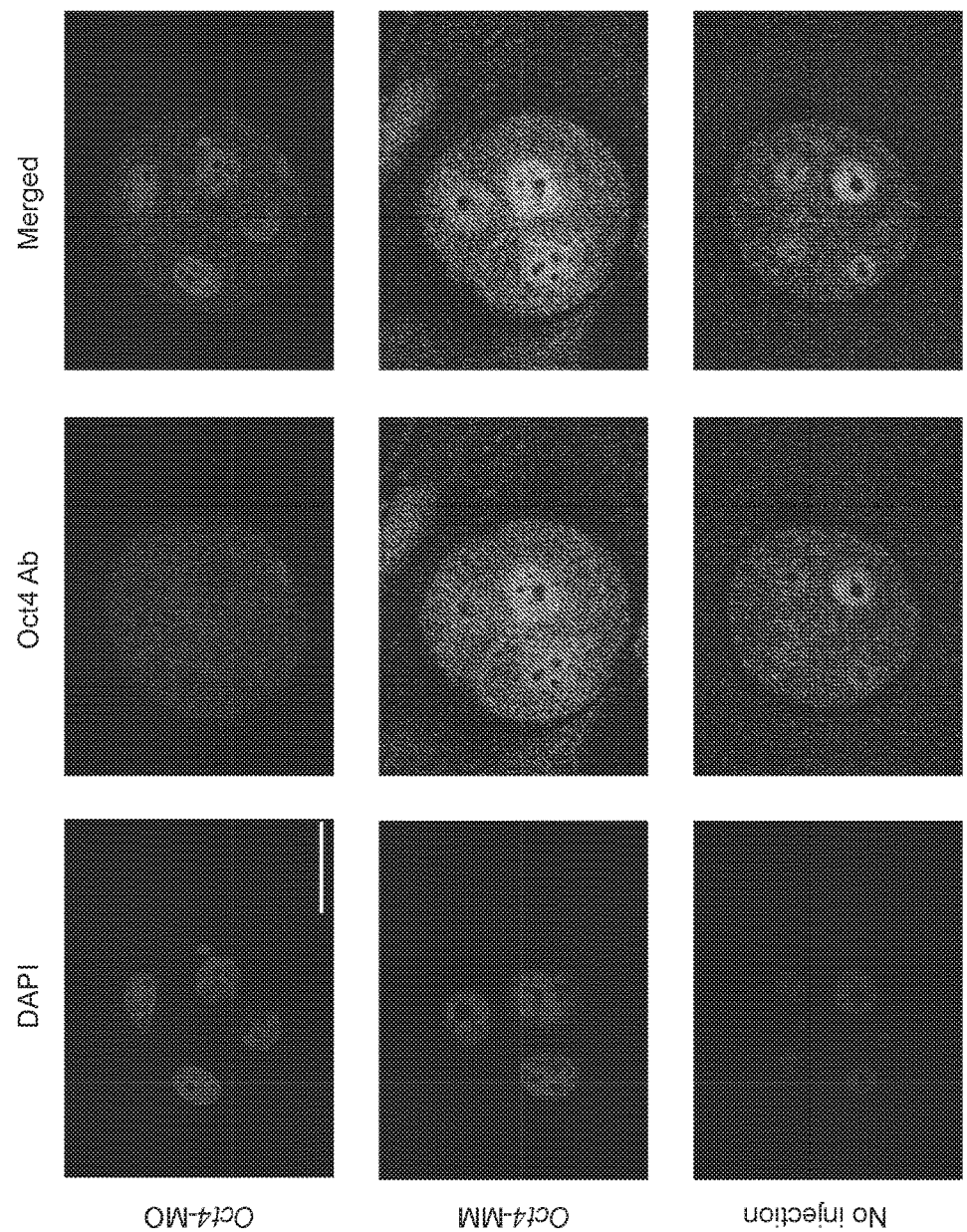
FIG. 10 shows that decreased Oct4 expression was evident by the 4-cell stage in Oct4-MO-injected embryos. Oct4 signal was absent in embryos injected with Oct4-MO, but its nuclear localization was present in uninjected and mismatch controls. Scale bar 40 µm.
Figure 11:
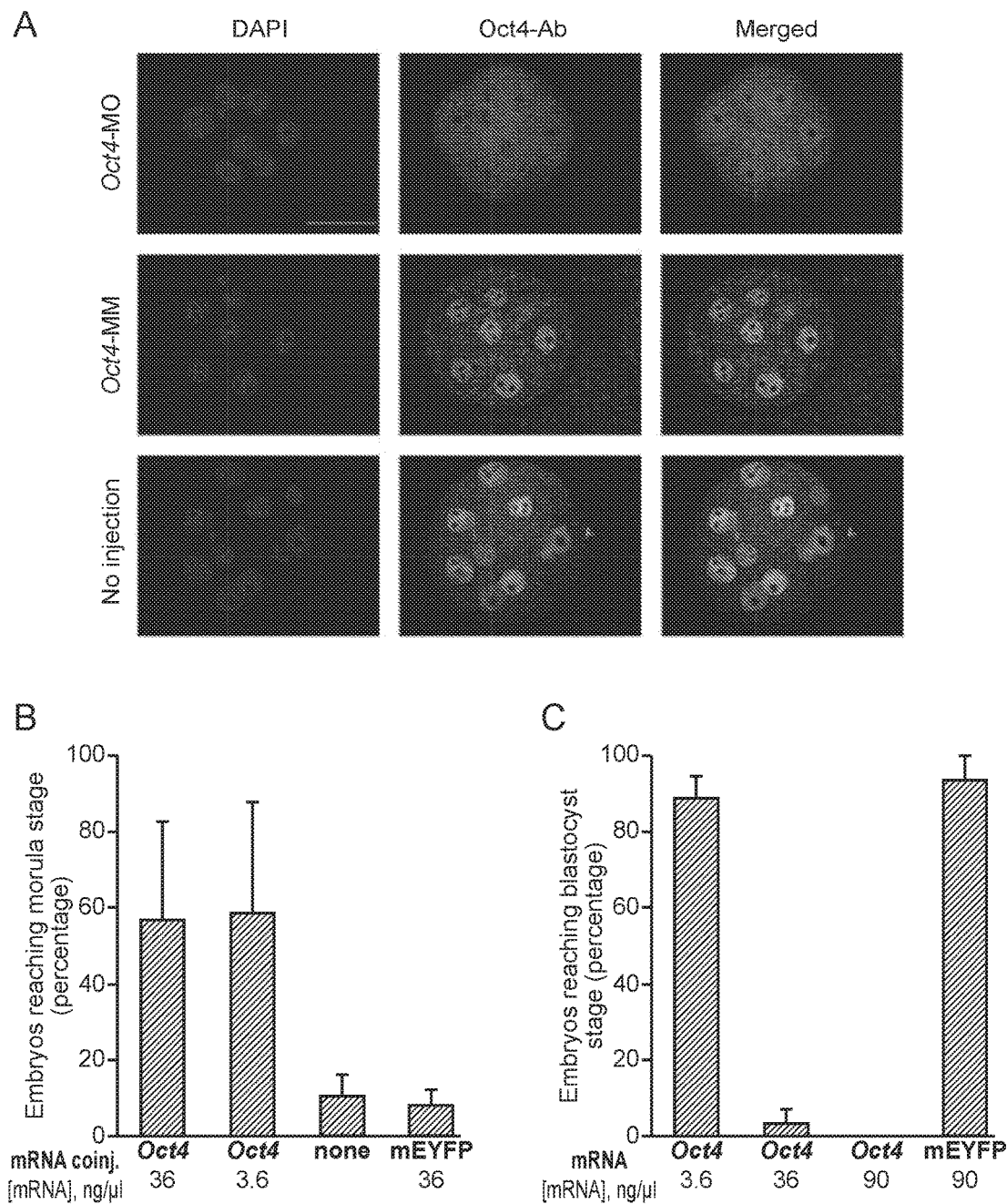
FIG. 11, Panel A, shows that nuclear Oct4 expression is absent in Oct4-MO-injected embryos (top panel) but present in Oct4-MM-injected embryos and uninjected. Panel B shows that compared to no coinjection or mEYFP mRNA coinjection, coinjection of 36 or 3.6 ng/µL of Oct4 mRNA resulted in partial rescue of the Oct4-MO-induced phenotype by specifically decreasing the arrest rates at the 1- to multicell stages, which resulted in higher rates blastocyst development ($p<0.01$). Panel C shows that overexpression of Oct4 mRNA induced higher developmental arrest in a dose-dependent manner, such that blastocyst rates are significantly lower after injection of Oct4 mRNA at 36 or 90 ng/µL, compared to overexpression of mEYFP ($p<0.01$). Gene overexpression was validated by q-PCR or immunocytochemistry (data not shown). (Scale bar=40 µm).
Figure 12:
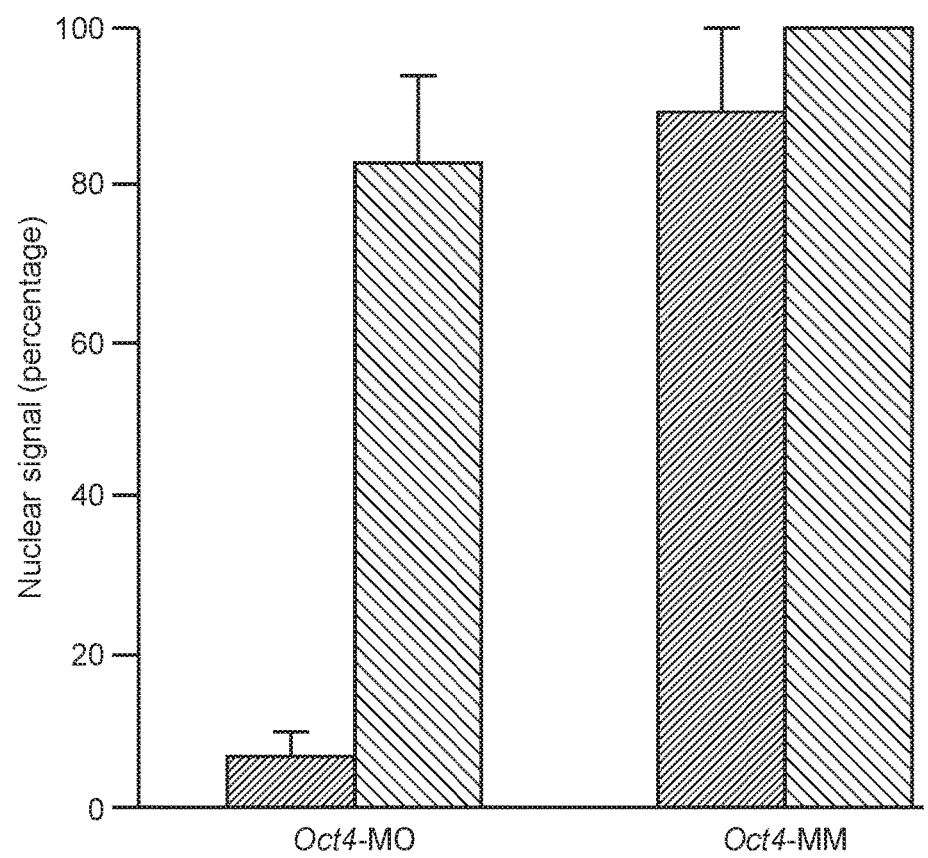
FIG. 12 shows decreased Oct4 expression at the multicell stage in Oct4-MO-injected embryos. Only 6.4±3.2% of Oct4-MO-injected embryos showed nuclear Oct4 signal, while 88.9±11.1% of Oct4-MM-injected embryos and 82.7±10.9% of uninjected control embryos showed unequivocal nuclear Oct4 expression at the multicell stage; $p<0.05$.
Figure 13:
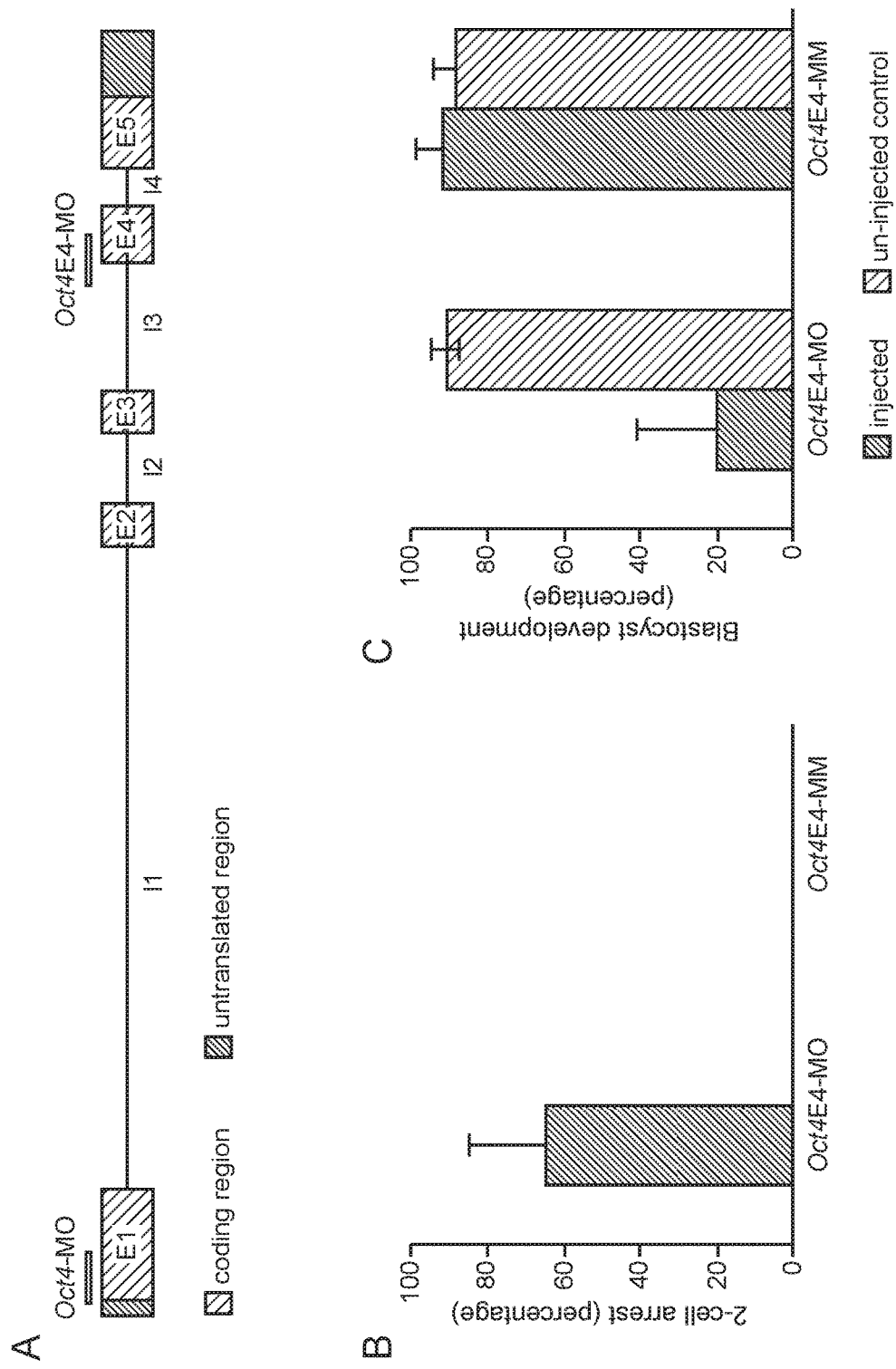
FIG. 13 shows confirmation of the requirement of Oct4 in early embryo development by Oct4E4-MO, an antisense morpholino that targets the splice site of exon 4 of Oct4. Panel A shows sites targeted by the two morpholinos, Oct4-MO and Oct4E4-MO. Oct4-MO targets the 25 nucleotides starting at the ATG start site, while Oct4E4-MO targets the splice site at the intron (I)-exon (E) boundary of the $4^{th}$ exon (E4). Removal of E4 is expected to result in a protein product that lacks the DNA-binding and activation domains. Panel B shows that 64.6±19.9% of embryos injected with Oct4E4-MO, while none that were injected with the mismatch control, Oct4E4-MM, arrested at the 2-cell stage. Panel C shows that blastocyst development is severely compromised after injection of Oct4E4-MO compared to the mismatch control, Oct4E4-MM.

By combining MO-mediated gene knockdown with global gene expression profiling and single-embryo level quantitative RT-PCR (q-PCR), we determined the influence of Oct4 on gene expression, and analyzed the Oct4-regulated gene network in the early embryo (FIG. 6 and FIG. 7). Consistent with the literature, we confirmed Oct4 gene expression at the 1-cell stage (FIG. 8). After 1-cell embryos were microinjected with 0.6 mM Oct4-MO, the rate of developmental arrest at the 1- to multicell stages was dramatically higher than that observed for uninjected and mismatch (Oct4-MM) controls (FIG. 9, panels A and B). Of embryos injected with Oct4-MO that reached the multicell stage, 86.8±8.3% arrested and did not form morulae, compared to 10.5±10.5% embryos injected with Oct4-MM (p<0.01; data not shown). Most remarkably, none of the Oct4-MO-injected embryos developed to blastocysts, compared to relatively high blastocyst rates of Oct4-MM-injected and uninjected embryos (p<0.01; FIG. 9, panel C). Further, the specificity of Oct4-MO is supported by the direct relationship between the phenotype severity and presumed "gene-dosage" as titrated by Oct4-MO concentration (FIG. 9, panels D and E). Oct4 protein expression was indeed reduced in Oct4-MO-injected embryos at the 4-cell (FIG. 10) and multi-cell stages (FIG. 11, panel A, and FIG. 12). Injection of another MO, targeting an intron-exon boundary in Oct4, confirmed that disruption of Oct4 function is detrimental to development before the blastocyst stage (FIG. 13, panels A-C).

The critical function of Oct4 at the 1- to 2-cell transition was embryo-autonomous. The effects of Oct4 knockdown could not be rescued by media conditioned by uninjected embryos or the in vivo environment provided by transferring injected embryos to oviducts of appropriately timed surrogate mothers (data not shown). Co-injection of low (3.6 ng/μL) or high (3.6 ng/μL) concentrations of unaltered, full-length Oct4 mRNA with 0.6 mM Oct4-MO resulted in a decrease in the percentage of embryos arresting at the 1- to multicell stages, compared to co-injection of control mRNA encoding a modified enhanced yellow fluorescent protein (mEYFP) (FIG. 11, panel B). No embryos co-injected with Oct4 mRNA arrested at the multicell stage, while 80.0±5.2% arrested after co-injection of mEYFP mRNA (p<0.01; data not shown). Thus, co-injection of Oct4 mRNA, but not control mRNA, partially rescued the Oct4-MO-induced multicell stage arrest phenotype. The failure of achieving full rescue of the phenotype may be due to insufficient Oct4 expression after co-injection of Oct4 mRNA at the low concentration, inappropriately high Oct4 expression at the high concentration, or relative instability of the in vitro transcribed Oct4 mRNA compared to Oct4-MO; further, these possibilities are not mutually exclusive. Hence, we next tested whether Oct4 over-expression itself would interfere with development.

Injection of Oct4 mRNA resulted in over-expression as quantified by q-PCR, but did not cause ectopic expression of Oct4 protein (data not shown). Oct4 over-expression indeed induced developmental arrest in a dosage-dependent manner, while injection of comparable or greater amounts of mEYFP mRNA interfered minimally with blastocyst development (FIG. 11, panel C). The "gene dosage" effect of Oct4 RNA injection may be due to enhanced Oct4 functions in transcriptional regulation, or Oct4 over-production may allow non-specific promoter-binding, or extra Oct4 causes inappropriate sequestration and subsequent inactivation of co-factors. Collectively, these data definitively showed Oct4 expression was required, and that its correct level was critical to early embryo development, just as pluripotency of ESCs depends on a precise range of Oct4 expression levels (Stefanovic S & Puceat M (2007) *Cell Cycle* 6, 8-10).

TABLE 7

Summary of the Number of Embryos Tested and the Number of Experiments Performed for Each Condition

| Experiment | Condition | No. Injected Embryos | No. Uninjected Embryos | No. experiments |
|---|---|---|---|---|
| Ccna2 knockdown | Ccna2-MO 0.75 mM | 94 | 65 | 8 |
|  | Ccna2-MM 0.75 mM | 75 | 101 | 9 |
| Ccna2-MO Immunocytochemistry | Ccna2-MO 0.75 mM | 26 | 28 | 3 |
| Ccna2 "gene dosage" | Ccna2-MO, 0.5 mM | 39 | 30 | 3 |
|  | Ccna2-MO, 0.25 mM | 50 | 29 | 3 |
| Oct4 knockdown | Oct4-MO, 0.60 mM | 41 | 37 | 4 |
|  | Oct4-MM, 0.60 mM | 57 | 30 | 3 |
|  | Oct4-MO, 0.40 mM | 79 | 25 | 3 |
|  | Oct4-MO, 0.20 mM | 63 | 30 | 3 |
|  | Oct4E4-MO, 0.60 mM | 35 | 30 | 3 |
|  | Oct4E4-MM, 0.60 mM | 32 | 30 | 3 |
| Oct4-MO Immunocytochemistry | Oct4-MO, 0.60 mM | 32 | 22 | 3 |
|  | Oct4-MM, 0.60 mM | 20 | 20 | 3 |
| Rescue | 0.036 µg/µl Oct4 mRNA + 0.60 mM Oct4-MO | 32 | 30 | 3 |
|  | 0.036 µg/µl EYFP mRNA + 0.60 mM Oct4-MO | 72 | 30 | 3 |
| Overexpression | 0.09 µg/µl Oct4 mRNA | 24 | 20 | 3 |
|  | 0.036 µg/µl Oct4 mRNA | 33 | 25 | 3 |
|  | 3.6 ng/µl Oct4 mRNA | 35 | 30 | 3 |
|  | 0.09 µg/µl EYFP mRNA | 41 | 20 | 2 |
| Oct4-MO/Conditioned Media | Oct4-MO, 0.60 mM, conditioned media | 20 | 20 | 2 |
|  | Oct4-MO, 0.60 mM, unconditioned media | 20 | 20 | 2 |
| Ccna2-MO gene chip | Ccna2-MO, 0.75 mM | 60 | 60 | 3 |
| Oct4-MO gene chip | Oct4-MO, 0.6 mM | 60 | 60 | 3 |
| Oct4-MO single embryo QPCR | Oct4-MO, 0.60 mM, 2-cell stage | 14-20 | 14-20 | 3-5 |
|  | Control-MO, 0.60 mM, 2-cell stage | 5-10 | n/a | 2 |

Example 5

Gene Regulation by Oct4

Figure 14:
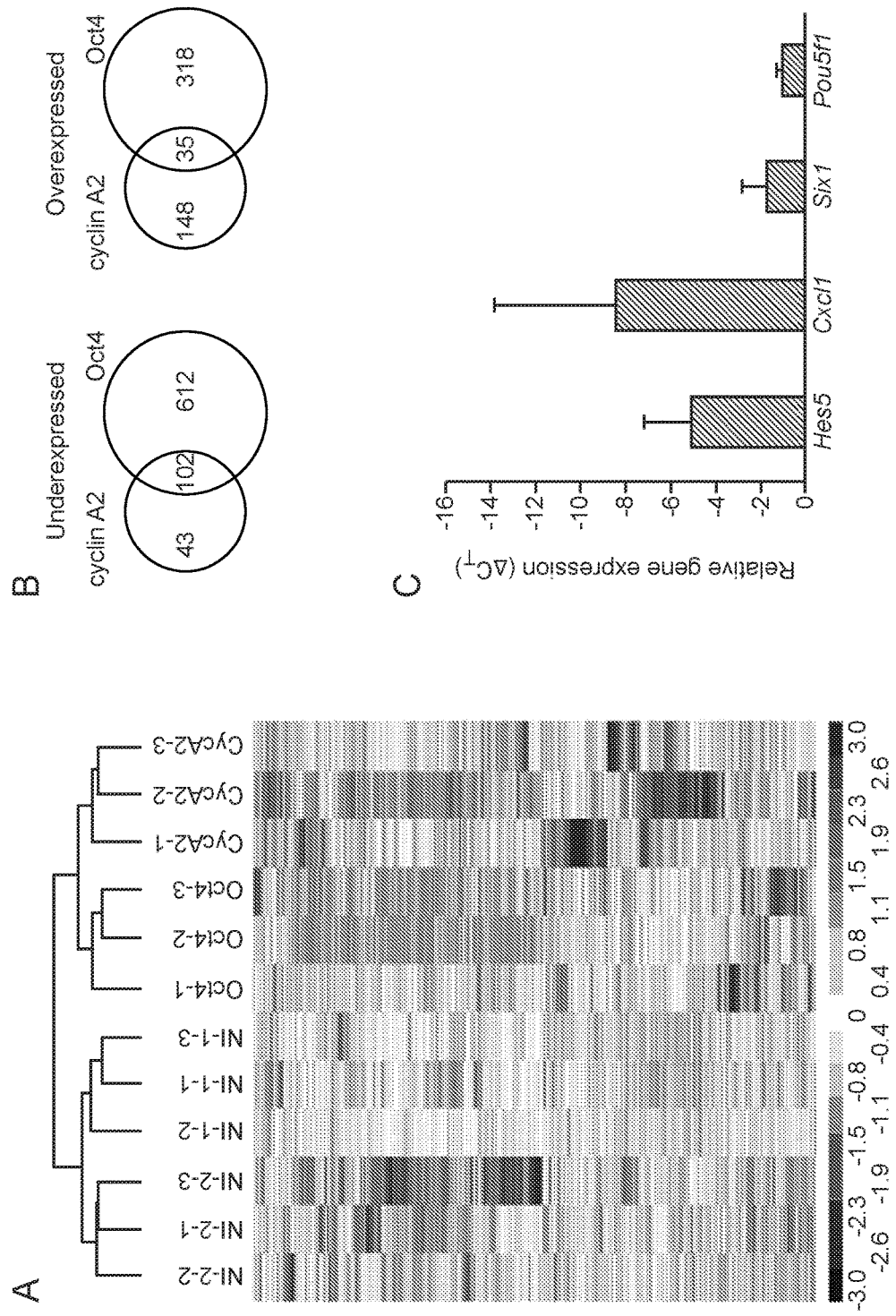
FIGS. 14 and 15 show gene regulation by Oct4.

To dissect the mechanisms of Oct4 function, we compared the global gene expression profile of Oct4 knockdown embryos to the effects of Ccna2 knockdown and to uninjected controls at the mid-2-cell stage. The goal was to identify differential gene expression that coincides with the first major wave of embryonic genome activation at the mid-2-cell stage (Hamatani T, Carter M G, Sharov A A, & Ko M S (2004) *Dev Cell* 6, 117-1317; Wang Q T, et al. (2004) *Dev Cell* 6, 133-1448) (Tables 8, A and B, 9, A and B). Analysis by an unsupervised algorithm showed that the embryo samples clustered according to the experimental conditions, which further supported the specific and non-random effects of gene knockdown (FIG. 14, panel A). At an arbitrary threshold false detection rate (FDR) of 0.05, the Oct4-regulated gene set is five times larger compared to the number of genes changing expression in response to cyclin A2 knockdown (FIG. 14, panel B). The different sizes of the under-expressed versus over-expressed Oct4-knockdown gene sets suggest that Oct4 may be predominantly activating rather than repressing transcription (FIG. 14, panel B). Some of the Oct4 candidate target genes have previously been identified as putative Oct4 targets based on mESC chromatin immunoprecipitation (ChIP) data or genomic sequence analysis of Oct4-binding sites (Thou Q, Chipperfield H, Melton D A, & Wong W H (2007) *Proc Natl Acad Sci USA* 104, 16438-16443) (Table 10).

The list of cyclin A2-regulated genes was rich in genes encoding factors for chromatin modification and remodelling (p=0.005), nucleotide metabolism (p=0.01), and chromosome organization (p=0.01; Tables 11 A and B). Oct4-regulated genes were significantly enriched for translation (p=$1.1\times10^{-4}$) and RNA processing functions (p=$3.0\times10^{-5}$) (Tables 11, C and D). Comparison of our data with published Oct4-regulated networks in mouse ESCs indicates that Oct4 has distinct and specific post-transcriptional and translational regulatory functions mediated by its control of genes encoding subunits in eukaryotic translation initiation factors (Eif), including Eif3c, and Eif3b. Interestingly, these two Eif subunits are evolutionarily conserved from yeast to human, and are amongst the six subunits comprising the functional core of mammalian Eif3, the largest of the Eif complexes (Masutani M, Sonenberg N, Yokoyama S, & Imataka H (2007) *Embo J* 26, 3373-3383). In addition to its embryo-specific function, Oct4 also controls the expression of genes encoding post-transcriptional regulators Dppa5 and Piwil2 (also known as Mili), as it does in ESCs (data not shown). Dppa5 is an embryo-, germ cell- and ESC-specific RNA-binding protein whose role in maternal-embryonic transition is not known. However, Piwil2 and its bound pi-RNAs, are known for their role in regulating retrotransposons in the fully-grown mouse oocyte (Watanabe T, et al. (2008) *Nature* 453, 539-543.26). Collectively, our data indicate that the Oct4 has a distinct, developmental stage-specific role in controlling genes encoding post-transcriptional regulators, in addition to its conserved functions shared amongst pluripotent cell types.

Table 8A: Genes that have Higher Expression Levels in Oct4-MO-Injected Compared to Uninjected Embryos (Following the Examples Section)

Table 8B: Genes that have Lower Expression Levels in Oct4-MO-Injected Compared to Uninjected Embryos (Following the Examples Section)

Table 9A: Genes that have Higher Expression Levels in Ccna2-MO-Injected Compared to Uninjected Embryos (Following the Examples Section Table 9B: Genes that have Lower Expression Levels in Ccna2-MO-Injected Compared to Uninjected Embryos (Following the Examples Section)

TABLE 10

Oct4 Candidate Target Genes That Have Putative Oct4 Binding Sites Based on Genomic Sequence Analysis or Mouse ESC Chromatin Precipitation (ChIP) Data Downregulated in Oct4 knockdown embryos:

1700021F05Rik: RIKEN cDNA 1700021F05 gene
2900073H19Rik: RIKEN cDNA 2900073H19 gene
Arhgap8: Rho GTPase activating protein 8
Cbfa2t2h: core-binding factor, runt domain, alpha subunit 2, translocated to, 2 homolog (human)
Cdt1: chromatin licensing and DNA replication factor 1
Dido1: death inducer-obliterator 1
Dpm1: dolichol-phosphate (beta-D) mannosyltransferase 1
Dppa5: developmental pluripotency associated 5
Eif4e2: eukaryotic translation initiation factor 4E member 2
Elovl6: ELOVL family member 6, elongation of long chain fatty acids (yeast)
Etv5: ets variant gene 5
Fkbp4: FK506 binding protein 4
Gnb2l1: guanine nucleotide binding protein (G protein), beta polypeptide 2 like 1
Hexb: hexosaminidase B
Igf2bp1: insulin-like growth factor 2 mRNA binding protein 1
Klf9: Kruppel-like factor 9
Mkrn1: makorin, ring finger protein, 1
Mtf2: metal response element binding transcription factor 2
Myg1: melanocyte proliferating gene 1
Pa2g4: proliferation-associated 2G4
Pitpnc1: phosphatidylinositol transfer protein, cytoplasmic 1
Ppm1a: protein phosphatase 1A, magnesium dependent, alpha isoform
Rest: RE1-silencing transcription factor
Rif1 /// LOC671598: Rap1 interacting factor 1 homolog (yeast) /// similar to Telomere-associated protein RIF1 (Rap1-interacting factor 1 homolog) (mRif1)
Slc19a3: solute carrier family 19 (sodium/hydrogen exchanger), member 3
Slc22a12: solute carrier family 22 (organic anion/cation transporter), member 12
Slc25a36: solute carrier family 25, member 36
Tfrc: transferrin receptor
Tnpo3: transportin 3
Ube2h: ubiquitin-conjugating enzyme E2H
Ube2o: ubiquitin-conjugating enzyme E2O
Zfp297b: zinc finger protein 297B Upregulated in Oct4 knockdown embryos BC022623: cDNA sequence BC022623
2810429O05Rik: RIKEN cDNA 2810429O05 gene
Blcap: bladder cancer associated protein homolog (human)
Icosl: icos ligand
Sox2: SRY-box containing gene 2
Bcas2: breast carcinoma amplified sequence 2
Ldlr: low density lipoprotein receptor
Zfp219: zinc finger protein 219
Arl4c /// LOC632433: ADP-ribosylation factor-like 4C /// similar to ADP-ribosylation factor-like protein 7
Tcl1: T-cell lymphoma breakpoint 1
Dcp1a: decapping enzyme
Nes: nestin
Rbpsuh: Recombining binding protein suppressor of hairless (*Drosophila*)

TABLE 11A

Functional Categories That Were Enriched In Downregulated Genes In The Ccna2 Knockdown Model

| GOBPID | P-value | Term |
|---|---|---|
| GO:0050875 | 1.1E−3 | cellular physiological process** |
| GO:0016568 | 4.0E−3 | chromatin modification* |
| GO:0042254 | 4.0E−3 | ribosome biogenesis and assembly** |
| GO:0006338 | 4.8E−3 | chromatin remodeling* |
| GO:0007028 | 0.01 | cytoplasm organization and biogenesis** |

TABLE 11A-continued

Functional Categories That Were Enriched In Downregulated Genes In The Ccna2 Knockdown Model

| GOBPID | P-value | Term |
|---|---|---|
| GO:0044237 | 0.01 | cellular metabolism** |
| GO:0007582 | 0.01 | physiological process |
| GO:0006139 | 0.01 | nucleobase, nucleoside, nucleotide and nucleic acid metabolism* |
| GO:0008152 | 0.01 | metabolism |
| GO:0006376 | 0.01 | mRNA splice site selection* |
| GO:0006413 | 0.01 | translational initiation** |
| GO:0007001 | 0.01 | chromosome organization and biogenesis (sensu Eukaryota)* |
| GO:0007001 | | |
| GO:0007001 | | |
| GO:0006996 | 0.01 | organelle organization and biogenesis* |
| GO:0007046 | 0.01 | ribosome biogenesis** |
| GO:0043170 | 0.02 | macromolecule metabolism** |
| GO:0051276 | 0.02 | chromosome organization and biogenesis |
| GO:0006325 | 0.02 | establishment and/or maintenance of chromatin architecture |
| GO:0006323 | 0.02 | DNA packaging* |
| GO:0016043 | 0.02 | cell organization and biogenesis |
| GO:0044238 | 0.03 | primary metabolism** |
| GO:0000245 | 0.03 | spliceosome assembly |
| GO:0006486 | 0.03 | protein amino acid glycosylation |
| GO:0009059 | 0.03 | macromolecule biosynthesis** |
| GO:0043413 | 0.03 | biopolymer glycosylation |
| GO:0009101 | 0.04 | glycoprotein biosynthesis |
| GO:0006364 | 0.04 | rRNA processing |
| GO:0006412 | 0.04 | protein biosynthesis** |
| GO:0006259 | 0.04 | DNA metabolism |
| GO:0016072 | 0.04 | rRNA metabolism** |
| GO:0009100 | 0.05 | glycoprotein metabolism |

Notes:
**Indicates the categories that were enriched in the Oct4 data set as well.
*indicates functional categories that were specifically enriched in Ccna2 knockdown.

TABLE 11B

Functional Categories That Were Enriched In Upregulated Genes In The Ccna2 Knockdown Model

| GOBPID | P-value | Term |
|---|---|---|
| GO:0044262 | 7.1E−4 | cellular carbohydrate metabolism |

TABLE 11C

Functional Categories That Were Enriched In Downregulated Genes In The Oct4 Knockdown Model

| GOBPID | P-value | Term |
|---|---|---|
| GO:0006412 | 1.8E−7 | protein biosynthesis** |
| GO:0009059 | 1.3E−6 | macromolecule biosynthesis** |
| GO:0006413 | 3.6E−6 | translational initiation** |
| GO:0009058 | 1.8E−5 | biosynthesis |
| GO:0044249 | 2.1E−5 | cellular biosynthesis |
| GO:0042254 | 2.3E−5 | ribosome biogenesis and assembly** |
| GO:0006396 | 3.0E−5 | RNA processing* |
| GO:0007046 | 3.3E−5 | ribosome biogenesis** |
| GO:0016070 | 3.9E−5 | RNA metabolism** |
| GO:0007028 | 7.0E−5 | cytoplasm organization and biogenesis** |
| GO:0043037 | 1.1E−4 | Translation* |
| GO:0043170 | 1.2E−4 | macromolecule metabolism** |
| GO:0019538 | 1.6E−4 | protein metabolism |
| GO:0044238 | 3.1E−4 | primary metabolism** |
| GO:0044267 | 3.1E−4 | cellular protein metabolism |

TABLE 11C-continued

Functional Categories That Were Enriched In Downregulated Genes In The Oct4 Knockdown Model

| GOBPID | P-value | Term |
|---|---|---|
| GO:0050875 | 3.3E−4 | cellular physiological process** |
| GO:0044237 | 5.3E−4 | cellular metabolism** |
| GO:0044260 | 5.7E−4 | cellular macromolecule metabolism |

Note:
**Indicates categories that were enriched in the Ccna2 data set as well.
*indicates functional categories that were specifically enriched in Oct4 knockdown.

TABLE 11D

Functional Categories That Were Enriched In Upregulated Genes In The Oct4 Knockdown Model

| GOBPID | P-value | Term |
|---|---|---|
| GO:0044262 | 2.0E−4 | Alcohol metabolism |

Example 6

Oct4 Function at the 1- to 2-Cell Stage

In order to understand the role of Oct4 in reprogramming the early embryo, we examined its role in embryonic genome activation and maternal transcript degradation. Overall, Oct4 regulates gene expression pertinent to basic machinery required for the entire spectrum of gene regulation, including transcription involving all three RNA polymerases, translation, RNA processing such as regulation of polyadenylation, and mRNA degradation proteins (Table 12). High levels of mRNA from developmental genes, such as Six1, Nestin, and Hoxa3, indicated that Oct4 was required for their repression, while excessive levels of maternal transcripts that would normally be rapidly degraded, such as Zar1 and Nobox1, indicated that Oct4 knockdown interfered with the mRNA degradation machinery. Thus, Oct4 has developmental stage- and cell-specific functions, and has an important role in the processes that mark maternal-embryonic transition.

Figure 15:
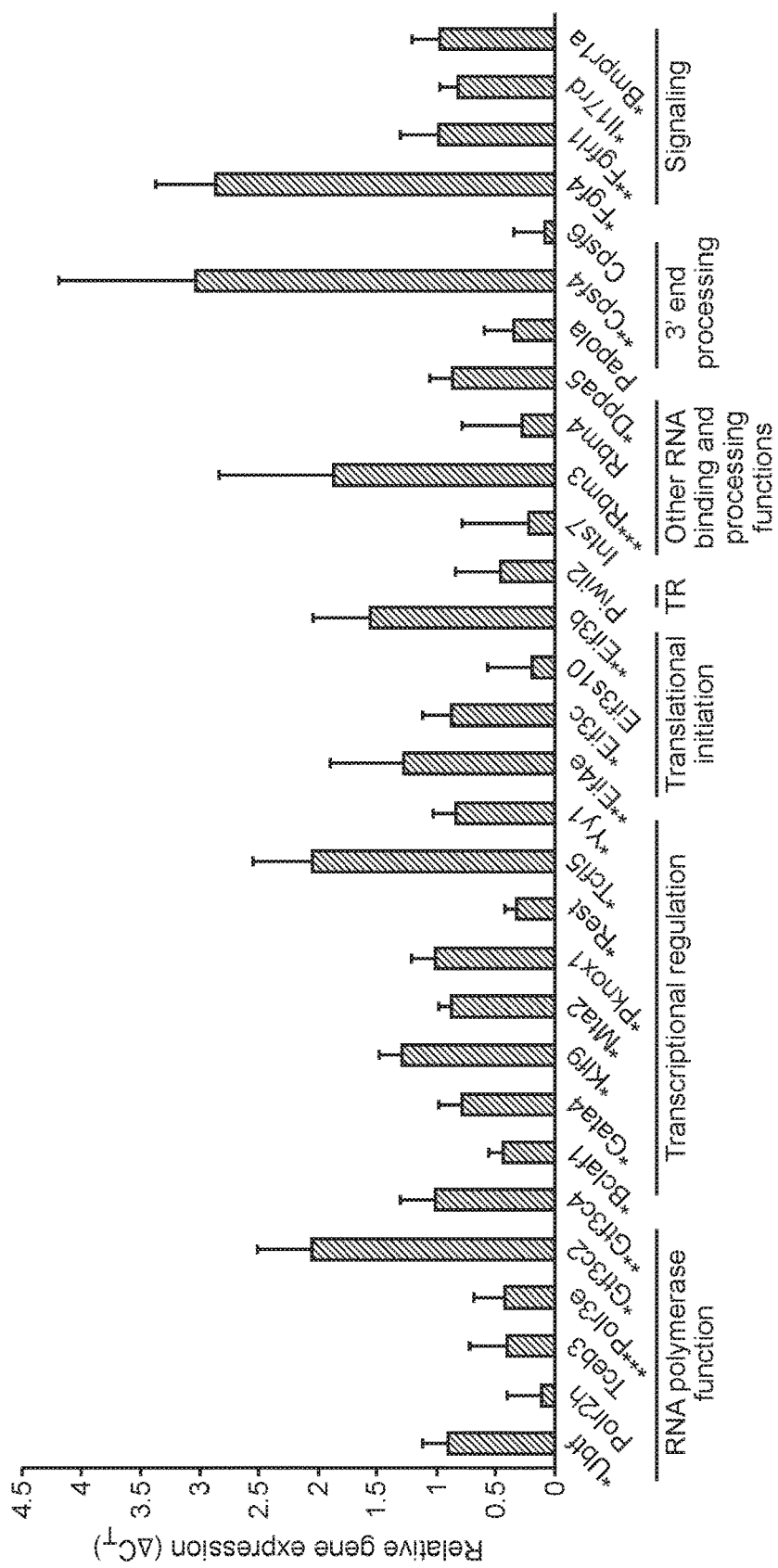

To further define the Oct4-regulated gene network, we selected 42 genes representing transcriptional, post-transcriptional and signaling functions for q-PCR assays. We analyzed RNA from single Oct4-MO-injected and control embryos and focused on genes that were under-expressed in Oct4 knockdown. After removing data related to 3 genes for which there were technical difficulties, expression changes of 39 genes were appropriately measured based on analysis using a linear model (See Methods and Materials). Of those, 34 or ~87% showed altered expression levels in Oct4 knockdown in the expected directions (FIG. 14, panel C and FIG. 15), while 5 genes, including Sox2, did not change (data not shown). 21 of the 34 genes, or ~62%, showed statistically significant differential expression by q-PCR at p<0.05 or less, while injection of a control MO did not alter expression of any of the genes assayed (data not shown). Thus, we have proven that Oct4 directly or indirectly regulates genes encoding the entire spectrum of transcriptional and post-transcriptional regulators at the 1- to 2-cell stages.

Our single-embryo data allowed us to go beyond simply validating our gene chip data. Methods using samples comprised of pooled cells or embryos, generate relative gene expression that represents an average of all cells assayed, but they cannot discern between genes that are consistently differentially regulated versus those with a tendency towards stochastic changes; similarly, rare outlier embryos expressing unique transcriptomes are not recognized (Bengtsson M, Stahlberg A, Rorsman P, & Kubista M (2005) *Genome Res* 15, 1388-1392; Chang H H, et al. (2008) *Nature* 453, 544-547; Warren L, Bryder D, Weissman I L, & Quake S R (2006) *Proc Natl Acad Sci USA* 103, 17807-17812). By analyzing quantitative expression data at the single-embryo level, we were able to make this discrimination. We presume genes whose relative expression is consistent amongst single embryos have a higher likelihood to be essential nodes in a gene regulatory network, which is expected to respond to perturbations in a consistent and predictable manner. The gene set was restricted to genes whose differential expression (represented by the difference in threshold cycles, $\Delta C_T$) $\Delta C_T$ is greater than expression differences amongst single embryos (represented by standard error of the mean, s.e.m.).

Figure 16:
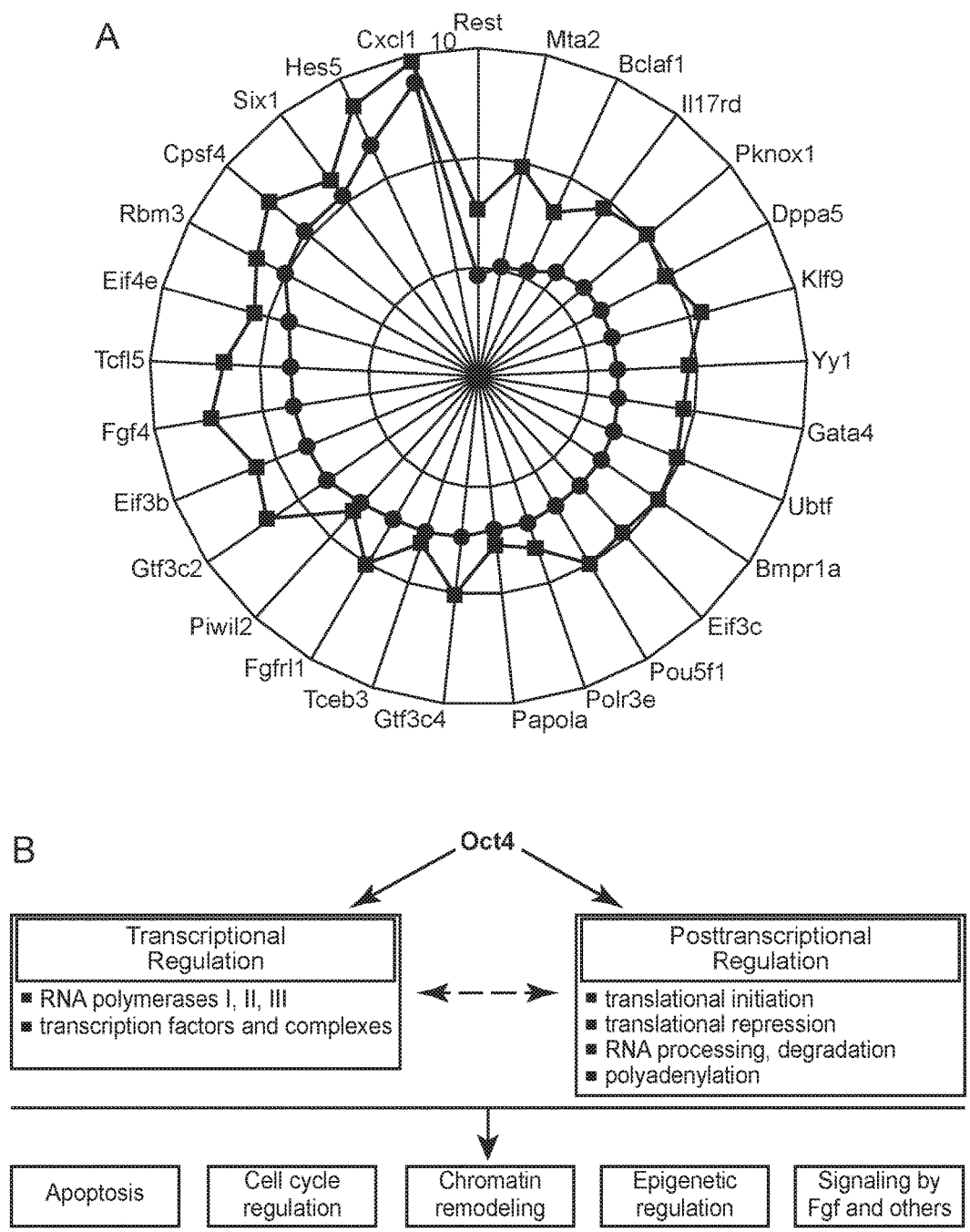
FIG. 16 shows models of Oct4 function at the 1- to 2-cell stage. Panel A shows genes whose Absolute ($\Delta C_T$) (red) is greater than its s.e.m. (blue), are ordered clockwise based on increasing s.e.m. (Log scale.) Panel B shows proposed regulation of various modules by Oct4 via transcriptional and post-transcriptional mechanisms.

We propose a hierarchy in the Oct4-regulated gene network in which 29 genes are ordered based on their increasing s.e.m., or inter-embryo variation and presumed decreasing biological significance in this network (FIG. 16, panel A). Taken together, we have identified and ranked potential key nodes of this network in a quantitative fashion.

The data shows that in the unique developmental context of maternal-embryonic transition, concomitant with massive mRNA degradation and dramatic reprogramming, Oct4 controls the expression of many transcriptional regulators. Oct4 also maintains the expression of many genes, such as Eif3c, Papola, Piwil2, Eif3b, Eif4e, Rbm3 and Cpsf4, that are involved in the post-transcriptional control. Through its influence on both the transcriptional and post-transcriptional regulators, Oct4 can directly or indirectly affect many essential processes, such as chromatin remodelling, epigenetic regulation, apoptosis, cell cycle regulation, and signalling, during early developmental program (FIG. 16, panel B).

TABLE 12

Candidate Oct4-Regulated Genes That Function In Transcription, Translation, RNA Processing, Chromatin Remodeling, Signaling, Apoptosis And The Cell Cycle.

| | Gene Symbol | Fold change | False detection rate (FDR) | T. P-value |
|---|---|---|---|---|
| POL I transcription | | | | |
| upstream binding transcription factor, RNA polymerase I | Ubtf | 0.49 | 0.02667 | 0.00424 |
| arginyl-tRNA synthetase | Rars | 0.47 | 0.03200 | 0.00131 |
| POL II transcription | | | | |
| BTAF1 RNA polymerase II, B-TFIID transcription factor-associated, (Mot1 homolog, *S. cerevisiae*) | Btaf1 | 0.12 | 0.03834 | 0.00833 |
| mediator of RNA polymerase II transcription, subunit 8 homolog (yeast) | Med8 | 0.25 | 0.03405 | 0.00142 |
| transcription elongation factor B (SIII), polypeptide 3 | Tceb3 | 0.29 | 0.01471 | 0.00001 |
| TAF9 RNA polymerase II, TATA box binding protein (TBP)-associated factor | Taf9 | 0.30 | 0.02151 | 0.00027 |
| polymerase (RNA) II (DNA directed) polypeptide H | Polr2h | 0.42 | 0.02586 | 0.00859 |
| elongation factor RNA polymerase II 2 | Ell2 | 0.49 | 0.03696 | 0.00098 |
| cofactor required for Sp1 transcriptional activation, subunit 2 | Med14 | 0.50 | 0.03794 | 0.00156 |
| POL III transcription | | | | |
| general transcription factor IIIC, polypeptide 4 | Gtf3c4 | 0.07 | 0.00000 | 0.00002 |
| general transcription factor IIIC, polypeptide 5 | Gtf3c5 | 0.34 | 0.03209 | 0.00212 |
| BRF2, subunit of RNA polymerase III transcription initiation factor, BRF1-like | Brf2 | 0.34 | 0.04385 | 0.05104 |
| general transcription factor IIIC, polypeptide 2, beta | Gtf3c2 | 0.35 | 0.03314 | 0.00047 |
| general transcription factor III C 1 | Gtf3c1 | 0.47 | 0.03303 | 0.00236 |
| polymerase (RNA) III (DNA directed) polypeptide A | Polr3a | 0.55 | 0.04421 | 0.01694 |
| polymerase (RNA) III (DNA directed) polypeptide E | Polr3e | 0.56 | 0.03366 | 0.00134 |
| Translational control, RNA processing, and posttranscriptional regulation Translational initiation | | | | |
| eukaryotic translation initiation factor 2C, 5 | Eif2c5 | 0.09 | 0.01370 | 0.00022 |
| eukaryotic translation initiation factor 5B | Eif5b | 0.14 | 0.03802 | 0.00002 |
| eukaryotic translation initiation factor 3, subunit 9 (eta) | Eif3b | 0.29 | 0.03803 | 0.00358 |
| eukaryotic translation initiation factor 3, subunit 8 | Eif3c | 0.36 | 0.00000 | 0.00016 |
| eukaryotic translation initiation factor 3, subunit 3 (gamma) | Eif3h | 0.42 | 0.03226 | 0.00485 |
| eukaryotic translation initiation factor 3, subunit 4 (delta) | Eif3g | 0.47 | 0.04924 | 0.01507 |
| integrin beta 4 binding protein | Eif6 | 0.53 | 0.02756 | 0.00236 |
| eukaryotic translation initiation factor 4, gamma 1 | Eif4g1 | 0.59 | 0.04065 | 0.00041 |
| eukaryotic translation initiation factor 2, subunit 1 alpha | Eif2s1 | 0.60 | 0.04879 | 0.00311 |
| eukaryotic translation initiation factor 4E /// hypothetical LOC630527 | Eif4e | 0.65 | 0.03742 | 0.00177 |
| eukaryotic translation initiation factor 3, subunit 10 (theta) | Eif3s10 | 0.66 | 0.04070 | 0.01798 |
| Translational repression | | | | |
| piwi-like homolog 2 (*Drosophila*) | Piwil2 | 0.34 | 0.02778 | 0.00051 |
| eukaryotic translation initiation factor 4E member 2 | Eif4e2 | 0.46 | 0.02553 | 0.01084 |
| 3' end processing | | | | |
| poly (A) polymerase alpha | Papola | 0.10 | 0.02475 | 0.00014 |
| cleavage and polyadenylation specific factor 6 | Cpsf6 | 0.20 | 0.03256 | 0.00009 |
| cleavage and polyadenylation specific factor 4 | Cpsf4 | 0.48 | 0.03542 | 0.00233 |

TABLE 12-continued

Candidate Oct4-Regulated Genes That Function In Transcription, Translation, RNA Processing, Chromatin Remodeling, Signaling, Apoptosis And The Cell Cycle.

| | Gene Symbol | Fold change | False detection rate (FDR) | T. P-value |
|---|---|---|---|---|
| Translational termination | | | | |
| eukaryotic translation termination factor 1 | Etf1 | 0.36 | 0.02717 | 0.00207 |
| Nonsense mediated decay (NMD) | | | | |
| eukaryotic translation initiation factor 3, subunit 6 | Eif3e | 0.21 | 0.00000 | 0.00000 |
| Other RNA binding and processing | | | | |
| integrator complex subunit 7 | Ints7 | 0.10 | 0.02757 | 0.00004 |
| RNA binding motif protein 3 | Rbm3 | 0.20 | 0.03791 | 0.00037 |
| RNA binding motif protein 4 | Rbm4 | 0.42 | 0.04967 | 0.00236 |
| developmental pluripotency associated 5 | Dppa5 | 0.46 | 0.03672 | 0.00786 |
| RNA binding motif protein 5 | Rbm5 | 0.52 | 0.03415 | 0.00245 |
| proliferation-associated 2G4 | Pa2g4 | 0.70 | 0.04956 | 0.01729 |
| Pre-mRNA processing and transport | | | | |
| Heterogeneous nuclear ribonucleoprotein U | | 0.18 | 0.03688 | 0.00020 |
| PRP4 pre-mRNA processing factor 4 homolog (yeast) | Prpf4 | 0.34 | 0.03828 | 0.00128 |
| RNA, U transporter 1 | Snupn | 0.35 | 0.01681 | 0.00227 |
| PRP38 pre-mRNA processing factor 38 (yeast) domain containing B | Prpf38b | 0.48 | 0.04103 | 0.00548 |
| protein phosphatase 1G (formerly 2C), magnesium-dependent, gamma isoform | Ppm1g | 0.48 | 0.02463 | 0.00012 |
| heterogeneous nuclear ribonucleoprotein A/B | Hnrpab | 0.58 | 0.03233 | 0.00100 |
| heterogeneous nuclear ribonucleoprotein A1 | Hnrpa1 | 0.63 | 0.04981 | 0.00961 |
| heterogeneous nuclear ribonucleoprotein K | Hnrpk | 0.64 | 0.04473 | 0.01239 |
| heterogeneous nuclear ribonucleoprotein M | Hnrpm | 0.63 | 0.04884 | 0.00724 |
| Transcriptional regulation | | | | |
| homeodomain interacting protein kinase 3 | Hipk3 | 0.17 | 0.04003 | 0.00031 |
| Kruppel-like factor 9 | Klf9 | 0.17 | 0.00000 | 0.00020 |
| nuclear respiratory factor 1 | Nrf1 | 0.20 | 0.01923 | 0.00073 |
| integrator complex subunit 4 | Ints4 | 0.34 | 0.03520 | 0.00080 |
| homeodomain interacting protein kinase 1 | Hipk1 | 0.35 | 0.01786 | 0.00073 |
| Pbx/knotted 1 homeobox | Pknox1 | 0.37 | 0.03796 | 0.00484 |
| proline, glutamic acid and leucine rich protein 1 | Pelp1 | 0.40 | 0.02415 | 0.00573 |
| core-binding factor, runt domain, alpha subunit 2, translocated to, 2 homolog (human) | | 0.41 | 0.04076 | 0.02903 |
| YY1 transcription factor | Yy1 | 0.43 | 0.03853 | 0.00074 |
| GATA binding protein 4 | Gata4 | 0.45 | 0.03963 | 0.00325 |
| metastasis-associated gene family, member 2 | Mta2 | 0.51 | 0.03395 | 0.00326 |
| BCL2-associated transcription factor 1 | Bclaf1 | 0.54 | 0.02664 | 0.00242 |
| RE1-silencing transcription factor | Rest | 0.62 | 0.03827 | 0.00983 |
| ets variant gene 5 | Etv5 | 0.50 | 0.04900 | 0.00576 |
| makorin, ring finger protein, 1 | Mkrn1 | 0.58 | 0.03793 | 0.00310 |
| Chromatin remodeling, epigenetic regulation | | | | |
| jumonji domain containing 1B | Kdm3b | 0.14 | 0.03770 | 0.00132 |
| jumonji, AT rich interactive domain 1C (Rbp2 like) | Kdm5c | 0.23 | 0.01408 | 0.00075 |
| sirtuin 1 ((silent mating type information regulation 2, homolog) 1 (S. cerevisiae) | Sirt1 | 0.28 | 0.01136 | 0.00002 |
| methyltransferase like 2 | Mettl2 | 0.37 | 0.03333 | 0.00010 |
| jumonji domain containing 1A | Kdm3a | 0.38 | 0.04874 | 0.00764 |
| SWI/SNF related, matrix associated, actin dependent regulator of chromatin, subfamily c, member 1 | Rsc8 | 0.41 | 0.03665 | 0.01049 |
| jumonji, AT rich interactive domain 1B (Rbp2 like) | Kdm5b | 0.57 | 0.03738 | 0.00388 |
| eukaryotic translation initiation factor 2, subunit 3, structural gene X-linked /// similar to eukaryotic translation initiation factor 2, subunit 3, structural gene X-linked | | 0.57 | 0.04905 | 0.00183 |
| Histone H3-specific HAT activity | | | | |
| general transcription factor IIIC, polypeptide 4 | Gtf3c4 | 0.07 | 0.00000 | 0.00002 |
| general transcription factor IIIC, polypeptide 5 | Gtf3c5 | 0.34 | 0.03209 | 0.00212 |
| GCN5 general control of amino acid synthesis-like 2 (yeast) | Gcn5 | 0.34 | 0.02525 | 0.00159 |
| general transcription factor IIIC, polypeptide 2, beta | Gtf3c2 | 0.35 | 0.03314 | 0.00047 |
| general transcription factor III C 1 | Gtf3c1 | 0.47 | 0.03303 | 0.00236 |
| H3 histone, family 3A | H3f3a | 0.53 | 0.04006 | 0.00865 |
| Signaling pathways (Fgf4, Bmp, Toll, Egf, Mapk, Erk, Igf2, Amp) | | | | |
| fibroblast growth factor 4 | Fgf4 | 0.09 | 0.02591 | 0.00088 |
| signaling intermediate in Toll pathway-evolutionarily conserved | Ecsit | 0.17 | 0.01935 | 0.00000 |

TABLE 12-continued

Candidate Oct4-Regulated Genes That Function In Transcription, Translation, RNA Processing, Chromatin Remodeling, Signaling, Apoptosis And The Cell Cycle.

| | Gene Symbol | Fold change | False detection rate (FDR) | T. P-value |
|---|---|---|---|---|
| protein kinase, AMP-activated, gamma 1 non-catalytic subunit | Prkag1 | 0.19 | 0.03786 | 0.00010 |
| insulin-like growth factor 2 mRNA binding protein 1 | Imp1 | 0.26 | 0.04930 | 0.00047 |
| bone morphogenetic protein receptor, type 1A | Bmpr1a | 0.35 | 0.02347 | 0.00005 |
| fibroblast growth factor receptor-like 1 | Fgfrl1 | 0.34 | 0.03349 | 0.01815 |
| interleukin 17 receptor D | Il17rd | 0.35 | 0.01961 | 0.00052 |
| mitogen activated protein kinase 1 | Mapk1 | 0.39 | 0.04889 | 0.00710 |
| splicing factor, arginine/serine-rich 15 /// similar to splicing factor, arginine/serine-rich 15 | Sfrs15 | 0.47 | 0.02113 | 0.00047 |
| protein phosphatase 1A, magnesium dependent, alpha isoform | Ppm1a | 0.46 | 0.02525 | 0.00280 |
| protein kinase C, delta | Prkcd | 0.45 | 0.03465 | 0.02184 |
| insulin-like growth factor 2 receptor | Igf2r | 0.53 | 0.04738 | 0.00600 |
| Apoptosis | | | | |
| junction-mediating and regulatory protein | Jmy | 0.21 | 0.00000 | 0.00036 |
| sphingosine-1-phosphate phosphatase 1 | Sgpp1 | 0.23 | 0.01538 | 0.00160 |
| cathepsin B | Ctsb | 0.28 | 0.00000 | 0.00024 |
| death inducer-obliterator 1 | Dido1 | 0.46 | 0.03440 | 0.00196 |
| Cell cycle, DNA replication, DNA repair, cell division, chromosome segregation, cell growth, cell size | | | | |
| origin recognition complex, subunit 4-like (*S. cerevisiae*) | Orc4l | 0.17 | 0.01852 | 0.00383 |
| purine rich element binding protein B | Purb | 0.29 | 0.02669 | 0.00019 |
| chromosome segregation 1-like (*S. cerevisiae*) | Cse1l | 0.34 | 0.03254 | 0.00002 |
| minichromosome maintenance deficient 5, cell division cycle 46 (*S. cerevisiae*) | Mcm5 | 0.34 | 0.01852 | 0.00004 |
| kinesin family member 11 | Kif11 | 0.34 | 0.01938 | 0.00170 |
| replication factor C (activator 1) 2 | Rfc3 | 0.40 | 0.04420 | 0.00919 |
| kinesin family member 22 | Kif22 | 0.42 | 0.02667 | 0.00033 |
| protein phosphatase 2 (formerly 2A), catalytic subunit, beta isoform | Ppp2cb | 0.43 | 0.03243 | 0.00658 |
| centromere protein E | Cenpe | 0.54 | 0.03801 | 0.00299 |
| Rap1 interacting factor 1 homolog (yeast) /// similar to Telomere-associated protein RIF1 (Rap1-interacting factor 1 homolog) (mRif1) | mRif1 | 0.63 | 0.04515 | 0.00228 |

Example 6

Determination of Probability of Live Birth Event

In the US, 7.3 million couples suffer from clinical infertility, for which more than ~120,000 IVF treatment cycles are performed per year. IVF is the most effective treatment for many infertility couples, but it is largely empiric, and may not result in a live birth for some couples despite multiple attempts. IVF treatment has revolutionized how physicians can help subfertile patients, but success rates with the use of autologous oocytes appear to have reached a plateau in the past decade. At an average cost of $12,000 per cycle, IVF treatment alone costs health care payers, most of whom are the couples themselves, more than $1 billion per year. However, the decision-making process for IVF can be daunting because IVF counseling and management decisions are often made based on the woman's chronological age, with non-standardized ways to adjust for various estimates of ovarian reserve and embryo quality. Further, quality of care is thought to vary amongst IVF clinics, but head-to-head comparisons are not possible in the absence of scientifically and rigorously defined prognostic stratification of patients. For a treatment that is physically, emotionally, and financially demanding, patients may feel that they are rolling the dice when deciding on whether to start or repeat IVF treatment. Consequently, there may be incongruence in patient- or self-selection for IVF, such that some patients with truly poor prognosis may develop unrealistic expectations, while others with truly good prognosis may miss opportunities for effective treatment. Although numerous publications have reported variables, including chronological age of the female patient, that are significantly associated with IVF outcomes, their contribution relative to outcomes is not clear, and we are even less certain how to directly apply those findings to counsel patients.

Accordingly, in the example we applied MART to analyze dichotomous live birth outcomes of a larger, four-year data set on 3338 fresh, non-oocyte donor IVF cycles and their associated embryos, including subsequent transfer of cryopreserved embryos from 2003 to 2006. Importantly, 57 variables pertaining to clinical diagnoses, treatment response, and embryo developmental parameters from 1,879 fresh, first-cycles were used to generate prediction models in an unbiased manner, with no pre-selection of variables based on previous literature. We identified four prognostic factors—the percentage of blastocysts (Blast Rate), total number of embryos (Embryo Number), total amount of gonadotropins required (TG), and endometrial thickness (EndoTh)—that determine live birth outcomes. The prognostic contribution of other variables, such as age and the number of 8-cell stage embryos on day 3, were optional once these four prognostic variables were known. Finally, the results show how our approach and findings can be applied to immediately improve patient counseling and management protocols, and how these rigorously defined prognostic criteria can fuel our concerted effort to improve quality assurance and decrease rates of multiple gestation.

Figure 17:
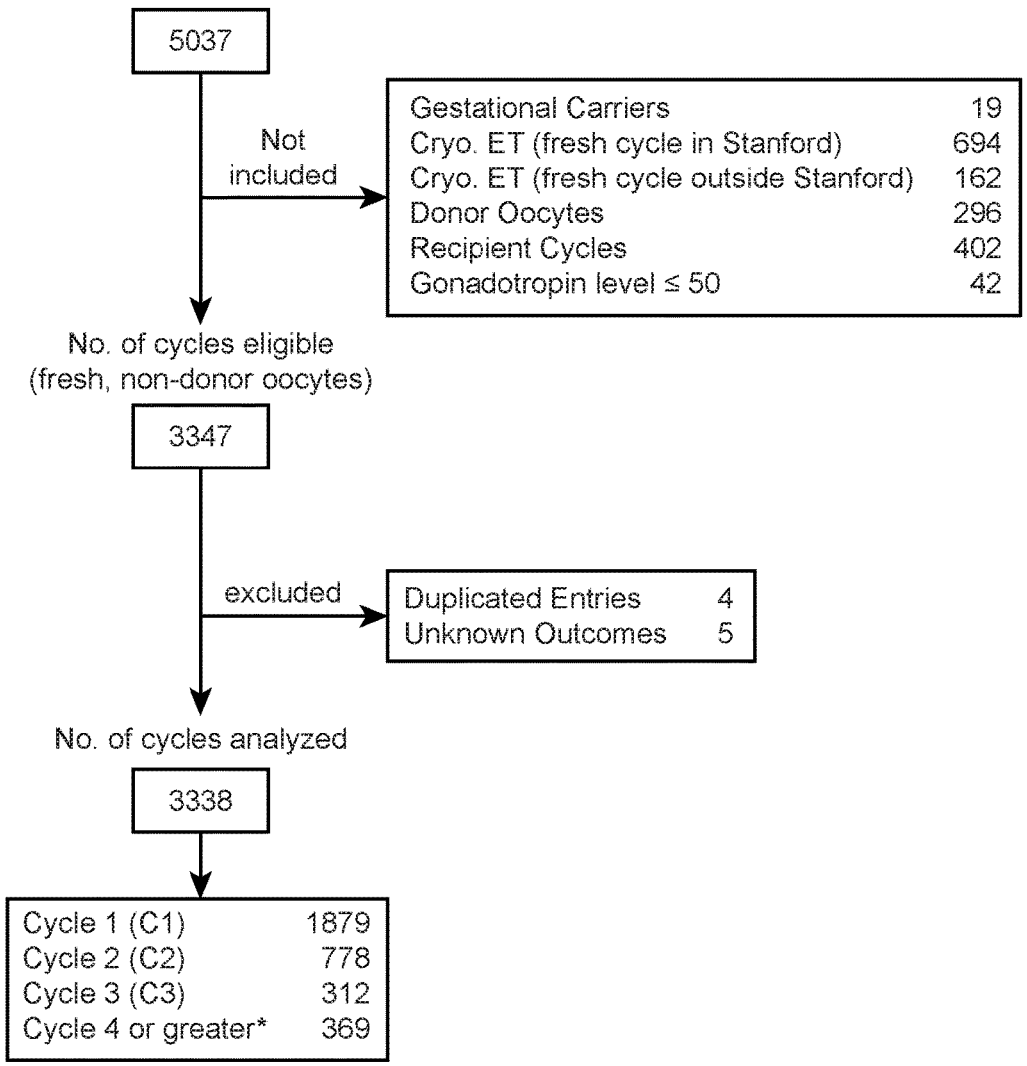
FIG. 17 shows a summary of the data source for the live birth analysis. The numbers in the boxes indicate the number of fresh cycles performed in the Stanford IVF center through 2003-06. The cycles that were not included were related to: gestational carriers, Cryo. ET or cryopreserved embryo transfer (cycles which utilized frozen embryos, irrespective of whether the cycle was performed at Stanford or outside), donor oocytes (non-self oocytes), recipient cycles and cycles in which no gonadotropin was injected. 9 cycles were excluded from analysis for duplicated entries and unknown outcomes. The cycles analyzed were further classified into Cycles 1, 2, 3 or beyond, depending on the number of times the patient returned for a fresh IVF cycle.
Figure 18:
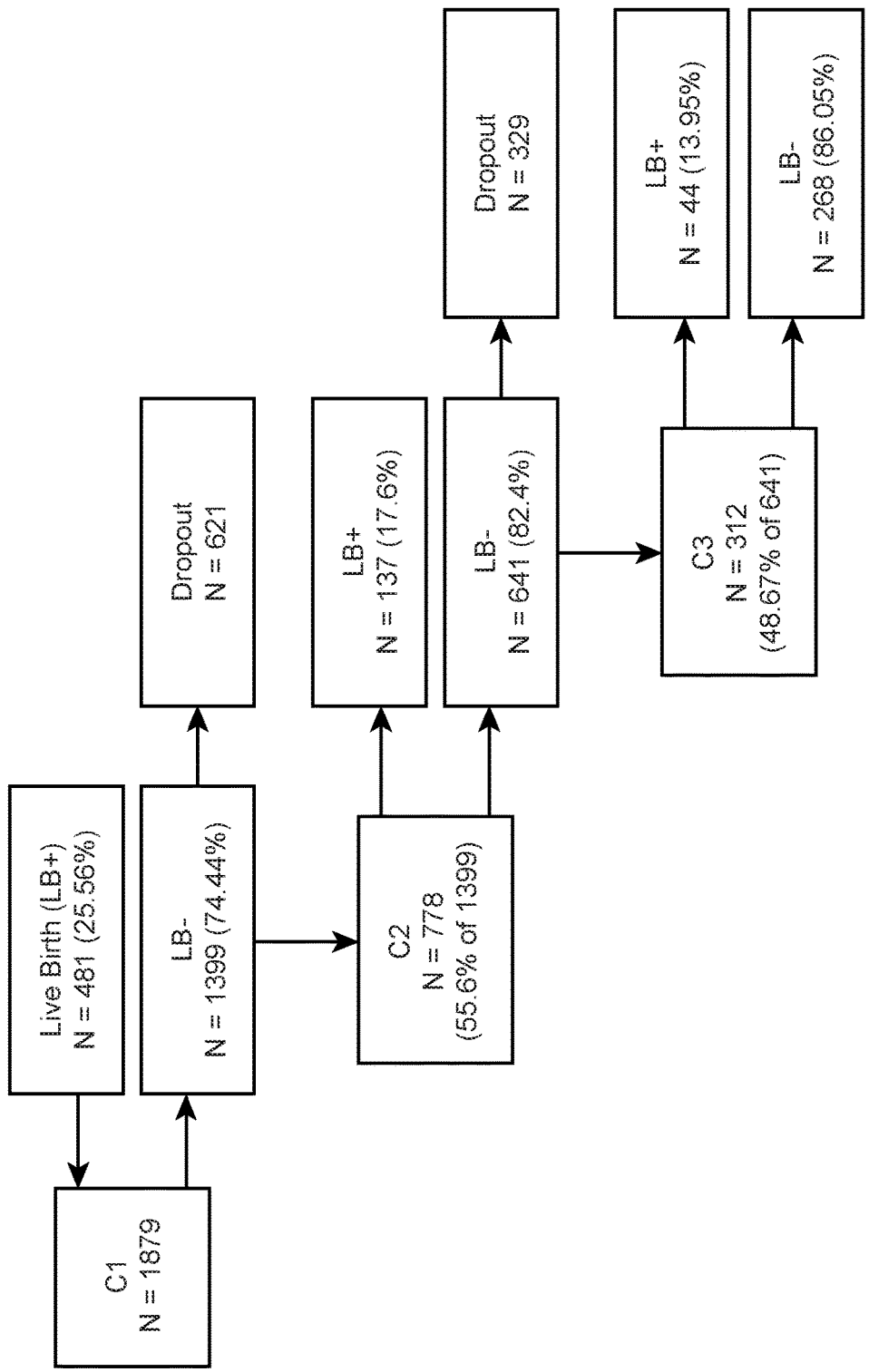
FIG. 18 shows a summary of live birth outcomes. Different boxes represented C1 (first-IVF cycle), C2 (second-IVF cycle), and C3 (third-IVF cycle). Each box shows the number of cycles with live birth (LB+) or no live birth (LB−) outcomes, the percentage of the total number (N) of cycles analyzed and the number of patients that dropped out and did not return.

Between Jan. 1, 2003 to Dec. 31, 2006, 5037 IVF treatments were performed in total, with annual volumes that were comparable across years. Of those, 3347 were fresh IVF cycles that used the patients' own oocytes and that fulfilled inclusion criteria. After applying exclusion criteria, 3338 cycles remained, of which 1879 were first-IVF cycles (C1), 778 were second-IVF cycles performed for patients who did not have live birth outcomes in C1 and who returned for their second treatment (C2); 312 were third-IVF cycles (C3); 369 cycles were fourth, fifth and sixth cycles, which were not analyzed (FIG. 17 and FIG. 18).

Figure 19:
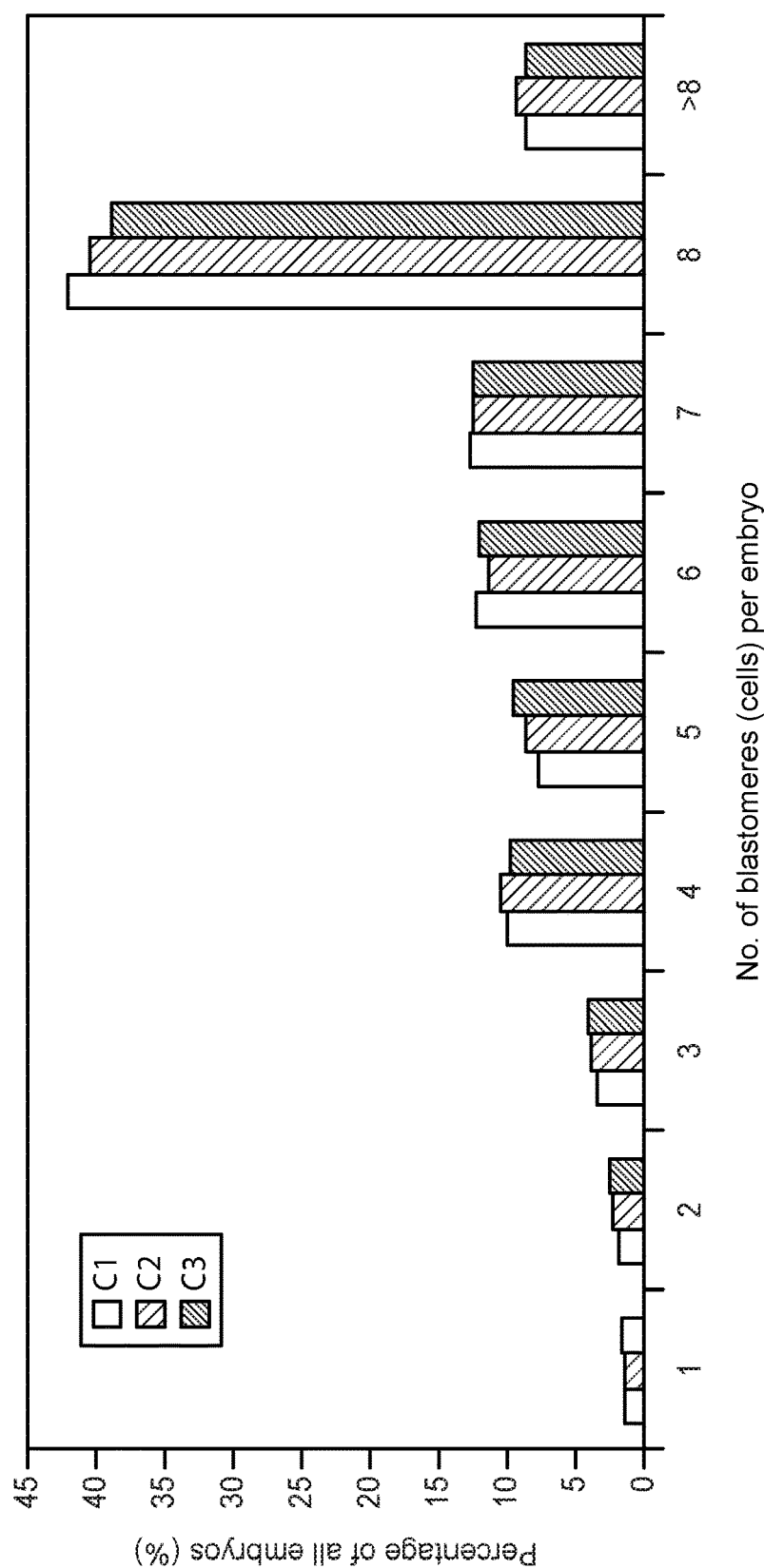
FIG. 19 is a graph showing distribution of embryos with respect to developmental stage. The distribution of 2969 fresh, non-donor IVF cases from all three cycles according to their cell number on day 3 of in vitro culture. The number of cells per embryo and the maximum number of embryos (~40%) that had 8 cells were similar amongst cycles C1 (no fill pattern), C2 (horizontal fill pattern), and C3 (vertical fill pattern).

Data from C1, C2, and C3 were subsequently analyzed separately. Overall, 41% % of embryos had 8 blastomeres, the developmentally appropriate cell number, while 17% % of embryos had <4 cells, and 33% % had 5-7 cells, and 9% % had more than 8 cells (FIG. 19). This profile of in vitro human embryo development in IVF was consistent with previous reports. Further, the number of blastomeres formed by 10,687, 3,932 and 1,573 embryos by Day 3 of in vitro culture in C1, C2, and C3, were not significantly different, which suggested that embryo development was comparable amongst the first three cycles (p=0.6; FIG. 19).

We used C1 data only to generate our prediction models, because patients dropped out for a variety of reasons for which there were no controls (FIG. 18), and we did not want significant prognostic factors to be masked by cycle number; we did not know whether the drop out rates were comparable amongst patient subsets that varied in their prognoses. Consistent with other reports, a significant number of patients who had no live births dropped out after each unsuccessful cycle, and did not return for subsequent treatments. Nonetheless, C2 and C3 data were used to test whether the prediction models held true for subsequent treatments.

Variables Associated with Live Birth Outcomes

We first focused on 1879 C1 cycles and their associated 10,687 embryos that satisfied all inclusion and exclusion criteria. We systematically examined the association of each of 57 variables with live birth outcomes. These variables were chosen based on the quality and completeness of data entry, rather than prior scientific or clinical knowledge. Pair-wise logistic regression confirmed significant association of many variables with live birth outcomes, including patient's age, male partner's age, Day 3 FSH, and the number of prior clinical pregnancy losses (p<0.05) (Table 13). As expected, diminished ovarian reserve (DOR), a clinical diagnosis based on poor ovarian response in previous non-IVF infertility treatments or clomid challenge test, was highly negatively associated with live birth outcomes (p<0.0001), while the diagnosis of polycystic ovarian syndrome, which tends to increase ovarian response, was positively associated with live births (p<0.0001).

TABLE 13

Variables and their association with IVF live birth outcomes.

Table 13A. Continuous Variables

| Variables | Estimate[1] | S.E. | p-value | Mean[5] | StDev |
|---|---|---|---|---|---|
| Pre-IVF | | | | | |
| Age of patient | −1.27E−01 | 1.24E−02 | 4.12E−24 | 40.99 | 4.56 |
| Age of male partner | −6.31E−02 | 1.02E−02 | 2.28E−09 | 42.95 | 5.82 |
| Body mass index | −4.55E−03 | 6.17E−03 | 5.55E−01 | 24.90 | 9.75 |
| No. of previous pregnancies[2] | −1.16E−01 | 4.29E−02 | 1.07E−02 | 1.04 | 1.33 |
| No. of previous term deliveries[3] | −3.05E−02 | 9.05E−02 | 7.49E−01 | 0.27 | 0.60 |
| Spontaneous miscarriages[4] | −2.01E−01 | 7.36E−02 | 1.04E−02 | 0.41 | 0.82 |
| Serum d.3 FSH (IU/L) | −6.93E−02 | 1.60E−02 | 2.89E−05 | 8.05 | 4.92 |
| Year | 2.24E−02 | 4.73E−02 | 6.83E−01 | 4.32 | 1.12 |
| Pre-OR | | | | | |
| Total amount of recombinant FSH (IU/L) | −4.46E−04 | 3.94E−05 | 1.15E−28 | 3,512.03 | 1,587.94 |
| Total amount of human menopausal gonadotropins (IU/L) | −1.01E−03 | 1.18E−04 | 4.69E−17 | 1,257.11 | 544.11 |
| Total amount of gonadotropin | −3.55E−04 | 3.14E−05 | 1.36E−28 | 4,769.14 | 1,990.39 |
| Endometrial Thickness (mm) | 2.22E−01 | 2.66E−02 | 2.94E−16 | 10.00 | 2.10 |
| No. of sperm motile after wash (million/mL) | −3.92E−04 | 2.92E−04 | 2.53E−01 | 128.41 | 244.60 |
| No. of sperm motile before wash (million/mL) | −2.71E−04 | 3.39E−04 | 5.22E−01 | 106.46 | 198.93 |
| Post-IVF | | | | | |
| Total no. of oocytes | 1.06E−01 | 8.66E−03 | 2.53E−33 | 10.24 | 6.63 |
| Percentage of normal and mature oocytes | 3.36E+00 | 5.86E−01 | 2.69E−08 | 0.80 | 0.38 |
| Normal fertilization (%) | 1.32E+00 | 2.40E−01 | 9.74E−08 | 0.65 | 0.24 |
| Unfertilized eggs (%) | −1.08E+00 | 2.48E−01 | 2.79E−05 | 0.27 | 0.23 |
| Abnormally fertilized eggs (%) | −9.87E−01 | 4.34E−01 | 3.56E−02 | 0.08 | 0.14 |
| Total number of embryos | 1.78E−01 | 1.21E−02 | 2.43E−47 | 5.92 | 4.94 |
| Blastocyst development (%) | 3.05E+00 | 2.41E−01 | 3.03E−35 | 0.15 | 0.23 |
| Compaction on day 3 | 2.66E−01 | 2.76E−01 | 4.51E−01 | 0.09 | 0.19 |
| Average no. of cells per embryos | 2.90E−01 | 4.57E−02 | 7.05E−10 | 6.76 | 1.32 |
| No. embryos arrested at? 4 cells | −1.32E−02 | 2.74E−03 | 3.00E−06 | 16.69 | 23.44 |
| No. of 8-cell embryos | 2.59E−01 | 2.25E−02 | 1.71E−29 | 2.73 | 2.74 |
| Percentage of 8 cell embryos (%) | 9.40E−03 | 1.89E−03 | 1.50E−06 | 40.49 | 29.09 |
| No. of embryos cryopreserved | 3.23E+00 | 2.88E−01 | 2.33E−28 | 0.11 | 0.19 |
| Average grade of embryos | −1.49E−01 | 1.11E−01 | 2.53E−01 | 1.83 | 0.61 |
| Total no. of transferred embryos | 9.59E−02 | 3.51E−02 | 1.04E−02 | 2.28 | 1.49 |
| Average no. of cells per transferred embryos | 5.37E−01 | 6.02E−02 | 2.07E−18 | 7.41 | 1.24 |

TABLE 13-continued

Variables and their association with IVF live birth outcomes.

| | | | | | |
|---|---|---|---|---|---|
| Average grade of transferred embryos | −6.33E−01 | 1.24E−01 | 8.24E−07 | 1.62 | 0.62 |
| No. of transferred embryos arrested with ? 4 cells | −2.36E−02 | 3.29E−03 | 7.12E−13 | 8.56 | 24.50 |
| No. of 8 cell embryos transferred | 3.26E−01 | 5.43E−02 | 5.59E−09 | 1.47 | 1.07 |
| Percentage of 8 cell embryos transferred | 1.67E−02 | 1.62E−03 | 3.65E−24 | 59.61 | 39.12 |

Table 13B. Categorical Variables

| Variables | Estimate | S.E. | p-value | Mean[6] | StDev |
|---|---|---|---|---|---|
| *Pre-IVF* | | | | | |
| Diminished ovarian reserve | −1.07E+00 | 1.23E−01 | 1.40E−17 | 0.39 | 0.49 |
| Polycystic ovarian syndrome | 7.58E−01 | 1.66E−01 | 1.01E−05 | 0.09 | 0.29 |
| Unexplained female infertility | 5.74E−01 | 1.70E−01 | 1.37E−03 | 0.09 | 0.28 |
| Other causes for infertility | −2.52E−01 | 1.14E−01 | 4.19E−02 | 0.34 | 0.47 |
| Tubal disease | −9.40E−02 | 1.66E−01 | 6.24E−01 | 0.12 | 0.32 |
| Uterine Fibroids | −1.87E−01 | 1.95E−01 | 4.51E−01 | 0.09 | 0.28 |
| Endometriosis | −9.18E−02 | 1.53E−01 | 6.23E−01 | 0.14 | 0.35 |
| Male infertility | 4.51E−02 | 1.07E−01 | 7.09E−01 | 0.42 | 0.49 |
| Tubal Ligation | 4.09E−02 | 3.72E−01 | 9.12E−01 | 0.02 | 0.14 |
| Hydrosalpinx | −7.22E−02 | 2.97E−01 | 8.08E−01 | NA | NA |
| Season: summer | 9.88E−02 | 1.54E−01 | 6.15E−01 | 0.22 | 0.42 |
| Season: winter | 1.32E−01 | 1.42E−01 | 4.63E−01 | 0.30 | 0.46 |
| Season: fall | 3.27E−01 | 1.54E−01 | 5.05E−02 | 0.20 | 0.40 |
| *Pre-OR* | | | | | |
| Oral contraception | 7.33E−01 | 1.85E−01 | 1.39E−04 | 0.87 | 0.34 |
| Sperm collected surgically | 1.57E−01 | 2.57E−01 | 6.23E−01 | 0.04 | 0.20 |
| Sperm collection from frozen | 2.61E−01 | 3.21E−01 | 5.22E−01 | 0.03 | 0.16 |
| Sperm from donor | −4.03E−01 | 4.56E−01 | 4.84E−01 | 0.02 | 0.13 |
| *Post-IVF* | | | | | |
| Assisted Hatching | −8.58E−01 | 1.26E−01 | 4.03E−11 | 0.33 | 0.47 |
| Day 5 Embryo transfer | 1.42E+00 | 1.20E−01 | 6.89E−31 | 0.27 | 0.44 |
| Antagonist protocol | −1.35E+00 | 1.21E−01 | 6.30E−28 | 0.47 | 0.50 |
| Flare protocol | −1.70E+00 | 1.84E−01 | 8.98E−20 | 0.18 | 0.39 |
| Echotip catheter | 6.83E−01 | 1.47E−01 | 7.64E−06 | 0.14 | 0.35 |
| Other catheter | −2.69E−01 | 4.67E−01 | 6.24E−01 | 0.02 | 0.13 |
| Performance of ICSI | 3.34E−01 | 1.07E−01 | 3.07E−03 | 0.41 | 0.49 |

FOOTNOTE:
Each variable was tested for its association with live birth outcomes in IVF by logistic regression, which gave estimate, standard error of the estimate (S.E.), p-value, mean and standard deviation (S.D.). Results for continuous variables and categorical variables were listed in Table 1A and Table 1B, respectively.
[1]Positive and negative estimates indicate association with positive and negative pregnancy outcomes, respectively.
[2]Number of previous clinical pregnancies as defined by positive serum human chorionic gonadotropin (hCG) or pregnancy test.
[3]Number of previous deliveries carried to term, 37 wks.
[4]Miscarriages refer to developmental arrest or clinical pregnancy loss at or after 5 wks gestation. Season, seemingly irrelevant, was included as a negative control.

We noted that many pairs of variables, such as age and total amount of gonadotropins used, were highly correlated with one another (Table 14). Although these findings are consistent with the presumed complex and poorly understood biological mechanisms amongst ovarian aging, ovarian hormone production and egg quality, those interactions could not be studied well by ANOVA using Chi-square statistics tests (data not shown), presumably because they do not interact in a linear fashion, or multiple conditions may affect the nature of the interactions.

We chose to analyze data and generate prediction models by constructing boosted classification trees by MART® to identify non-redundant prognostic variables. MART® is a robust method used to identify interactive structure of variables that are predictive of outcomes. The use of cross-validation and boosting in parameter selection and model assessment in MART® also preserve parsimony and prevent over-fitting. Finally, MART does not presume the absence or presence of interactions, or the nature of the interactions.
Table 14a and 14B. Correlation Between Every Pair of Variables.

TABLE 14A

| | Age of patient | Age of spouse | Body Mass Index | No. of previous pregnancies | No. of previous term deliveries | Spontaneous miscarriages | Serum d.2 FSH | Year | Total amount of FSH (IU/ml) | Total amount of HMg (IU/L) | Total amount of gonadotropin (IU/L) | Endometrial thickness (mm) | Total no. of sperm motile after wash (mill/mL) | Total no. of sperm motile before wash (mill/mL) | Total no. of oocytes | Percentage of normal and mature oocytes | Normal fertilization (%) |
|---|---|---|---|---|---|---|---|---|---|---|---|---|---|---|---|---|---|
| Pre-IVF Variables |
| Age of patient | 1.00 | 0.56 | 0.04 | 0.22 | 0.13 | 0.14 | 0.17 | −0.27 | 0.43 | 0.33 | 0.44 | −0.16 | 0.04 | 0.05 | −0.37 | −0.20 | −0.05 |
| Age of spose | 0.56 | 1.00 | 0.01 | 0.10 | 0.09 | 0.06 | 0.08 | −0.19 | 0.23 | 0.19 | 0.24 | −0.12 | −0.06 | −0.05 | −0.20 | −0.08 | −0.05 |
| Body Mass Index | 0.04 | 0.01 | 1.00 | 0.08 | 0.05 | 0.05 | −0.04 | 0.07 | 0.07 | 0.00 | 0.00 | −0.05 | −0.01 | 0.00 | 0.06 | −0.05 | −0.04 |
| No. of previous pregnancies | 0.22 | 0.10 | 0.08 | 1.00 | 0.56 | 0.70 | 0.01 | −0.01 | 0.08 | 0.06 | 0.08 | −0.07 | 0.07 | 0.05 | −0.04 | −0.16 | 0.00 |
| No. of previous term deliveries | 0.13 | 0.09 | 0.05 | 0.56 | 1.00 | 0.14 | 0.05 | −0.01 | 0.02 | 0.00 | 0.02 | 0.05 | 0.01 | 0.02 | 0.00 | −0.09 | 0.01 |
| Spontaneous miscarriages | 0.14 | 0.06 | 0.05 | 0.70 | 0.14 | 1.00 | −0.02 | 0.01 | 0.06 | 0.05 | 0.06 | −0.07 | 0.05 | 0.03 | −0.02 | −0.13 | 0.00 |
| Serum d.2 FSH | 0.17 | 0.08 | −0.04 | 0.01 | 0.05 | −0.02 | 1.00 | 0.03 | 0.35 | 0.28 | 0.36 | −0.11 | 0.00 | 0.00 | −0.30 | −0.13 | −0.06 |
| Year | −0.27 | −0.19 | 0.07 | −0.01 | −0.01 | 0.01 | 0.03 | 1.00 | −0.05 | −0.06 | −0.06 | −0.04 | −0.11 | −0.08 | 0.11 | −0.01 | 0.04 |
| Pre-OR Variables |
| Total amount of FSH (IU/ml) | 0.43 | 0.23 | 0.00 | 0.08 | 0.02 | 0.06 | 0.35 | −0.05 | 1.00 | 0.66 | 0.98 | −0.16 | 0.01 | 0.03 | −0.55 | −0.06 | −0.05 |
| Total amount of HMg (IU/L) | 0.33 | 0.19 | 0.00 | 0.06 | 0.00 | 0.05 | 0.28 | −0.06 | 0.66 | 1.00 | 0.80 | −0.11 | 0.01 | 0.03 | −0.44 | −0.09 | −0.06 |
| Total amount of gonadotropin (IU/L) | 0.44 | 0.24 | 0.00 | 0.08 | 0.02 | 0.06 | 0.36 | −0.06 | 0.98 | 0.80 | 1.00 | −0.16 | 0.02 | 0.03 | −0.56 | −0.07 | −0.05 |
| Endometrial thichness (mm) | −0.16 | −0.12 | −0.05 | −0.07 | 0.05 | −0.07 | −0.11 | −0.04 | −0.16 | −0.11 | −0.16 | 1.00 | 0.01 | 0.01 | 0.14 | 0.37 | 0.01 |
| Total no. of sperm motile after wash (mill/mL) | 0.04 | −0.06 | −0.01 | 0.07 | 0.01 | 0.05 | 0.00 | −0.11 | 0.01 | 0.01 | 0.02 | 0.01 | 1.00 | 0.62 | −0.03 | −0.19 | 0.01 |
| Total no. of sperm motile before wash (mill/mL) | 0.05 | −0.05 | 0.00 | 0.05 | 0.02 | 0.03 | 0.00 | −0.08 | 0.03 | 0.03 | 0.03 | 0.01 | 0.62 | 1.00 | 0.01 | −0.08 | −0.01 |
| Post-IVF Variables |
| Total no. of oocytes | −0.37 | −0.20 | 0.06 | −0.04 | 0.00 | −0.02 | −0.30 | 0.11 | −0.55 | −0.44 | −0.56 | 0.14 | −0.03 | 0.01 | 1.00 | 0.13 | 0.03 |
| Percentage of normal and mature oocytes | −0.20 | −0.08 | −0.05 | −0.16 | −0.09 | −0.13 | −0.13 | −0.01 | −0.06 | −0.09 | −0.07 | 0.37 | −0.19 | −0.08 | 0.13 | 1.00 | −0.04 |
| Normal fertilization (%) | −0.05 | −0.05 | −0.04 | 0.00 | 0.01 | 0.00 | −0.06 | 0.04 | −0.05 | −0.06 | −0.05 | 0.01 | 0.01 | −0.01 | 0.03 | −0.04 | 1.00 |
| Unfertilized eggs (%) | 0.01 | 0.03 | 0.03 | −0.02 | −0.01 | −0.02 | 0.06 | −0.08 | 0.04 | 0.03 | 0.04 | 0.01 | −0.04 | −0.04 | −0.01 | 0.05 | −0.83 |
| Abnormally fertilized eggs (%) | 0.06 | 0.03 | 0.01 | 0.04 | 0.00 | 0.02 | −0.01 | 0.07 | 0.02 | 0.05 | 0.03 | −0.02 | 0.05 | 0.09 | −0.03 | −0.01 | −0.35 |
| Total no. of embryos | −0.34 | −0.20 | 0.02 | −0.03 | 0.00 | −0.01 | −0.27 | 0.10 | −0.45 | −0.36 | −0.46 | 0.21 | −0.01 | −0.02 | 0.87 | 0.48 | 0.39 |
| Blastocyst | −0.35 | −0.21 | 0.06 | 0.01 | 0.03 | 0.02 | −0.20 | 0.19 | −0.41 | −0.32 | −0.42 | 0.12 | 0.00 | −0.01 | 0.47 | 0.03 | 0.15 |

TABLE 14A-continued

| | Age of patient | Age of spose | Body Mass Index | No. of previous pregnancies | No. of previous term deliveries | Spontaneous miscarriages | Serum d.2 FSH | Year | Total amount of FSH (IU/ml) | Total amount of HMg (IU/L) | Total amount of gonadotropin (IU/L) | Endometrial thichness (mm) | Total no. of sperm motile after wash (mill/mL) | Total no. of sperm motile before wash (mill/mL) | Total no. of oocytes | Percentage of normal and mature oocytes | Normal fertilization (%) |
|---|---|---|---|---|---|---|---|---|---|---|---|---|---|---|---|---|---|
| development (%) Compaction on d.3 (%) | 0.09 | 0.05 | -0.04 | 0.04 | 0.01 | 0.02 | -0.02 | -0.24 | -0.05 | -0.04 | -0.05 | -0.01 | 0.01 | -0.01 | -0.04 | 0.02 | 0.05 |
| Average no. of cells per embryo | 0.00 | -0.01 | 0.04 | 0.07 | 0.02 | 0.05 | -0.01 | -0.04 | -0.06 | -0.07 | -0.06 | 0.05 | 0.02 | 0.02 | 0.03 | 0.02 | -0.01 |
| No. of embryos arrested at = 4 cells | -0.03 | 0.00 | -0.01 | -0.04 | 0.00 | -0.04 | 0.00 | 0.08 | 0.02 | 0.04 | 0.03 | -0.04 | -0.03 | 0.00 | 0.00 | 0.01 | -0.03 |
| No. of 8 cell embryos | -0.23 | -0.14 | 0.06 | 0.02 | 0.02 | 0.01 | -0.22 | 0.02 | -0.41 | -0.32 | -0.42 | 0.13 | 0.00 | -0.01 | 0.65 | 0.03 | 0.26 |
| Percentage of 8 cell embryos (%) | 0.03 | 0.01 | 0.03 | 0.05 | 0.01 | 0.02 | -0.06 | -0.10 | -0.08 | -0.06 | -0.08 | 0.06 | 0.01 | 0.04 | 0.06 | 0.01 | 0.05 |
| Cryopreserved embryos (%) | -0.37 | -0.24 | 0.03 | -0.04 | -0.02 | -0.04 | -0.19 | 0.11 | -0.37 | -0.31 | -0.38 | 0.10 | 0.03 | 0.01 | 0.43 | 0.00 | 0.17 |
| Average grade of embryos | -0.05 | -0.03 | -0.08 | 0.04 | 0.03 | 0.04 | -0.01 | 0.16 | 0.04 | 0.02 | 0.04 | 0.01 | -0.04 | 0.01 | -0.02 | 0.01 | 0.01 |
| Total no. of embryos transferred | 0.13 | 0.08 | -0.03 | -0.02 | -0.05 | -0.03 | -0.13 | -0.07 | 0.02 | 0.04 | 0.03 | 0.11 | 0.02 | 0.00 | 0.08 | 0.59 | 0.23 |
| Average no. of cells per transferred embryo | -0.16 | -0.10 | 0.04 | 0.03 | 0.01 | 0.04 | -0.12 | -0.01 | -0.21 | -0.18 | -0.22 | 0.10 | 0.01 | 0.00 | 0.28 | 0.02 | 0.11 |
| Average grade of embryos transferred | 0.11 | 0.06 | -0.08 | 0.04 | 0.03 | 0.04 | 0.08 | 0.12 | 0.20 | 0.14 | 0.20 | -0.05 | -0.05 | 0.02 | -0.23 | -0.03 | -0.06 |
| No. of transferred embryos with arrest at = 4 cells | 0.09 | 0.06 | -0.01 | -0.01 | 0.01 | -0.03 | 0.08 | 0.04 | 0.15 | 0.13 | 0.15 | -0.07 | -0.02 | 0.02 | -0.19 | 0.01 | -0.12 |
| No. of 8 cell embryos transferred | 0.03 | 0.04 | 0.04 | 0.00 | 0.00 | -0.02 | -0.14 | -0.10 | -0.18 | -0.11 | -0.17 | 0.08 | 0.02 | -0.01 | 0.29 | -0.01 | 0.18 |
| Percentage of 8 cell embryos transferred (%) | -0.19 | -0.10 | 0.04 | 0.00 | 0.01 | -0.01 | -0.16 | -0.02 | -0.30 | -0.21 | -0.30 | 0.13 | 0.01 | 0.01 | 0.36 | 0.03 | 0.15 |

TABLE 14B

| | Un-fertilized eggs (%) | Ab-normally fertilized eggs (%) | Total no. of embryos | Blas-tocyst devel-opment (%) | Com-paction on d.3 (%) | Average no. of cells per embryo | No. of embryos arrested at = 4 cells | No. of 8 cell embryos | Percentage of 8 cell embryos (%) | Cryopre-served embryos (%) | Average grade of embryos | Total no. of embryos transferred | Average no. of cells per transferred embryo | Average grade of embryos transferred | No. of transferred embryos with arrest at = 4 cells | No. of 8 cell embryos transferred | Percentage of 8 cell embryos transferred (%) |
|---|---|---|---|---|---|---|---|---|---|---|---|---|---|---|---|---|---|
| Pre-IVF Variables | | | | | | | | | | | | | | | | | |
| Age of patient | 0.01 | 0.06 | −0.34 | −0.35 | 0.09 | 0.00 | −0.03 | −0.23 | 0.03 | −0.37 | −0.05 | 0.13 | −0.16 | 0.11 | 0.09 | 0.03 | −0.19 |
| Age of spose | 0.03 | 0.03 | −0.20 | −0.21 | 0.05 | −0.01 | 0.00 | −0.14 | 0.01 | −0.24 | −0.03 | 0.08 | −0.10 | 0.06 | 0.06 | 0.04 | −0.10 |
| Body Mass Index | 0.03 | 0.01 | 0.02 | 0.06 | −0.04 | 0.04 | −0.01 | 0.06 | 0.03 | 0.03 | −0.08 | −0.03 | 0.04 | 0.08 | −0.01 | 0.04 | 0.04 |
| No. of previous pregnancies | −0.02 | 0.04 | −0.03 | 0.01 | 0.04 | 0.07 | −0.04 | 0.02 | 0.05 | −0.04 | 0.04 | −0.02 | 0.03 | 0.04 | −0.01 | 0.00 | 0.00 |
| No. of previous term deliveries | −0.01 | 0.00 | 0.00 | 0.03 | 0.01 | 0.02 | 0.00 | 0.02 | 0.01 | −0.02 | 0.03 | −0.05 | 0.01 | 0.03 | 0.01 | 0.00 | 0.01 |
| Spontaneous miscarriages | −0.02 | 0.02 | −0.01 | 0.02 | 0.02 | 0.05 | −0.04 | 0.01 | 0.02 | −0.04 | 0.04 | −0.03 | 0.04 | 0.04 | −0.03 | −0.02 | −0.01 |
| Serum d.2 FSH | 0.06 | −0.01 | −0.27 | −0.20 | −0.02 | −0.01 | 0.00 | −0.22 | −0.06 | −0.19 | −0.01 | −0.13 | −0.12 | 0.08 | 0.08 | −0.14 | −0.16 |
| Year | −0.08 | 0.07 | 0.10 | 0.19 | −0.24 | −0.04 | 0.08 | 0.02 | −0.10 | 0.11 | 0.16 | −0.07 | −0.01 | 0.12 | 0.04 | −0.10 | −0.02 |
| Pre-OR Variables | | | | | | | | | | | | | | | | | |
| Total amount of FSH (IU/ml) | 0.04 | 0.02 | −0.45 | −0.41 | −0.05 | −0.06 | 0.02 | −0.41 | −0.08 | −0.37 | 0.04 | 0.02 | −0.21 | 0.20 | 0.15 | −0.18 | −0.30 |
| Total amount of HMg (IU/L) | 0.03 | 0.05 | −0.36 | −0.32 | −0.04 | −0.07 | 0.04 | −0.32 | −0.06 | −0.31 | 0.02 | 0.04 | −0.18 | 0.14 | 0.13 | −0.11 | −0.21 |
| Total amount of gonadotropin (IU/L) | 0.04 | 0.03 | −0.46 | −0.42 | −0.05 | −0.06 | 0.03 | −0.42 | −0.08 | −0.38 | 0.04 | 0.03 | −0.22 | 0.20 | 0.15 | −0.17 | −0.30 |
| Endometrial thichness (mm) | 0.01 | −0.02 | 0.21 | 0.12 | −0.01 | 0.05 | −0.04 | 0.13 | 0.06 | 0.10 | 0.01 | 0.11 | 0.10 | −0.05 | −0.07 | 0.08 | 0.13 |
| Total no. of sperm motile after wash (mil/mL) | −0.04 | 0.05 | −0.01 | 0.00 | 0.01 | 0.02 | −0.03 | 0.00 | 0.01 | 0.03 | −0.04 | 0.02 | 0.01 | −0.05 | −0.02 | 0.02 | 0.01 |
| Total no. of sperm motile before wash (mil/mL) | −0.04 | 0.09 | −0.02 | −0.01 | −0.01 | 0.02 | 0.00 | −0.01 | 0.04 | 0.01 | 0.01 | 0.00 | 0.00 | 0.02 | 0.02 | −0.01 | 0.01 |
| Post-IVF Variables | | | | | | | | | | | | | | | | | |
| Total no. of oocytes | −0.01 | −0.03 | 0.87 | 0.47 | −0.04 | 0.03 | 0.00 | 0.65 | 0.06 | 0.43 | −0.02 | 0.08 | 0.28 | −0.23 | −0.19 | 0.29 | 0.36 |
| Percentage of normal and mature oocytes | 0.05 | −0.01 | 0.48 | 0.03 | 0.02 | 0.02 | 0.01 | 0.03 | 0.01 | 0.00 | 0.01 | 0.59 | 0.02 | −0.03 | 0.01 | −0.01 | 0.03 |
| Normal fertilization (%) | −0.83 | −0.35 | 0.39 | 0.15 | 0.05 | −0.01 | −0.03 | 0.26 | 0.05 | 0.17 | 0.01 | 0.23 | 0.11 | −0.06 | −0.12 | 0.18 | 0.15 |
| Unfertilized eggs (%) | 1.00 | −0.24 | −0.34 | −0.17 | −0.04 | −0.02 | 0.05 | −0.24 | −0.05 | −0.18 | −0.01 | −0.18 | −0.12 | 0.06 | 0.12 | −0.16 | −0.14 |
| Abnormally fertilized eggs (%) | −0.24 | 1.00 | −0.11 | 0.03 | −0.01 | 0.06 | −0.03 | −0.04 | 0.00 | 0.00 | −0.01 | −0.09 | 0.02 | 0.00 | 0.01 | −0.04 | −0.01 |
| Total no. of embryos | −0.34 | −0.11 | 1.00 | 0.52 | −0.02 | 0.02 | −0.01 | 0.77 | 0.07 | 0.49 | 0.00 | 0.24 | 0.31 | −0.24 | −0.22 | 0.33 | 0.40 |
| Blastocyst | −0.17 | 0.03 | 0.52 | 1.00 | 0.00 | 0.25 | −0.20 | 0.61 | 0.26 | 0.69 | −0.18 | −0.26 | 0.34 | −0.35 | −0.22 | 0.18 | 0.44 |

TABLE 14B-continued

| | Unfertilized eggs (%) | Abnormally fertilized eggs (%) | Total no. of embryos | Blastocyst development (%) | Compaction on d.3 (%) | Average no. of cells per embryo | No. of embryos arrested at = 4 cells | No. of 8 cell embryos | Percentage of 8 cell embryos (%) | Cryopreserved embryos (%) | Average grade of embryos | Total no. of embryos transferred | Average no. of cells per transferred embryo | Average grade of embryos transferred | No. of transferred embryos with arrest at = 4 cells | No. of 8 cell embryos transferred | Percentage of 8 cell embryos transferred (%) |
|---|---|---|---|---|---|---|---|---|---|---|---|---|---|---|---|---|---|
| development (%) Compaction on d.3 (%) | −0.04 | −0.01 | −0.02 | 0.00 | 1.00 | 0.13 | −0.90 | 0.08 | 0.19 | 0.03 | −0.30 | 0.00 | 0.10 | −0.27 | −0.06 | 0.10 | 0.13 |
| Average no. of cells per embryo | −0.02 | 0.06 | 0.02 | 0.25 | 0.13 | 1.00 | −0.82 | 0.33 | 0.57 | 0.22 | −0.38 | −0.09 | 0.77 | −0.37 | −0.59 | 0.33 | 0.42 |
| No. of embryos arrested at = 4 cells | 0.05 | −0.03 | −0.01 | −0.20 | −0.09 | −0.82 | 1.00 | −0.27 | −0.47 | −0.18 | 0.29 | 0.06 | −0.62 | 0.27 | 0.78 | −0.27 | −0.34 |
| No. of 8 cell embryos | −0.24 | −0.04 | 0.77 | 0.61 | 0.08 | 0.33 | −0.27 | 1.00 | 0.53 | 0.60 | −0.21 | −0.09 | 0.43 | −0.42 | −0.30 | 0.53 | 0.64 |
| Percentage of 8 cell embryos (%) | −0.05 | 0.00 | 0.07 | 0.26 | 0.19 | 0.57 | −0.47 | 0.53 | 1.00 | 0.23 | −0.34 | −0.11 | 0.46 | −0.37 | −0.36 | 0.60 | 0.77 |
| Cryopreserved embryos (%) | −0.18 | 0.00 | 0.49 | 0.69 | 0.03 | 0.22 | −0.18 | 0.60 | 0.23 | 1.00 | −0.17 | −0.32 | 0.32 | −0.33 | −0.20 | 0.17 | 0.42 |
| Average grade of embryos | −0.01 | −0.01 | 0.00 | −0.18 | −0.30 | −0.38 | 0.29 | −0.21 | −0.34 | −0.17 | 1.00 | 0.09 | −0.26 | 0.86 | 0.16 | −0.18 | −0.23 |
| Total no. of embryos transferred | −0.18 | −0.09 | 0.24 | −0.26 | 0.00 | −0.09 | 0.06 | −0.09 | −0.11 | −0.32 | 0.09 | 1.00 | −0.14 | 0.16 | 0.06 | 0.39 | −0.21 |
| Average no. of cells per transferred embryo | −0.12 | 0.02 | 0.31 | 0.34 | 0.10 | 0.77 | −0.62 | 0.43 | 0.46 | 0.32 | −0.26 | −0.14 | 1.00 | −0.39 | −0.76 | 0.42 | 0.55 |
| Average grade of embryos transferred | 0.06 | 0.00 | −0.24 | −0.35 | −0.27 | −0.37 | 0.27 | −0.42 | −0.37 | −0.33 | 0.86 | 0.16 | −0.39 | 1.00 | 0.27 | −0.30 | −0.43 |
| No. of transferred embryos with arrest at = 4 cells | 0.12 | 0.01 | −0.22 | −0.22 | −0.06 | −0.59 | 0.78 | −0.30 | −0.36 | −0.20 | 0.16 | 0.06 | −0.76 | 0.27 | 1.00 | −0.35 | −0.43 |
| No. of 8 cell embryos transferred | −0.16 | −0.04 | 0.33 | 0.18 | 0.10 | 0.33 | −0.27 | 0.53 | 0.60 | 0.17 | −0.18 | 0.39 | 0.42 | −0.30 | −0.35 | 1.00 | 0.73 |
| Percentage of 8 cell embryos transferred (%) | −0.14 | −0.01 | 0.40 | 0.44 | 0.13 | 0.42 | −0.34 | 0.64 | 0.77 | 0.42 | −0.23 | −0.21 | 0.55 | −0.43 | −0.42 | 0.73 | 1.00 |

IVF Treatment Time Point-Specific Prognostic Factors and Models

Figure 20:
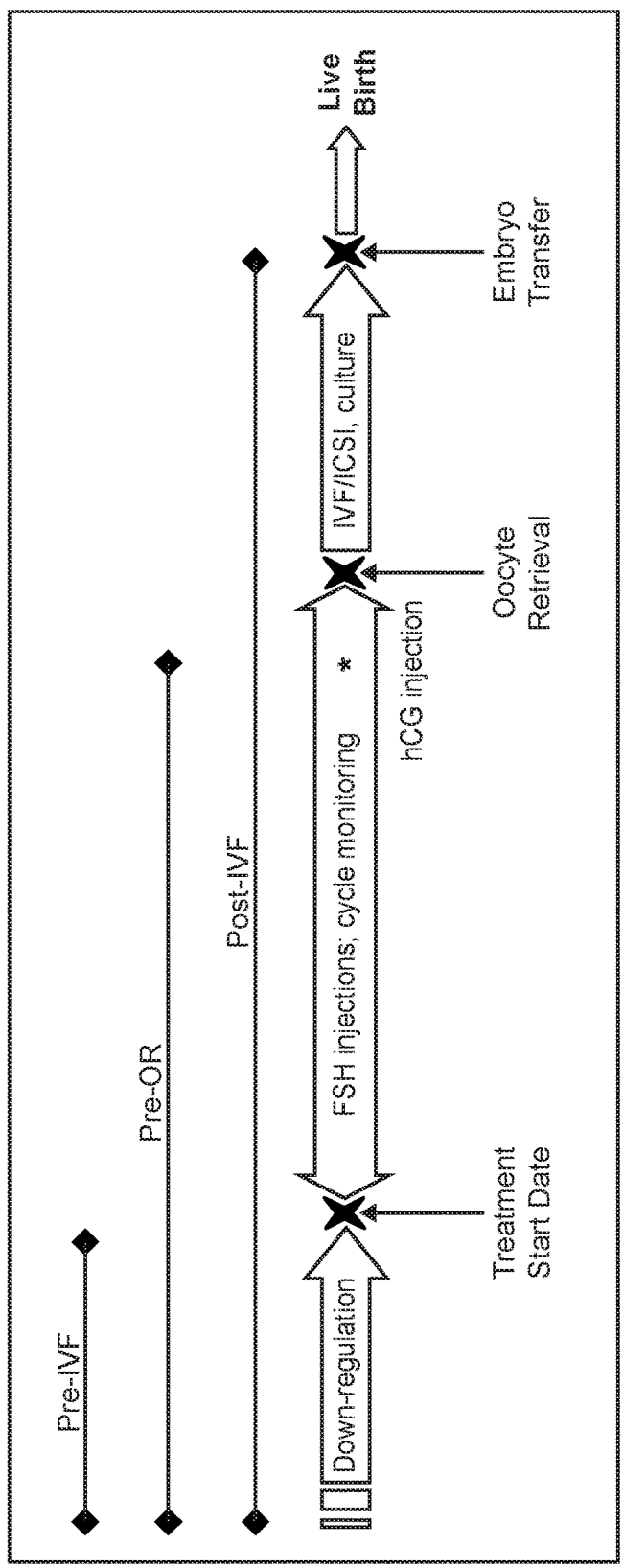
FIG. 20 shows prediction models and their temporal relationship with a typical IVF cycle. An IVF cycle comprises of down-regulation of endogenous gonadotropins and the menstrual cycle using oral contraceptive pill (OCP), periodic FSH injections and cycle monitoring by ultrasound with or without serum estradiol, followed by hCG injection to simulate endogenous LH surge, oocyte retrieval, fertilization by IVF or ICSI, in vitro embryo culture, embryo transfer, and cryopreservation of excess embryos. The three black stars represent the points at which patients can take an informed decision about further treatment options and whether to continue treatment. The Pre-IVF model extends until the treatment start date. The Pre-OR (oocyte retrieval) model extends until the hCG injection. The Post-IVF model includes all variables until embryo transfer.

Consistent with our goal to facilitate real life decision-making, we used boosted tree from MART to generate three prediction models, each of which utilized variables that would be available at a specific time point during IVF planning and treatment. As shown by the schematics in FIG. 20, the Pre-IVF model was limited to 21 variables primarily pertaining to patients' baseline characteristics, clinical diagnoses; the Pre-oocyte retrieval (Pre-OR) model utilized the same 21 variables pertaining to patient's response to ovarian stimulation in addition to 9 variables used in the Pre-IVF model, for a total of 30 variables; the Post-IVF model used all variables in Pre-IVF and Pre-OR in addition to data pertaining to embryo development, and embryo parameters related to transfer or cryopreservation for a total of 57 variables.

Pre-IVF Model.

Figure 21A:
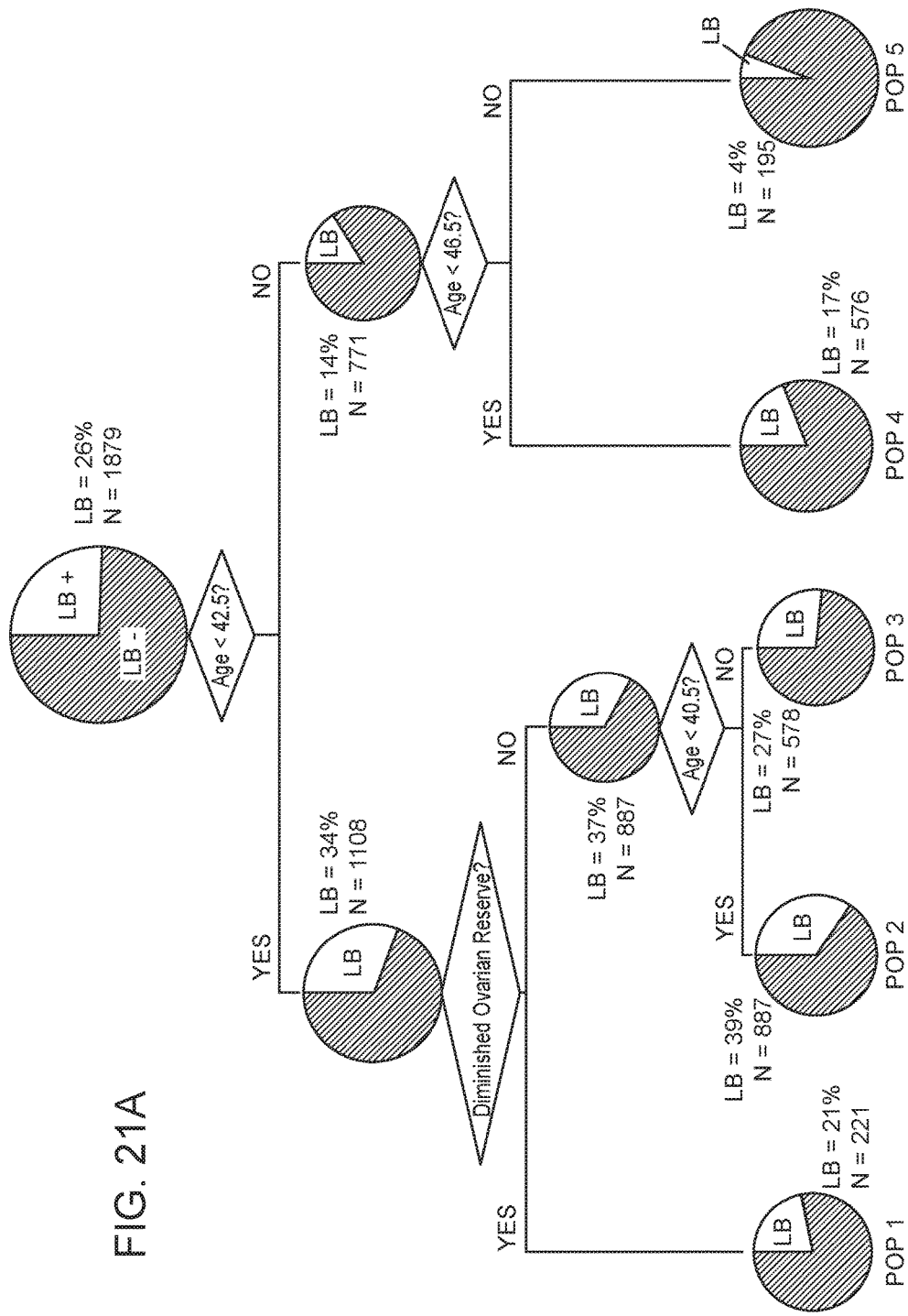

MART analysis of 1879 C1 patients with respect to 21 continuous and categorical variables that are known prior to starting IVF treatment (see Table 13), showed that each of patient's age and the diagnosis of diminished ovarian reserve (DOR) alone, as well as their interaction, predicted live birth outcomes. At our center, DOR has been routinely used to describe patients who showed a history of poor response to ovarian stimulation by gonadotropins in controlled ovarian hyperstimulation/intrauterine insemination (COH/IUI) treatment. While the presence of DOR is a negative predictor for LB, it only pertained to ~12% of the population. The rest of the patients were stratified by age. However, the model identified age thresholds (i.e. 40.5, 42.5, and 46.5) that were vastly different from thresholds (i.e. <35, 36-37, 38-40, 41-42, >42) that are arbitrarily and commonly used in the literature (ref). Overall, 5 patient subsets, hereafter populations, were discerned by this model with LB rates of 21%, 39%, 27%, 17%, and 4% for 222 (12% of all C1 patients), 690 (37%), 176 (9%), 581 (31%), and 199 (11%) patients, respectively (FIG. 21A).

Pre-OR Model.

Figure 21B:
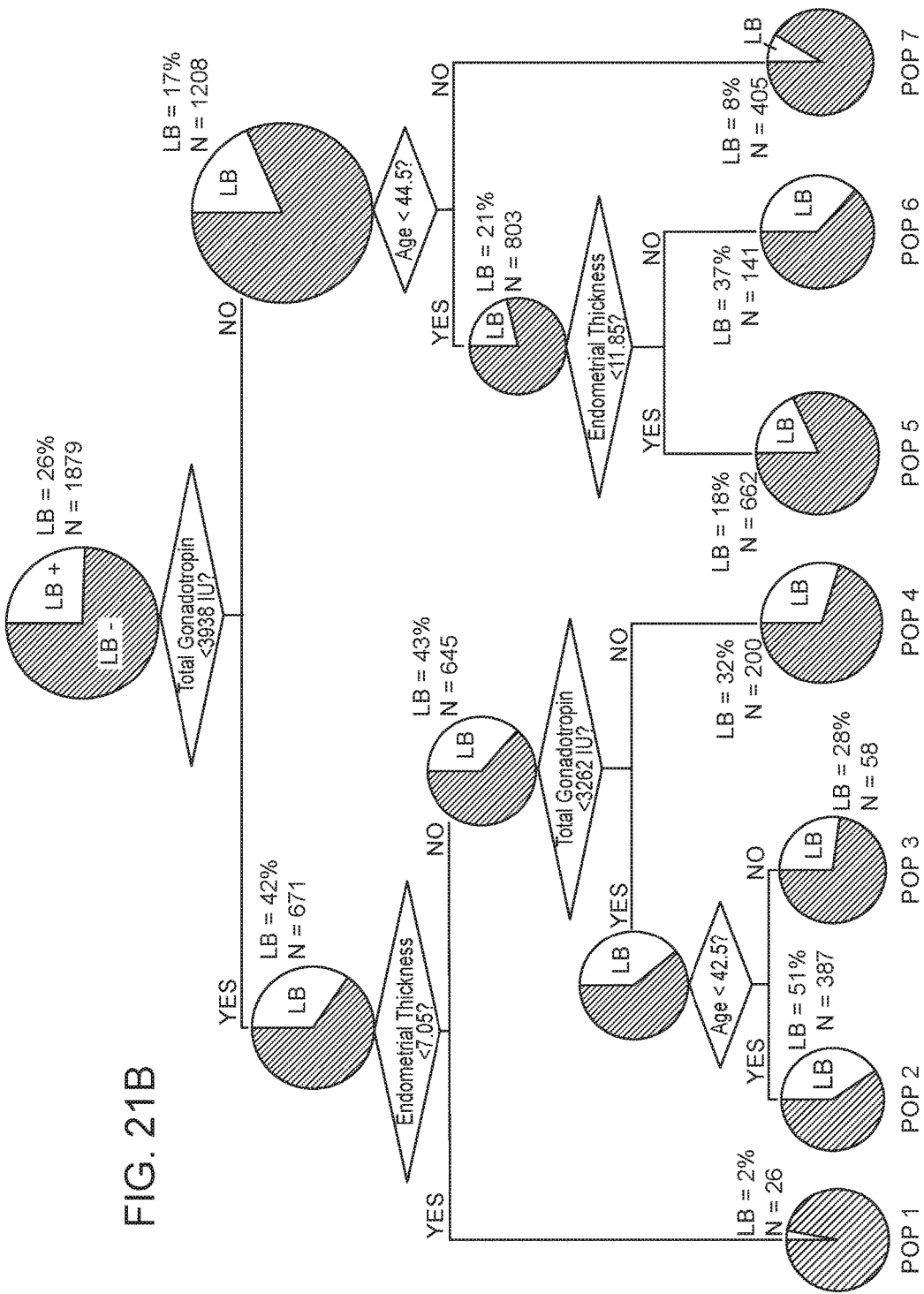

In this model, 30 variables known by the time of oocyte retrieval, from the same population comprising 1879 C1 patients, were analyzed by MART. Three independent prognostic factors were identified—total amount of gonadotropins required (TG), age, and endometrial thickness (EndoTh). Again, although each of these prognostic factors had been reported to be associated with LB outcomes, for the first time, we are objectively defining their thresholds and the nature of their potential interaction, which are critical for clinical application. Overall, this model identified 7 distinct populations with respect to their LB rates spanning 2%, 51%, 28%, 32%, 18%, 37%, and 8% for 26 (1.4% of all C1 patients), 387 (21%), 58 (3%), 200 (11%), 662 (35%), 141 (8%), and 405 (22%) patients in Populations (Pops) 1 to 7 (FIG. 21B). In addition to precisely parsed populations, the striking findings were the miniscule chance of LB outcomes for patients who had EndoTh <7.05 mm (Pop 1), those who fared poorly according to all 3 prognostic factors (Pop 5); and Age >44.5 (Pop 7). A mere combination of Pops 1, 5, and 7 showed that 1119 or ~60% of all C1 patients had a very low LB rate of 13.5%.

Post-IVF Model.

The Post-IVF model was generated by MART based on all 57 variables listed in Table 1. Of note, this analysis was restricted to 1664 of the 1879 C1 patients because 215 patients did not complete their IVF treatment and had "cycle cancellation" primarily due to suboptimal ovarian response. Four significant prognostic factors—Blast Rate, Embryo Number, TG, and EndoTh sufficed to differentiate 6 populations with LB rates ranging from 7%, 39%, 17%, 54%, 36%, and 72% for 361 (19% of patients analyzed), 96 (5.5%), 643 (40%), 316 (19%), 198 (12%), and 95 (6%) patients in Populations 1 to 6 (FIG. 21C).

Model Validation in Returning Patients and an Independent Data Set.

Figure 22:
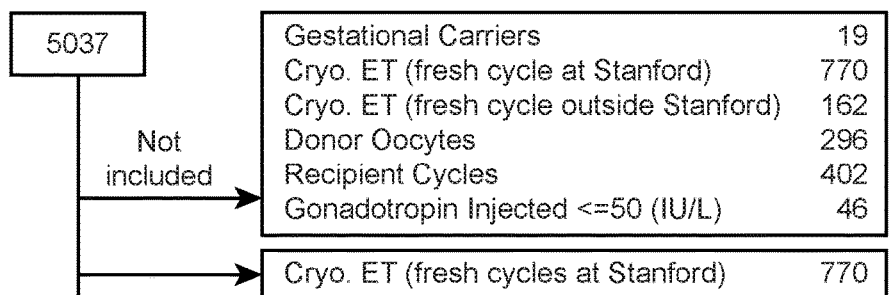
FIG. 22 shows inclusion and exclusion criteria for 2007 data set.
Figure 22:
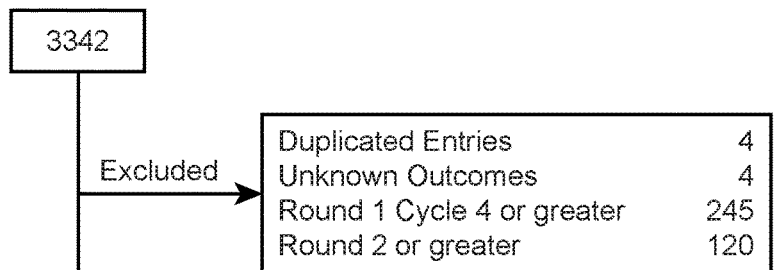
Figure 22:
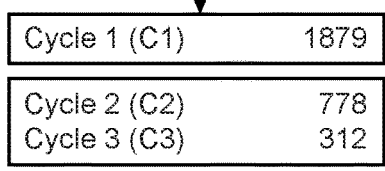

We validated our models by testing whether live birth rates amongst populations are significantly different in related data sets comprised of patients whose C1 did not result in a live birth and who returned for repeat treatment in 778 $2^{nd}$ cycles (C2) and 312 $3^{rd}$-cycles (C3). To further validate our results, we also tested an independent data set comprised of C1 data from 343 non-redundant patients who had IVF treatment in 2007. (See FIG. 22) Interestingly, we noted that the composition of the overall IVF patient population altered in between cycles, and between data sets.

Figure 23:
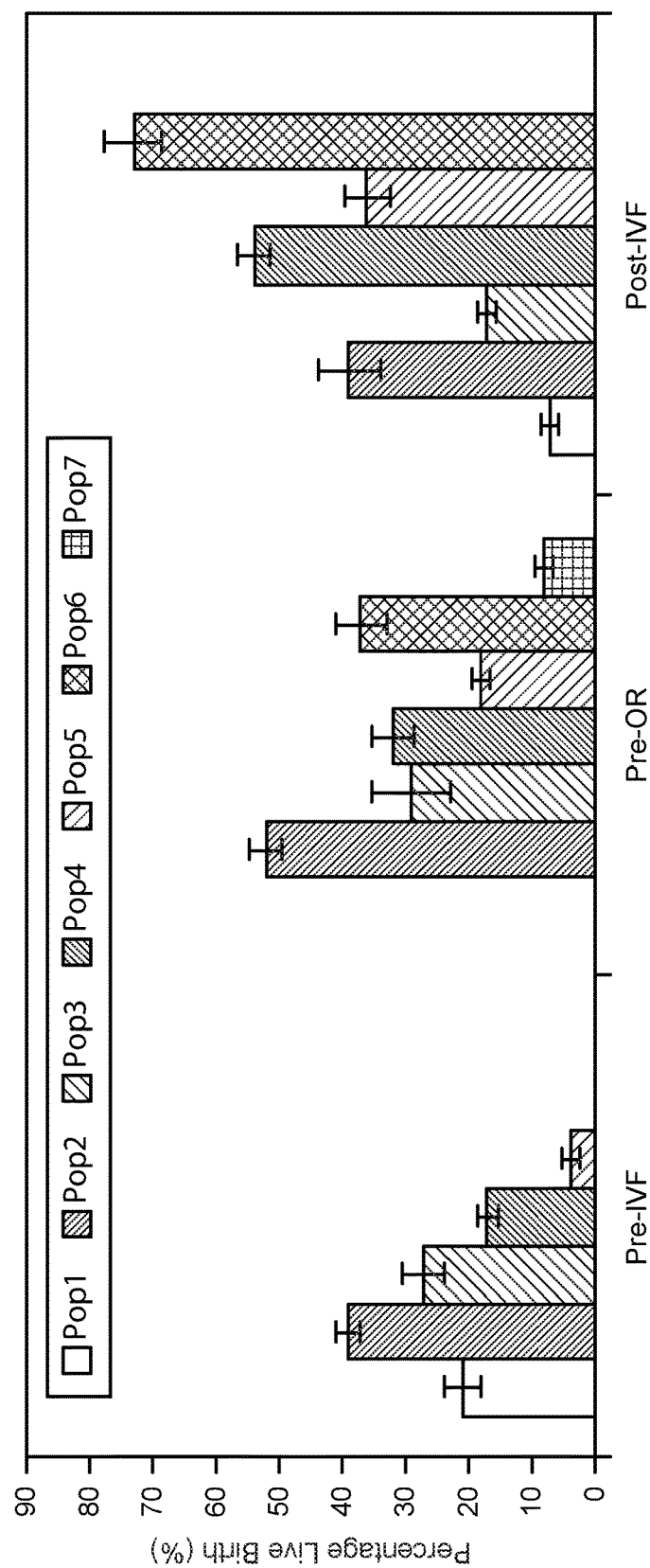
FIG. 23 shows that Pre-IVF, Pre-OR and Post-IVF models identify distinct populations with differential live birth rates.

We tested differential live birth rates amongst populations by ANOVA Chi-square test, which revealed that differential LB outcomes amongst populations remained significantly different in C2 and C3 from the 2003-2006 data set as well as C1 from the independent data set from 2007, for each of the Pre-IVF, Pre-OR, and Post-IVF models with p-values at 1.17E-50, 8.69E-71, and 1.64E-96, respectively (FIG. 23).

Then we validated our models in a different way, by testing whether the live birth rates of each prognostically-defined population was stable and unaltered amongst C1, C2, C3 of 2003-2006 data (inter-cycle, hereafter), and between C1 of 2007 and C1 of 2003-2006 data sets. The inter-cycle comparison showed that all populations remained similar for the Pre-OR and Post-IVF models; in the Pre-IVF model, only Pop 2 and Pop 4 showed that their live birth rates altered amongst cycles (p=0.02). (See Table 15 for p-values of inter-cycle comparisons.) Further, comparison of populations between the 2003-2006 and 2007 data sets indicated that the Pre-IVF and Post-IVF models, and most of the Pre-OR models have remained constant and highly reproducible (p≥0.5); Pops 1 and 6 of the Pre-OR model had differential live birth outcomes between the two data sets.

TABLE 15

Live birth rates were compared between age-based control model and each of Pre-IVF, Pre-OR and Post-IVF models across populations for each age group.

| | Age groups | | | | |
|---|---|---|---|---|---|
| | <35 | 35-37 | 38-40 | 41-42 | >=43 |
| Pre-IVF | 0.6 | 0.1 | 0.01 | NA | NA |
| Pre-OR | 0.04 | 1.8E-04 | 3.2E-07 | 4.1E-05 | 2.1E-06 |
| Post-IVF | 3.2E-07 | 3.7E-05 | 9.5E-16 | 3.7E-05 | 1.6E-09 |

Collectively, our results showed that all three models were effective in stratifying patients with differential live birth rates, and this ability to stratify by prognosis is reproducible in subsequent cycles and in an independent data set, despite changes in the composition of the general IVF patient population. Further, we confirmed that the prognostic stratification and live birth prediction used in each model were reproducible and validated in an independent data set, as well as in repeat cycles of returning patients.

Models Predicted Live Birth Outcomes More Specifically than Age.

Figure 24A:
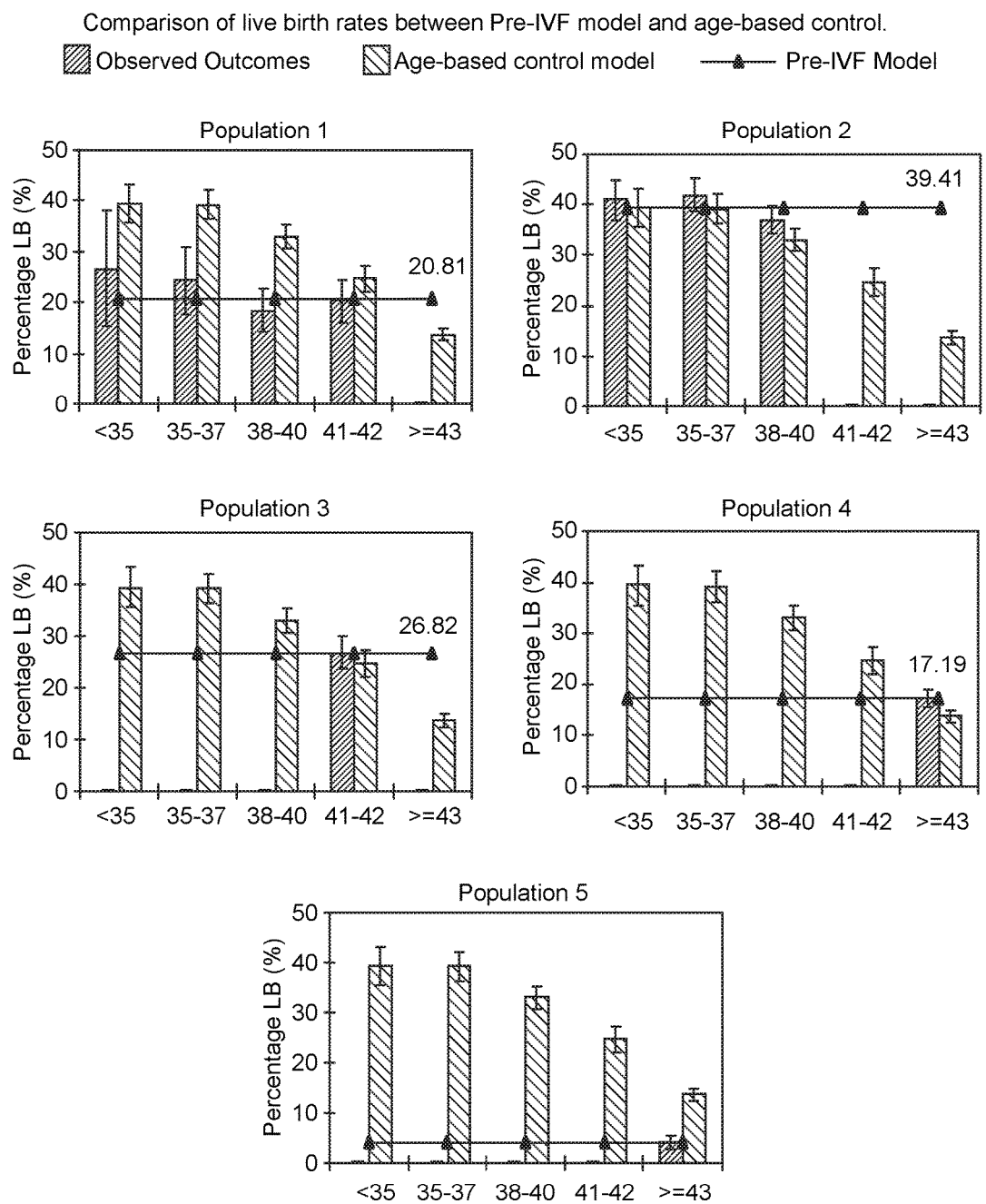
FIGS. 24A, 24B, and 24C show comparison of live birth rates between Pre-IVF (FIG. 23A), Pre-OR- (FIG. 23 B), Post-IVF models and an age-based control model.
Figure 24B:
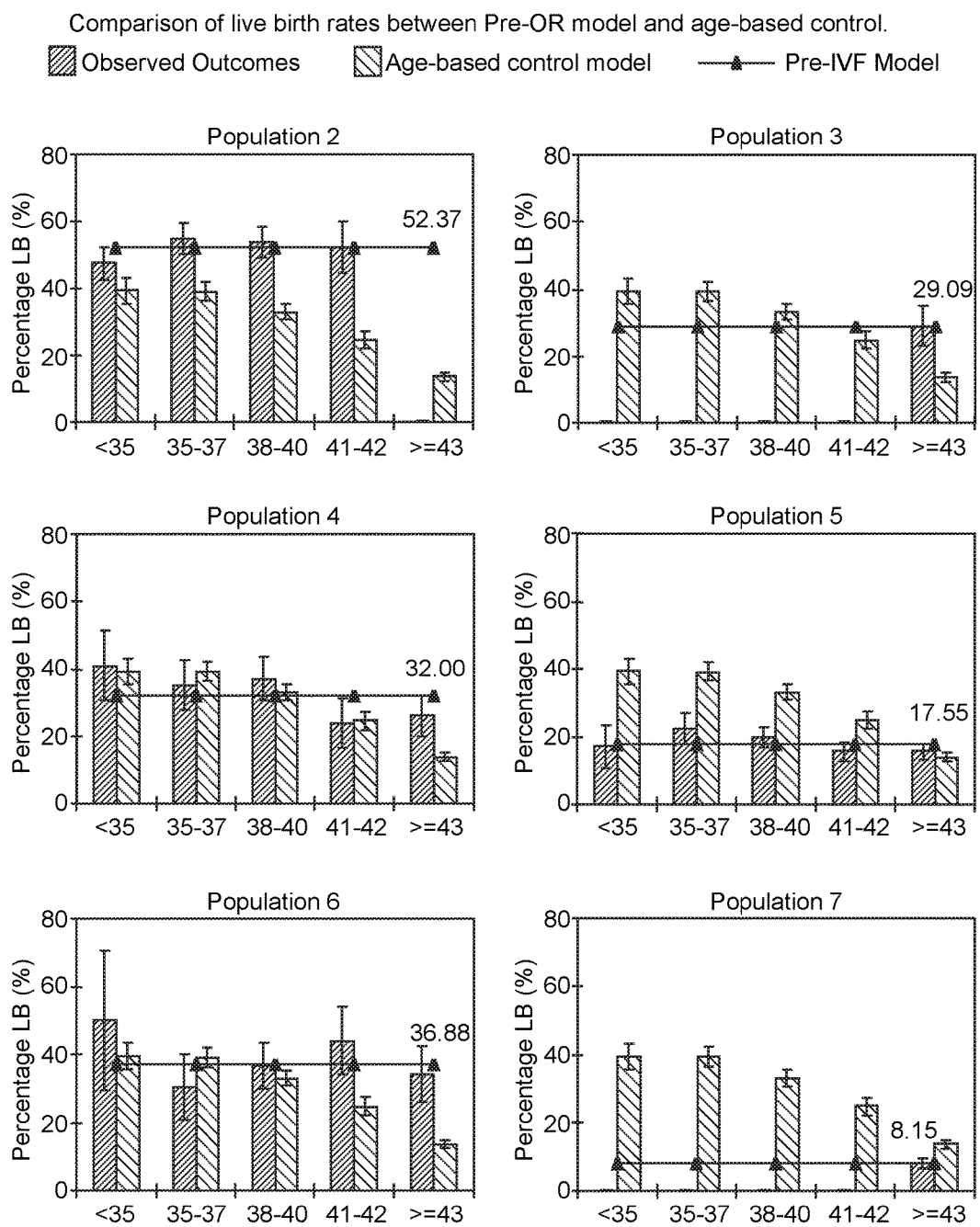
Figure 24C:
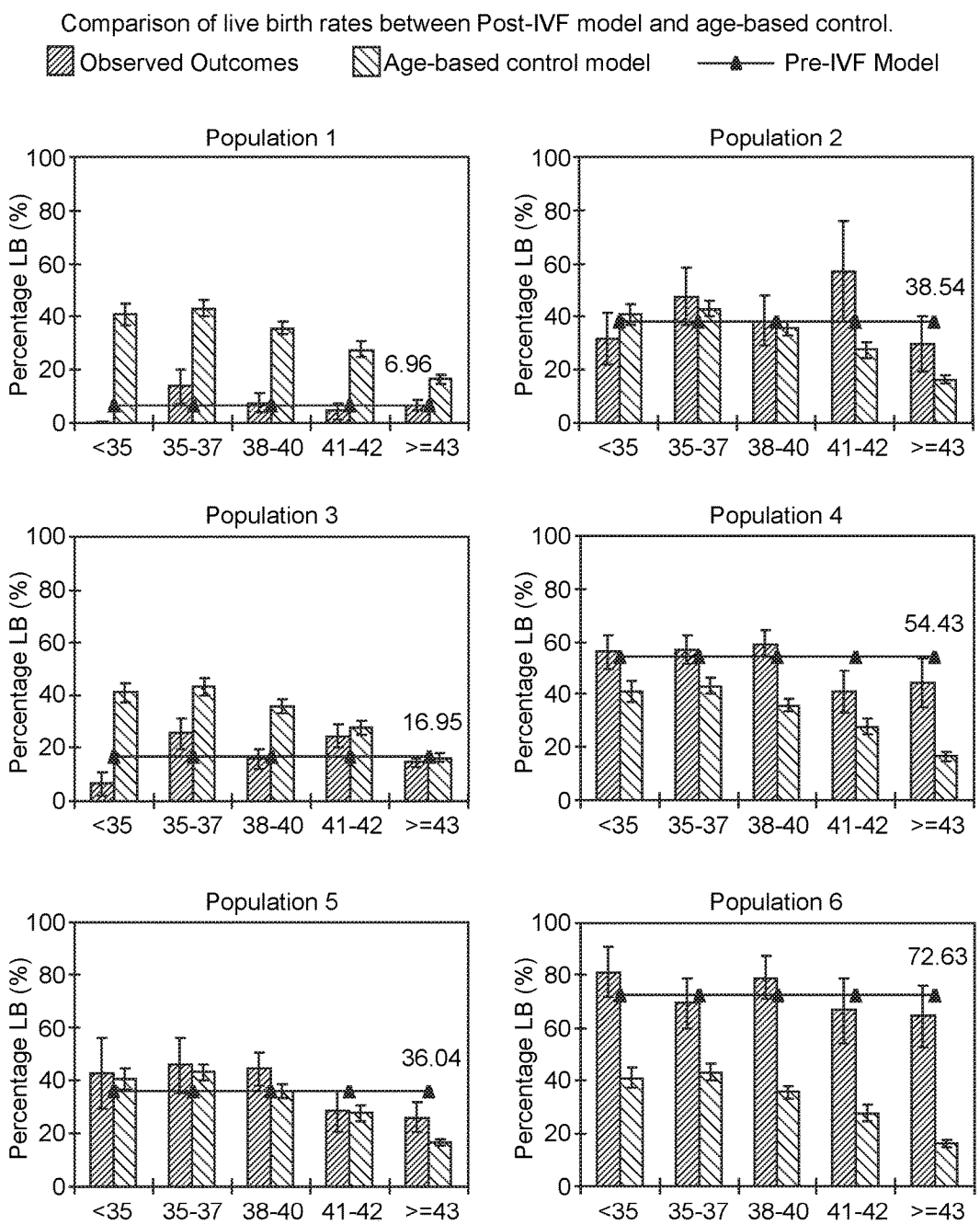

We tested whether these prediction models defined patient populations better and more specifically than an age-based control model (hereafter, control). (See Methods for age-based control model details.) We show the population-specific, observed live birth outcomes compared to live birth rates predicted by the control for each five age categories, <35, 35-37, 38-40, 41-42, and >43 (FIG. 24A-C). Here, age categories were defined by conventional standards used by the Society for Assisted Reproductive Technologies (SART) national registry and most of the literature (ref). These comparisons highlight the tendency for age to overestimate or underestimate live birth rates. For example, the control model tends to overestimate live birth rates in Pop 1 of the Pre-IVF model, Pops 5 and 7 of the Pre-OR model, and Pops 1 and 3 of the Post-IVF model (FIG. 24A-C). In the comparison with the Pre-OR model, control model also tends to underestimate live birth rates in Pops 2 and 3, and in age groups 41-42 and >43 of Pop 6, while comparison with the Post-IVF model, age tends to underestimate Pops 4 and 6.

We compared each of Pre-IVF, Pre-OR and Post-IVF models to the control with respect to the live birth rates in each of five age categories. Both the Pre-OR and Post-IVF models predicted live birth rates significantly better than the control model across populations in all five age groups (p-values range from 0.04 to 0.5E-16, see Table 15 for all p-values of these comparisons). In the Pre-IVF model, in which age is a key prognostic factor, the Pre-IVF model predicted outcomes better than the control for the age group 38-40, presumably because it also considers the diagnosis of diminished ovarian reserve (p=0.01). In summary, amongst patients who are undergoing their first fresh IVF cycle 17.7% of patients would receive more accurate and personalized live birth outcomes prediction from using the Pre-IVF model and 76% of patients would benefit from using the Pre-OR model. The utility of the Post-IVF model is to facilitate decision-making regarding subsequent IVF treatment in the event that live birth does not result from the first treatment, its use as a prediction tool for subsequent cycles is analyzed more in-depth later.

Prognostic Stratification Predicts Subsequent and Cumulative Live Birth Rates

Figure 25:
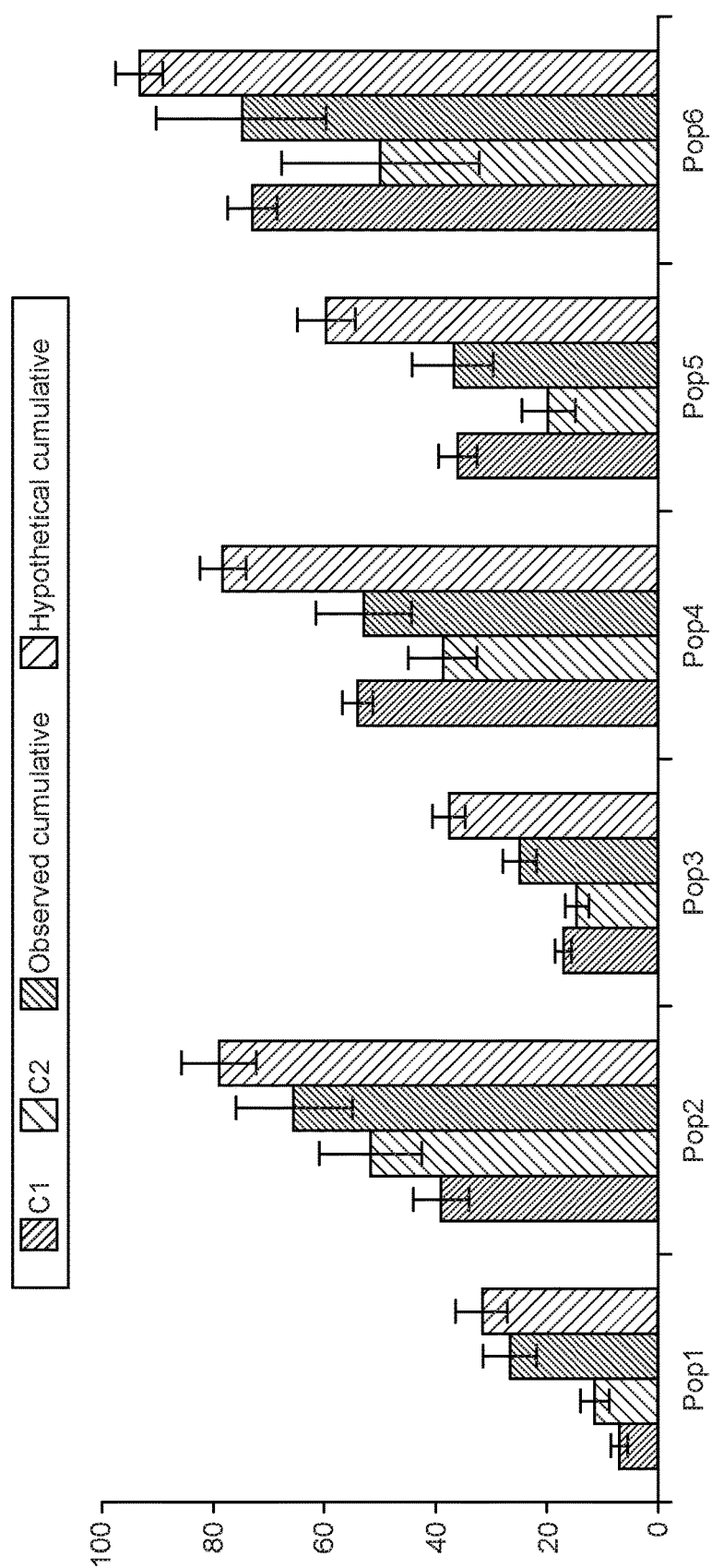
FIG. 25 shows that Post-IVF model C1 population assignment predicts differential live birth rates in C2 and cumulative live birth rates in subsequent cycles (C2 and C3).
Figure 26:
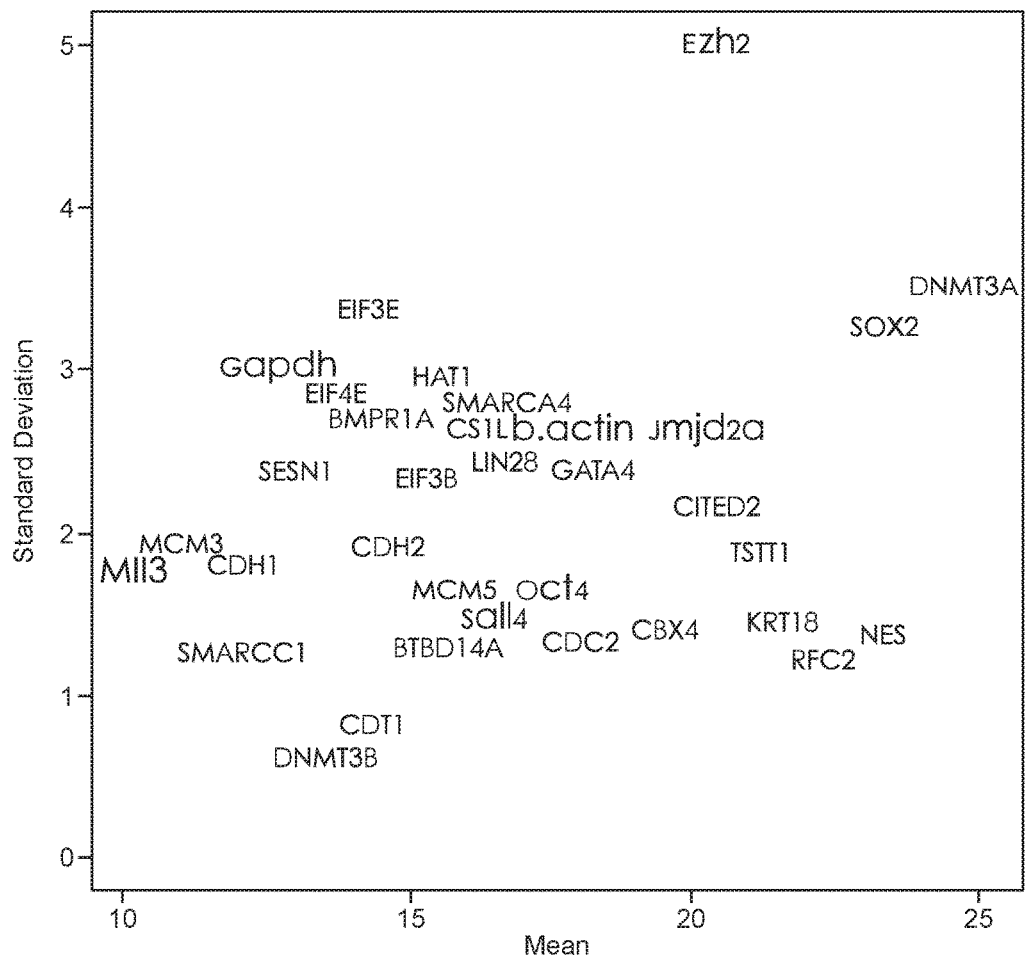
FIG. 26 shows results of gene chip experiments performed at the 1-cell stage.
Figure 27:
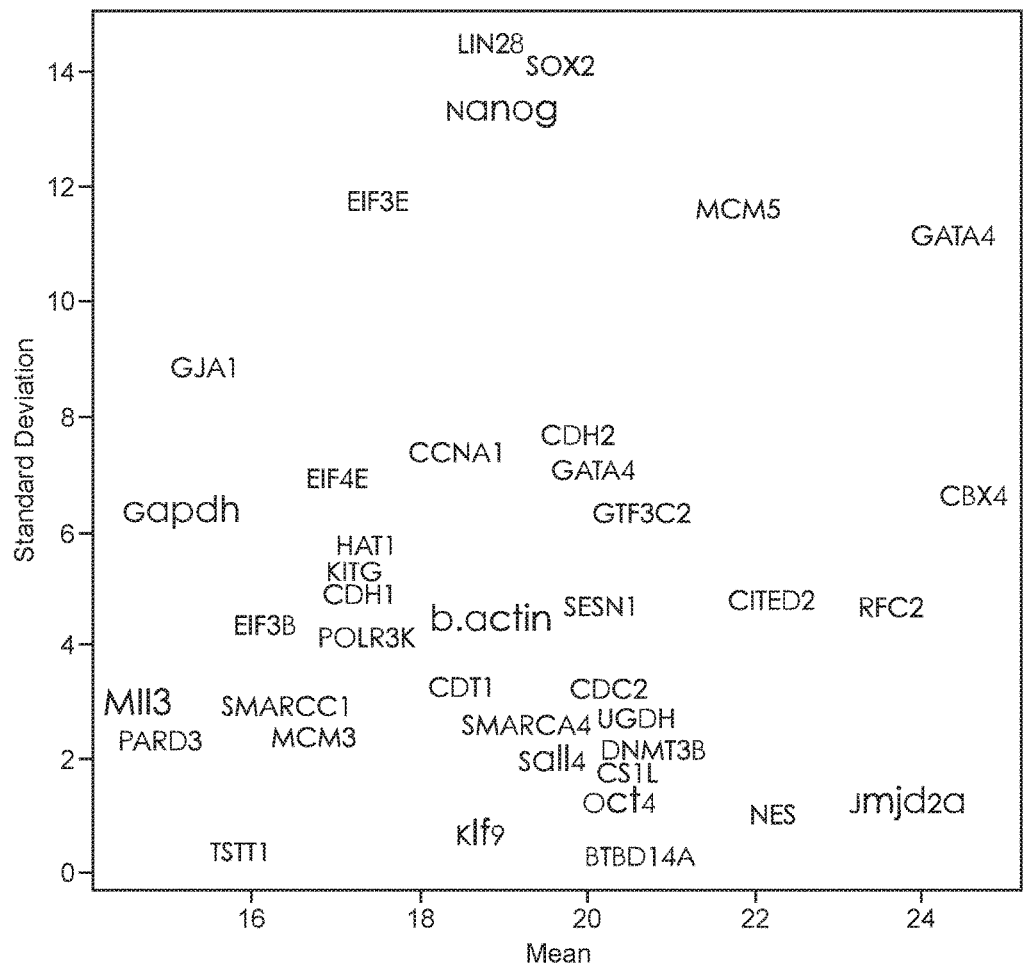
FIG. 27 shows results of gene chip experiments performed at the 4-cell stage.
Figure 28:
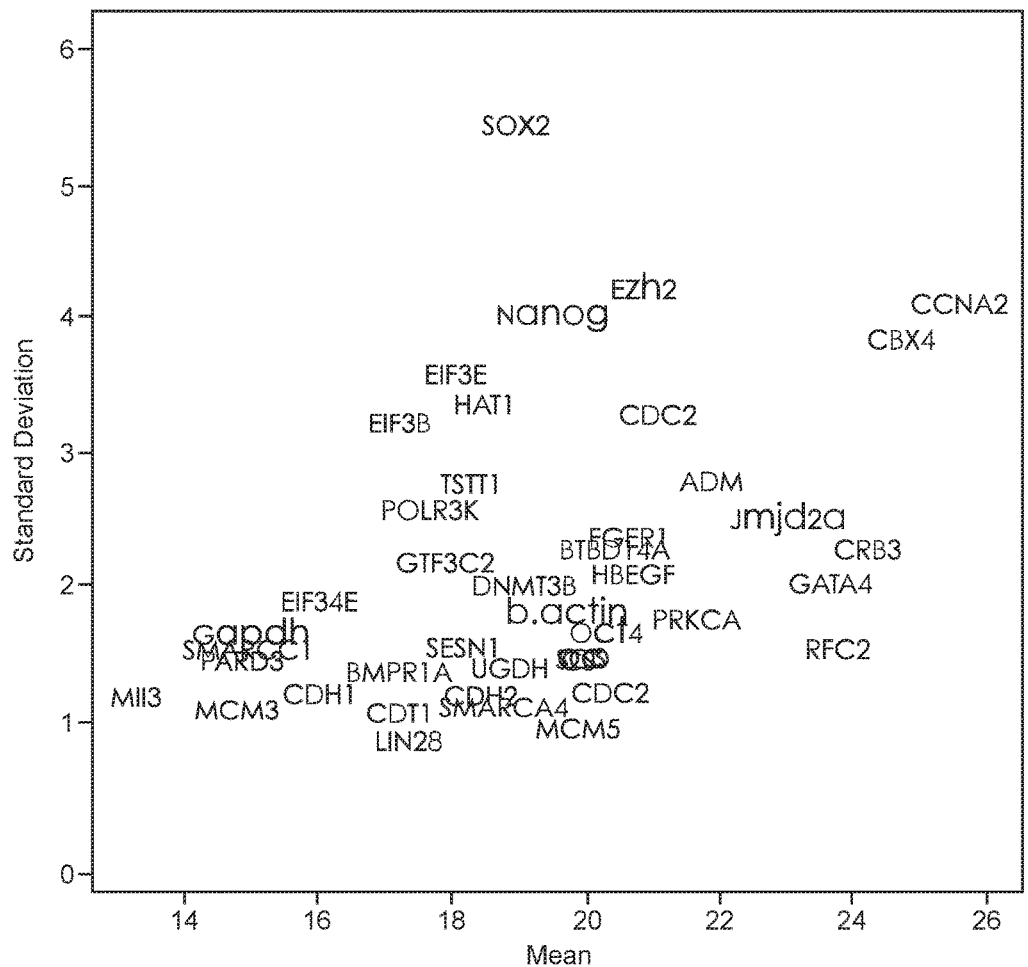
FIG. 28 shows results of gene chip experiments performed at the 8-cell stage.
Figure 29:
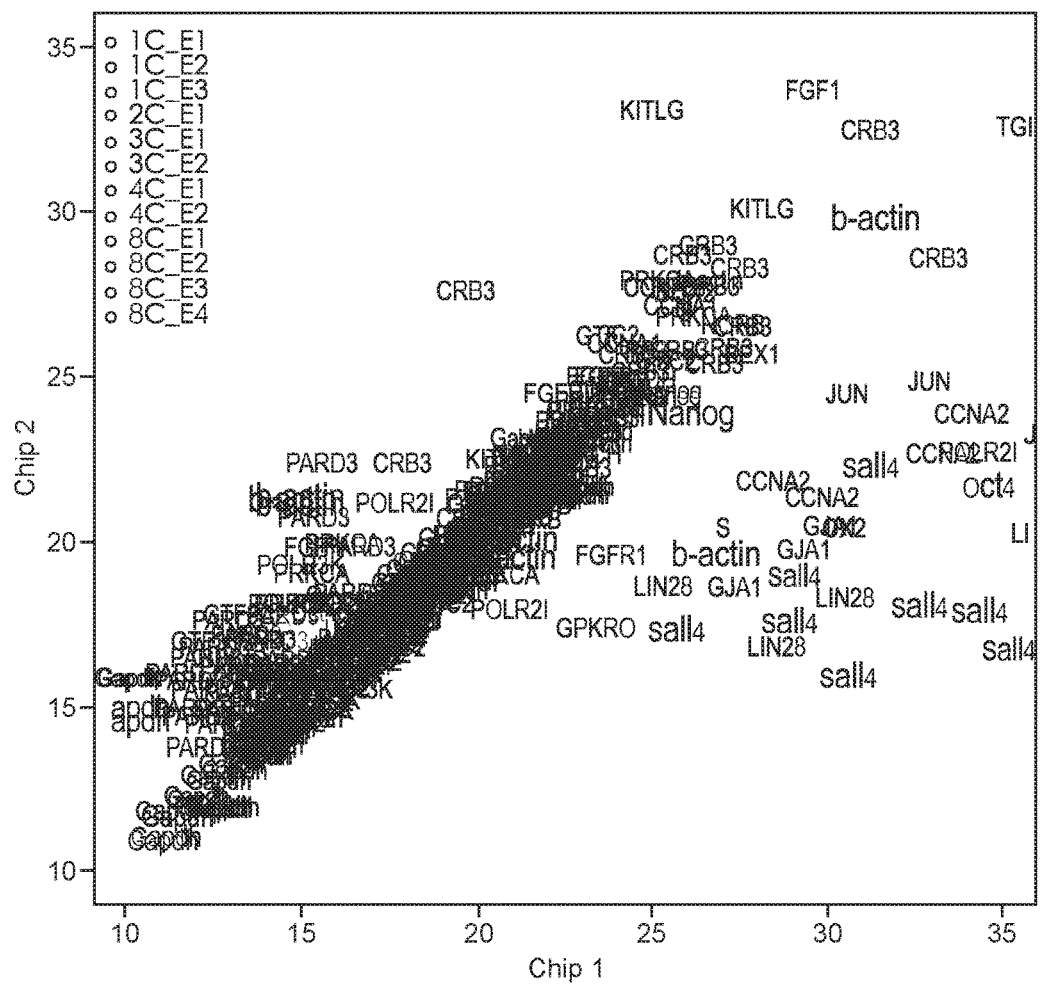
FIG. 29 shows a correlation of two gene chip experiments showing expression of a panel of genes at various cell stages.
Figure 30:
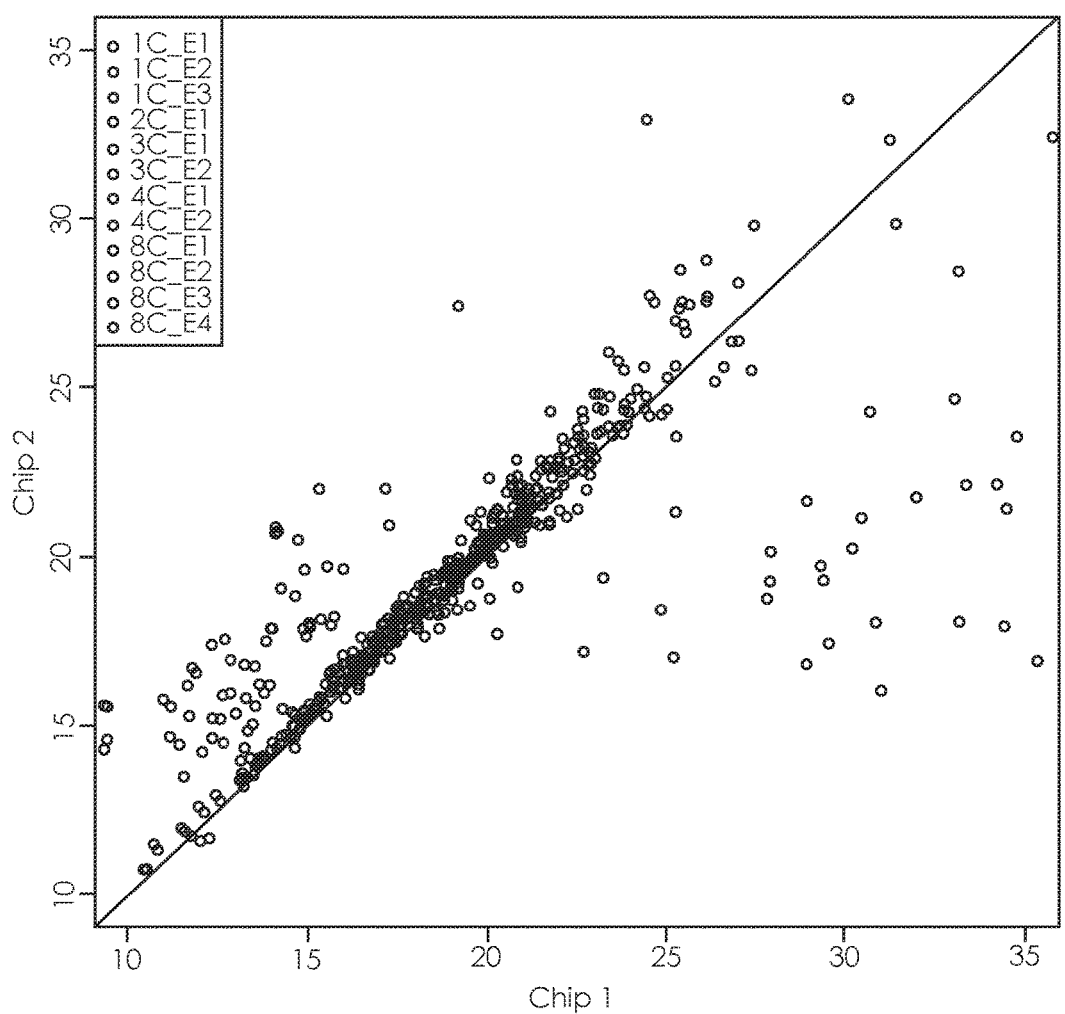
FIG. 30 shows a correlation of two gene chip experiments showing expression of a panel of genes at various cell stages.

We asked whether population assignment in C1 predicts live birth rates in C2 and the cumulative live birth rates in C2 and C3, for patients who do not have a live birth from C1. These questions precisely address the frequent scenario in which a couple needs to decide whether to repeat IVF treatment after an unsuccessful cycle. We addressed these questions by assigning patients to populations based on the Post-IVF model, followed by tracking patients' outcomes in C2 and C3. We considered both observed and hypothetical cumulative live birth rates. The observed cumulative rates were conservatively calculated based on the actual patients who returned for C2 and C3; the nominator was number of live births in C2 and C3, and the denominator was the total number of C2 cycles. The hypothetical cumulative rates were calculated based on the probability of having live birth outcomes in C2 or C3, and assumed that the patients who dropped out were no different from the ones who returned; therefore, they are not affected by the limited number of patients who chose to have C3. Specifically, C1 assignment to Pops 1 and 3 resulted in observed cumulative live birth rates of 15.1% and 18.4%, respectively, and 27.5% for Pop 5. In contrast, Pops 2, 4 and 6 had much higher cumulative live birth rates of 56.7%, 42.9%, and 75%, respectively; the hypothetical cumulative live birth rates had a trend towards being slightly higher (FIG. 25). Therefore, population assignment based on prognostic factors in C1 re-defines the IVF population into subsets that have distinct and predictable cumulative live birth rates in C2 and C3.

Gradient Boost Analysis to Identify Relative Importance of Preselected Patient Variables We used gradient boosted machine (GBM) to perform analyses to determine the "relative influence" of each variable on live birth outcomes for all three models. Briefly, we performed 10-fold cross validation for 1879, 1879, and 1664 fresh cycles for Pre-IVF, Pre-OR, and Post-IVF models, respectively. The optimal numbers of trees were 4677, 8680, and 10,745 for Pre-IVF, Pre-OR, and Post-IVF models, respectively; 25,000 trees (i.e. more than the minimum required) were analyzed for each model. The results are shown in Tables 16A, 16B, and 16C. The variables are ranked according to decreasing relative influence/importance such that the most important variables are ranked at the top. The numbers for relative influence add up to 100 in each model.

These GBM outputs contain thousands of trees which cannot be visualized and are conceptually too abstract for most scientific and clinical discussions. Therefore, we chose the top variables for further analysis to construct simpler tree models that could be visualized with Rpart. The advantages of simpler tree models were that they were conceptually more easily understood by scientists, clinicians, and lay people; distinct sub-populations can be characterized and subjected to further analyses to address specific questions, and to explore the utility of the models.

Tables 16a, 16B, and 16C. List of Variables and their Relative Importance in Determining Live Birth Outcomes in the Pre-IVF, Pre-OR and Post-IVF Model Respectively.

TABLE 16A

Pre-IVF Model
Pre-IVF model

| Variables | Relative Importance |
| --- | --- |
| Age of patient | 45.38 |
| Diminished ovarian reserve | 14.82 |
| Age of spouse | 11.55 |
| Serum d. 3 FSH (IU/L) | 10.71 |
| Body Mass Index | 6.37 |
| Polycystic ovarian syndrome | 2.88 |
| Season | 1.75 |
| Unexplained female infertility | 1.35 |
| Spontaneous miscarriages | 0.97 |
| Year | 0.89 |
| Other causes of female infertility | 0.76 |
| No. of previous pregnancies | 0.74 |
| No. of previous term deliveries | 0.64 |
| Endometriosis | 0.51 |
| Tubal disease | 0.48 |
| Tubal ligation | 0.09 |
| Male infertility only | 0.07 |
| Uterine fibroids | 0.02 |
| Hydrosalpinx | 0.01 |
| Male infertility causes | 0.01 |

TABLE 16B

Pre-OR Model
Pre-OR model

| Variables | Relative Importance |
| --- | --- |
| Total amount of gonadotropin | 35.22 |
| Endometrial Thickness | 17.58 |
| Age of patient | 14.16 |
| No. of sperm motile after wash (million/mL) | 8.05 |

TABLE 16B-continued

Pre-OR Model
Pre-OR model

| Variables | Relative Importance |
|---|---|
| No. of sperm motile before wash (million/mL) | 6.87 |
| Sperm collection | 6.03 |
| Age of spouse | 4.27 |
| Body Mass Index | 2.91 |
| Serum d. 3 FSH (IU/L) | 2.41 |
| Season | 0.75 |
| Spontaneous miscarriages | 0.39 |
| Unexplained female infertility | 0.39 |
| No. of previous term deliveries | 0.26 |
| Year | 0.26 |
| No. of previous pregnancies | 0.21 |
| Other causes of female infertility | 0.10 |
| Endometriosis | 0.04 |
| Male infertility only | 0.02 |
| Tubal ligation | 0.02 |
| Polycystic ovarian syndrome | 0.02 |
| Tubal disease | 0.02 |
| Sperm from donor | 0.00 |
| Hydrosalpinx | 0.00 |
| Uterine fibroids | 0.00 |
| Male infertility causes | 0.00 |

TABLE 16C

Post-IVF Model
Post-IVF model

| Variables | Relative Importance |
|---|---|
| Blastocyst development (%) | 27.30 |
| Total amount of gonadotropin | 10.58 |
| Total no. of embryos | 8.95 |
| Endometrial Thickness | 7.24 |
| Flare protocol | 6.13 |
| Average no. of cells per embryo | 4.97 |
| Catheter used | 4.04 |
| Percentage of 8 cell embryos | 3.54 |
| Serum d. 3 FSH (IU/L) | 3.17 |
| Body Mass Index | 3.16 |
| No. of sperm motile before wash (million/mL) | 2.99 |
| No. of sperm motile after wash (million/mL) | 2.88 |
| Age of patient | 2.56 |
| Average grade of embryos | 2.49 |
| Day of embryo transfer | 1.88 |
| Season | 1.32 |
| Spontaneous miscarriages | 0.93 |
| No. of previous term deliveries | 0.74 |
| Oral contraceptive pills | 0.68 |
| Sperm collection | 0.58 |
| Unfertilized eggs (%) | 0.56 |
| No. embryos arrested at = 4 cells | 0.54 |
| Compaction on day 3 | 0.51 |
| Normal fertilization (%) | 0.48 |
| Abnormally fertilized eggs (%) | 0.48 |
| Percentage of normal and mature oocytes | 0.48 |
| No. of previous pregnancies | 0.26 |
| Year | 0.17 |
| Polycystic ovarian syndrome | 0.12 |
| Unexplained female infertility | 0.11 |
| Tubal disease | 0.05 |
| Male infertility only | 0.05 |
| Male infertility causes | 0.03 |
| Endometriosis | 0.02 |
| Other causes of female infertility | 0.01 |
| Uterine fibroids | 0.01 |
| Tubal ligation | 0.00 |
| Sperm from donor | 0.00 |
| Hydrosalpinx | 0.00 |
| Performance of ICSI | 0.00 |
| Assisted Hatching | 0.00 |

Example 7

Determination of Molecular Fingerprint for Normal Vs. Abnormal Human Embryos

We successfully tested the expression of a panel of genes in dissociated blastomeres of control cryopreserved-thawed human embryos that are at the 1-cell, 4-cell, and 8-cell stages. (Patients donated those control embryos to research because they had completed their families.) We analyzed the data by considering both standard deviation and mean. The results of gene chip experiments on the 1-cell, 4-cell, and 8-cell stages are provided in FIGS. 25-30. These results show the utility of gene expression analysis at the single-cell level as well examining expression of many genes simultaneously. As such, the results show that the fingerprinting analysis for the embryos could be used to provide information that may improve prediction of live birth outcomes for subsequent IVF cycles.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

TABLE 8A

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 12561 | 0610039J04Rik: RIKEN cDNA 0610039J04 gene | 726.94 | 952.88 | 925.99 | 702.03 | 806.57 | 331 | 405.8 | 335.4 | 516.81 | 1.682481163 | 0.04796748 | 0.09424119 | 11.4121 |
| 17702 | 0610040J01Rik: RIKEN cDNA 0610040J01 gene | 408.14 | 292.64 | 232.51 | 164.99 | 152.49 | 79.1 | 50.46 | 95.62 | 57.89 | 3.108117559 | 0.027310924 | 0.06003501 | 19.3713 |
| 14297 | 1110007M04Rik: RIKEN cDNA 1110007M04 gene | 1261.71 | 969.97 | 1148.54 | 891.24 | 883.27 | 742.9 | 514.8 | 528.3 | 552.68 | 1.643608215 | 0.047535211 | 0.09174589 | 11.9566 |
| 23774 | 1300003B13Rik: RIKEN cDNA 1300003B13 gene | 366.9 | 654.15 | 629.58 | 353.58 | 521.61 | 292.6 | 233.5 | 199.1 | 273.86 | 1.761395346 | 0.047778709 | 0.09288628 | 11.6452 |
| 2769 | 1500005A01Rik: RIKEN cDNA 1500005A01 gene | 190.67 | 162.34 | 88.43 | 60.38 | 43.44 | 74.49 | 60.43 | 32.43 | 37.65 | 2.858882197 | 0.048085485 | 0.09187593 | 12.0161 |
| 22816 | 1500011B03Rik: RIKEN cDNA 1500011B03 gene | 322.26 | 247.98 | 673.66 | 122.44 | 129.61 | 103.8 | 91.83 | 188.2 | 110.61 | 3.332395687 | 0.028446389 | 0.06021882 | 19.6218 |
| 22897 | 1500041J02Rik: RIKEN cDNA 1500041J02 gene | 1893.92 | 1849.2 | 1693.29 | 1451 | 1424 | 1116 | 1066 | 1017 | 1101.9 | 1.515255995 | 0.046834345 | 0.09180399 | 11.8767 |
| 39273 | 1700013H16Rik: RIKEN cDNA 1700013H16 gene | 758.43 | 675.7 | 737.99 | 758.17 | 463.94 | 313.6 | 215 | 215.7 | 339.42 | 1.884057091 | 0.045634921 | 0.08490741 | 12.9579 |
| 39378 | 1700080O16Rik /// LOC665895 /// LOC671223 /// LOC676479: RIKEN cDNA 1700080O16 gene /// similar to melanoma antigen family A, 5 /// similar to melanoma antigen family A, 5 /// similar to melanoma antigen family A, 5 | 200.58 | 99.12 | 179.18 | 2.68 | 13.11 | 53.79 | 4.95 | 4.98 | 14.24 | 10.21610667 | 0.010416667 | 0.0375 | 38.9031 |
| 25993 | 1700129I15Rik: RIKEN cDNA 1700129I15 gene | 669.05 | 306.9 | 110.37 | 38.64 | 337.75 | 62.42 | 8.11 | 130.2 | 9.06 | 3.706501527 | 0.032414911 | 0.06916261 | 16.8302 |
| 1469 | 1810021J13Rik: RIKEN cDNA 1810021J13 gene | 197.73 | 84.01 | 193.51 | 54.69 | 91.43 | 27.17 | 26.09 | 36.55 | 61.85 | 3.191953791 | 0.03257329 | 0.06910423 | 16.8574 |
| 38853 | 1810044A24Rik: RIKEN cDNA 1810044A24 gene | 327.76 | 445.4 | 180.89 | 194.87 | 99.06 | 230.3 | 90.63 | 104.2 | 122.74 | 2.266582724 | 0.044401544 | 0.08662162 | 12.7189 |
| 14361 | 2010109N14Rik: RIKEN cDNA 2010109N14 gene | 2153.09 | 1615.8 | 2175.97 | 1431.2 | 1545.7 | 1498 | 990.7 | 1212 | 998.06 | 1.548963257 | 0.036834925 | 0.07317417 | 15.5482 |
| 12883 | 2010109N14Rik: RIKEN cDNA 2010109N14 gene | 137.6 | 388.98 | 247.94 | 70.02 | 143.76 | 72.7 | 44.83 | 53.42 | 47.03 | 3.587733926 | 0.023560209 | 0.0575829 | 21.1602 |
| 4342 | 2010301N04Rik: RIKEN cDNA 2010301N04 gene | 1336.22 | 1283.4 | 1702.28 | 919.13 | 704.51 | 611.2 | 198 | 869.9 | 354.78 | 2.363351515 | 0.019047619 | 0.04355556 | 28.4416 |
| 4343 | 2410022L05Rik: RIKEN cDNA 2410022L05 gene | 1587.18 | 1243 | 1840.86 | 1006.1 | 799.09 | 735.3 | 264.5 | 1067 | 383.1 | 2.195358325 | 0.020833333 | 0.04227431 | 29.5735 |
| 7831 | 2510042P03Rik: RIKEN cDNA 2510042P03 gene | 609.91 | 476.61 | 483.28 | 205.72 | 292.53 | 253.9 | 143.3 | 227.1 | 130.33 | 2.506046408 | 0.026923077 | 0.06301282 | 18.4494 |
| 38903 | 2600010E01Rik: RIKEN cDNA 2600010E01 gene | 303.78 | 312.45 | 368.93 | 57.76 | 100.13 | 37.76 | 33.32 | 102.2 | 59.89 | 5.037893122 | 0.01010101 | 0.03750842 | 38.2228 |
| 12473 | 2610001J05Rik: RIKEN cDNA 2610001J05 gene | 296.77 | 409.38 | 503.49 | 245.92 | 295.87 | 217.2 | 127.3 | 127.2 | 112.09 | 2.149210241 | 0.042988741 | 0.08313886 | 13.1993 |
| 17629 | 2610200G18Rik: RIKEN cDNA 2610200G18 gene | 507.41 | 353.97 | 562.56 | 226.7 | 318.05 | 160 | 138.3 | 150 | 181.72 | 2.424181549 | 0.02284264 | 0.05854484 | 20.816 |
| 8796 | 2610204L23Rik: RIKEN cDNA 2610204L23 gene | 2035.34 | 2238.2 | 2213.21 | 1158 | 1919.6 | 996.2 | 1310 | 1294 | 1439.4 | 1.598253609 | 0.035814607 | 0.07222846 | 15.755 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 13166 | 2610206B13Rik: RIKEN cDNA 2610206B13 gene | 225.38 | 66.31 | 200.47 | 99.87 | 45.82 | 54.05 | 28.4 | 45.37 | 49.13 | 3.050830647 | 0.03313253 | 0.07128514 | 16.2151 |
| 15069 | 2700060E02Rik: RIKEN cDNA 2700060E02 gene | 1283.21 | 1570.9 | 1406.02 | 866.04 | 1267.3 | 698.8 | 686.8 | 853.4 | 876.63 | 1.623218225 | 0.047315742 | 0.09020625 | 12.2015 |
| 12465 | 2810026P18Rik: RIKEN cDNA 2810026P18 gene | 2572.92 | 1625.6 | 2626.66 | 1339.2 | 1910.7 | 1650 | 1370 | 1348 | 1217.5 | 1.544918909 | 0.02722323 | 0.06469449 | 17.9141 |
| 1357 | 2810037C14Rik: RIKEN cDNA 2810037C14 gene | 1234.26 | 1441.4 | 1159.06 | 686.13 | 824.88 | 637.2 | 505.8 | 807.8 | 513.31 | 1.929321084 | 0.027184466 | 0.06282848 | 18.5328 |
| 7425 | 2810405K02Rik: RIKEN cDNA 2810405K02 gene | 178.7 | 133.85 | 23.59 | 37.21 | 19.15 | 47.42 | 21.42 | 5.11 | 43.31 | 3.872134547 | 0.047822374 | 0.09246513 | 11.7588 |
| 2836 | 2810429O05Rik: RIKEN cDNA 2810429O05 gene | 545.26 | 616.74 | 406.07 | 256.07 | 314.66 | 153.4 | 93.44 | 189.3 | 192.29 | 2.615411559 | 0.024390244 | 0.05095238 | 24.3184 |
| 8173 | 2900092E17Rik: RIKEN cDNA 2900092E17 gene | 364.43 | 535.89 | 536.98 | 201.3 | 208.16 | 223.1 | 249.4 | 258.8 | 279.55 | 2.023952855 | 0.034950071 | 0.07232525 | 15.8264 |
| 31900 | 3 days neonate thymus cDNA, RIKEN full-length enriched library, clone: A630060L04 product: unclassifiable, full insert sequence | 217.23 | 198.01 | 208.5 | 35.11 | 62.24 | 25.96 | 128.6 | 54.01 | 42.21 | 3.58368285 | 0.026156942 | 0.06102616 | 18.9222 |
| 23783 | 3110040M04Rik /// LOC668050 /// LOC668055 /// LOC671025 /// LOC671035 /// LOC671043 /// LOC671049 /// LOC676755 /// LOC676758: RIKEN cDNA 3110040M04 gene /// similar to U2-associated SR140 protein /// hypothetical protein LOC668055 /// similar to U2-associated SR140 protein /// similar to U2-associated SR140 protein /// similar to U2-associated SR140 protein /// similar to U2-associated SR140 protein /// similar to U2-associated SR140 protein | 262.9 | 66.64 | 204.12 | 24.31 | 69.95 | 13.99 | 53.82 | 27.08 | 11.49 | 5.319577352 | 0.019607843 | 0.04245098 | 28.9087 |
| 24812 | 3110045A19Rik: RIKEN cDNA 3110045A19 gene | 133.79 | 102.29 | 11.36 | 16.34 | 11.54 | 14.64 | 9.74 | 11.08 | 9.95 | 6.752353664 | 0.035664336 | 0.07221445 | 15.7371 |
| 41988 | 4930406H16Rik: Nalp4e: RIKEN cDNA 4930406H16 gene /// NACHT, leucine rich repeat and PYD containing 4E | 504.28 | 1414.9 | 933.88 | 507.4 | 694.22 | 548.5 | 512.1 | 494.6 | 292.39 | 1.871318333 | 0.045098039 | 0.08532353 | 12.8793 |
| 25457 | 4930452B06Rik: RIKEN cDNA 4930452B06 gene | 159.43 | 56.45 | 170.72 | 54.77 | 36.42 | 26.26 | 16.28 | 39.2 | 26.39 | 3.87918243 | 0.029668412 | 0.06595695 | 17.569 |
| 27714 | 4930455F23Rik: RIKEN cDNA 4930455F23 gene | 534.1 | 677.74 | 522.3 | 346.74 | 399.19 | 274.9 | 281.7 | 256.8 | 176.61 | 1.997868651 | 0.047457627 | 0.09223446 | 11.7332 |
| 12139 | 4934307C03Rik: RIKEN cDNA 4934307C03 gene | 132.88 | 24.46 | 352.91 | 23.21 | 29.24 | 24.42 | 23.67 | 16.78 | 20.79 | 7.389037724 | 0.023746702 | 0.05663149 | 21.4433 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 5148 | 4933411K20Rik: RIKEN cDNA 4933411K20 gene | 738.65 | 1039.5 | 815.98 | 385.61 | 591.61 | 566 | 375.2 | 430.3 | 545.57 | 1.792608768 | 0.048440066 | 0.09399288 | 11.4661 |
| 39323 | 4933416M07Rik: RIKEN cDNA 4933416M07 gene | 131.45 | 240.96 | 376.74 | 164.45 | 78.57 | 97.69 | 70.38 | 90 | 47.91 | 2.729143898 | 0.042071197 | 0.08097807 | 13.6443 |
| 29217 | 4933427D06Rik: RIKEN cDNA 4933427D06 gene | 908.64 | 946.8 | 1089.77 | 626.62 | 734.75 | 426.3 | 393.3 | 601.6 | 587.3 | 1.747950978 | 0.047619048 | 0.09166961 | 11.9754 |
| 32880 | 5330427D05Rik: RIKEN cDNA 5330427D05 gene | 288.66 | 223.45 | 219.68 | 127.67 | 89.86 | 117.7 | 46.92 | 105.9 | 66.56 | 2.639125809 | 0.047120419 | 0.09182373 | 11.9053 |
| 12662 | 5730507H05Rik: RIKEN cDNA 5730507H05 gene | 812.73 | 648.02 | 809.21 | 424.8 | 297.08 | 456.7 | 492.6 | 353.6 | 405.37 | 1.868164517 | 0.035161744 | 0.07214721 | 15.7684 |
| 10438 | 5830415L20Rik: RIKEN cDNA 5830415L20 gene | 1798.9 | 1735.1 | 1623.57 | 447.1 | 794.05 | 612.1 | 547.7 | 578.6 | 472.45 | 2.988146002 | 0 | 0.02944444 | 58.7902 |
| 10605 | 6430548M08Rik: RIKEN cDNA 6430548M08 gene | 172.77 | 77.66 | 129.96 | 52.6 | 22.23 | 16.06 | 21.88 | 26.12 | 38.85 | 4.280297063 | 0.038167939 | 0.07466497 | 15.0198 |
| 26997 | 6720463M24Rik: RIKEN cDNA 6720463M24 gene | 217.15 | 218.01 | 225.79 | 73.98 | 49.43 | 68.05 | 56.28 | 107.7 | 70.8 | 3.10166827 | 0.032786885 | 0.07150025 | 16.1248 |
| 31488 | 7420416P09Rik: RIKEN cDNA 7420416P09 gene | 891.83 | 777.85 | 767.35 | 491.65 | 642.89 | 411.6 | 237.4 | 519.4 | 353.02 | 1.835126771 | 0.048171276 | 0.09178709 | 12.027 |
| 29615 | A230048G03Rik /// LOC670614: RIKEN cDNA A230048G03 gene /// similar to CG2747-PB, isoform B | 171.76 | 66.93 | 163.5 | 48.01 | 41.96 | 51.96 | 61.61 | 18.34 | 49.85 | 2.960217863 | 0.043032787 | 0.08315232 | 13.2034 |
| 22603 | A230062G08Rik: RIKEN cDNA A230062G08 gene | 322.83 | 261.74 | 354.1 | 323.26 | 201.66 | 68.32 | 42.84 | 53.83 | 127.44 | 2.29686181 | 0.047858942 | 0.09292751 | 11.655 |
| 41840 | A430033K04Rik: RIKEN cDNA A430033K04 gene | 1229.01 | 998.13 | 1215.48 | 461.08 | 557.03 | 342.2 | 761 | 837.6 | 205.38 | 2.175946907 | 0.016877637 | 0.04720113 | 26.7452 |
| 15795 | A830039H10Rik: RIKEN cDNA A830039H10 gene | 285.01 | 249.94 | 242.98 | 101.83 | 100.81 | 86.69 | 105.9 | 99.37 | 94.16 | 2.642649682 | 0.042253521 | 0.0812026 | 13.6501 |
| 14842 | Adcy3: adenylate cyclase 3 | 758.96 | 864.83 | 804.58 | 572.29 | 686.9 | 438.5 | 319.3 | 409.5 | 337.76 | 1.757014688 | 0.048333333 | 0.09301667 | 11.6011 |
| 27502 | Adult male medulla oblongata cDNA, RIKEN full-length enriched library, clone: 6330441D15 product: hypothetical protein, full insert sequence | 149.12 | 176.59 | 33.92 | 30.73 | 59.6 | 50.95 | 19.27 | 31.34 | 26.32 | 3.296182576 | 0.042900919 | 0.0831018 | 13.1896 |
| 42166 | Agrp: Agouti related protein | 231.44 | 178.62 | 94.37 | 33.38 | 179.24 | 13.68 | 1 | 3.54 | 25.21 | 3.940089826 | 0.033182504 | 0.07107089 | 16.2397 |
| 30358 | AI449441: expressed sequence AI449441 | 151.46 | 251.91 | 122.96 | 52.19 | 97.84 | 34.47 | 27.9 | 63.13 | 28.11 | 3.466802793 | 0.044847328 | 0.08782443 | 12.5897 |
| 27056 | Akap7: A kinase (PRKA) anchor protein 7 | 474.68 | 818.9 | 809.2 | 330.68 | 516.16 | 412.1 | 350.4 | 355.2 | 259.52 | 1.891006214 | 0.028520499 | 0.0653773 | 17.7396 |
| 40856 | Arhgef15: Rho guanine nucleotide exchange factor (GEF) 15 | 75.81 | 156.72 | 162.47 | 102.39 | 39.12 | 15.89 | 18.53 | 57.97 | 26.4 | 3.034959662 | 0.04506232 | 0.08746245 | 12.6344 |
| 14676 | Arl4c /// LOC632433: ADP-ribosylation factor-like 4C /// similar to ADP-ribosylation factor-like protein 7 | 311.79 | 210.2 | 41.38 | 104.69 | 73.13 | 31.74 | 50.31 | 49.49 | 54.66 | 3.095269491 | 0.042752868 | 0.08291971 | 13.3239 |
| 14653 | Arpc5l: actin related protein 2/3 complex, subunit 5-like | 2473.77 | 2293.9 | 2924.51 | 1813.4 | 2433.6 | 1537 | 1353 | 1754 | 1246.7 | 1.517524443 | 0.048559671 | 0.0937668 | 11.4908 |
| 40302 | Arrdc3: arrestin domain containing 3 | 183.69 | 264.91 | 361.58 | 62.76 | 138.75 | 89.69 | 46.24 | 105.3 | 72.66 | 3.144010245 | 0.026209677 | 0.06090726 | 18.9442 |
| 18069 | Arx: aristaless related | 297.32 | 299.7 | 123.78 | 72.45 | 57.19 | 29.97 | 24.05 | 38.12 | 24.48 | 5.853975473 | 0.016129032 | 0.03553763 | 46.1316 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 29021 | Ascl1: achaete-scute complex homolog-like 1 (*Drosophila*) homeobox gene (*Drosophila*) | 78.29 | 281.43 | 176.69 | 53.61 | 123.08 | 40.97 | 87.55 | 31.01 | 24.18 | 2.976748058 | 0.046793761 | 0.09179376 | 11.8701 |
| 7414 | Atp6v1g1: ATPase, H+ transporting, lysosomal V1 subunit G1 | 814.9 | 317.26 | 545.09 | 311.05 | 237.03 | 227 | 233.4 | 269.9 | 361.16 | 2.046137987 | 0.042708333 | 0.08292361 | 13.3161 |
| 27011 | Atp8a1: ATPase, aminophospholipid transporter (APLT), class I, type 8A, member 1 | 113.19 | 302.99 | 336.88 | 111.03 | 98.91 | 55.24 | 45.16 | 134.9 | 41.74 | 3.092585368 | 0.024615385 | 0.05401026 | 22.9511 |
| 10707 | Atp6d4: ATP binding domain 4 | 644.58 | 851.86 | 1031.97 | 378.68 | 582.62 | 175.6 | 246.6 | 575.3 | 407.51 | 2.137051719 | 0.026788714 | 0.05929315 | 19.8453 |
| 26830 | AU022751: expressed sequence AU022751 | 1575.02 | 1805.1 | 1927.95 | 1006.1 | 1485.3 | 930.7 | 1148 | 1148 | 924.02 | 1.598423276 | 0.037974684 | 0.07783659 | 14.1867 |
| 28921 | AU041783: expressed sequence AU041783 | 728.29 | 1031.6 | 715.32 | 268.18 | 470.17 | 621.1 | 289.7 | 297.9 | 348.87 | 2.1562451 | 0.03485064 | 0.07223803 | 15.8165 |
| 17440 | Aurkc: aurora kinase C | 1462.84 | 1182.8 | 1533.48 | 1312.5 | 1219.2 | 927.9 | 377.4 | 555.4 | 561.63 | 1.687182324 | 0.047372954 | 0.09207293 | 11.8231 |
| 15571 | Auts2: autism susceptibility candidate 2 | 892.1 | 1352.7 | 1127.84 | 816.47 | 892.95 | 829.9 | 561.9 | 507.8 | 366.68 | 1.696647131 | 0.047493404 | 0.09168279 | 11.9562 |
| 8718 | AW060207: expressed sequence AW060207 | 432.59 | 609.26 | 574.19 | 250.29 | 379.24 | 218.9 | 259.2 | 166.6 | 184.98 | 2.214784968 | 0.026946108 | 0.06165669 | 18.8051 |
| 29405 | AW146299: expressed sequence AW146299 | 284.07 | 216.2 | 332.39 | 121.93 | 161.67 | 105.2 | 66.41 | 71.03 | 112.37 | 2.607562828 | 0.036290323 | 0.07364247 | 15.4019 |
| 29099 | B230312I18Rik: RIKEN cDNA B230312I18 gene | 420.5 | 374.15 | 459.33 | 169.13 | 94.51 | 275.9 | 97.89 | 101.3 | 61.44 | 3.134479828 | 0.016949153 | 0.04735876 | 26.7539 |
| 11389 | B930041F14Rik: RIKEN cDNA B930041F14 gene | 26.1 | 145.4 | 149.78 | 15.65 | 34.72 | 7.96 | 30.02 | 31.98 | 43.39 | 3.924749572 | 0.036096257 | 0.07358289 | 15.378 |
| 35357 | B930096F20Rik: RIKEN cDNA B930096F20 gene | 232.53 | 102.36 | 229.72 | 30.99 | 16.44 | 13.59 | 17.81 | 40.92 | 54.55 | 6.478600115 | 0.010309278 | 0.03721649 | 38.8416 |
| 33323 | B930096F20Rik: RIKEN cDNA B930096F20 gene | 162.51 | 79.13 | 176.86 | 11.2 | 5.38 | 6.12 | 14.66 | 19.82 | 13.65 | 11.81702668 | 0.018691589 | 0.03785047 | 36.9537 |
| 30001 | BB176347: Expressed sequence BB176347 | 141.82 | 106.11 | 79.54 | 18.32 | 14.54 | 23.04 | 8.15 | 16.92 | 11.44 | 7.087328211 | 0.029616725 | 0.06619048 | 17.5516 |
| 27229 | BC010981: cDNA sequence BC010981 | 388.39 | 149.2 | 438 | 121.27 | 178.69 | 160.1 | 120.7 | 85.02 | 190.36 | 2.279043147 | 0.03271028 | 0.07022845 | 16.5397 |
| 10371 | BC021367: cDNA sequence BC021367 | 255.84 | 599.36 | 133.32 | 56.72 | 58.42 | 9.17 | 12.43 | 144.6 | 45.71 | 6.045808997 | 0.015151515 | 0.03744949 | 34.4898 |
| 10893 | BC022623: cDNA sequence BC022623 | 784.51 | 724.29 | 716.83 | 301.14 | 357.98 | 339.1 | 388.4 | 240.7 | 107.29 | 2.566144551 | 0.021912351 | 0.04861886 | 26.0618 |
| 28308 | BC047219: cDNA sequence BC047219 | 402.73 | 298.41 | 481.25 | 99.48 | 304.76 | 138.3 | 227.8 | 47.95 | 55.07 | 2.707649679 | 0.02690583 | 0.05922272 | 19.8718 |
| 31719 | BC052883: cDNA sequence BC052883 | 3547.69 | 3957.6 | 3518.81 | 3150.9 | 2830 | 3065 | 843.8 | 1089 | 690.96 | 1.889427057 | 0.024390244 | 0.05562782 | 21.7701 |
| 14991 | Bcas2: breast carcinoma amplified sequence 2 | 933.79 | 898.82 | 1023.13 | 656.47 | 683.52 | 725.1 | 238.6 | 384.1 | 299.55 | 1.911914063 | 0.037546934 | 0.07496454 | 14.8965 |
| 4790 | Blcap: bladder cancer associated protein homolog (human) | 1031.43 | 970.72 | 1005.09 | 398.98 | 455.59 | 428.7 | 593.8 | 433.6 | 467.82 | 2.1646422 | 0.025236593 | 0.0544428 | 23.1594 |
| 7998 | Btf3: basic transcription factor 3 | 1578.04 | 1824.5 | 1702.45 | 1348.1 | 1356.3 | 1018 | 743.3 | 874.9 | 818.67 | 1.657623607 | 0.03609816 | 0.07552147 | 14.7389 |
| 27083 | C030048B08Rik: RIKEN cDNA C030048B08 gene | 408.49 | 460.05 | 549.24 | 205.03 | 223.41 | 242.7 | 206.1 | 243.9 | 160.9 | 2.211756263 | 0.036991369 | 0.07569667 | 14.7567 |
| 31101 | C330046E03: hypothetical protein C330046E03 | 4819.33 | 3225.1 | 3559.24 | 755.8 | 537.22 | 920.6 | 495.6 | 490.6 | 1006.3 | 5.517476831 | 0 | 0.005 | 199.636 |
| 43660 | C80008: expressed sequence C80008 | 387.88 | 488.55 | 927.38 | 95.78 | 305.61 | 74.02 | 92.37 | 277.2 | 122.15 | 3.730232751 | 0.018867925 | 0.03821803 | 32.1199 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 41465 | C87977: expressed sequence C87977 | 1813.37 | 1754 | 1731.6 | 1381 | 1479.5 | 1226 | 879 | 1054 | 758.51 | 1.563607178 | 0.0472103 | 0.09198283 | 11.8126 |
| 22912 | Calcocol: calcium binding and coiled coil domain 1 | 551.7 | 236.85 | 422.22 | 259.49 | 280.12 | 113.5 | 190.8 | 154.3 | 163.4 | 2.084497585 | 0.044790652 | 0.08589094 | 12.8067 |
| 8101 | Camk2g: calcium/calmodulin-dependent protein kinase II gamma | 336.31 | 254.03 | 256.42 | 116.66 | 94.65 | 136.1 | 97.12 | 109.2 | 105.92 | 2.567339761 | 0.04613936 | 0.08864721 | 12.4665 |
| 11172 | Car9: carbonic anhydrase 9 | 471.81 | 315.93 | 321.74 | 92.43 | 324.34 | 121.6 | 91.77 | 148.2 | 106.79 | 2.507101133 | 0.045 | 0.08457333 | 13.0189 |
| 270 | Carhsp1: calcium regulated heat stable protein 1 | 783.29 | 492.05 | 805.9 | 323.58 | 378.15 | 367.8 | 428.5 | 461.3 | 410.2 | 1.756676458 | 0.038106236 | 0.077602 | 14.2229 |
| 15424 | Cdc102a /// LOC672218: coiled-coil domain containing 102A /// similar to CG31638-PA | 88.88 | 90.52 | 37.42 | 3.07 | 8.66 | 4.42 | 4.14 | 2.85 | 2.42 | 16.96557121 | 0.027027027 | 0.06286358 | 18.4783 |
| 4096 | Cdc56: coiled-coil domain containing 56 | 392.74 | 395.1 | 319.83 | 208.46 | 301.88 | 148.4 | 177.1 | 110 | 108.37 | 2.101282392 | 0.044310171 | 0.08402148 | 13.0746 |
| 22624 | Cdc69: Coiled-coil domain containing 69 | 962.65 | 1366.1 | 1349.11 | 634.59 | 688.1 | 744 | 606.2 | 369.6 | 463.47 | 2.098090669 | 0.019230769 | 0.0436859 | 28.4695 |
| 22741 | Cdc69: coiled-coil domain containing 69 | 1132.93 | 1623.1 | 1851.99 | 805.4 | 1046.3 | 856 | 984.6 | 482 | 775.42 | 1.861933951 | 0.022535211 | 0.05503286 | 22.1289 |
| 22623 | Cdc69: coiled-coil domain containing 69 | 1050.67 | 1566.1 | 1589.84 | 762.24 | 1001.9 | 968.9 | 918.1 | 524.8 | 763.31 | 1.703329676 | 0.027079304 | 0.06286912 | 18.4874 |
| 16411 | Ccni: cyclin I | 493.47 | 644.26 | 702.9 | 315.9 | 404.45 | 474.9 | 206.1 | 318.3 | 253.34 | 1.865932038 | 0.042944785 | 0.08317314 | 13.192 |
| 16410 | Ccni: cyclin I | 995.58 | 940.06 | 798.15 | 555.77 | 798.27 | 475.2 | 498.2 | 513.86 | 309.27 | 1.735447687 | 0.045499505 | 0.08530828 | 12.9222 |
| 44690 | Ccnjl: cyclin J-like | 710.33 | 626.07 | 346.33 | 315.27 | 210.57 | 294 | 79.62 | 182.2 | 113.19 | 2.816638072 | 0.017647059 | 0.03870588 | 31.472 |
| 329 | Cd24a: CD24a antigen | 1205 | 1433.8 | 1104.89 | 719.21 | 978.74 | 647.6 | 776.5 | 731.8 | 580.28 | 1.688576461 | 0.047178538 | 0.08963306 | 12.3197 |
| 6122 | Cdc25b: cell division cycle 25 homolog B (S. cerevisiae) | 1318 | 1113.9 | 1472.91 | 1078.3 | 923.92 | 886.1 | 576.7 | 563.7 | 362.23 | 1.778541969 | 0.036144578 | 0.07362784 | 15.3818 |
| 15802 | Cdc9111: CDC91 cell division cycle 91-like 1 (S. cerevisiae) | 49.58 | 345.26 | 607.45 | 52.03 | 65.68 | 20.93 | 52.8 | 45.12 | 27.03 | 7.604916727 | 0 | 0.03 | 60.8874 |
| 12970 | Cdca1: cell division cycle associated 1 | 674.36 | 667 | 543.88 | 296.75 | 413.81 | 246.4 | 141.6 | 321.8 | 221.52 | 2.296412693 | 0.022038567 | 0.05520661 | 21.9807 |
| 42049 | Cdk9: cyclin-dependent kinase 9 (CDC2-related kinase) | 139.64 | 199.95 | 196.21 | 14.31 | 19.14 | 29.4 | 35.55 | 8.3 | 51.82 | 6.76003028 | 0.014285714 | 0.03807143 | 33.6461 |
| 8112 | Cdkal1: CDK5 regulatory subunit associated protein 1-like 1 | 879.67 | 767.38 | 813.54 | 253.82 | 513.83 | 385.5 | 494.5 | 208.3 | 137.41 | 2.468897841 | 0.022177419 | 0.04872312 | 26.1509 |
| 3196 | Cebpb: CCAAT/enhancer binding protein (C/EBP), beta | 132 | 304.11 | 204.27 | 35.5 | 57.66 | 60.4 | 8.94 | 15.35 | 29.75 | 6.169364162 | 0.018404908 | 0.03862986 | 31.7317 |
| 19532 | Chchd5: coiled-coil-helix-coiled-coil-helix domain containing 5 | 220.46 | 43.46 | 183.56 | 95.26 | 39.57 | 75.13 | 40.76 | 8.84 | 10.24 | 3.317123795 | 0.042857143 | 0.0835 | 13.1659 |
| 21181 | Chchd7: coiled-coil-helix-coiled-coil-helix domain containing 7 | 143.11 | 45.85 | 147.48 | 54.41 | 37.61 | 40.61 | 18.63 | 32.67 | 27.57 | 3.181465721 | 0.045320197 | 0.08514614 | 12.9126 |
| 14624 | Chd4: chromodomain helicase DNA binding protein 4 | 618.5 | 949.18 | 1142.49 | 391 | 589.16 | 319.2 | 415.8 | 423.6 | 527.37 | 2.033097654 | 0.0243309 | 0.05852393 | 20.5004 |
| 15480 | Chd4: chromodomain helicase DNA binding protein 4 | 1585.68 | 1818.1 | 1935.42 | 1226.8 | 1598.3 | 1198 | 946.6 | 909.1 | 980.36 | 1.556702038 | 0.044834308 | 0.0858642 | 12.8114 |
| 15075 | Clu: clusterin | 196.31 | 133.06 | 97.6 | 58.66 | 66.23 | 26.33 | 41.53 | 27.45 | 12.04 | 3.676972098 | 0.04567079 | 0.08815414 | 12.5518 |
| 2308 | Cml1: camello-like 1 | 47.86 | 117.93 | 133.93 | 4.92 | 25.59 | 4.56 | 62.29 | 5.09 | 4.57 | 5.601196038 | 0.032520325 | 0.06910569 | 16.8467 |
| 14516 | Cnot3: CCR4-NOT transcription complex, subunit 3 | 796.98 | 668.81 | 778.76 | 366.48 | 721.23 | 392.7 | 402.2 | 266.4 | 437.76 | 1.735481277 | 0.048182587 | 0.09296422 | 11.6855 |
| 3016 | Cops7b: COP9 (constitutive photomorphogenic) homolog, subunit 7b (Arabidopsis thaliana) | 630.4 | 592.56 | 784.56 | 381.57 | 313.14 | 269.3 | 386 | 255.5 | 166.93 | 2.265261447 | 0.027422303 | 0.06459476 | 17.9807 |
| 9970 | Csrp1: cysteine and glycine- | 592.11 | 830.02 | 1000.51 | 402.09 | 254.56 | 515.3 | 117.8 | 186.2 | 282.36 | 2.755708736 | 0.014388489 | 0.03784173 | 33.681 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 42439 | Cxcl1: chemokine (C—X—C motif) ligand 1 rich protein 1 | 22.86 | 80.3 | 90.94 | 1.97 | 4.77 | 2.02 | 4.71 | 2.48 | 4.31 | 19.16090819 | 0.033639144 | 0.07090724 | 16.3534 |
| 3504 | Cxcl1: chemokine (C—X—C motif) ligand 1 | 47.52 | 119.73 | 89.85 | 17.25 | 11.6 | 15.44 | 9.7 | 10.43 | 6.75 | 7.224954335 | 0.036904762 | 0.07630159 | 14.5178 |
| 16786 | Cxcr4: chemokine (C—X—C motif) receptor 4 | 358.53 | 513.32 | 197.69 | 121.26 | 183.91 | 87.45 | 18.1 | 32.91 | 17.61 | 4.637672361 | 0.010526316 | 0.03778947 | 38.9113 |
| 30909 | Cyp11a1: cytochrome P450, family 11, subfamily a, polypeptide 1 | 258.01 | 292.08 | 442.1 | 107.55 | 178.36 | 106.1 | 178.5 | 12.51 | 54.95 | 3.11031348 | 0.032051282 | 0.06915064 | 16.7746 |
| 41238 | Cyp3: cysteine-rich perinuclear theca 3 | 423.83 | 155.74 | 395.11 | 142.52 | 146.78 | 84.29 | 153.7 | 281.9 | 54.27 | 2.257667006 | 0.036855037 | 0.07558149 | 14.7418 |
| 17076 | D10Jhu81e: DNA segment, Chr 10, Johns Hopkins University 81 expressed | 1166.3 | 278.18 | 584.98 | 41.06 | 273.73 | 194.1 | 342.2 | 66.45 | 240.74 | 3.504143933 | 0.01744186 | 0.0394186 | 31.3457 |
| 21185 | D10Wsu102e: DNA segment, Chr 10, Wayne State University 102, expressed | 2792.95 | 2498.7 | 2814.16 | 1716.1 | 1847 | 1338 | 1962 | 1712 | 1576.6 | 1.596805904 | 0.026666667 | 0.06302222 | 18.3654 |
| 31660 | D11Ertd497e: DNA segment, Chr 11, ERATO Doi 497, expressed | 1363.15 | 1027.4 | 1189.28 | 742.66 | 758.15 | 478.8 | 680.6 | 595 | 536.27 | 1.888339413 | 0.027726433 | 0.06448552 | 18.0557 |
| 32944 | D130073L02Rik: RIKEN cDNA D130073L02 gene | 1475.86 | 1476.2 | 1683.68 | 818.11 | 1061.5 | 984.4 | 665.5 | 689 | 969.73 | 1.787029488 | 0.03442619 | 0.0715377 | 16.1158 |
| 19130 | D14Ertd500e: DNA segment, Chr 14, ERATO Doi 500, expressed | 681.58 | 601.92 | 716.43 | 390.44 | 459.16 | 256.8 | 360.4 | 265.9 | 425.26 | 1.853614907 | 0.045226131 | 0.08424791 | 13.0523 |
| 29688 | D2Ertd612e: DNA segment, Chr2, ERATO Doi 612, expressed | 319.43 | 176.06 | 370.14 | 220.95 | 120.36 | 106 | 116.2 | 108.1 | 103.63 | 2.233105886 | 0.043294615 | 0.08247448 | 13.4481 |
| 7623 | D2Ertd750e: DNA segment, Chr 2, ERATO Doi 750, expressed | 394.9 | 506.08 | 652.28 | 243.42 | 291.26 | 438 | 219.8 | 255.7 | 110.89 | 1.9925724 | 0.047619048 | 0.09278752 | 11.6257 |
| 17383 | Dbnd1: dysbindin (dystrobrevin binding protein 1) domain containing 1 | 464.15 | 301.44 | 304.82 | 104.24 | 166.01 | 137.6 | 190.5 | 70.39 | 112.63 | 2.739969027 | 0.037174721 | 0.07516316 | 14.8291 |
| 41824 | Dbx1: developing brain homeobox 1 | 276.19 | 187.2 | 124.35 | 38.52 | 58.77 | 7.62 | 29.55 | 11.63 | 10.84 | 7.49047346 | 0.01459854 | 0.03824818 | 33.796 |
| 6290 | Dcp1a: decapping enzyme | 577.73 | 499.84 | 520.9 | 251.84 | 361.9 | 184 | 289.1 | 278.2 | 245.94 | 1.984530675 | 0.04600939 | 0.08865102 | 12.4452 |
| 542 | Dctn3: dynactin 3 | 540.25 | 352.08 | 532.14 | 252.9 | 202.65 | 271.3 | 222 | 154 | 123.8 | 2.322461258 | 0.02244389 | 0.05806318 | 20.7509 |
| 1811 | Ddit3: DNA-damage inducible transcript 3 | 499.34 | 650.01 | 844 | 254.47 | 351.31 | 188.1 | 199 | 274.8 | 371.53 | 2.432175213 | 0.027727273 | 0.05471591 | 22.2271 |
| 9363 | Ddx19a /// Ddx19b: DEAD (Asp-Glu-Ala-Asp) box polypeptide 19a /// DEAD (Asp-Glu-Ala-Asp) box polypeptide 19b | 1578.61 | 1941.1 | 1533.78 | 1167.2 | 1152.7 | 885.9 | 897.4 | 1007 | 1064.7 | 1.636896915 | 0.048 | 0.09173926 | 12.0151 |
| 2222 | Ddx19a: DEAD (Asp-Glu-Ala-Asp) box polypeptide 19a | 1009.15 | 1114.6 | 1292.36 | 497.39 | 638.59 | 587.9 | 581.9 | 501.6 | 556.5 | 2.031071632 | 0.024154589 | 0.0584219 | 20.4566 |
| 36061 | Dgat1: diacylglycerol O-acyltransferase 1 | 289.38 | 324.34 | 39.41 | 98.71 | 107.58 | 55.58 | 34.36 | 61.27 | 22.93 | 3.43364088 | 0.027600849 | 0.059908 | 19.4349 |
| 24651 | Dhfr: dihydrofolate reductase | 426.78 | 75.47 | 340.75 | 63.57 | 73.72 | 47.34 | 58.38 | 22.96 | 36.07 | 5.582042114 | 0.018867925 | 0.03471698 | 49.1336 |
| 16466 | Dhrs3: dehydrogenase/reductase (SDR family) member 3 | 175.77 | 358.46 | 397.37 | 163.62 | 207.39 | 44.67 | 59.21 | 66.67 | 115.31 | 2.836482105 | 0.02247191 | 0.05490637 | 22.1263 |
| 36303 | Diras2: DIRAS family, GTP- | 83.58 | 244.42 | 311.89 | 57.09 | 96.41 | 29.57 | 84.61 | 77.33 | 98.72 | 2.884141257 | 0.03164557 | 0.06949895 | 16.6642 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 14159 | binding RAS-like 2 Dmpk: dystrophia myotonica-protein kinase | 130.39 | 64.65 | 251.65 | 43.94 | 24.65 | 45.01 | 36.88 | 47.29 | 31.12 | 3.903097558 | 0.044573643 | 0.08648256 | 12.7504 |
| 18463 | Dnajb5: DnaJ (Hsp40) homolog, subfamily B, member 5 | 173.41 | 174.8 | 38.49 | 23.48 | 43.07 | 40.6 | 23.62 | 34.57 | 27 | 4.021004471 | 0.024943311 | 0.05890401 | 20.0001 |
| 1165 | Dnalc4: dynein, axonemal, light chain 4 | 627.08 | 485.5 | 527.62 | 152.51 | 208.44 | 124.3 | 259.5 | 384 | 378.63 | 2.176154117 | 0.037783375 | 0.07515533 | 14.9173 |
| 4618 | Dscr6: Down syndrome critical region homolog 6 (human) | 364.43 | 202.42 | 53.05 | 100.55 | 71.25 | 41.67 | 57.79 | 52.26 | 26.72 | 3.539858383 | 0.033383915 | 0.07102175 | 16.2903 |
| 14348 | Dsp: desmoplakin | 348.74 | 368.07 | 172.59 | 17.12 | 59.21 | 37.98 | 120.1 | 62.81 | 35.6 | 5.344951923 | 0.018181818 | 0.03509091 | 48.1504 |
| 44606 | Dynlt3: dynein light chain Tctex-type 3 | 1184.16 | 850.7 | 1225.34 | 804.47 | 862.49 | 821.8 | 513.8 | 484.1 | 546.26 | 1.616793787 | 0.044487427 | 0.0865087 | 12.7286 |
| 30501 | E130311K13Rik: RIKEN cDNA E130311K13 gene | 292.14 | 72.05 | 149.12 | 73.07 | 44.21 | 47.25 | 43.95 | 46.76 | 53.87 | 3.321212513 | 0.048373645 | 0.09281346 | 11.6139 |
| 1360 | Egr1: early growth response 1 | 863.82 | 594.38 | 874.96 | 651.4 | 743.85 | 349.3 | 362.2 | 301.7 | 296.64 | 1.725097598 | 0.047790803 | 0.0904749 | 12.1522 |
| 28198 | Ehd2 /// LOC673251: EH-domain containing 2 /// similar to EH-domain containing 2 | 552.22 | 499.34 | 187.9 | 118.31 | 170.8 | 197.3 | 120 | 329.7 | 107.65 | 2.375217983 | 0.024691358 | 0.0582963 | 20.6613 |
| 3769 | Ehf: ets homologous factor | 422.95 | 299.88 | 362.77 | 181.23 | 308.34 | 201 | 118.5 | 82.28 | 115.52 | 2.156471301 | 0.048128342 | 0.09172906 | 12.0251 |
| 6059 | Eif2ak1: eukaryotic translation initiation factor 2 alpha kinase 1 | 601.03 | 422.26 | 534.76 | 313.33 | 270.08 | 133.6 | 249.2 | 221.6 | 232.52 | 2.194034895 | 0.032019704 | 0.06823755 | 16.968 |
| 22574 | Eif2b1: eukaryotic translation initiation factor 2B, subunit 1 (alpha) | 639.36 | 591.13 | 452.83 | 426.81 | 356.95 | 299.3 | 292.9 | 218.6 | 271.63 | 1.804037146 | 0.047939445 | 0.09294365 | 11.6628 |
| 41276 | Emx2: empty spiracles homolog 2 (Drosophila) | 234.91 | 298.01 | 341.22 | 97.13 | 165.98 | 119.9 | 85.52 | 182 | 66.68 | 2.437578428 | 0.037585421 | 0.078265 | 14.0886 |
| 27167 | Faah: fatty acid amide hydrolase | 147.03 | 240.15 | 277.1 | 108.99 | 47.52 | 58.21 | 61.45 | 124.1 | 50.02 | 2.950192081 | 0.030252101 | 0.06778151 | 17.1504 |
| 316 | Fabp5 /// LOC628298 /// LOC637129 /// LOC669559 /// LOC672321: fatty acid binding protein 5, epidermal /// similar to Fatty acid-binding protein, epidermal (E-FABP) (Psoriasis-associated fatty acid-binding protein homolog) (PA-FABP) (Keratinocyte lipid-binding protein) /// similar to Fatty acid-binding protein, epidermal (E-FABP) (Psoriasis-associated fatty acid-binding protein homolog) (PA-FABP) (Keratinocyte lipid-binding protein) /// similar to | 1266.08 | 1469.8 | 1868.49 | 809.42 | 1034.2 | 1028 | 272.5 | 598 | 286.82 | 2.285431361 | 0.019417476 | 0.04377023 | 28.5422 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| | Fatty acid-binding protein, epidermal (E-FABP) (Psoriasis-associated fatty acid-binding protein homolog) (PA-FABP) (Keratinocyte lipid-binding protein) | | | | | | | | | | | | | |
| 317 | Fabp5: fatty acid binding protein 5, epidermal | 436.27 | 439.2 | 537.34 | 241.63 | 390.24 | 301.4 | 62.47 | 184.3 | 99.47 | 2.208430053 | 0.048387097 | 0.09106631 | 12.0981 |
| 1371 | Fabp9: fatty acid binding protein 9, testis | 409.89 | 270.29 | 333.46 | 189.49 | 58.21 | 125.5 | 90.91 | 122.6 | 177.68 | 2.652431605 | 0.029900332 | 0.06765227 | 17.1013 |
| 38293 | Fank1: fibronectin type 3 and ankyrin repeat domains 1 | 2043.72 | 1333.2 | 2424.93 | 1297.9 | 895.96 | 1029 | 224.5 | 906.6 | 897.4 | 2.20974613 | 0.014705882 | 0.03808824 | 33.9309 |
| 38294 | Fank1: fibronectin type 3 and ankyrin repeat domains 1 | 924.97 | 617.49 | 1115.41 | 530.43 | 486.47 | 334.5 | 325.3 | 374.2 | 450.52 | 2.125114436 | 0.022792023 | 0.0548433 | 22.228 |
| 28859 | Fbxw14 /// LOC668758 /// LOC673189: F-box and WD-40 domain protein 14 /// similar to F-box and WD-40 domain protein 14 /// similar to F-box and WD-40 domain protein 14 | 1689.47 | 1449.1 | 1379.4 | 771.7 | 977.11 | 774 | 924.7 | 979.8 | 930.52 | 1.686457855 | 0.04250797 | 0.08190932 | 13.5148 |
| 17631 | Fetub: fetuin beta | 339.98 | 98.9 | 176.78 | 28.16 | 22.02 | 28.89 | 47.19 | 149.6 | 27.08 | 4.064701416 | 0.030050083 | 0.06791319 | 17.1106 |
| 18896 | Fgf1: fibroblast growth factor 1 | 681.86 | 369.41 | 720.7 | 327.77 | 349.5 | 445.6 | 311.8 | 285.3 | 249.7 | 1.799219174 | 0.038548753 | 0.07857143 | 14.042 |
| 16430 | G6pdx: glucose-6-phosphate dehydrogenase X-linked | 1968.98 | 1787.5 | 2156.26 | 787.91 | 1751.9 | 1060 | 912.4 | 963.3 | 1065.4 | 1.807953743 | 0.022900763 | 0.05866836 | 20.8236 |
| 20610 | Galm: galactose mutarotase | 325.39 | 308.96 | 339.4 | 107.5 | 239.54 | 178.8 | 127.7 | 148.9 | 72.69 | 2.225459947 | 0.047488584 | 0.09021005 | 12.2255 |
| 32346 | Gas2l1: growth arrest-specific 2 like 1 | 161.84 | 235.35 | 19.91 | 17.07 | 61.3 | 43.92 | 20.12 | 11.33 | 52.21 | 4.050497694 | 0.045454545 | 0.0852668 | 12.9177 |
| 12777 | Gch1: GTP cyclohydrolase 1 | 398.77 | 412.01 | 533.59 | 236.21 | 254.72 | 224.9 | 133.7 | 148.3 | 134.69 | 2.37426818 | 0.0373599 | 0.07496056 | 14.8721 |
| 38302 | Ghitm: Growth hormone inducible transmembrane protein | 167.4 | 64.72 | 61.47 | 5.07 | 13.4 | 2.06 | 3.34 | 4.13 | 8.35 | 16.15350757 | 0.037714286 | 0.07841524 | 14.1066 |
| 27801 | Gm129: gene model 129, (NCBI) | 962.68 | 506.38 | 860.85 | 158.2 | 317.4 | 272.4 | 320.2 | 434.4 | 279.11 | 2.615437289 | 0.014925373 | 0.03823383 | 34.0765 |
| 31138 | Gm1568: gene model 1568, (NCBI) | 543.23 | 1089.3 | 807.32 | 324.93 | 568.66 | 388.6 | 233.9 | 198.5 | 219.96 | 2.522390451 | 0.01754386 | 0.04565789 | 27.2403 |
| 16058 | Gm428 /// LOC623180 /// LOC623197 /// LOC623210 /// LOC623219: gene model 428, (NCBI) /// hypothetical LOC623180 /// hypothetical LOC623197 /// hypothetical LOC623210 /// hypothetical LOC623219 | 1914.89 | 1546.2 | 1987.58 | 718.98 | 1301.8 | 938 | 1086 | 1344 | 986.94 | 1.709161859 | 0.026694045 | 0.06009582 | 19.1631 |
| 17875 | Gna14: guanine nucleotide binding protein, alpha 14 | 300.19 | 342.97 | 390.91 | 109.58 | 273.46 | 141.3 | 122.7 | 96.2 | 128.54 | 2.372264281 | 0.037558685 | 0.07721831 | 14.351 |
| 27857 | Gnaz: guanine nucleotide binding protein, alpha z subunit | 291.26 | 148.83 | 411.78 | 101.45 | 157.63 | 114.7 | 126.2 | 93.34 | 143.95 | 2.311190092 | 0.045837231 | 0.08869036 | 12.4247 |
| 3764 | Gnb4: guanine nucleotide binding protein, beta 4 | 800.06 | 500.22 | 743.39 | 483.85 | 537.75 | 253.1 | 157.9 | 393.7 | 258.05 | 1.960947433 | 0.033674963 | 0.07097609 | 16.075 |
| 1723 | Gng3: guanine nucleotide binding protein (G protein), | 1141.11 | 1006.1 | 938.92 | 376.96 | 611.22 | 390.9 | 606.5 | 482.2 | 588.54 | 2.019579614 | 0.026369168 | 0.06075727 | 19.0026 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 38463 | Gng3: guanine nucleotide binding protein (G protein), gamma 3 subunit | 29.31 | 68.46 | 318.22 | 20.93 | 10.51 | 15.87 | 14.53 | 12.26 | 10.91 | 9.786848606 | 0.04808476 | 0.09437924 | 11.4171 |
| 14851 | Gng5: guanine nucleotide binding protein (G protein), gamma 5 subunit | 751.62 | 1021.2 | 1032.02 | 380.3 | 617.1 | 541.3 | 307.9 | 450.5 | 359.29 | 2.111806714 | 0.021428571 | 0.05125 | 24.5286 |
| 19438 | Gprc5b: G protein-coupled receptor, family C, group 5, member B | 306.88 | 118.93 | 6.69 | 4.77 | 9.28 | 5.32 | 8.02 | 2.74 | 32.26 | 13.86440135 | 0.023346304 | 0.05102464 | 25.4672 |
| 14609 | Grina: glutamate receptor, ionotropic, N-methyl D-asparate-associated protein 1 (glutamate binding) | 1034.42 | 812.15 | 1228.38 | 477.25 | 540.8 | 546.5 | 285.4 | 670.3 | 531.6 | 2.015164771 | 0.027088036 | 0.0592927 | 19.9298 |
| 15539 | Grn: granulin | 1352.59 | 514.79 | 1057.39 | 324.87 | 349.47 | 237.6 | 326.6 | 429.6 | 434.48 | 2.782090489 | 0.012820513 | 0.03683761 | 41.8478 |
| 21945 | Grn: granulin | 1042.32 | 422.35 | 831.7 | 282.08 | 293.46 | 176.8 | 252.5 | 333.1 | 327.99 | 2.756746699 | 0.017094017 | 0.03763533 | 35.8799 |
| 44280 | Gyg: glycogenin | 1636.26 | 1537.6 | 1912.79 | 587.38 | 955.09 | 642.4 | 640.7 | 735.8 | 665.37 | 2.406956662 | 0.01754386 | 0.03795322 | 36.2379 |
| 16505 | Gyg: glycogenin | 1843.18 | 1330 | 1474.57 | 451.38 | 788.27 | 545 | 633.2 | 808.2 | 736.02 | 2.346160253 | 0.01863354 | 0.03867495 | 31.8723 |
| 21695 | Hadhsc: L-3-hydroxyacyl-Coenzyme A dehydrogenase, short chain | 176.86 | 172.31 | 47.15 | 7.97 | 25.17 | 8.67 | 37.31 | 48.56 | 24.68 | 5.202415332 | 0.024475524 | 0.05073427 | 24.4128 |
| 20748 | Hba-a1: hemoglobin alpha, adult chain 1 | 145.01 | 91.26 | 185.79 | 31.03 | 31.41 | 48.27 | 14.05 | 70.23 | 28.93 | 3.769739193 | 0.037667072 | 0.07575132 | 14.6733 |
| 34409 | Hdlbp: High density lipoprotein (HDL) binding protein | 65.43 | 20.02 | 222.9 | 4.86 | 15.41 | 2.9 | 23.01 | 5.26 | 6.4 | 10.66217151 | 0.048414023 | 0.09280467 | 11.6202 |
| 21722 | Hes5: hairy and enhancer of split 5 (Drosophila) | 77.81 | 670.65 | 255.74 | 37.89 | 6.51 | 4.11 | 5.4 | 49.42 | 10.01 | 17.72013411 | 0 | 0.03571429 | 76.3251 |
| 14548 | Hes6: hairy and enhancer of split 6 (Drosophila) | 874.59 | 449.21 | 52.72 | 14.43 | 115.08 | 53.85 | 47.95 | 155.1 | 45.4 | 6.375581853 | 0 | 0.03063063 | 57.3556 |
| 294 | Hey1: hairy/enhancer-of-split related with YRPW motif 1 | 782.14 | 951.79 | 1330.97 | 370.68 | 579.38 | 458.1 | 340.9 | 320.2 | 328.5 | 2.556469371 | 0.019900498 | 0.04260365 | 29.0333 |
| 40573 | Hist2h2be: histone 2, H2be | 45.26 | 112.92 | 234.65 | 9.51 | 47.79 | 32.3 | 12.23 | 14.75 | 13.01 | 6.062659156 | 0.032357473 | 0.07042116 | 16.4512 |
| 15290 | Hk1: hexokinase 1 | 97.53 | 40.72 | 292.16 | 23.48 | 13.09 | 10.02 | 17.7 | 8.41 | 70.37 | 6.016775005 | 0.045279383 | 0.08702954 | 12.6818 |
| 1997 | Hnmt: histamine N-methyltransferase | 291.41 | 218.29 | 287.13 | 133.75 | 161.6 | 140.3 | 63.03 | 104.4 | 82.11 | 2.325899764 | 0.042619543 | 0.08295565 | 13.3018 |
| 20448 | Hoxa3: homeo box A3 | 67.37 | 168.06 | 195.07 | 30.43 | 54.67 | 3.04 | 114.4 | 21.42 | 18.67 | 3.549198236 | 0.036643026 | 0.07695823 | 14.4359 |
| 38029 | Hspa1a: heat shock protein 1A | 99.91 | 395.12 | 430.36 | 63.95 | 34.34 | 2.89 | 11.27 | 190.3 | 15.72 | 5.810743776 | 0 | 0.02886179 | 56.2068 |
| 20415 | Hspa1b: heat shock protein 1B | 665.51 | 521.22 | 682.91 | 384.53 | 418.07 | 300.9 | 177.6 | 256.6 | 240.21 | 2.103200405 | 0.026717557 | 0.06280534 | 18.4144 |
| 20345 | Hspa12a: heat shock protein 12A | 1356.32 | 1044 | 604.27 | 612.34 | 519.36 | 458.8 | 326.2 | 890.6 | 200.5 | 1.997912074 | 0.030201342 | 0.06785794 | 17.1351 |
| 11286 | Hspa1b: heat shock protein 1B | 603.12 | 550.63 | 273.69 | 292.64 | 253.66 | 243.1 | 178.7 | 397.6 | 109.8 | 1.934869094 | 0.04518664 | 0.08519974 | 12.8968 |
| 1396 | Hspa2: heat shock protein 2 | 1671.68 | 1450.9 | 1466.81 | 768.33 | 1325.6 | 888 | 653 | 1010 | 758.87 | 1.698705433 | 0.041845494 | 0.08110515 | 13.6108 |
| 3507 | Icos1: icos ligand | 698.31 | 470.26 | 803.79 | 259.27 | 478.54 | 329.9 | 299.9 | 350.5 | 227.76 | 2.027216478 | 0.030508475 | 0.06688701 | 17.2922 |
| 14244 | Id2: inhibitor of DNA binding 2 | 159.2 | 175.61 | 225 | 87.31 | 76.02 | 44.55 | 20.82 | 47.44 | 37.67 | 3.567827666 | 0.036262204 | 0.0725709 | 15.7007 |
| 3942 | Ier3: immediate early response 3 | 135.39 | 282.8 | 200.44 | 43.45 | 88.87 | 51.5 | 102.8 | 52.75 | 30 | 3.349649403 | 0.032407407 | 0.07047325 | 16.4563 |
| 5812 | Igh-VJ558 /// LOC238447 /// LOC544903 /// LOC544907: immunoglobulin heavy chain (J558 family) /// similar to | 796.82 | 447.15 | 483.63 | 357.22 | 539.3 | 266.5 | 77.64 | 114.2 | 116.29 | 2.348686715 | 0.047531993 | 0.09001828 | 12.2414 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 18787 | immunoglobulin heavy chain variable region /// similar to immunoglobulin mu-chain /// similar to anti-poly(dC) monoclonal antibody heavy chain | 797.55 | 862.17 | 1017.87 | 636.48 | 680.07 | 589 | 200.3 | 400.2 | 302.52 | 1.906748702 | 0.041980624 | 0.08096161 | 13.6303 |
| 40325 | Ing3: inhibitor of growth family, member 3 | 2692.54 | 2321.2 | 2684.68 | 1690.3 | 1802.6 | 1778 | 1643 | 1631 | 1533.5 | 1.527618507 | 0.035150646 | 0.07234338 | 15.8472 |
| 16512 | Insig1: insulin induced gene 1 | 789.3 | 575.41 | 867.38 | 269.32 | 522.82 | 348.8 | 278.6 | 292.6 | 194.46 | 2.341447296 | 0.022900763 | 0.05101781 | 25.2531 |
| 2812 | Irf1: interferon regulatory factor 1 | 348.55 | 332.29 | 138.19 | 5.68 | 121.77 | 63.47 | 127.6 | 69.42 | 60.1 | 3.656465546 | 0.017857143 | 0.04482143 | 27.5757 |
| 18056 | Irx3: Iroquois related homeobox 3 (Drosophila) | 602.24 | 988.31 | 1038.91 | 552.93 | 662.74 | 418.5 | 555.2 | 457.9 | 546.34 | 1.646726537 | 0.042268041 | 0.08298625 | 13.2595 |
| 1704 | Itga9: integrin alpha 9 | 824.08 | 580.75 | 436.92 | 74.84 | 119.42 | 26.57 | 109.4 | 37.89 | 28.35 | 9.290272138 | 0 | 0.02583333 | 113.684 |
| 38760 | Jun: Jun oncogene | 455.34 | 326.78 | 526.39 | 276.27 | 277.62 | 210.1 | 85.33 | 54.31 | 126.1 | 2.541487006 | 0.028697572 | 0.05972774 | 19.7266 |
| 17540 | Kalrn: kalirin, RhoGEF kinase | 253.97 | 94.35 | 476.89 | 62.84 | 42.18 | 56.37 | 133.6 | 55.74 | 24.75 | 4.395844986 | 0.020661157 | 0.04779614 | 26.4773 |
| 38646 | Kcnq1: potassium voltage-gated channel, subfamily Q, member 1 | 341.25 | 421.32 | 771.62 | 218.81 | 258.08 | 529 | 77.71 | 47.73 | 84.33 | 2.524106842 | 0.047169811 | 0.09193539 | 11.8117 |
| 25517 | Kif13a: Kinesin family member 13A | 338.53 | 277.95 | 398.92 | 132.82 | 85.27 | 159.4 | 147.6 | 148.5 | 106.19 | 2.604290899 | 0.029801325 | 0.06786424 | 17.0703 |
| 16345 | Kif24: kinesin family member 24 | 1515.8 | 1527.5 | 1239.11 | 1454.6 | 785.49 | 962.1 | 538.2 | 329.8 | 445.64 | 1.896626556 | 0.026966292 | 0.05925094 | 19.8985 |
| 13958 | Klhl13: kelch-like 13 (Drosophila) | 2740.69 | 2312.3 | 3295.47 | 1762 | 2507 | 1685 | 1417 | 2027 | 1678.1 | 1.507554068 | 0.045105566 | 0.087508 | 12.6371 |
| 5980 | Ldhb: lactate dehydrogenase B | 335.33 | 308.94 | 424.04 | 117.76 | 245.41 | 172 | 99.41 | 87.75 | 147.65 | 2.456054441 | 0.038283063 | 0.07753674 | 14.2499 |
| 29964 | Ldlr: low density lipoprotein receptor | 349.24 | 268.52 | 370.69 | 153.24 | 103.08 | 147.7 | 93.05 | 223.7 | 96.65 | 2.418344628 | 0.033873343 | 0.07123711 | 16.0846 |
| 916 | Ldlrad3: low density lipoprotein receptor class A domain containing 3 | 1297.45 | 1170.9 | 1328.72 | 919.12 | 927.65 | 845 | 526.8 | 632.3 | 506.16 | 1.742963703 | 0.036451169 | 0.07264099 | 15.6391 |
| 21355 | Llgl1: lethal giant larvae homolog 1 (Drosophila) | 2299.11 | 2394 | 2530.26 | 1703.4 | 2212.2 | 1824 | 1271 | 1373 | 1270.7 | 1.496467727 | 0.04749788 | 0.09230421 | 11.7338 |
| 32615 | Lmo7: LIM domain only 7 | 218.5 | 275.91 | 425.72 | 86.21 | 127.38 | 61.45 | 46.82 | 105.4 | 143.32 | 3.22507492 | 0.026315789 | 0.06088394 | 18.9799 |
| 14891 | LOC240444: Similar to Potassium voltage-gated channel subfamily G member 2 (Voltage-gated potassium channel subunit Kv6.2) (Cardiac potassium channel subunit) | 1517.86 | 1912.8 | 1961.88 | 1213.5 | 1373.7 | 1085 | 657.6 | 832.6 | 661.9 | 1.851793474 | 0.023890785 | 0.05119454 | 24.0588 |
| 19912 | LOC545161 /// LOC637273: similar to Peroxiredoxin 1 (Thioredoxin peroxidase 2) (Thioredoxin-dependent peroxide reductase 2) (Osteoblast specific factor 3) (OSF-3) (Macrophage 23 kDa stress protein) /// similar to Peroxiredoxin-1 (Thioredoxin peroxidase 2) (Thioredoxin-dependent peroxide reductase 2) (Osteoblast-specific factor 3) (OSF-3) (Macrophage 23 kDa stress protein) | 226.98 | 259.54 | 118.5 | 143.89 | 63.21 | 9.37 | 10.47 | 15.52 | 12.43 | 4.747302758 | 0.018957346 | 0.04349131 | 28.4084 |
| 34813 | LOC574530: metallothionein 1K LOC627488 /// LOC627520 | 3712.88 | 3330.1 | 4059.81 | 2547.1 | 3079.4 | 2572 | 1852 | 2591 | 2371.8 | 1.479044054 | 0.036719706 | 0.07589147 | 14.7015 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| | /// LOC667692 /// LOC667695 /// LOC673990: similar to THO complex subunit 4 (Tho4) (RNA and export factor binding protein 1) (REF1-I) (Ally of AML-1 and LEF-1) (Aly/REF) /// similar to THO complex subunit 4 (Tho4) (RNA and export factor binding protein 1) (REF1-I) (Ally of AML-1 and LEF-1) (Aly/REF) /// similar to THO complex subunit 4 (Tho4) (RNA and export factor binding protein 1) (REF1-I) (Ally of AML-1 and LEF-1) (Aly/REF) /// similar to THO complex subunit 4 (Tho4) (RNA and export factor binding protein 1) (REF1-I) (Ally of AML-1 and LEF-1) (Aly/REF) | | | | | | | | | | | | | |
| 36676 | LOC665521 /// LOC665546 /// LOC665755 /// LOC66203: similar to PRAME family member 8 /// similar to PRAME family member 8 /// similar to PRAME family member 8 /// similar to PRAME family member 8 | 1690.74 | 1078.8 | 1867.35 | 435.93 | 1040.6 | 413.3 | 298 | 288.9 | 409.86 | 3.212720848 | 0 | 0.02811594 | 69.6907 |
| 35372 | LOC666806: similar to X-linked eukaryotic translation initiation factor 1A | 1437.33 | 1258.1 | 1431.69 | 830.47 | 904.29 | 911.7 | 639.8 | 803.3 | 394.95 | 1.840602429 | 0.028508772 | 0.06025585 | 19.6427 |
| 23907 | LOC677447: similar to RIKEN cDNA 5730590G19-like | 169.23 | 96.13 | 289.52 | 47.67 | 49.17 | 46.11 | 50.1 | 30.45 | 38.54 | 4.235078614 | 0.026415094 | 0.06295597 | 18.313 |
| 2237 | Lypd3: Ly6/Plaur domain containing 3 | 398.36 | 354 | 401.18 | 228.49 | 210.36 | 118.7 | 246.3 | 99.17 | 235.65 | 2.026189368 | 0.047863248 | 0.09232479 | 11.7737 |
| 22323 | Lysmd3: LysM, putative peptidoglycan-binding, domain containing 3 | 453.85 | 368.82 | 661.12 | 92.84 | 321.95 | 197.1 | 125 | 290.1 | 91.81 | 2.6523721 | 0.026748971 | 0.0601166 | 19.1722 |
| 14392 | Marcksl1 /// LOC673071: MARCKS-like 1 /// similar to MARCKS-related protein (MARCKS-like protein 1) (Macrophage myristoylated alanine-rich C kinase | 1185.33 | 1143.2 | 1024.39 | 984.94 | 699.06 | 786.1 | 242.8 | 549.7 | 257.94 | 1.904808706 | 0.034833091 | 0.07184809 | 15.9639 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 14326 | Marcksl1: MARCKS-like 1 | 1090.15 | 1065.5 | 915.39 | 902.84 | 654.38 | 711.6 | 198.7 | 505.8 | 271.67 | 1.892871561 | 0.036890646 | 0.07380764 | 15.2728 |
| 9962 | Mbd2: methyl-CpG binding domain protein 2 | 705.4 | 147.62 | 1019.73 | 112.36 | 370.48 | 107.5 | 65.92 | 14.24 | 271.83 | 3.974764411 | 0.014288714 | 0.036 | 43.8036 |
| 1105 | Mea1: male enhanced antigen 1 | 542.92 | 668.6 | 745.81 | 373.15 | 443.27 | 291.3 | 373 | 331.2 | 364.96 | 1.798256252 | 0.047787611 | 0.09168732 | 11.9939 |
| 14305 | Mm.10009.3 | 245.87 | 217.16 | 188.38 | 53.3 | 153.42 | 55.43 | 78.1 | 79.43 | 58.1 | 2.726819875 | 0.04253112 | 0.08289765 | 13.2956 |
| 43719 | Mm.150985.1 | 393 | 518.17 | 908.05 | 363.36 | 370.12 | 406.2 | 195.3 | 152.2 | 111.3 | 2.276315543 | 0.045053869 | 0.08550767 | 12.8666 |
| 4333 | Mm.25004.1 | 145.84 | 123.93 | 76.52 | 26.6 | 44.95 | 15.88 | 28.28 | 3.92 | 34.91 | 4.481558173 | 0.037313433 | 0.07497512 | 14.8637 |
| 9278 | Mm.37131.1 | 290.79 | 409.6 | 147.87 | 153.64 | 67.38 | 113.6 | 173 | 47.35 | 77.8 | 2.681312429 | 0.035100287 | 0.07225406 | 15.847 |
| 38596 | Mm.454490.1 | 458.52 | 300.11 | 583.52 | 157.64 | 158.29 | 215.6 | 52.94 | 334 | 76.83 | 2.696759027 | 0.024193548 | 0.05605735 | 21.6519 |
| 22096 | Mm.69144.1 | 564.45 | 289.9 | 595.48 | 130.38 | 120.9 | 231.2 | 100.7 | 88.48 | 177.73 | 3.41381462 | 0.012345679 | 0.0373251 | 41.2274 |
| 21487 | Mm.9772.3 | 207.88 | 220.36 | 148.09 | 29.05 | 85.16 | 103.9 | 122.9 | 53.97 | 65.17 | 2.504911335 | 0.04757859 | 0.0923676 | 11.7365 |
| 8468 | Mocs2: molybdenum cofactor synthesis 2 | 451.72 | 641.1 | 548.64 | 204.64 | 269.88 | 172.8 | 296.6 | 378.2 | 132.88 | 2.256395453 | 0.0297028 | 0.06585082 | 17.5962 |
| 29403 | Mrpl9: mitochondrial ribosomal protein L9 | 687.37 | 522.93 | 342.88 | 378.66 | 145.59 | 253.6 | 220.5 | 250.8 | 282.44 | 2.028206166 | 0.043112513 | 0.08283912 | 13.3899 |
| 6034 | Mrps23: mitochondrial ribosomal protein S23 | 189.41 | 237.99 | 295.52 | 122.32 | 119.68 | 82.57 | 55.82 | 57.01 | 56.99 | 2.924492809 | 0.035310734 | 0.07228343 | 15.7753 |
| 44561 | Mrps23: mitochondrial ribosomal protein S23 | 133.78 | 165.37 | 174.49 | 82.76 | 82.15 | 57.97 | 48.91 | 9.82 | 35.54 | 2.986851647 | 0.048430493 | 0.09099851 | 12.1046 |
| 18672 | Mt4: metallothionein 4 | 471.49 | 401.25 | 465.5 | 283.03 | 160.15 | 374.6 | 77.11 | 182.5 | 150.05 | 2.180449535 | 0.037926675 | 0.07498946 | 14.9389 |
| 8584 | Mtap: methylthioadenosine phosphorylase | 301.33 | 399.52 | 615.48 | 133.87 | 304.21 | 110.8 | 88.98 | 14.43 | 153.22 | 3.268395635 | 0.025559105 | 0.05434505 | 23.2205 |
| 3549 | Mthfd2: methylenetetrahydrofolate dehydrogenase (NAD+ dependent), methenyltetrahydrofolate cyclohydrolase | 983.54 | 1203.2 | 1182.24 | 590.25 | 760.27 | 536.8 | 554.4 | 527.2 | 690.45 | 1.841304716 | 0.02661597 | 0.06293409 | 18.3588 |
| 27588 | Mxd1: MAX dimerization protein 1 | 993.73 | 911.74 | 644.1 | 466.93 | 617.29 | 512.7 | 418 | 374.6 | 279.54 | 1.910455702 | 0.029255319 | 0.06550827 | 17.6984 |
| 6161 | Mxd1: MAX dimerization protein 1 | 181.67 | 333.48 | 504.31 | 168.5 | 123.99 | 172.7 | 110.9 | 62.78 | 111.84 | 2.716133587 | 0.029462738 | 0.06636049 | 17.5011 |
| 20325 | Myo5b: myosin Vb | 768.64 | 656.09 | 488.09 | 409.12 | 389.77 | 359 | 270.7 | 380 | 263.4 | 1.844641373 | 0.044616877 | 0.08649855 | 12.7532 |
| 29664 | Myom2: myomesin 2 | 1192.6 | 1602.7 | 1540.02 | 1131.7 | 1059.7 | 972 | 571.8 | 941.8 | 785.78 | 1.587230631 | 0.04340381 | 0.082537 | 13.4485 |
| 28881 | Nalp4f: NACHT, leucine rich repeat and PYD containing 4F | 2150.11 | 2492.3 | 2718.12 | 1515.2 | 1789.6 | 1160 | 566.2 | 1035 | 625.39 | 2.199965628 | 0.010638298 | 0.03808511 | 38.9565 |
| 11528 | Nalp6: NACHT, leucine rich repeat and PYD containing 6 | 317.78 | 138.89 | 39.96 | 17.77 | 77.33 | 22.29 | 55.67 | 9.16 | 5.59 | 5.288642777 | 0.031695721 | 0.06955098 | 16.6649 |
| 41896 | Nalp9b: NACHT, LRR and PYD containing protein 9b | 743.42 | 818.13 | 815.08 | 320.66 | 556.55 | 474.3 | 285.5 | 410.1 | 285.42 | 2.037874176 | 0.026974952 | 0.06290944 | 18.4675 |
| 18033 | Ncoa4 /// LOC627557: nuclear receptor coactivator 4 /// similar to nuclear receptor coactivator 4 | 552.62 | 540.61 | 580.1 | 250.08 | 280.29 | 212.8 | 299.8 | 200.4 | 190.95 | 2.333403057 | 0.027108434 | 0.06128514 | 18.8762 |
| 21797 | Ndrg1: N-myc downstream regulated gene 1 | 760.12 | 747.8 | 336.89 | 280.11 | 487.1 | 357.4 | 374.4 | 244.3 | 197.19 | 1.901454324 | 0.031796502 | 0.0690938 | 16.7306 |
| 4919 | Ndrl: N-myc downstream regulated-like | 442.34 | 476.68 | 210.38 | 300.65 | 162.3 | 171.9 | 239.9 | 189.1 | 144.37 | 1.869588969 | 0.048053024 | 0.0935156 | 11.5462 |
| 10414 | Nefl: neurofilament, light | 1726.22 | 1655.4 | 1459.28 | 902.95 | 1121 | 600.9 | 759.2 | 965.7 | 548.27 | 1.976692432 | 0.022813688 | 0.05089987 | 25.2396 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 2584 | Nes: nestin polypeptide | 259.68 | 196.54 | 282.1 | 75.72 | 199.89 | 71.08 | 119.4 | 87.37 | 86.2 | 2.308404202 | 0.046753247 | 0.09178066 | 11.8681 |
| 6998 | Neurog2: neurogenin 2 | 231.05 | 418.13 | 218.55 | 123.46 | 78.36 | 80.47 | 63.67 | 209.6 | 71.81 | 2.766114122 | 0.047928513 | 0.09439751 | 11.403 |
| 9918 | Nobox: NOBOX oogenesis homeobox | 396.92 | 408.09 | 475.01 | 129.03 | 371.41 | 87.59 | 172.8 | 98.82 | 245.05 | 2.317449397 | 0.038327526 | 0.07741773 | 14.2596 |
| 17216 | Nudcd2: NudC domain containing 2 | 1083.58 | 1300.2 | 1922.19 | 656.24 | 404.23 | 762.1 | 293 | 236.5 | 633.56 | 2.884501117 | 0.01298701 | 0.03791861 | 41.8566 |
| 2861 | Nudcd2: NudC domain containing 2 | 653.94 | 528.12 | 803.02 | 415.16 | 310.05 | 389.2 | 346.4 | 283.8 | 405.47 | 1.846517339 | 0.047745358 | 0.09168288 | 11.986 |
| 3960 | Nupr1: nuclear protein 1 | 312.62 | 225.23 | 176.51 | 47.1 | 36.87 | 54.82 | 8.86 | 46.3 | 100.04 | 4.859757135 | 0.018099548 | 0.04529412 | 27.5871 |
| 3961 | Nupr1: nuclear protein 1 | 208.1 | 133.13 | 133.4 | 11.64 | 27.13 | 47.78 | 1.98 | 17.52 | 68.53 | 5.437392599 | 0.029982363 | 0.06595532 | 17.6434 |
| 2981 | Oas1c: 2′-5′ oligoadenylate synthetase 1C | 1384.52 | 1483.8 | 1747.71 | 600.25 | 1009 | 720.6 | 552.8 | 343.8 | 414.35 | 2.535773144 | 0.0090099 | 0.03722772 | 37.9655 |
| 1142 | Oas1d /// Oas1e: 2′-5′ oligoadenylate synthetase 1D /// 2′-5′ oligoadenylate synthetase 1E | 2035.81 | 1982.1 | 2708.21 | 777.35 | 1074.7 | 732.5 | 695 | 757.1 | 651.09 | 2.869641642 | 0 | 0.02992754 | 53.6191 |
| 19318 | Obfc2b: oligonucleotide/oligosaccharide-binding fold containing 2B | 433.1 | 115.04 | 679.94 | 161.64 | 146 | 98.16 | 107.4 | 78.98 | 143.91 | 3.336675225 | 0.020512821 | 0.04188034 | 29.5008 |
| 10199 | Odf2: outer dense fiber of sperm tails 2 | 1037.05 | 1156.3 | 1111.85 | 662.64 | 858.1 | 614 | 392.7 | 651.3 | 460.77 | 1.81630428 | 0.035 | 0.0724 | 15.828 |
| 22813 | Osbp2: oxysterol binding protein 2 | 269.05 | 335.57 | 568.18 | 144.89 | 117.87 | 130.8 | 68.72 | 106.4 | 53.36 | 3.771121722 | 0.016666667 | 0.04731944 | 26.6072 |
| 43535 | Pak7: P21 (CDKN1A)-activated kinase 7 | 394.46 | 1077 | 817.61 | 505.83 | 477.53 | 544 | 153 | 241.8 | 217.14 | 2.13996971 | 0.027322404 | 0.06455373 | 17.9674 |
| 41333 | Paqr5: progestin and adipoQ receptor family member V | 724.43 | 758.22 | 613.93 | 502.88 | 471.52 | 563.1 | 113.6 | 175.4 | 120.97 | 2.153154125 | 0.032102729 | 0.06917603 | 16.7783 |
| 849 | Pdlim1: PDZ and LIM domain 1 (elfin) | 300.99 | 412.46 | 570 | 141.35 | 241.6 | 138.6 | 163.9 | 202.1 | 181.18 | 2.402069959 | 0.033923304 | 0.07121436 | 16.0941 |
| 41503 | Pex10 /// LOC668173 /// LOC671348: peroxisome biogenesis factor 10 /// similar to peroxisome biogenesis factor 10 isoform 1 /// similar to Peroxisome assembly protein 10 (Peroxin-10) (Peroxisome biogenesis factor 10) (RING finger protein 69) | 280.61 | 206.54 | 96.17 | 72.22 | 80.02 | 54.72 | 83.5 | 24.39 | 29.12 | 3.391691136 | 0.028776978 | 0.06503597 | 17.8229 |
| 12239 | Pgam5: phosphoglycerate mutase family member 5 | 110.6 | 127.3 | 151.21 | 91.12 | 15.55 | 11.93 | 56.81 | 11.64 | 29.05 | 3.601203147 | 0.046956522 | 0.09189855 | 11.8815 |
| 6474 | Phkg1: phosphorylase kinase gamma 1 | 178.41 | 106.98 | 171.74 | 40.05 | 80.47 | 88.56 | 39.25 | 46.03 | 40.22 | 2.732560225 | 0.04787234 | 0.09175532 | 11.9989 |
| 4052 | Pitpnm2: phosphatidylinositol transfer protein, membrane-associated 2 | 84.85 | 63.94 | 331.06 | 11.48 | 54.66 | 9.66 | 23.36 | 16.57 | 16.8 | 7.24137931 | 0.046918123 | 0.08945109 | 12.2952 |
| 19362 | Plac8: placenta-specific 8 | 662.3 | 661.38 | 795.38 | 468 | 575.56 | 338.1 | 183 | 196.8 | 196.89 | 2.164105864 | 0.033823529 | 0.07121569 | 16.08 |
| 20205 | Plec1 /// LOC671535: plectin 1 /// similar to poly (ADP-ribose) polymerase family, member 10 | 121.35 | 70.86 | 157.14 | 22.86 | 52.58 | 29.9 | 14.04 | 42.18 | 35.14 | 3.552109812 | 0.047738693 | 0.09283082 | 11.6437 |
| 27915 | Plekhg1: pleckstrin homology domain containing, family G | 1853.45 | 1666.1 | 1893.1 | 1079.7 | 1334.2 | 984 | 491.4 | 722.9 | 597.2 | 2.078008684 | 0.015873016 | 0.0412522 | 29.9928 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 11164 | Plk2: polo-like kinase 2 (with RhoGef domain) member 1 (Drosophila) | 498.11 | 383.42 | 423.89 | 177.35 | 110.99 | 143.6 | 134.9 | 38.56 | 65.38 | 3.89207078 | 0.016949153 | 0.03774011 | 35.7785 |
| 15242 | Pofut2: protein O-fucosyltransferase 2 | 1778.06 | 1154.3 | 2374.19 | 882.1 | 1201.9 | 822.3 | 491.1 | 875.2 | 1214.3 | 1.934223068 | 0.02484472 | 0.05419255 | 23.0226 |
| 14202 | Pofut2: protein O-fucosyltransferase 2 | 841.36 | 629.59 | 1545.03 | 432.55 | 580.35 | 395.1 | 328.1 | 451.2 | 735.19 | 2.064043252 | 0.042842215 | 0.08301289 | 13.3317 |
| 10997 | Pold3: polymerase (DNA-directed), delta 3, accessory subunit | 1231.65 | 1183.2 | 1391.33 | 824.72 | 900.21 | 640.4 | 329.6 | 569.7 | 526.55 | 2.007913041 | 0.023980815 | 0.05843325 | 20.4291 |
| 34590 | Pold3: polymerase (DNA-directed), delta 3, accessory subunit | 423.34 | 669.16 | 843.98 | 290.44 | 334.78 | 246.5 | 303.9 | 237.9 | 260.63 | 2.313402702 | 0.024523161 | 0.05544959 | 21.8711 |
| 38961 | Ppp1r3d: protein phosphatase 1, regulatory subunit 3D | 575.14 | 503.37 | 526.53 | 166.64 | 221.68 | 213.9 | 94.06 | 104 | 89.52 | 3.607723257 | 0.009615385 | 0.03676282 | 37.8147 |
| 36182 | Ppp4c: protein phosphatase 4, catalytic subunit | 571.66 | 453.52 | 340.78 | 131.19 | 406.4 | 205.3 | 175.5 | 111.2 | 158.93 | 2.299802602 | 0.035050072 | 0.07244158 | 15.8315 |
| 14726 | Prdx1: peroxiredoxin 1 | 2781.18 | 3417.9 | 3506.42 | 2190.9 | 2626.8 | 2285 | 1226 | 1574 | 1195.6 | 1.749054555 | 0.017094017 | 0.04625356 | 26.9776 |
| 14063 | Prdx1: peroxiredoxin 1 | 2078.16 | 2456.5 | 2879.78 | 1833.6 | 1734.2 | 1642 | 870.6 | 902.3 | 801.35 | 1.904999994 | 0.022088353 | 0.04886212 | 26.0918 |
| 13692 | Prdx1: peroxiredoxin 1 | 1982.74 | 2435.2 | 2494.71 | 1597.2 | 1890.1 | 1553 | 859.4 | 1144 | 886.29 | 1.743495 | 0.023460411 | 0.05467253 | 22.4906 |
| 295 | Prdx1: peroxiredoxin 1 | 687.71 | 1005.3 | 1004.39 | 538.28 | 643.24 | 491.2 | 434.4 | 689.3 | 439.9 | 1.666929311 | 0.041019956 | 0.08053954 | 13.8032 |
| 12996 | Prdx2: peroxiredoxin 2 | 2137.92 | 1606.1 | 1921.64 | 1079.9 | 1587.9 | 1273 | 690.7 | 1588 | 625.66 | 1.655379356 | 0.037457435 | 0.07846008 | 14.0576 |
| 2801 | Prdx2: peroxiredoxin 2 | 3503.34 | 3323.1 | 3762.91 | 2292.1 | 2644.3 | 1942 | 2586 | 2530 | 2441.4 | 1.467059107 | 0.041800643 | 0.08119328 | 13.6017 |
| 42136 | Prmt3: protein arginine N-methyltransferase 3 | 165 | 52.27 | 96.5 | 11.63 | 3.78 | 14.62 | 15.11 | 34.44 | 6.54 | 7.286809104 | 0.035302594 | 0.07236792 | 15.8727 |
| 2615 | Prss8: protease, serine, 8 (prostasin) | 471.01 | 140.12 | 249.79 | 75.51 | 130.38 | 26.33 | 79.43 | 130.7 | 70.09 | 3.36008118 | 0.029151943 | 0.06553592 | 17.6734 |
| 8719 | Pstpip1: proline-serine-threonine phosphatase-interacting protein 1 | 44.1 | 110.11 | 91.14 | 10.97 | 19.4 | 25.08 | 18.91 | 12.49 | 10.27 | 5.052512356 | 0.047161572 | 0.09181659 | 11.9108 |
| 43158 | Ptdss2: phosphatidylserine synthase 2 | 1203.34 | 418.9 | 557.48 | 508.13 | 304.61 | 307.9 | 188.3 | 147 | 386.5 | 2.366084658 | 0.046685341 | 0.08895425 | 12.3985 |
| 41102 | Rab3gap1: RAB3 GTPase activating protein subunit 1 | 460.17 | 347.13 | 470.57 | 199.81 | 233.06 | 254.1 | 132.1 | 145 | 138.52 | 2.317921277 | 0.026266417 | 0.06385866 | 18.2065 |
| 16961 | Rap2b: RAP2B, member of RAS oncogene family | 808.09 | 565.99 | 369.3 | 354.3 | 287.58 | 166.3 | 57.48 | 218.1 | 87 | 2.978227632 | 0.018604651 | 0.04384496 | 28.1739 |
| 8013 | Rasl11b: RAS-like, family 11, member B | 426.89 | 253.01 | 172 | 67.51 | 155.36 | 83.97 | 28.63 | 67.32 | 76.13 | 3.557587906 | 0.022988506 | 0.0580613 | 20.1914 |
| 16931 | Rassf1: Ras association (RalGDS/AF-6) domain family 1 | 551.69 | 251.68 | 515.62 | 171.98 | 181.71 | 219.6 | 213.6 | 114.1 | 183.5 | 2.43250620 | 0.024767802 | 0.05414861 | 23.0186 |
| 6797 | Rassf5: Ras association (RalGDS/AF-6) domain family 5 | 720.77 | 665.14 | 560.86 | 336.47 | 286.71 | 262.6 | 254.6 | 257.9 | 267.99 | 2.336764273 | 0.022099448 | 0.05517495 | 22.0115 |
| 19264 | Rbm7: RNA binding motif protein 7 | 1311.84 | 1104.7 | 1399.09 | 852.61 | 1194.9 | 761.2 | 564.4 | 793.3 | 454.85 | 1.651371739 | 0.044444444 | 0.08668921 | 12.7196 |
| 30077 | Rbpsuh: Recombining binding protein suppressor of hairless (Drosophila) | 229.78 | 181.62 | 164.15 | 47.11 | 63.14 | 54.63 | 33.26 | 159.1 | 37.35 | 2.917131272 | 0.047963801 | 0.09049472 | 12.1646 |
| 17285 | Rdh11: retinol dehydrogenase 11 | 266.28 | 352.96 | 301.12 | 131.17 | 93.27 | 93.1 | 130.5 | 206.4 | 92.85 | 2.463127752 | 0.039370079 | 0.07937008 | 13.9553 |
| 3831 | Rela: v-rel | 1165.05 | 845.26 | 817.64 | 573.79 | 604.68 | 707 | 323.3 | 379.4 | 435.95 | 1.870281638 | 0.047038328 | 0.09183798 | 11.8894 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 19286 | reticuloendotheliosis viral oncogene homolog A (avian) | 496.13 | 531.04 | 541.91 | 329.27 | 450.19 | 238 | 210.9 | 214.8 | 230.19 | 1.875420574 | 0.048006509 | 0.09429889 | 11.4137 |
| 3543 | Rexo2: REX2, RNA exonuclease 2 homolog (S. cerevisiae) | 982.72 | 955.41 | 1090.21 | 552.53 | 601.28 | 456.3 | 215.4 | 392.9 | 290.79 | 2.413808495 | 0.018181818 | 0.04524242 | 27.6143 |
| 3542 | Rgs2: regulator of G-protein signaling 2 | 755.61 | 753.62 | 945.56 | 289.77 | 380.15 | 277.6 | 309.3 | 389.5 | 287.36 | 2.539035188 | 0.022140221 | 0.05134071 | 24.8558 |
| 38623 | Rgs2: regulator of G-protein signaling 2 | 439.17 | 401.76 | 570.74 | 252.29 | 232.03 | 224.9 | 47.94 | 265.8 | 134.38 | 2.439949995 | 0.035714286 | 0.07222222 | 15.7414 |
| 40641 | Rnd1: Rho family GTPase 1 | 341.36 | 140.63 | 50.42 | 22.78 | 40.06 | 50.85 | 49.94 | 22.23 | 23.68 | 5.081702778 | 0.031862745 | 0.06855664 | 16.9255 |
| 996 | Rnd3: Rho family GTPase 3 | 236.49 | 269.23 | 240.29 | 57.64 | 90.84 | 104.7 | 34.95 | 86.4 | 66.49 | 3.383342026 | 0.027196653 | 0.06002789 | 19.3316 |
| 995 | Rnd3: Rho family GTPase 3 | 346.48 | 273.15 | 396.01 | 104.43 | 242.51 | 112.8 | 134.1 | 41.05 | 157.66 | 2.563194024 | 0.031897927 | 0.06903775 | 16.7571 |
| 44629 | Rnf185: Ring finger protein 185 | 3391.02 | 3265.6 | 3308.22 | 2163.5 | 2326.9 | 1837 | 1543 | 1821 | 2169 | 1.680373212 | 0.022222222 | 0.05532407 | 22.0213 |
| 19135 | Rnf185: ring finger protein 185 | 3100.72 | 2881.4 | 3164.78 | 1942 | 2217.8 | 1890 | 2233 | 2234 | 2296.7 | 1.427717853 | 0.047833935 | 0.09054753 | 12.1523 |
| 19484 | Sc5d: sterol-C5-desaturase (fungal ERG3, delta-5-desaturase) homolog (S. cerevisiae) | 156.19 | 125.87 | 470.87 | 12.69 | 92.23 | 44.12 | 37.46 | 10.13 | 75.32 | 5.53726788 | 0.026768642 | 0.06290631 | 18.417 |
| 21214 | Scarb2: scavenger receptor class B, member 2 | 412.98 | 136.41 | 11.58 | 17.91 | 8.27 | 79.58 | 23.24 | 12.15 | 32.61 | 6.456837017 | 0.048995984 | 0.09481928 | 11.3271 |
| 14524 | Sdhc: succinate dehydrogenase complex, subunit C, integral membrane protein | 655.46 | 629.8 | 569.58 | 133.4 | 248.7 | 128 | 367.2 | 95.09 | 439.58 | 2.627289338 | 0.023715415 | 0.05048748 | 25.7165 |
| 16404 | Sh3bp2: SH3-domain binding protein 2 | 939.44 | 869.33 | 963.81 | 543.92 | 577.31 | 563.7 | 456.3 | 460.2 | 392.82 | 1.851886733 | 0.036885246 | 0.0731102 | 15.5576 |
| 11436 | Six1: sine oculis-related homeobox 1 homolog (Drosophila) | 890.55 | 896.49 | 591.29 | 257.89 | 404.29 | 126.8 | 116.8 | 139.6 | 145.28 | 3.995178901 | 0 | 0.02714286 | 66.8915 |
| 16644 | Slc20a1: solute carrier family 20, member 1 | 755.61 | 816.13 | 1040.94 | 591.52 | 587.71 | 537.5 | 338.8 | 299.8 | 249.93 | 2.00568847 | 0.036745407 | 0.07408136 | 15.2304 |
| 5126 | Slc25a15: solute carrier family 25 (mitochondrial carrier ornithine transporter), member 15 | 2097.82 | 2285.9 | 2519.54 | 1552.6 | 1649.2 | 1444 | 801.2 | 1031 | 1205.9 | 1.796727072 | 0.024657534 | 0.05515982 | 21.9246 |
| 42635 | Slc7a14: Solute carrier family 7 (cationic amino acid transporter, y+ system), member 14 | 850.08 | 861.15 | 971.47 | 367.62 | 635.72 | 604.9 | 171.7 | 384 | 263.26 | 2.210530653 | 0.024213075 | 0.05830508 | 20.4881 |
| 15341 | Slc9a3r1: solute carrier family 9 (sodium/hydrogen exchanger), isoform 3 regulator 1 | 1945.59 | 1874.9 | 1042.14 | 1213.4 | 1279.4 | 924.9 | 732.2 | 1247 | 905.41 | 1.543013175 | 0.04248366 | 0.08125999 | 13.6676 |
| 15340 | Slc9a3r1: solute carrier family 9 (sodium/hydrogen exchanger), isoform 3 regulator 1 | 1511.18 | 1791 | 882.39 | 908.38 | 1070.8 | 773.7 | 603.5 | 1141 | 742.49 | 1.597206796 | 0.04744186 | 0.08977984 | 12.3407 |
| 29662 | Slco4a1: solute carrier organic anion transporter family, member 4a1 | 1518.9 | 1099.7 | 758.84 | 781.47 | 590.77 | 472.9 | 410.2 | 560.3 | 482.97 | 2.047771782 | 0.023752969 | 0.05806809 | 20.3739 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 22832 | Smurf1 /// LOC640390: SMAD specific E3 ubiquitin protein ligase 1 /// similar to Smad ubiquitination regulatory factor 1 (Ubiquitin-protein ligase SMURF1) (Smad-specific E3 ubiquitin ligase 1) (hSMURF1) | 353.27 | 405.72 | 431.46 | 185.4 | 183.4 | 173.3 | 130.3 | 182.9 | 293.86 | 2.071951336 | 0.04549763 | 0.08836651 | 12.5257 |
| 7515 | Snap29: synaptosomal-associated protein | 1533.29 | 1209.3 | 1300.59 | 1097.4 | 921.79 | 856.9 | 676.1 | 678.9 | 687.34 | 1.644127897 | 0.047818792 | 0.09289989 | 11.6499 |
| 15156 | Snord22: small nucleolar RNA, C/D box 22 | 244.55 | 88.91 | 292.33 | 138.36 | 78.77 | 71.21 | 96.16 | 68.67 | 49.02 | 2.492243971 | 0.041755889 | 0.08124197 | 13.5908 |
| 10772 | Snrpb2: U2 small nuclear ribonucleoprotein B | 1280 | 1540.4 | 1365.87 | 675.42 | 748.01 | 668.4 | 399.1 | 607.5 | 397.8 | 2.394785166 | 0.013513514 | 0.03754505 | 33.014 |
| 20449 | Snrpb2: U2 small nuclear ribonucleoprotein B | 1101.45 | 1113.1 | 1328.87 | 444.18 | 372.6 | 458.6 | 607.3 | 424.6 | 345.21 | 2.67191229 | 0.016260163 | 0.03837398 | 35.0616 |
| 1262 | Sox2: SRY-box containing gene 2 | 258.38 | 397.22 | 227.54 | 100.5 | 112.85 | 106.8 | 94.1 | 81.95 | 80.38 | 3.06347995 | 0.032307692 | 0.07045128 | 16.4379 |
| 7733 | Srd5a2l: steroid 5 alpha-reductase 2-like | 951.51 | 803.16 | 917.18 | 539.46 | 538.83 | 573.3 | 345.4 | 553.4 | 479.19 | 1.763841853 | 0.042576419 | 0.08121543 | 13.679 |
| 37863 | Ssr3: signal sequence receptor, gamma | 878.88 | 551.79 | 1339.32 | 496.85 | 533.72 | 503.9 | 432 | 471.5 | 368.38 | 1.974066235 | 0.036986301 | 0.07271233 | 15.6044 |
| 17274 | St3gal5: ST3 beta-galactoside alpha-2,3-sialyltransferase 5 | 585.5 | 294.61 | 591.89 | 101.96 | 252.48 | 156 | 129.7 | 214.2 | 153.36 | 2.921765366 | 0.015037594 | 0.03827068 | 34.2305 |
| 10512 | Stat6: signal transducer and activator of transcription 6 | 280.93 | 369.43 | 537.91 | 177.71 | 247.51 | 140.3 | 74.96 | 158.2 | 163.26 | 2.47054207 | 0.03856041 | 0.07460154 | 15.0996 |
| 5687 | Surf5: surfeit gene 5 | 808.83 | 625.57 | 901.86 | 425.58 | 600.45 | 367.5 | 196.1 | 219.1 | 363.82 | 2.150727493 | 0.024630542 | 0.05834154 | 20.6282 |
| 16783 | Taf13: TAF13 RNA polymerase II, TATA box binding protein (TBP)-associated factor | 2786.83 | 2273 | 2785.38 | 1860.7 | 2037.4 | 1751 | 1700 | 1367 | 1418.5 | 1.548259965 | 0.030769231 | 0.06631909 | 17.421 |
| 14515 | Taok3: TAO kinase 3 | 840.36 | 751.13 | 664 | 644.14 | 406.28 | 520.9 | 288.5 | 201 | 341.2 | 1.877923992 | 0.042726348 | 0.08343845 | 13.1523 |
| 21642 | Tax1bp3 /// Rpl13: Tax1 (human T-cell leukemia virus type I) binding protein 3 /// ribosomal protein L13 | 871.73 | 903.94 | 1048.44 | 382.12 | 394.43 | 282.3 | 507.1 | 145.2 | 438.71 | 2.627237926 | 0.016666667 | 0.04101852 | 30.5599 |
| 502 | Taz: tafazzin | 510.91 | 478.79 | 738.95 | 285.8 | 194.27 | 193.5 | 116.3 | 261.3 | 97.64 | 3.009750152 | 0.023529412 | 0.05086275 | 25.5673 |
| 6617 | Tcl1: T-cell lymphoma breakpoint 1 | 4221.74 | 3745.3 | 4210.23 | 2520.7 | 3350.8 | 3381 | 2300 | 2780 | 3125.2 | 1.394976158 | 0.044399596 | 0.08380424 | 13.0961 |
| 19537 | Thedc1: thioesterase domain containing 1 | 749.49 | 760.8 | 818.91 | 422.7 | 601.57 | 400.7 | 231.5 | 336.5 | 417.73 | 1.932376769 | 0.036599764 | 0.07688705 | 14.4348 |
| 20152 | Thrap3: thyroid hormone receptor associated protein 3 | 308.4 | 324.33 | 307.94 | 159.33 | 140.04 | 211.4 | 90.03 | 100.2 | 151.4 | 2.207264707 | 0.048242028 | 0.09426547 | 11.4399 |
| 16803 | Tle6: transducin-like enhancer of split 6, homolog of Drosophila E(spl) | 1270.14 | 833.99 | 1229.7 | 374.24 | 654.97 | 691.3 | 407.2 | 562.4 | 495.75 | 2.092904854 | 0.017241379 | 0.04622126 | 27.0809 |
| 15195 | Tm2d2: TM2 domain containing 2 | 934.68 | 572.01 | 641.41 | 527.63 | 320.67 | 388.1 | 290.4 | 286.3 | 252.38 | 2.079960494 | 0.041896362 | 0.08087468 | 13.7569 |
| 21204 | Tmed10 /// LOC634748: transmembrane emp24-like trafficking protein 10 (yeast) | 371.69 | 689.99 | 932.01 | 227.36 | 344.45 | 312 | 356.4 | 335.3 | 331.6 | 2.090851887 | 0.029307282 | 0.06547661 | 17.7043 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 15880 | Tmed10 /// LOC634748: transmembrane emp24-like trafficking protein 10 (yeast) /// similar to transmembrane trafficking protein | 293.24 | 526.59 | 744.83 | 183.86 | 260.8 | 259 | 306.9 | 282.8 | 262.97 | 2.01075635 | 0.042769857 | 0.08350984 | 13.1531 |
| 15864 | Tmed10 /// LOC634748: transmembrane emp24-like trafficking protein 10 (yeast) /// similar to transmembrane trafficking protein | 325.23 | 522.46 | 807.94 | 214.86 | 292.41 | 263.9 | 328.4 | 287.9 | 276.07 | 1.990478194 | 0.048141892 | 0.09307995 | 11.6733 |
| 21746 | Tmem109: transmembrane protein 109 | 658.76 | 639.21 | 690.17 | 367.58 | 528.21 | 245.5 | 273.8 | 272.9 | 273.33 | 2.027348928 | 0.036 | 0.07345778 | 15.3724 |
| 14887 | Tmem109: transmembrane protein 109 | 827.27 | 787.55 | 910.96 | 487.81 | 701.24 | 347.9 | 350.2 | 365 | 381.93 | 1.917784713 | 0.037974684 | 0.07493671 | 14.9506 |
| 8336 | Tmem38a: transmembrane protein 38a | 965.95 | 199.02 | 508.25 | 119.7 | 369.44 | 96.15 | 251.5 | 101.5 | 150.48 | 3.073850902 | 0.024561404 | 0.05080702 | 24.4359 |
| 10674 | Tor1a: torsin family 1, member A (torsin A) | 1760.16 | 1607.9 | 1566.85 | 1294.5 | 1207 | 1120 | 851.9 | 880.3 | 816.44 | 1.599693348 | 0.047144152 | 0.09024781 | 12.187 |
| 7470 | Tpbg: trophoblast glycoprotein | 135.67 | 173.87 | 65.62 | 38.44 | 9.01 | 28.02 | 6.79 | 31.8 | 103.96 | 3.441519127 | 0.047454702 | 0.0919931 | 11.8366 |
| 20812 | Tpi1: triosephosphate isomerase 1 | 723.43 | 510.71 | 278.29 | 243.4 | 202.66 | 199.6 | 498.9 | 79.81 | 92.94 | 2.2962923 6 | 0.0368608 8 | 0.07673801 | 14.4886 |
| 22085 | Transcribed locus | 244.72 | 168.35 | 553.92 | 235.2 | 92.48 | 72.5 | 7.42 | 50.24 | 1 | 4.21493331 | 0.035410765 | 0.07242682 | 15.7775 |
| 43618 | Transcribed locus | 1331.08 | 1132.8 | 759.97 | 700.03 | 776.17 | 653.8 | 600.2 | 448.6 | 142.5 | 1.941371472 | 0.0390625 | 0.07442274 | 15.175 |
| 30279 | Transcribed locus | 115.59 | 77.5 | 3.01 | 1 | 6.1 | 4.39 | 6.91 | 7.21 | 3.07 | 13.67503487 | 0.042162162 | 0.08108468 | 13.6466 |
| 31948 | Transcribed locus | 948.04 | 695.42 | 1011.76 | 481.07 | 569.52 | 551.4 | 635.4 | 513.4 | 462.89 | 1.652432858 | 0.046961326 | 0.08948742 | 12.2985 |
| 36521 | Transcribed locus | 163.5 | 288.96 | 275.95 | 153.58 | 132.29 | 129 | 127.8 | 62.86 | 77.98 | 2.131349485 | 0.049114332 | 0.094635 | 11.3498 |
| 14557 | Transcribed locus, moderately similar to XP_574723.1 PREDICTED: similar to LRRGT00097 [Rattus norvegicus] | 389.93 | 446.02 | 354.24 | 146.9 | 73.38 | 178.6 | 150.5 | 243.5 | 285.69 | 2.207018682 | 0.045135406 | 0.0843096 | 13.0436 |
| 31203 | Transcribed locus, weakly similar to XP_417295.1 PREDICTED: similar to TAF3 protein [Gallus gallus] | 833.28 | 557.28 | 868.7 | 344.25 | 284.45 | 400.2 | 464.4 | 244.1 | 342.7 | 2.172271392 | 0.022727273 | 0.05269481 | 23.5482 |
| 16554 | Trip: Trf (TATA binding protein-related factor)-proximal protein homolog (Drosophila) | 1346.13 | 1510.8 | 1419.34 | 707.69 | 420.35 | 502.5 | 668.7 | 1297 | 686.12 | 1.997305029 | 0.023323615 | 0.0545967 | 22.442 |
| 11566 | Trip11: thyroid hormone receptor interactor 11 | 259.32 | 592.74 | 496.79 | 341.11 | 199.04 | 280 | 193.4 | 155.1 | 127.48 | 2.081494398 | 0.037878788 | 0.07494108 | 14.9376 |
| 39305 | Troap: trophinin associated protein | 208.07 | 262.5 | 390.33 | 82.47 | 98.83 | 71.69 | 101.3 | 44.16 | 107.74 | 3.401287978 | 0.025114155 | 0.0585312 | 20.0849 |
| 8651 | Trpc2: transient receptor potential cation channel, subfamily C, member 2 | 1159.04 | 683.82 | 924.49 | 504.31 | 574.63 | 394.4 | 398.4 | 456.4 | 182.58 | 2.204436195 | 0.02359882 | 0.05485742 | 22.5014 |
| 17247 | Ttk: Ttk protein kinase | 442.51 | 328.09 | 595.94 | 156.99 | 233.89 | 156.6 | 291.1 | 218.8 | 142.18 | 2.278383087 | 0.037859008 | 0.07429939 | 15.191 |
| 20704 | Tubb2b: tubulin, beta 2b | 2089.18 | 1881.4 | 2187.75 | 1223.2 | 1598.2 | 1370 | 901.7 | 1304 | 685.75 | 1.739163956 | 0.02832244 | 0.06042847 | 19.5561 |
| 1904 | Ube2a: ubiquitin-conjugating enzyme E2A, RAD6 homolog | 668.24 | 817.55 | 665.53 | 322.75 | 424.91 | 331.9 | 208 | 371.1 | 379.5 | 2.110968831 | 0.036401099 | 0.07271978 | 15.6237 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 6873 | (S. cerevisiae) Ube2i /// LOC546265 /// LOC669417: ubiquitin-conjugating enzyme E2I /// similar to Chain A, Human Ubiquitin-Conjugating Enzyme Ubc9 /// similar to Ubiquitin-conjugating enzyme E2 I (Ubiquitin-protein ligase I) (Ubiquitin carrier protein I) (SUMO-1-protein ligase) (Ubiquitin-conjugating enzyme UbcE2A) | 881.06 | 714.36 | 770.75 | 667.98 | 572.39 | 299.1 | 178.7 | 412.2 | 456.5 | 1.829369083 | 0.049193548 | 0.09460215 | 11.3561 |
| 34066 | Ube2w: ubiquitin-conjugating enzyme E2W (putative) | 257.73 | 223.92 | 304.28 | 83.65 | 208.87 | 56.27 | 64.14 | 66.41 | 62.1 | 2.903110225 | 0.032258065 | 0.07035842 | 16.4371 |
| 30305 | Umodl1: uromodulin-like 1 | 918.71 | 1173.2 | 1195.72 | 468.99 | 479.34 | 394.6 | 140.4 | 315.4 | 169.66 | 3.340415155 | 0 | 0.02952381 | 59.0622 |
| 27170 | Unc5a: unc-5 homolog A (C. elegans) | 251.93 | 17.43 | 149.64 | 24.49 | 31.01 | 22.93 | 71.25 | 19.8 | 14.94 | 4.543975708 | 0.036948749 | 0.07631307 | 14.5235 |
| 18877 | Vil2: villin 2 | 241.97 | 205.21 | 109.2 | 76.45 | 75.17 | 88.63 | 56.94 | 39.13 | 59.75 | 2.809503371 | 0.038596491 | 0.07755945 | 14.307 |
| 36640 | Wdr27: WD repeat domain 27 | 258.28 | 184.34 | 219.19 | 117.86 | 87.15 | 48.94 | 74.51 | 75.45 | 48.47 | 2.925903002 | 0.0375 | 0.07488333 | 14.8953 |
| 40438 | Wdr40b: WD repeat domain 40B | 412.95 | 601.38 | 440.4 | 258.01 | 180.34 | 165.1 | 177.8 | 333.6 | 44.28 | 2.509864477 | 0.034023669 | 0.07133136 | 16.1014 |
| 20216 | Wdr82: WD repeat domain containing 82 | 930.14 | 666.97 | 795.89 | 478.36 | 548.79 | 548.8 | 439.9 | 334.8 | 377.74 | 1.754141621 | 0.047417443 | 0.09220999 | 11.7317 |
| 44710 | Wfdc3: WAP four-disulfide core domain 3 | 840.41 | 352.61 | 513.04 | 317.4 | 228.96 | 204.5 | 83.53 | 153.4 | 181.23 | 2.918761708 | 0.024647887 | 0.0509507 | 24.4457 |
| 4516 | Xlr3a /// Xlr3b /// MGC76689: X-linked lymphocyte-regulated 3A /// X-linked lymphocyte-regulated 3B /// hypothetical protein LOC574437 | 360.83 | 588.71 | 622.92 | 230.28 | 410.11 | 221.9 | 206 | 332.5 | 245.03 | 1.910945836 | 0.036817102 | 0.07669438 | 14.4846 |
| 6776 | Xmr /// LOC546272 /// LOC619991 /// LOC664810 /// LOC664861 /// LOC664877 /// LOC664890 /// LOC664906 /// LOC664923 /// LOC664944 /// LOC664989: Xmr protein /// similar to Xlr-related, meiosis regulated /// similar to Xlr-related, meiosis regulated /// similar to Synaptonemal complex protein 3 (SCP-3) /// similar to Xlr-related, meiosis regulated /// similar to Xlr-related, meiosis regulated /// similar to Xlr-related, meiosis regulated /// similar to Xlr-related, meiosis regulated /// similar to Xlr-related, meiosis regulated | 402.45 | 431.9 | 419.31 | 132.31 | 243.77 | 319 | 93.22 | 113 | 120.66 | 2.453418398 | 0.029411765 | 0.06629181 | 17.4967 |

TABLE 8A-continued

| Row | Gene | Oct4.1 | Oct4.2 | Oct4.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 6777 | similar to Xlr-related, meiosis regulated Xmr /// LOC546272 /// LOC619991 /// LOC664810 /// LOC664861 /// LOC664877 /// LOC664890 /// LOC664906 /// LOC664923 /// LOC664944 /// LOC664989: Xmr protein /// similar to Xlr-related, meiosis regulated /// similar to Xlr-related, meiosis regulated /// similar to Synaptonemal complex protein 3 (SCP-3) /// similar to Xlr-related, meiosis related /// similar to Xlr-related, meiosis regulated /// similar to Xlr-related, meiosis regulated /// similar to Xlr-related, meiosis regulated /// similar to Xlr-related, meiosis regulated /// similar to Xlr-related, meiosis regulated | 416.14 | 408.25 | 408.94 | 135.94 | 270.28 | 290.5 | 105.7 | 134.5 | 133.3 | 2.304945055 | 0.038860104 | 0.0744905 | 15.1475 |
| 15133 | Ywhaq: tyrosine 3-monooxygenase/tryptophan 5-monooxygenase activation protein, theta polypeptide | 823.51 | 1230.4 | 1166.2 | 689.41 | 787.92 | 682.6 | 668.7 | 504.4 | 743.91 | 1.579678045 | 0.048561151 | 0.09080635 | 12.127 |
| 14866 | Ywhaz: tyrosine 3-monooxygenase/tryptophan 5-monooxygenase activation protein, zeta polypeptide | 1349.62 | 789.35 | 427.74 | 385.13 | 670.02 | 394.3 | 284.5 | 439.5 | 466.58 | 1.944403621 | 0.048956661 | 0.09480203 | 11.319 |
| 27398 | Zar1: zygote arrest 1 | 308.67 | 302.35 | 296.84 | 96.91 | 62.32 | 61.6 | 36.14 | 73.34 | 105 | 4.17109646 | 0.016853933 | 0.04059925 | 30.8299 |
| 8460 | Zfp219: zinc finger protein 219 | 362.85 | 474.33 | 421.09 | 139.56 | 154.27 | 248.9 | 222.6 | 276.2 | 128.61 | 2.150613169 | 0.041622199 | 0.08153682 | 13.5586 |
| 15729 | Zfp3612: zinc finger protein 36, C3H type-like 2 | 1493.92 | 1568.6 | 1661.69 | 1083.2 | 1187.2 | 1122 | 833.5 | 1041 | 686.1 | 1.587178186 | 0.047877145 | 0.09053899 | 12.154 |
| 20879 | Zfp422-rs1: zinc finger protein 422, related sequence 1 | 807.14 | 637.1 | 963.93 | 639.73 | 531.32 | 551.3 | 241.2 | 450.1 | 320.33 | 1.761665271 | 0.049153908 | 0.09463336 | 11.3527 |
| 24731 | Zfp444: zinc finger protein 444 | 153.25 | 73.77 | 591 | 9.86 | 2.23 | 35.58 | 45.91 | 75.68 | 121.03 | 5.63588136 | 0.041202673 | 0.08044915 | 13.8348 |
| 7994 | Zfp503: zinc finger protein 503 | 499.68 | 1344.6 | 631.84 | 248.83 | 28.76 | 97.85 | 46.17 | 549 | 78.64 | 4.71964318 | 0.02 | 0.036 | 49.7065 |
| 7995 | Zfp503: zinc finger protein 503 | 201.34 | 138.04 | 36.43 | 20 | 36.65 | 32.65 | 17.34 | 48.18 | 62.9 | 3.452232225 | 0.04757548 | 0.08998411 | 12.2507 |
| 44691 | Zfp68: zinc finger protein 68 | 836.97 | 770.67 | 353.93 | 367.82 | 511.34 | 379.8 | 260.4 | 345.8 | 315.87 | 1.798780376 | 0.037125749 | 0.07644311 | 14.5373 |
| 8911 | Zfp71-rs1: zinc finger protein 71, related sequence 1 | 118.31 | 304.51 | 288.84 | 100.79 | 115.62 | 155.5 | 55.72 | 138.6 | 55.13 | 2.290505311 | 0.043478261 | 0.08252033 | 13.4658 |
| 17202 | Zfp90: zinc finger protein 90 | 148.51 | 168.8 | 284.96 | 41.22 | 44.14 | 22.58 | 38.95 | 17.6 | 56.83 | 5.44256658 | 0.024539877 | 0.05421268 | 22.8885 |
| 1832 | Zmat2: zinc finger, matrin type 2 | 271.97 | 245.47 | 570.3 | 68.8 | 63.18 | 133.6 | 110.3 | 99.83 | 40.13 | 4.218008376 | 0.023972603 | 0.05133562 | 24.0851 |

TABLE 8B

| Row | Gene | Oct. 4, 2001 | Oct. 4, 2002 | Oct. 4, 2003 | NI1.1 | NI1.2 | NI1.3 | NI2.1 | NI2.2 | NI2.3 | foldchange | fdr | t.pvals |
|---|---|---|---|---|---|---|---|---|---|---|---|---|---|
| 52 | transferrin receptor | 624.69 | 241.34 | 260.79 | 1658.5 | 1221.5 | 1475.4 | 2092.4 | 1394.63 | 2043.46 | 0.227967388 | 0 | 0.00015951 |
| 154 | eukaryotic translation initiation factor 3, subunit 8 | 1574.05 | 898.06 | 884.18 | 3064.3 | 2464 | 3091 | 3612.2 | 2968.05 | 3465.95 | 0.359626325 | 0 | 0.00015921 |
| 785 | transmembrane emp24 protein transport domain containing 6 | 158.97 | 64.18 | 182.56 | 508.83 | 418.62 | 577.06 | 745.64 | 731.85 | 729.56 | 0.218619664 | 0 | 0.000222179 |
| 1785 | cathepsin B | 725.96 | 401.03 | 413.68 | 1480.9 | 1297.2 | 1599.4 | 2070.4 | 1870.47 | 2628.6 | 0.28148163 | 0 | 0.00024093 |
| 4369 | ATP-binding cassette, sub-family F (GCN20), member 1 | 415.1 | 244.32 | 320.89 | 937.07 | 895.73 | 1089.1 | 1088.9 | 1163.3 | 2060.89 | 0.270972664 | 0 | 0.0003167 |
| 4798 | junction-mediating and regulatory protein | 143.62 | 100.64 | 83.34 | 547.49 | 231.34 | 463.45 | 532.88 | 603.44 | 674.49 | 0.214602255 | 0 | 0.00036372 |
| 4799 | junction-mediating and regulatory protein | 290.52 | 233.15 | 287.38 | 1194 | 1060.9 | 1111.5 | 1676.9 | 1290.77 | 1588.17 | 0.204752955 | 0 | 6.13E-006 |
| 5181 | acylphosphatase 1, erythrocyte (common) type | 16.91 | 108.49 | 111.19 | 532.02 | 571.18 | 559.42 | 528.01 | 477.38 | 466.65 | 0.15095098 | 0 | 0.00038783 |
| 7126 | transferrin receptor | 689.39 | 491.5 | 251.38 | 1428.2 | 1227 | 1221.1 | 2092 | 1833.64 | 2227.85 | 0.285602903 | 0 | 0.00068689 |
| 10805 | RIKEN cDNA 9130011I15 gene | 285.53 | 256.11 | 271.55 | 782.98 | 735.67 | 749.47 | 1214.6 | 1679.66 | 1121.66 | 0.258811622 | 0 | 0.0002899 |
| 10887 | phosphatidylserine synthase 2 | 708.39 | 150.51 | 190.22 | 1424.2 | 1092.5 | 1221.8 | 1035.7 | 1127.98 | 1999.15 | 0.265555293 | 0 | 0.00127543 |
| 12367 | Kruppel-like factor 9 | 42.96 | 50.16 | 156.96 | 413.31 | 485.3 | 353.82 | 523.55 | 415.15 | 759.55 | 0.16950669 | 0 | 0.00019734 |
| 13878 | general transcription factor IIIC, polypeptide 4 | 27.87 | 16.57 | 35.71 | 474.48 | 220.1 | 217.44 | 516.42 | 384.03 | 566.54 | 0.067380969 | 0 | 2.35E-005 |
| 13972 | eukaryotic translation initiation factor 3, subunit 6 | 203.48 | 187.05 | 266.56 | 1013.4 | 919.72 | 998.66 | 1287.5 | 1098.19 | 1049.17 | 0.206416571 | 0 | 1.86E-006 |
| 14002 | phosphatidylserine synthase 2 | 602.84 | 152.26 | 203.21 | 1152.7 | 870.06 | 1008.7 | 1052.6 | 1114.61 | 1781.74 | 0.274571264 | 0 | 0.00102264 |
| 14683 | diacylglycerol kinase, epsilon | 190.03 | 434.95 | 115.62 | 1081.8 | 777.24 | 733.1 | 1097.9 | 905.2 | 997.74 | 0.264831986 | 0 | 0.00044972 |
| 15504 | torsin family 2, member A | 231.7 | 99.13 | 132.44 | 803.51 | 625.23 | 692.06 | 515.53 | 1579.92 | 860.9 | 0.18249246 | 0 | 0.00031663 |
| 15713 | acylphosphatase 1, erythrocyte (common) type | 9.09 | 70.55 | 99.27 | 431.09 | 432.79 | 469.83 | 452.15 | 386.11 | 368.38 | 0.140854607 | 0 | 0.00068273 |
| 15791 | eukaryotic translation initiation factor 3, subunit 6 | 117.88 | 107.21 | 148.87 | 614.35 | 581.81 | 595.12 | 849.71 | 634.84 | 809.58 | 0.183070977 | 0 | 2.91E-006 |
| 18122 | acylphosphatase 1, erythrocyte (common) type | 24.1 | 104.37 | 109.38 | 657.52 | 691.59 | 706.49 | 594.96 | 581.28 | 463.27 | 0.12873771 | 0 | 0.00010853 |
| 18375 | solute carrier family 19 (sodium/hydrogen exchanger), member 3 | 227.44 | 127.66 | 156.95 | 731.75 | 478.33 | 711.17 | 1053 | 795.48 | 1291.81 | 0.202330925 | 0 | 0.0001809 |
| 19172 | transmembrane protein 111 | 330.63 | 240.26 | 230.31 | 1271.5 | 949.26 | 808.68 | 1152.8 | 998.66 | 1763.99 | 0.230733122 | 0 | 7.44E-005 |
| 21863 | Kruppel-like factor 9 | 126.03 | 324.94 | 264.78 | 1413.6 | 1073.9 | 1024.2 | 1693.1 | 992.37 | 1695.4 | 0.181373344 | 0 | 8.56E-005 |
| 21873 | eukaryotic translation initiation factor 3, subunit 8 | 688.45 | 338.22 | 292.12 | 1367.9 | 940 | 1082 | 1811.8 | 1859.33 | 2228.32 | 0.283934988 | 0 | 0.00112513 |
| 22149 | phosphatidylserine synthase 2 | 1200.27 | 227.6 | 292.55 | 2416.8 | 1922 | 2063.5 | 1639.9 | 1905.6 | 3229.72 | 0.261113788 | 0 | 0.00137219 |
| 22419 | eukaryotic translation initiation factor 3, subunit 6 | 253.42 | 148.89 | 203.42 | 867.23 | 627.04 | 653.69 | 1252.5 | 944.86 | 908.52 | 0.23058519 | 0 | 7.39E-005 |
| 27213 | DNA segment, Chr 19, Brigham & Women's Genetics 1357 expressed | 566.7 | 267.24 | 1036.42 | 1513.8 | 1213 | 2166.7 | 2823.8 | 2513.75 | 3203.16 | 0.278448166 | 0 | 0.00268403 |
| 28204 | galactosidase, beta 1 | 426.39 | 169.6 | 51.27 | 1713.4 | 1707.9 | 1919 | 2551.5 | 2521.75 | 2747.95 | 0.098357318 | 0 | 0.00014849 |
| 28632 | ankyrin repeat domain 38 | 29.64 | 6.72 | 16.18 | 346.3 | 291.12 | 247.57 | 166 | 148.99 | 316.27 | 0.069302556 | 0 | 4.02E-005 |
| 29867 | RIKEN cDNA 4933433K01 gene | 145.78 | 41.38 | 31.11 | 448.82 | 321.98 | 385.46 | 480.01 | 555.13 | 902.54 | 0.141095173 | 0 | 0.00031856 |
| 33396 | Transcribed locus | 352.3 | 82.9 | 105.87 | 670.9 | 481.47 | 592.69 | 1401.6 | 1113.63 | 1247.74 | 0.196466957 | 0 | 0.00143556 |
| 41050 | RIKEN cDNA 4930427A07 gene | 225.06 | 114.11 | 217.2 | 462.21 | 493.17 | 756.34 | 822.19 | 1212.27 | 977.74 | 0.23355437 | 0 | 0.00068706 |
| 29064 | ubiquitin specific peptidase 22 | 470.08 | 134.25 | 91.36 | 877.44 | 673.24 | 719.13 | 843.91 | 842.44 | 1309.02 | 0.264260671 | 0.01064 | 0.00127129 |

TABLE 8B-continued

| Row | Gene | Oct. 4, 2001 | Oct. 4, 2002 | Oct. 4, 2003 | NI1.1 | NI1.2 | NI1.3 | NI2.1 | NI2.2 | NI2.3 | foldchange | fdr | t.pvals |
|---|---|---|---|---|---|---|---|---|---|---|---|---|---|
| 21759 | eukaryotic translation initiation factor 3, subunit 8 | 873.58 | 406.65 | 383.89 | 1537.6 | 1184.1 | 1444.6 | 1689.9 | 1790.34 | 2140.93 | 0.340049716 | 0.01111 | 0.00060111 |
| 22191 | ribosomal protein L24 /// similar to ribosomal protein L24 /// similar to ribosomal protein L24 | 1172.49 | 672.1 | 952.29 | 1781.4 | 1430.2 | 1946.1 | 2400.7 | 2576.5 | 2545.94 | 0.441122173 | 0.01124 | 0.0018963 |
| 2935 | sirtuin 1 ((silent mating type information regulation 2, homolog) 1 (S. cerevisiae) | 159.78 | 122.53 | 182.71 | 551.66 | 431.36 | 568.18 | 612.19 | 521.34 | 692.06 | 0.275421332 | 0.01136 | 2.03E-005 |
| 4370 | ATP-binding cassette, sub-family F (GCN20), member 1 | 427.95 | 279.01 | 441.26 | 1100.4 | 946.89 | 1266 | 1325.4 | 1128.42 | 2317.25 | 0.284061348 | 0.01136 | 0.00045761 |
| 16122 | Transcribed locus | 93.98 | 30.44 | 15.4 | 215.29 | 193.76 | 209.2 | 360.32 | 327.29 | 349.09 | 0.168971872 | 0.01149 | 0.00047997 |
| 153 | eukaryotic translation initiation factor 3, subunit 8 | 475.14 | 206.19 | 253.03 | 1108.7 | 888.34 | 784.61 | 1267.7 | 1026.05 | 1313.35 | 0.292501663 | 0.01163 | 0.00024627 |
| 8022 | ATP-binding cassette, sub-family F (GCN20), member 2 | 152.19 | 156.91 | 162.97 | 363.57 | 305.96 | 451.65 | 884.29 | 887.81 | 683.59 | 0.263957035 | 0.01163 | 0.00200161 |
| 28457 | solute carrier family 30 (zinc transporter), member 1 | 233.42 | 27.36 | 61.68 | 315.4 | 343.75 | 619.79 | 393.91 | 491.5 | 503.8 | 0.241710549 | 0.01176 | 0.00194384 |
| 21824 | thioredoxin-like 2 | 294.52 | 175.68 | 266.05 | 909.58 | 693.73 | 804.9 | 643.13 | 850.93 | 762.17 | 0.315686342 | 0.0119 | 4.42E-005 |
| 7389 | inositol polyphosphate-5-phosphatase E | 25.77 | 21.31 | 39.99 | 241.41 | 177.04 | 187.24 | 342.97 | 181.11 | 290.47 | 0.122613079 | 0.01205 | 1.28E-005 |
| 16808 | cathepsin B | 130.23 | 101.77 | 67.38 | 288.01 | 181.13 | 261.76 | 690.28 | 580.37 | 717.78 | 0.22018659 | 0.0122 | 0.00427226 |
| 39214 | 1-acylglycerol-3-phosphate O-acyltransferase 5 (lysophosphatidic acid acyltransferase, epsilon) | 499.54 | 525.47 | 363.14 | 1210.6 | 1108.5 | 1066.1 | 1281.2 | 1561.27 | 1458.73 | 0.361200628 | 0.0125 | 7.86E-005 |
| 3399 | abhydrolase domain containing 6 | 156.99 | 100 | 43.52 | 553.9 | 326.89 | 296.3 | 593.6 | 167.18 | 618.84 | 0.235075546 | 0.01266 | 0.00413915 |
| 53 | transferrin receptor | 409.32 | 206.62 | 95.99 | 595.48 | 591.14 | 503.44 | 983.73 | 948.43 | 1145.38 | 0.298653411 | 0.01316 | 0.00301392 |
| 9791 | PQ loop repeat containing 2 | 13.76 | 7.56 | 6.29 | 292.48 | 156.56 | 55.45 | 60.34 | 219.02 | 172.47 | 0.057742178 | 0.01333 | 0.00024888 |
| 7125 | transferrin receptor | 361.01 | 329.39 | 377.07 | 974.9 | 842.63 | 895.37 | 1430.9 | 1069.76 | 1417.72 | 0.321952338 | 0.01351 | 0.00011751 |
| 14950 | eukaryotic translation initiation factor 2C, 5 | 44.09 | 7.7 | 7.32 | 207.56 | 115.15 | 151.62 | 314.47 | 175.57 | 291.88 | 0.094105473 | 0.0137 | 0.00022399 |
| 18250 | apoptotic peptidase activating factor 1 | 36.46 | 51.69 | 50.02 | 277.53 | 197.48 | 388.51 | 297.58 | 228.07 | 287.72 | 0.164793159 | 0.01389 | 8.99E-006 |
| 10657 | jumonji, AT rich interactive domain 1C (Rbp2 like) | 55.24 | 122.77 | 112.59 | 314.35 | 218.11 | 459.64 | 670.73 | 493.09 | 411.48 | 0.226376879 | 0.01408 | 0.00075321 |
| 43911 | gb: BM122336 /DB_XREF = gi: 17106104 /DB_XREF = L0508F03 /FEA = EST /CLONE = L0508F03-3 /CNT = 3 /TID = Mm.218397.1 /TIER = ConsEnd /STK = 2 /UG = Mm.218397 /UG_TITLE = ESTs | 75.29 | 12.69 | 9.34 | 166.18 | 32.25 | 202.06 | 433.2 | 516.27 | 301.93 | 0.117828669 | 0.01449 | 0.00986852 |
| 18703 | transcription elongation factor B (SIII), polypeptide 3 | 231.44 | 240.04 | 198.89 | 638.35 | 629.15 | 741.99 | 859.61 | 921.16 | 783.83 | 0.293116226 | 0.01471 | 1.39E-005 |
| 16204 | protective protein for beta-galactosidase | 474.09 | 446.21 | 267.96 | 1117.8 | 569.65 | 1350.3 | 1365.1 | 642.54 | 1356.92 | 0.371197851 | 0.01493 | 0.00629467 |
| 15395 | Vacuolar protein sorting 54 (yeast) | 714.94 | 245.49 | 144.2 | 1535.2 | 886.77 | 1048.1 | 1134.2 | 921.8 | 1216.19 | 0.327673024 | 0.01515 | 0.00227705 |
| 4980 | sphingosine-1-phosphate phosphatase 1 | 262.03 | 173.69 | 51.88 | 1215.3 | 589.36 | 577.14 | 509.63 | 536.21 | 763.86 | 0.232661338 | 0.01538 | 0.0016041 |

TABLE 8B-continued

| Row | Gene | Oct. 4, 2001 | Oct. 4, 2002 | Oct. 4, 2003 | NI1.1 | NI1.2 | NI1.3 | NI2.1 | NI2.2 | NI2.3 | foldchange | fdr | t.pvals |
|---|---|---|---|---|---|---|---|---|---|---|---|---|---|
| 54 | transferrin receptor | 434.35 | 354.1 | 332.55 | 1138.5 | 818.28 | 858.07 | 1238.7 | 1119.89 | 1324.05 | 0.345056322 | 0.01563 | 0.00010839 |
| 27902 | potassium inwardly-rectifying channel, subfamily K, member 6 | 44.82 | 139.14 | 63.27 | 323.91 | 232.15 | 319.5 | 516.23 | 473.27 | 565.17 | 0.203462224 | 0.01587 | 0.00046105 |
| 39802 | neuropilin (NRP) and tolloid (TLL)-like 2 | 87 | 64.53 | 146.38 | 522.51 | 475.14 | 750.45 | 427.95 | 275.96 | 347.24 | 0.212849871 | 0.01639 | 0.00032483 |
| 384 | ribosomal protein S15 | 256.87 | 118.98 | 155.05 | 330.72 | 201.23 | 1135.8 | 727.25 | 514.63 | 1106.92 | 0.264353593 | 0.01667 | 0.01955601 |
| 6466 | DB_XREF = gi: 14010854 /GEN = Usmg3 /FEA = FLmRNA /CNT = 2 /TID = Mm.218588.1 /TIER = FL /STK = 1 /UG = Mm.218588 /LL = 83678 /DEF = *Mus musculus* upregulated during skeletal muscle growth 3 (Usmg3), mRNA. /PROD = upregulated | 228.12 | 205.44 | 238.32 | 906 | 787.64 | 785.29 | 730.81 | 656.42 | 846.69 | 0.285126834 | 0.01667 | 3.78E−006 |
| 34766 | Vacuolar protein sorting 33A (yeast) | 315.2 | 115.51 | 221.53 | 607.77 | 456.63 | 589.67 | 807.65 | 809.12 | 987.11 | 0.306363391 | 0.01667 | 0.00105604 |
| 38885 | RNA, U transporter 1 | 515.79 | 234.67 | 214.8 | 722.54 | 562.88 | 810.9 | 985.1 | 1105.78 | 1283.74 | 0.352868063 | 0.01681 | 0.00227145 |
| 8821 | peptidase (mitochondrial processing) alpha | 73.11 | 56.51 | 41.28 | 381.32 | 318.1 | 307.73 | 329.1 | 251.1 | 518.94 | 0.16227585 | 0.01695 | 1.65E−005 |
| 10448 | RIKEN cDNA 2610028H07 gene | 638.95 | 517.06 | 757.25 | 1387 | 1282.6 | 1540.6 | 1558.4 | 2078.88 | 1484.02 | 0.410069668 | 0.01724 | 0.00022595 |
| 14001 | phosphatidylserine synthase 2 | 252.19 | 121.81 | 137.37 | 847.59 | 360.31 | 528.7 | 764.33 | 553.32 | 801.99 | 0.265216895 | 0.01724 | 0.0006063 |
| 21527 | DEAD (Asp-Glu-Ala-Asp) box polypeptide 49 | 173.52 | 35.84 | 59.84 | 496.4 | 167.03 | 182.83 | 391.02 | 405.54 | 415.71 | 0.26154586 | 0.01739 | 0.00468851 |
| 29344 | Adult male cecum cDNA, RIKEN full-length enriched library, clone: 9130409M07 product: hypothetical protein, full insert sequence | 90.7 | 19.1 | 227.83 | 613.93 | 432.25 | 327.99 | 562.83 | 671.26 | 386.9 | 0.225450393 | 0.01754 | 0.00292411 |
| 13579 | RIKEN cDNA 9430010O03 gene | 1276.81 | 930.39 | 852.58 | 2128.7 | 1524.5 | 2270.8 | 2042.7 | 2601.49 | 3336.82 | 0.440098756 | 0.0177 | 0.00221166 |
| 8699 | homeodomain interacting protein kinase 1 | 703.08 | 358.75 | 437.43 | 1281.1 | 954.65 | 1185.9 | 1575.7 | 1648.73 | 1861.89 | 0.352435769 | 0.01786 | 0.00072822 |
| 16053 | expressed sequence C77815 | 226.98 | 68.5 | 120.21 | 355.27 | 288.1 | 364.69 | 689.78 | 629.82 | 713.08 | 0.273413709 | 0.01786 | 0.00247561 |
| 33270 | gene model 104, (NCBI) | 167.88 | 96.62 | 189.61 | 623.96 | 423.95 | 354.11 | 625.11 | 416.17 | 774.69 | 0.282232077 | 0.01802 | 0.00055679 |
| 3951 | solute carrier family 25, member 36 | 196.31 | 138.07 | 287.87 | 552.92 | 426.31 | 612.23 | 716.16 | 716.8 | 838.71 | 0.322148103 | 0.01818 | 0.00045152 |
| 8247 | melanocyte proliferating gene 1 | 38.3 | 8.3 | 8.89 | 124.7 | 125.7 | 87.63 | 225.51 | 241.69 | 255.09 | 0.104666516 | 0.01835 | 0.00028537 |
| 24977 | origin recognition complex, subunit 4-like (*S. cerevisiae*) | 64.74 | 3.28 | 40.64 | 285.69 | 259.43 | 282.71 | 113.94 | 217.49 | 143.37 | 0.166831717 | 0.01852 | 0.00382844 |
| 28887 | deficient 5, cell division cycle 46 (*S. cerevisiae*) | 521.19 | 337.32 | 431.77 | 1405.9 | 1199.3 | 1296.8 | 1001.6 | 1386.43 | 1286.19 | 0.34061178 | 0.01852 | 3.87E−005 |
| 44778 | gb: BB473929 /DB_XREF = gi: 16439785 /DB_XREF = BB473929 /CLONE = D330003M06 /FEA = EST /CNT = 5 /TID = Mm.214471.1 /TIER = ConsEnd /STK = 3 /UG = Mm.214471 | 186.55 | 85.65 | 81.04 | 314.37 | 247.68 | 303.97 | 629.46 | 581.85 | 788.79 | 0.246493517 | 0.01887 | 0.00263775 |

TABLE 8B-continued

| Row | Gene | Oct. 4, 2001 | Oct. 4, 2002 | Oct. 4, 2003 | NI1.1 | NI1.2 | NI1.3 | NI2.1 | NI2.2 | NI2.3 | foldchange | fdr | t.pvals |
|---|---|---|---|---|---|---|---|---|---|---|---|---|---|
| | /UG_TITLE = ESTs, Weakly similar to ENV1_HUMAN RETROVIRUS-RELATED ENV POLYPROTEIN (*H. sapiens*) | | | | | | | | | | | | |
| 9574 | solute carrier family 1 (neuronal/epithelial high affinity glutamate transporter, system Xag), member 1 | 86.76 | 56.92 | 100.42 | 341.84 | 267.96 | 357.7 | 469.01 | 318.11 | 475.25 | 0.21893653 | 0.01905 | 4.04E-005 |
| 8320 | DEAD (Asp-Glu-Ala-Asp) box polypeptide 27 | 112.56 | 127.64 | 180.35 | 447.67 | 410.04 | 494.24 | 453.03 | 489.33 | 871.51 | 0.265681561 | 0.01908 | 0.00016822 |
| 5137 | nuclear respiratory factor 1 | 96.06 | 22.21 | 58.59 | 206.74 | 207.72 | 216.54 | 387.53 | 439.3 | 340.7 | 0.196671726 | 0.01923 | 0.00072954 |
| 12240 | kelch-like 21 (*Drosophila*) | 945.8 | 323.32 | 551.74 | 1286.9 | 1071.9 | 1407.3 | 2344.7 | 2073.51 | 1947.4 | 0.359439618 | 0.01923 | 0.00324608 |
| 1375 | signaling intermediate in Toll pathway-evolutionarily conserved | 36.01 | 35.11 | 41.82 | 287.35 | 199.74 | 197.73 | 218.85 | 209.08 | 241.65 | 0.166674956 | 0.01935 | 7.77E-007 |
| 20342 | kinesin family member 11 | 285.49 | 271.4 | 175.23 | 802.55 | 400.74 | 666.11 | 896.31 | 538.17 | 967.58 | 0.34279614 | 0.01938 | 0.00170065 |
| 32215 | RIKEN cDNA 4833426I09 gene | 123.19 | 52.54 | 98.29 | 403.04 | 266.83 | 290.65 | 664.64 | 325.8 | 820.34 | 0.197755566 | 0.01942 | 0.00102827 |
| 40316 | (human) | 76.89 | 53.93 | 138.9 | 311.28 | 272.58 | 273.85 | 386.44 | 406.16 | 550.1 | 0.245154312 | 0.01948 | 0.00031454 |
| 22448 | ribosomal protein L37a | 1002.33 | 507.96 | 700.13 | 1369.4 | 1086.7 | 1508.1 | 1821.2 | 2432.09 | 2770.43 | 0.402340412 | 0.01953 | 0.00609027 |
| 14883 | similar to tripartite motif-containing 43 | 2079.61 | 1375.77 | 1494.31 | 3821.7 | 3156.2 | 3686.6 | 3576.3 | 3726.61 | 3888.5 | 0.452940224 | 0.01961 | 0.00012531 |
| 17514 | dolichol-phosphate (beta-D) mannosyltransferase 1 | 258.66 | 211.61 | 223.09 | 752.95 | 658.07 | 688.27 | 654.69 | 634.23 | 705.73 | 0.338725042 | 0.01961 | 4.11E-006 |
| 20498 | interleukin 17 receptor D | 209.33 | 454.26 | 402.87 | 1218.7 | 961.8 | 1018.6 | 741.16 | 890.6 | 1180.07 | 0.354838495 | 0.01961 | 0.00052241 |
| 8691 | YLP motif containing 1 | 212.15 | 172.37 | 259.8 | 629.55 | 420.34 | 439.07 | 700.52 | 102.0 | 768.8 | 0.32391888 | 0.01969 | 0.00118415 |
| 1363 | protein tyrosine phosphatase, non-receptor type 1 | 179.44 | 81.35 | 70.37 | 316.61 | 354.23 | 389.06 | 459.26 | 401.39 | 646.69 | 0.257989125 | 0.01974 | 0.00033685 |
| 4707 | RIKEN cDNA 2310008H09 gene | 197.94 | 200.34 | 46.69 | 511.26 | 431.89 | 592.74 | 490.78 | 359.97 | 815.86 | 0.277889149 | 0.01984 | 0.00233408 |
| 29582 | HECT domain containing 1 | 631.08 | 441.62 | 450.4 | 1198 | 860.21 | 1101.7 | 1757.5 | 1238.84 | 1402.21 | 0.403019138 | 0.01987 | 0.00082061 |
| 12090 | pyridoxal (pyridoxine, vitamin B6) kinase | 799 | 486.45 | 774.66 | 1353.4 | 1207.1 | 1465.8 | 1752.2 | 1584.83 | 2835.54 | 0.403985912 | 0.02 | 0.00279501 |
| 19076 | B-cell receptor-associated protein 31 | 467.79 | 406.25 | 272.93 | 836.98 | 845.26 | 926.32 | 1177.4 | 1170.25 | 1387.16 | 0.361629108 | 0.02 | 0.00035378 |
| 22059 | DNA segment, Chr 9, ERATO Doi 720, expressed | 78.25 | 101.45 | 110.24 | 395.68 | 368.76 | 211.62 | 565.85 | 296.89 | 522.68 | 0.24555787 | 0.02 | 0.00042704 |
| 14968 | Casitas B-lineage lymphoma-like 1 | 59.21 | 39.31 | 73.98 | 227.96 | 165.93 | 243.84 | 387.77 | 297.25 | 353.48 | 0.205819011 | 0.02013 | 0.00013549 |
| 3646 | RIKEN cDNA 0610007P06 gene | 95.48 | 69.48 | 144.37 | 251.3 | 275.76 | 304.24 | 515.25 | 489.89 | 705.11 | 0.243418386 | 0.02016 | 0.00113655 |
| 7606 | caseinolytic peptidase X (*E. coli*) | 305.08 | 204.23 | 250.93 | 827.98 | 642.13 | 720.65 | 860.05 | 674.03 | 951.76 | 0.325125091 | 0.02041 | 4.40E-005 |
| 14623 | DNA segment, Chr 19, ERATO Doi 721, expressed | 1485.68 | 1003.23 | 618.92 | 2282.7 | 1674.9 | 1684 | 2958.2 | 2051.06 | 2943.84 | 0.457211329 | 0.02041 | 0.00546228 |
| 21740 | ubiquitin specific peptidase 22 | 61.29 | 89.92 | 72.62 | 339.83 | 313.96 | 288.37 | 464.56 | 442.81 | 598.41 | 0.182872129 | 0.02041 | 3.09E-005 |
| 40844 | RIKEN cDNA A530082C11 gene | 103.02 | 148.62 | 109.7 | 459.34 | 222.66 | 476.49 | 456.67 | 365.07 | 541.49 | 0.286582174 | 0.02049 | 0.0004431 |
| 41846 | DNA segment, Chr 14, Abbott 1 expressed | 186.91 | 203.53 | 137.66 | 493.13 | 316.45 | 653.17 | 637.61 | 639.35 | 503.72 | 0.325642915 | 0.02055 | 0.00045287 |
| 12366 | Kruppel-like factor 9 | 16.35 | 11.35 | 21.12 | 152.11 | 133.07 | 165.7 | 191.43 | 117.35 | 292.03 | 0.092841046 | 0.02066 | 1.05E-005 |

TABLE 8B-continued

| Row | Gene | Oct. 4, 2001 | Oct. 4, 2002 | Oct. 4, 2003 | NI.1.1 | NI.1.2 | NI.1.3 | NI.2.1 | NI.2.2 | NI.2.3 | foldchange | fdr | t.pvals |
|---|---|---|---|---|---|---|---|---|---|---|---|---|---|
| 16275 | ankyrin repeat domain 10 | 957.77 | 535.96 | 734 | 1791.6 | 1402.8 | 1508.8 | 1900.9 | 1549.28 | 1875.29 | 0.444274929 | 0.02069 | 0.00043489 |
| 15513 | solute carrier family 44, member 2 | 306.38 | 221.45 | 247.39 | 842.17 | 546.42 | 703.47 | 972.75 | 1046.06 | 1199.47 | 0.29229649 | 0.02083 | 0.00026173 |
| 30136 | DEAD/H (Asp-Glu-Ala-Asp/His) box polypeptide 31 | 298.29 | 107.94 | 733.56 | 541.89 | 894.27 | 2088.9 | 557.59 | 1736.89 | 1228.52 | 0.323432306 | 0.02083 | 0.02150807 |
| 5443 | phosphatidylinositol glycan, class N | 16.63 | 32.81 | 16.53 | 182.07 | 166.32 | 169.44 | 257.91 | 95.85 | 192.79 | 0.123959488 | 0.02098 | 3.41E-005 |
| 11492 | splicing factor, arginine/serine-rich 15 /// similar to splicing factor, arginine/serine-rich 15 | 1024.33 | 1160.82 | 1136.04 | 2097 | 1886.9 | 1968.6 | 2810.8 | 2721.99 | 2515.66 | 0.474425893 | 0.02113 | 0.00046687 |
| 512 | ribosomal protein L37a | 554.13 | 423.04 | 428.11 | 1126.8 | 809.26 | 769.11 | 1242.4 | 1292.95 | 1650.52 | 0.407856568 | 0.02128 | 0.00194373 |
| 19536 | TATA box binding protein (TBP)-associated factor | 311.53 | 245.56 | 144.13 | 955.42 | 630.33 | 651.71 | 788.7 | 630.81 | 1019.52 | 0.299891585 | 0.02151 | 0.00027298 |
| 13981 | bolA-like 2 (E. coli) | 1123.84 | 508.83 | 707.52 | 1607 | 1111.3 | 1182.5 | 2058.8 | 2007.06 | 2217.36 | 0.459584404 | 0.02174 | 0.00773939 |
| 16339 | CNDP dipeptidase 2 (metallopeptidase M20 family) | 29.26 | 96.28 | 61.29 | 542.76 | 229.08 | 165.59 | 150.97 | 419.23 | 414.14 | 0.194435338 | 0.02174 | 0.00246061 |
| 40577 | RIKEN cDNA D330037H05 gene /// similar to La-related protein 4 (La ribonucleoprotein domain family member 4) /// similar to La-related protein 4 (La ribonucleoprotein domain family member 4) | 2109.33 | 1591.5 | 1770.31 | 3282.8 | 2998.5 | 3238.5 | 4490.2 | 4321.16 | 4046.76 | 0.488976197 | 0.02198 | 0.00074647 |
| 23071 | RIKEN cDNA 3300001M20 gene | 252.81 | 164.8 | 211.21 | 708.72 | 562.73 | 499.17 | 858.23 | 902.18 | 429.21 | 0.317566612 | 0.02222 | 0.0005967 |
| 5178 | RIKEN cDNA 1700021F05 gene | 1666.18 | 665.55 | 1064.07 | 2327.8 | 1899.1 | 2094.8 | 2301 | 2524.08 | 2681.17 | 0.491153722 | 0.02339 | 0.00283379 |
| 9650 | bone morphogenetic protein receptor, type 1A | 216.85 | 211.07 | 155.24 | 631.62 | 531 | 550.21 | 566.68 | 440.17 | 655.89 | 0.345517942 | 0.02347 | 4.52E-005 |
| 20927 | ribosomal protein S15a | 1300.6 | 959.53 | 1013.49 | 2281.4 | 1908 | 2020.4 | 1644.5 | 2363.4 | 2951.07 | 0.497181577 | 0.02358 | 0.00167999 |
| 9017 | L-2-hydroxyglutarate dehydrogenase | 651.86 | 266.18 | 527.12 | 1034.2 | 590.33 | 965.17 | 1621.2 | 1345.63 | 1417.59 | 0.414435677 | 0.02367 | 0.00986099 |
| 19095 | ribosomal protein S25 | 1492.69 | 819.24 | 1298.17 | 1951 | 1634.9 | 2069.3 | 2782.6 | 3268.32 | 3608.72 | 0.471453683 | 0.02381 | 0.00935608 |
| 23146 | RIKEN cDNA 4933417E01 gene | 1387.41 | 981.03 | 1339 | 2342.5 | 1725.8 | 1965.4 | 2559.7 | 2606.75 | 2682.38 | 0.534117054 | 0.02392 | 0.00225043 |
| 14122 | ribosomal protein L37 /// similar to ribosomal protein L37 | 2088.46 | 1026.24 | 1539.86 | 2325.4 | 1980.6 | 2858.3 | 3213.9 | 3926.6 | 5118.59 | 0.47927296 | 0.02395 | 0.01585526 |
| 1918 | solute carrier family 12, member 2 | 967.39 | 592.93 | 609.84 | 1657.9 | 1103 | 1407.2 | 2393.4 | 1532.65 | 1828.34 | 0.437422461 | 0.0241 | 0.00251573 |
| 9201 | proline, glutamic acid and leucine rich protein 1 | 510.07 | 270.17 | 230.83 | 665.9 | 602.67 | 521.24 | 1107.5 | 1067.04 | 1083.99 | 0.400553843 | 0.02415 | 0.00573436 |
| 7982 | RIKEN cDNA 2610012O22 gene | 269.15 | 194.81 | 225.6 | 623.68 | 421.41 | 548.5 | 719.07 | 776.11 | 829.08 | 0.352009393 | 0.02424 | 0.0003918 |
| 6045 | Son of sevenless homolog 1 (Drosophila) | 324.06 | 248.6 | 173.51 | 684.56 | 368.73 | 779.87 | 937.33 | 493.55 | 698.66 | 0.376596765 | 0.02439 | 0.00317609 |
| 8238 | RIKEN cDNA 2900073H19 gene | 238.99 | 108.15 | 83.52 | 574.46 | 220.64 | 424.2 | 345.06 | 612.16 | 561.13 | 0.314620203 | 0.02439 | 0.00372284 |
| 1087 | (formerly 2C), magnesium-dependent, gamma isoform | 787.65 | 715.87 | 989.87 | 1836.5 | 1670.7 | 1777.8 | 1497.2 | 1797.05 | 1727.82 | 0.483825524 | 0.02463 | 0.00012463 |
| 12224 | solute carrier family 44, member 2 | 389.99 | 279.49 | 239.58 | 762.05 | 891.14 | 732.46 | 894.68 | 755.73 | 873.96 | 0.370287697 | 0.02469 | 5.28E-005 |
| 8376 | poly (A) polymerase alpha | 27.35 | 12.11 | 9.5 | 148.02 | 91.72 | 167.2 | 349.39 | 111.73 | 134.94 | 0.097627119 | 0.02475 | 0.00014113 |
| 15635 | DEAD (Asp-Glu-Ala-Asp) box polypeptide 54 | 1421.61 | 650.28 | 836.92 | 1354.5 | 1685.8 | 1727.6 | 2190.6 | 2797.01 | 3685.12 | 0.432837698 | 0.025 | 0.01163473 |

TABLE 8B-continued

| Row | Gene | Oct. 4, 2001 | Oct. 4, 2002 | Oct. 4, 2003 | NI1.1 | NI1.2 | NI1.3 | NI2.1 | NI2.2 | NI2.3 | foldchange | fdr | t.pvals |
|---|---|---|---|---|---|---|---|---|---|---|---|---|---|
| 22224 | WD repeat domain 81 | 30.24 | 51.94 | 30.12 | 149.76 | 94.94 | 145.32 | 314.53 | 347.69 | 678.34 | 0.129783079 | 0.025 | 0.00279921 |
| 6961 | defensin related cryptdin 3 | 151.47 | 120.24 | 161.96 | 432.42 | 333.51 | 435.02 | 555.4 | 446.67 | 466.28 | 0.32493163 | 0.0251 | 4.13E-005 |
| 2811 | metal response element binding transcription factor 2 | 1221.23 | 1231.8 | 963.63 | 2148.1 | 1573.3 | 2029 | 2913.6 | 2368.89 | 2633.34 | 0.500011371 | 0.02513 | 0.00216856 |
| 38660 | thioredoxin-like 2 /// similar to thioredoxin-like 2 | 256.9 | 121.83 | 146.19 | 592.86 | 461.89 | 532.76 | 354.26 | 505.22 | 432.44 | 0.364599938 | 0.02517 | 0.00046608 |
| 19232 | proteasome (prosome, macropain) subunit, beta type 4 | 308.03 | 183.74 | 228.7 | 497.19 | 390.48 | 588.01 | 679.25 | 828.99 | 1020.79 | 0.359811322 | 0.02521 | 0.0025591 |
| 7130 | GCN5 general control of amino acid synthesis-like 2 (yeast) | 166.77 | 199.37 | 129.42 | 236.69 | 512.49 | 594.15 | 527.41 | 562.67 | 457.51 | 0.342838958 | 0.02525 | 0.00158602 |
| 39148 | protein phosphatase 1A, magnesium dependent, alpha isoform | 928.91 | 352.17 | 441.26 | 1276.6 | 1065.7 | 1257 | 1597.5 | 1131.12 | 1120.34 | 0.462479307 | 0.02525 | 0.0028015 |
| 20760 | RIKEN cDNA 6330412F12 gene | 1221.12 | 833.76 | 1060.24 | 2026.1 | 1856.5 | 2309.3 | 2009.3 | 2276.23 | 2705.78 | 0.472593299 | 0.02532 | 0.00036731 |
| 30288 | RIKEN cDNA D630023B12 gene | 231.8 | 124.88 | 215.74 | 650.6 | 584.87 | 451.15 | 354.09 | 367.11 | 666.9 | 0.372339595 | 0.02534 | 0.00162651 |
| 6136 | matrix metallopeptidase 19 | 680.52 | 322.99 | 248.89 | 1034.6 | 954 | 994.51 | 1010.7 | 1245.39 | 922.69 | 0.406499315 | 0.02538 | 0.00106165 |
| 504 | glutamate dehydrogenase 1 | 522.62 | 453.19 | 388.25 | 953.35 | 635.51 | 724.4 | 1144.2 | 1119.64 | 1119.85 | 0.478871262 | 0.02542 | 0.00299594 |
| 19855 | acyl-CoA synthetase long-chain family member 4 | 127.18 | 124.68 | 134.3 | 543.08 | 402.43 | 284.25 | 500.48 | 291.57 | 601.29 | 0.294430254 | 0.02548 | 0.000421 |
| 10996 | methionyl aminopeptidase 1 | 241.66 | 153.56 | 132.59 | 424.1 | 450.43 | 589.31 | 730.27 | 394.02 | 744.54 | 0.316749033 | 0.02551 | 0.00058301 |
| 12146 | scaffold attachment factor B2 | 210.74 | 107.75 | 267.22 | 331.79 | 464.58 | 1217.3 | 391.51 | 663.29 | 603.91 | 0.31898202 | 0.02551 | 0.00753413 |
| 14456 | eukaryotic translation initiation factor 4E member 2 | 608.3 | 392.91 | 580.62 | 1063.5 | 641.07 | 821.13 | 1540.2 | 1462.72 | 1376.89 | 0.458135605 | 0.02553 | 0.01083693 |
| 24272 | ribosomal protein S21 | 2211.44 | 1389.97 | 1767.1 | 3057.7 | 2659.7 | 3238.2 | 3772.8 | 3453.75 | 5642.06 | 0.492033374 | 0.02564 | 0.00500878 |
| 20122 | histocompatibility 47 | 1061.18 | 593.13 | 563.78 | 1601.4 | 1273.8 | 1337.6 | 1610.6 | 1602.25 | 1546.14 | 0.494465907 | 0.02575 | 0.00117621 |
| 1829 | integrin beta 5 | 20.55 | 31.81 | 35.62 | 138.64 | 106.21 | 113.56 | 245.56 | 233.83 | 262.94 | 0.159856097 | 0.02577 | 0.0001947 |
| 8820 | peptidase (mitochondrial processing) alpha | 103.32 | 47.96 | 17.42 | 213.06 | 180.94 | 210.53 | 289.87 | 282.06 | 241.71 | 0.237912239 | 0.02577 | 0.00089259 |
| 8632 | polymerase (RNA) II (DNA directed) polypeptide H | 546.89 | 407.89 | 194.5 | 750.55 | 562.77 | 678.85 | 1016.1 | 1159.35 | 1244.52 | 0.424701322 | 0.02586 | 0.00859166 |
| 18309 | fibroblast growth factor 4 | 35.44 | 14.3 | 20.86 | 432.43 | 172.1 | 100.94 | 143.65 | 149.66 | 594.64 | 0.088614427 | 0.02591 | 0.00088338 |
| 29855 | ankyrin repeat domain 35 | 194.21 | 126.07 | 115.62 | 458.93 | 307.25 | 358.15 | 396.59 | 1145.29 | 528.2 | 0.272914247 | 0.02595 | 0.00318398 |
| 23808 | RIKEN cDNA 4632434I11 gene | 448.86 | 431.73 | 363.62 | 671.77 | 596.73 | 936.9 | 1130.6 | 1078.94 | 1163.22 | 0.446102905 | 0.02597 | 0.0029039 |
| 16734 | squamous cell carcinoma antigen recognized by T-cells 1 | 321.84 | 208.57 | 257.48 | 621.17 | 329.5 | 867.92 | 525.03 | 704.23 | 1019.17 | 0.387453221 | 0.02604 | 0.00692468 |
| 20423 | splicing factor, arginine/serine-rich 15 /// similar to splicing factor, arginine/serine-rich 15 | 1714.9 | 1723.34 | 1637.59 | 2614.4 | 2538.8 | 2537.6 | 4326.7 | 3486.43 | 3541.53 | 0.533024807 | 0.02609 | 0.00359332 |
| 21533 | ribosomal protein L41 | 2356.65 | 1636.04 | 2315.68 | 3506.7 | 3203.3 | 3590.5 | 4290.3 | 3926.82 | 4970.51 | 0.537155245 | 0.02618 | 0.00181749 |
| 11378 | gb: AV003927 /DB_XREF = gi: 4780777 /DB_XREF = AV003927 /CLONE = 0610038F02 /FEA = mRNA /CNT = 8 /TID = Mm.89136.2 /TIER = Stack /STK = 8 /UG = Mm.89136 /LL = 15078 /UG_GENE = H3f3a | 1053.61 | 887.11 | 842.46 | 1543.8 | 1584.5 | 1875.9 | 1827.2 | 1989.27 | 2602.7 | 0.487282112 | 0.0262 | 0.00095764 |

TABLE 8B-continued

| Row | Gene | Oct. 4, 2001 | Oct. 4, 2002 | Oct. 4, 2003 | NI.1.1 | NI.1.2 | NI.1.3 | NI.2.1 | NI.2.2 | NI.2.3 | foldchange | fdr | t.pvals |
|---|---|---|---|---|---|---|---|---|---|---|---|---|---|
| | /UG_TITLE = H3 histone, family 3A | | | | | | | | | | | | |
| 10575 | Yip1 domain family, member 4 | 1301.23 | 782.33 | 716.95 | 1652.4 | 1414.2 | 1672.3 | 2397.5 | 2218.58 | 2274.82 | 0.481613455 | 0.02632 | 0.00312624 |
| 27086 | RIKEN cDNA 6720458F09 gene | 514.62 | 69.3 | 305.05 | 616.13 | 470.79 | 506.67 | 1261.3 | 1536.3 | 928.03 | 0.334248254 | 0.02643 | 0.01918525 |
| 7894 | WD repeat domain 36 | 254.38 | 272.47 | 200.29 | 610.23 | 547.12 | 595.16 | 573.36 | 653.39 | 981.04 | 0.367214605 | 0.0265 | 0.00024551 |
| 20279 | UTP20, small subunit (SSU) processome component, homolog (yeast) | 265.64 | 117.47 | 77.53 | 395.94 | 294.27 | 367.33 | 559.06 | 746.95 | 535 | 0.317841679 | 0.02655 | 0.0029134 |
| 1828 | integrin beta 5 | 24.85 | 44.95 | 37.18 | 101.84 | 100.6 | 157.78 | 300.13 | 259.71 | 279.75 | 0.178328235 | 0.0266 | 0.00087414 |
| 11029 | F-box only protein 33 | 352.6 | 363.65 | 331.07 | 680.26 | 745.22 | 715.11 | 875.23 | 916.58 | 1126.49 | 0.414051304 | 0.0266 | 0.00023586 |
| 29619 | BCL2-associated transcription factor 1 | 2093.59 | 1414.28 | 1845.33 | 3045.3 | 2613.5 | 2893.6 | 4169.1 | 3260.8 | 3703.5 | 0.543864934 | 0.02664 | 0.00241845 |
| 7972 | kinesin family member 22 | 361.65 | 356.42 | 276.4 | 873.55 | 734.19 | 599.86 | 722.03 | 806.28 | 1047.44 | 0.415804823 | 0.02667 | 0.00033015 |
| 20855 | upstream binding transcription factor, RNA polymerase I | 926.95 | 606.37 | 732.79 | 1499.9 | 977.24 | 1296.7 | 1732.9 | 1838.77 | 1899.81 | 0.490214572 | 0.02667 | 0.00423551 |
| 3937 | purine rich element binding protein B | 92.81 | 87.2 | 83.07 | 292.59 | 182.12 | 245.32 | 380.5 | 365.18 | 322.38 | 0.294258119 | 0.02669 | 0.00018866 |
| 15556 | ataxin 10 | 17.33 | 32.34 | 12.45 | 228.41 | 198.1 | 179.58 | 181.72 | 19.95 | 77.06 | 0.140412739 | 0.02674 | 0.01259115 |
| 32318 | Guanine nucleotide binding protein (G protein), beta polypeptide 1-like | 38.16 | 26.14 | 37.97 | 167.8 | 192.62 | 140.2 | 315.19 | 211.09 | 159.05 | 0.172469328 | 0.02675 | 3.09E−005 |
| 20865 | transportin 3 | 498.71 | 536.39 | 322.85 | 1055.4 | 938.14 | 988.25 | 892.24 | 975.15 | 1289.64 | 0.442415456 | 0.02676 | 0.00038598 |
| 4981 | sphingosine-1-phosphate phosphatase 1 | 1139.7 | 516.96 | 256.51 | 1556.5 | 1386.4 | 1522.7 | 1138.2 | 1603.75 | 1205.39 | 0.454813871 | 0.02688 | 0.00679675 |
| 19730 | gb: M11310.1 /DB_XREF = gi: 192009 /FEA = FLmRNA /CNT = 3 /TID = Mm.1786.2 /TIER = FL /STK = 2 /UG = Mm.1786 /LL = 11821 /UG_GENE = Aprt /UG_TITLE = adenine phosphoribosyl transferase /DEF = Mouse adenine phosphoribosyltransferase (APRT), complete cds. /FL = gb: M11310.1 | 324.96 | 291.64 | 351.88 | 787.01 | 359.57 | 481.37 | 843.3 | 1266.51 | 1056.9 | 0.403982764 | 0.02688 | 0.01927971 |
| 22636 | glutamine fructose-6-phosphate transaminase 1 | 91.19 | 137.72 | 9.09 | 335.73 | 165.1 | 314.89 | 566.93 | 599.99 | 90.41 | 0.229613372 | 0.02691 | 0.02247234 |
| 2926 | ubiquitin-conjugating enzyme E2H | 294.34 | 174.38 | 235.24 | 787.87 | 546.3 | 553.52 | 647.84 | 590.18 | 714.62 | 0.366614327 | 0.02697 | 0.00012805 |
| 27358 | RIKEN cDNA 9630055N22 gene /// similar to Feline leukemia virus subgroup C receptor-related protein 1 (Feline leukemia virus subgroup C receptor) (hFLVCR) | 51.52 | 68.1 | 41.88 | 364.66 | 211.27 | 222.89 | 271.25 | 214.45 | 185.62 | 0.219706967 | 0.02698 | 4.17E−005 |
| 9307 | sorting nexin 6 | 301.12 | 372.14 | 208.12 | 830.58 | 453.64 | 637.73 | 836.86 | 766.12 | 1038.77 | 0.386256765 | 0.02703 | 0.00175737 |
| 16924 | torsin family 1, member B | 614.56 | 254.05 | 272.1 | 1028.7 | 649.17 | 887.96 | 740.56 | 964.62 | 1195.38 | 0.417351759 | 0.02703 | 0.00265516 |
| 13406 | RIKEN cDNA 1700081L11 gene | 279.8 | 322.06 | 289.78 | 766.08 | 332.23 | 382.41 | 846.57 | 836.8 | 863.11 | 0.442808899 | 0.02708 | 0.02078566 |

TABLE 8B-continued

| Row | Gene | Oct. 4, 2001 | Oct. 4, 2002 | Oct. 4, 2003 | NI1.1 | NI1.2 | NI1.3 | NI2.1 | NI2.2 | NI2.3 | foldchange | fdr | t.pvals |
|---|---|---|---|---|---|---|---|---|---|---|---|---|---|
| 4267 | eukaryotic translation termination factor 1 | 631.46 | 328.73 | 441.06 | 971.21 | 1389.4 | 1088.4 | 1011 | 1046.31 | 2206.07 | 0.363373978 | 0.02717 | 0.0020725 |
| 10910 | nucleoporin 107 | 200.91 | 280.21 | 189.53 | 608.9 | 413.29 | 503.35 | 667.94 | 577.6 | 680.86 | 0.388564112 | 0.02717 | 0.00027743 |
| 3500 | G patch domain containing 4 | 532.74 | 280.11 | 245.54 | 950.82 | 529.03 | 789.31 | 962.71 | 725.77 | 902.34 | 0.435553233 | 0.02727 | 0.00265492 |
| 16856 | solute carrier family 12, member 2 | 171.34 | 87.64 | 209.04 | 527.45 | 337.21 | 487.48 | 447.9 | 572.27 | 515.56 | 0.324128164 | 0.02732 | 0.00041255 |
| 23353 | GINS complex subunit 3 (Psf3 homolog) | 212.75 | 16.22 | 83.74 | 345.6 | 181.35 | 376.3 | 448.35 | 272.34 | 362.05 | 0.314915986 | 0.02737 | 0.00945197 |
| 11567 | thyroid hormone receptor associated protein 3 | 409.89 | 226.84 | 478.01 | 731.74 | 781.37 | 771.17 | 1117 | 1028.78 | 1020.12 | 0.409069141 | 0.0274 | 0.00102386 |
| 20123 | RIKEN cDNA D230025D16 gene | 566.99 | 244.72 | 230.85 | 773.96 | 545.87 | 752.66 | 969.51 | 843.84 | 1512.66 | 0.386240622 | 0.02747 | 0.00551593 |
| 23022 | gene model 608, (NCBI) | 19.79 | 34.73 | 13.36 | 118.5 | 152.45 | 170.4 | 284.71 | 124.46 | 269.07 | 0.121258675 | 0.02747 | 8.52E-005 |
| 957 | sarcosine dehydrogenase | 102.85 | 51.26 | 39.67 | 276.87 | 330.62 | 409.42 | 265.49 | 87.25 | 247.39 | 0.239672488 | 0.02752 | 0.00405166 |
| 11737 | integrin beta 4 binding protein | 1478.64 | 784.12 | 1168.22 | 2140.2 | 1696.4 | 2027.5 | 2235.5 | 2368.91 | 2496.33 | 0.529274561 | 0.02756 | 0.00235946 |
| 12467 | integrator complex subunit 7 | 15.64 | 11.95 | 9.45 | 107.56 | 81.04 | 69.17 | 167.85 | 135.22 | 200.6 | 0.097289347 | 0.02757 | 3.84E-005 |
| 28696 | cDNA sequence BC031781 | 206.5 | 200.11 | 102.8 | 539.87 | 415.28 | 426.91 | 561.46 | 529.25 | 585.07 | 0.3331829 | 0.02762 | 0.0002035 |
| 2616 | dodecenoyl-Coenzyme A delta isomerase (3,2 trans-enoyl-Coenyme A isomerase) | 213.16 | 144.86 | 245.49 | 656.83 | 765.69 | 443.88 | 467.21 | 472 | 709.62 | 0.343368713 | 0.02765 | 0.00043803 |
| 16782 | Traf and Tnf receptor associated protein | 86.91 | 90.66 | 92.25 | 320.57 | 262.64 | 310.65 | 271.8 | 329.04 | 442.44 | 0.278575632 | 0.02778 | 1.87E-005 |
| 17246 | piwi-like homolog 2 (Drosophila) | 194.88 | 162.18 | 83.38 | 485.71 | 471.02 | 370.39 | 490.29 | 309.46 | 467.42 | 0.339545695 | 0.02778 | 0.00050921 |
| 28263 | zinc finger protein 297B | 346.22 | 252.82 | 249.98 | 689.62 | 506.85 | 491.93 | 824.26 | 739.66 | 843.71 | 0.414557511 | 0.02778 | 0.00089669 |
| 13852 | CCR4-NOT transcription complex, subunit 1 | 624.54 | 555.94 | 435.99 | 1003.5 | 854.27 | 1131.5 | 1220.5 | 1252.71 | 1422.68 | 0.46955327 | 0.02788 | 0.00078009 |
| 23277 | biogenesis of lysosome-related organelles complex-1, subunit 2 | 79.81 | 76.06 | 64.03 | 325.63 | 170.46 | 148.71 | 292.97 | 413.85 | 462.88 | 0.242380821 | 0.02793 | 0.00148942 |
| 42753 | RIKEN cDNA 2010002M12 gene | 174.49 | 77.58 | 21.59 | 574.43 | 290.32 | 438.63 | 251.82 | 312.33 | 262.98 | 0.256896236 | 0.02799 | 0.00346194 |
| 20191 | cDNA sequence BC038286 /DB_XREF = gi: 12854789 /GEN = Hipk1 /FEA = mRNA /CNT = 3 /TID = Mm.160710.1 /TIER = ConsEnd /STK = 2 /UG = Mm.160710 /UG_TITLE = Mus musculus adult male testis cDNA, RIKEN full-length enriched library, clone: 4930557G23: homeodomain interacting protein kinase 1, full insert sequence /DEF = Mus musculus adult male testis cDNA, RIKEN full-length enriched library, clone: 4930557G23: homeodomain interacting protein kinase 1 | 125.97 | 73.92 | 68.54 | 284.36 | 290.06 | 209.54 | 343.44 | 337.31 | 491.7 | 0.274410783 | 0.028 | 0.00030981 |
| 39706 | | 615.34 | 546.59 | 659.88 | 1182.5 | 1131.4 | 1245.5 | 1548.5 | 1390.42 | 1818.55 | 0.438098857 | 0.02804 | 0.00032472 |
| 27310 | G patch domain and KOW motifs | 61.52 | 159.03 | 86.57 | 532.82 | 393.07 | 275.19 | 336.31 | 260.97 | 331.72 | 0.288364756 | 0.02809 | 0.00056609 |
| 15631 | Max dimerization protein 3 | 231.87 | 142.18 | 388.83 | 680.62 | 398.74 | 1726.9 | 635.95 | 544.19 | 1682.23 | 0.269158034 | 0.0282 | 0.01298519 |
| 1794 | translocase of inner | 445.43 | 218.47 | 297.38 | 1237.7 | 550.92 | 497.86 | 560.37 | 1173.81 | 1446.18 | 0.351674081 | 0.02825 | 0.01197186 |

TABLE 8B-continued

| Row | Gene | Oct. 4, 2001 | Oct. 4, 2002 | Oct. 4, 2003 | NI.1.1 | NI.1.2 | NI.1.3 | NI.2.1 | NI.2.2 | NI.2.3 | foldchange | fdr | t.pvals |
|---|---|---|---|---|---|---|---|---|---|---|---|---|---|
| 40394 | mitochondrial membrane 10 homolog (yeast) RIKEN cDNA A230097K15 gene | 542.56 | 392.94 | 536.72 | 1135.4 | 943.8 | 714.8 | 1147.6 | 1095.12 | 1136.24 | 0.476993833 | 0.0283 | 0.00099635 |
| 13932 | cytochrome c oxidase, subunit XVII assembly protein homolog (yeast) | 374.36 | 512.87 | 771.27 | 1560.4 | 816.01 | 1231.3 | 757.93 | 1492.77 | 1259.95 | 0.465978119 | 0.02834 | 0.00846149 |
| 12583 | nucleolar and coiled-body phosphoprotein 1 | 1396.29 | 962.28 | 1269.5 | 2433.1 | 1712.7 | 2129 | 2601.3 | 2478.57 | 2899.66 | 0.509051699 | 0.02841 | 0.00166888 |
| 44733 | RIKEN cDNA 2610510H03 gene | 1694.62 | 1302.55 | 1307.24 | 2154.8 | 2197.4 | 2580.1 | 2853.9 | 2696.93 | 3033.96 | 0.554799252 | 0.02841 | 0.00127502 |
| 24057 | RIKEN cDNA 6330548G22 gene | 1941.19 | 1205.89 | 1387.66 | 2922.2 | 2488.6 | 2691 | 2668.2 | 2814.66 | 3260.93 | 0.53838802 | 0.02846 | 0.00088299 |
| 9979 | G patch domain containing 4 | 1180.84 | 937.75 | 328.1 | 2341.4 | 1228.2 | 1953.3 | 2071.8 | 1558.28 | 1584.77 | 0.455720416 | 0.02857 | 0.00998652 |
| 15379 | sorbitol dehydrogenase | 27.38 | 63.24 | 77.06 | 217.25 | 225.56 | 241.16 | 303.1 | 194.63 | 333.28 | 0.221362658 | 0.02857 | 0.00015891 |
| 1395 | CD320 antigen | 376.3 | 186.45 | 150.95 | 519.75 | 347.27 | 458.89 | 885.75 | 732.05 | 898.14 | 0.371539753 | 0.02874 | 0.00681172 |
| 10147 | homeodomain interacting protein kinase 1 /// similar to homeodomain-interacting protein kinase 1 | 162.22 | 95.7 | 238.88 | 242.84 | 377.63 | 282.15 | 900.14 | 726.92 | 970.38 | 0.283880848 | 0.02874 | 0.01486244 |
| 40408 | zinc finger and BTB domain containing 11 | 154.16 | 137.47 | 107.76 | 393.41 | 317.18 | 313.89 | 408.57 | 545.45 | 573.96 | 0.312945159 | 0.02885 | 0.00024451 |
| 12344 | La ribonucleoprotein domain family, member 1 /// similar to la related protein isoform 1 | 383.9 | 74.36 | 193.38 | 510.75 | 581.65 | 447.49 | 684.6 | 681.6 | 1010.2 | 0.332784344 | 0.0289 | 0.00428131 |
| 801 | proteasome (prosome, macropain) subunit, alpha type 6 | 317.41 | 182.75 | 245.98 | 577.9 | 392.79 | 559.5 | 873.25 | 678.68 | 1083.53 | 0.358234609 | 0.02896 | 0.00296154 |
| 12365 | gb: AW545056 /DB_XREF = gi: 7187569 /DB_XREF = C0190C04-3 /CLONE = C0190C04 /FEA = mRNA /CNT = 182 /TID = Mm.29909.1 /TIER = Stack /STK = 60 /UG = Mm.29909 /LL = 69023 /UG_GENE = 1810005K14Rik /UG_TITLE = RIKEN cDNA 1810005K14 gene | 575.81 | 256.8 | 387.06 | 829.02 | 524.34 | 892.94 | 1101.1 | 1108.62 | 1025.51 | 0.44501485 | 0.02907 | 0.00545304 |
| 13580 | RIKEN cDNA 9430010O03 gene | 252.11 | 205.75 | 110.44 | 548.01 | 407.24 | 529.86 | 651.64 | 535.7 | 411.67 | 0.368533001 | 0.0293 | 0.00067634 |
| 29034 | jumonji, AT rich interactive domain 1A (Rbp2 like) | 37.2 | 22.61 | 18.65 | 222.58 | 113.9 | 160.57 | 93.92 | 144 | 233.42 | 0.162042152 | 0.02951 | 0.00011963 |
| 8637 | Bardet-Biedl syndrome 2 homolog (human) | 145.67 | 71.74 | 140.97 | 337.79 | 236.48 | 247.56 | 500.41 | 586.34 | 389.87 | 0.311844939 | 0.02961 | 0.00216673 |
| 21932 | Transcribed locus | 449.07 | 163.81 | 87.36 | 583.75 | 309.89 | 572.13 | 653.87 | 636.22 | 766.49 | 0.397598194 | 0.0297 | 0.00950051 |
| 24471 | TSC22 domain family 2 | 1111.19 | 838.9 | 701.35 | 1530.6 | 1318.9 | 1453.7 | 2101.3 | 2010.43 | 1899.33 | 0.514136405 | 0.0298 | 0.00250066 |
| 12713 | transportin 3 | 236.77 | 170.07 | 152.07 | 455.61 | 333.47 | 459.35 | 782.62 | 552.05 | 536.83 | 0.358283679 | 0.0299 | 0.00088863 |
| 4235 | zinc finger protein 644 | 25.19 | 29.71 | 183.22 | 387.55 | 173.75 | 307.41 | 242.2 | 191.55 | 329.75 | 0.291776181 | 0.03064 | 0.00413242 |
| 27956 | RIKEN cDNA 4933439C20 gene /// phosphatidylserine decarboxylase | 214.02 | 187.62 | 218.88 | 489.82 | 385.39 | 354.78 | 580.99 | 667.79 | 1214.05 | 0.336068371 | 0.03073 | 0.00567336 |

TABLE 8B-continued

| Row | Gene | Oct. 4, 2001 | Oct. 4, 2002 | Oct. 4, 2003 | NI1.1 | NI1.2 | NI1.3 | NI2.1 | NI2.2 | NI2.3 | foldchange | fdr | t.pvals |
|---|---|---|---|---|---|---|---|---|---|---|---|---|---|
| 14945 | proteasome (prosome, macropain) subunit, alpha type 6 | 673.17 | 339.26 | 437.73 | 823.99 | 814.83 | 842.51 | 1149.9 | 1450.18 | 1653.82 | 0.430618656 | 0.03081 | 0.00552425 |
| 8311 | cDNA clone IMAGE: 30031514 | 1455.82 | 885.16 | 844.81 | 1802.7 | 1683.2 | 1977.4 | 2026.2 | 1949.49 | 2208.37 | 0.547043051 | 0.03107 | 0.00167117 |
| 18423 | stromal antigen 2 | 448.64 | 362.26 | 221.01 | 1147.6 | 777.91 | 1089.8 | 665.09 | 575.32 | 749.19 | 0.412363183 | 0.03116 | 0.00282021 |
| 7826 | methionine adenosyltransferase II, alpha | 1253.06 | 613.26 | 919.4 | 1482.9 | 1372 | 1652.5 | 2217 | 1838.93 | 2120.48 | 0.521490234 | 0.03143 | 0.00499621 |
| 8396 | zinc finger protein 639 | 651.33 | 592 | 510.89 | 1190.3 | 1159.1 | 1416.3 | 1011.3 | 1284.01 | 1188.3 | 0.483970154 | 0.03152 | 0.00017759 |
| 19114 | WD repeat domain 36 | 205.63 | 144.93 | 118.6 | 423.92 | 347.67 | 404.86 | 409.04 | 556.77 | 672.92 | 0.333307284 | 0.03161 | 0.00038691 |
| 919 | ubiquitin A-52 residue ribosomal protein fusion product 1 /// similar to ubiquitin A-52 residue ribosomal protein fusion product 1 /// similar to ubiquitin A-52 residue ribosomal protein fusion product 1 /// similar to ubiquitin A-52 residue ribosomal protein fusion product 1 | 1179.37 | 800.7 | 703.02 | 1290.2 | 1670.2 | 1344.1 | 2225.4 | 1773.66 | 3566.28 | 0.452084904 | 0.0317 | 0.01417489 |
| 6104 | brix domain containing 1 | 189.12 | 152.83 | 356.96 | 579.34 | 457.58 | 505.53 | 797.43 | 691.14 | 566.73 | 0.388526162 | 0.03179 | 0.00117216 |
| 14528 | gene model 288, (NCBI) | 611.12 | 289.52 | 223.86 | 897.94 | 493.54 | 694.95 | 841.18 | 913.47 | 964.44 | 0.468003463 | 0.03188 | 0.00748606 |
| 14234 | ribosomal protein S3 | 1603.17 | 992.86 | 1195.88 | 2140 | 1511 | 1797.1 | 2583.6 | 2433.02 | 3136.49 | 0.557583805 | 0.03191 | 0.01375262 |
| 1610 | GRIP1 associated protein 1 | 156.21 | 52.05 | 43.1 | 267.72 | 230.72 | 274.17 | 284.24 | 349.37 | 343.89 | 0.287250516 | 0.03198 | 0.00064653 |
| 607 | arginyl-tRNA synthetase | 475.28 | 273.88 | 474.37 | 856.71 | 656.69 | 777.19 | 931.87 | 958.54 | 1034 | 0.469234899 | 0.032 | 0.00130575 |
| 8157 | general transcription factor IIIC, polypeptide 5 | 212.08 | 99.85 | 122.9 | 316.44 | 273.49 | 369.01 | 425.12 | 499.92 | 698.25 | 0.336786421 | 0.03209 | 0.00211539 |
| 10540 | peroxisome proliferative activated receptor, gamma, coactivator-related 1 | 902.33 | 445.31 | 392.62 | 1139.4 | 999.53 | 1033.5 | 1236.1 | 1335.21 | 2000.98 | 0.449403209 | 0.03215 | 0.00487984 |
| 17591 | zinc finger protein 292 | 33.35 | 44.66 | 45.16 | 200.8 | 146.72 | 175.4 | 256.79 | 209.89 | 116.94 | 0.222621866 | 0.03216 | 6.65E-005 |
| 16780 | histocompatibility 47 | 1837.26 | 1122.62 | 1324.02 | 2610 | 1889.2 | 2344.4 | 2583.7 | 2481.42 | 2674.07 | 0.587533816 | 0.03217 | 0.00342811 |
| 257 | eukaryotic translation initiation factor 3, subunit 3 (gamma) | 627.16 | 426.41 | 780.66 | 1198.3 | 1019.4 | 1204.3 | 1897.9 | 1173.9 | 2308.62 | 0.41675632 | 0.03226 | 0.00484988 |
| 13101 | heterogeneous nuclear ribonucleoprotein A/B | 1618.69 | 1405.47 | 1477.8 | 2463.2 | 2094 | 2498.9 | 2936.5 | 2830.56 | 2597.97 | 0.583869773 | 0.03233 | 0.00099967 |
| 33525 | Transcribed locus | 83.97 | 35.52 | 295.51 | 432.87 | 220.51 | 436.57 | 389.83 | 242.22 | 680.37 | 0.34549216 | 0.03235 | 0.01240034 |
| 2568 | ribosomal protein L30 /// similar to ribosomal protein L30 /// similar to ribosomal protein L30 /// similar to ribosomal protein L30 /// similar to ribosomal protein L30 | 1254.95 | 735.95 | 965.54 | 1689.5 | 1596.4 | 1943.3 | 1668.9 | 1958.22 | 2788.5 | 0.508643152 | 0.03235 | 0.00325586 |
| 7517 | RIKEN cDNA 1810009K13 gene | 143.62 | 57.05 | 68.62 | 322.65 | 136.04 | 252.87 | 427.73 | 276.99 | 553.43 | 0.273431114 | 0.03236 | 0.00435699 |
| 19614 | TIP41, TOR signalling pathway regulator-like (S. cerevisiae) | 1754.37 | 1366.54 | 1274.92 | 2383.4 | 2108.3 | 2070.9 | 2846.6 | 2746.03 | 2667.1 | 0.593140169 | 0.03241 | 0.0026507 |
| 5982 | protein phosphatase 2 (formerly 2A), catalytic subunit, beta isoform | 551.48 | 339.48 | 280.15 | 775 | 546.79 | 692.17 | 928.41 | 1201.26 | 1257.08 | 0.433687423 | 0.03243 | 0.00657847 |
| 9877 | influenza virus NS1A binding protein | 975.18 | 492.65 | 387.23 | 858.37 | 991.15 | 1163.2 | 1663.5 | 2058.91 | 1252.97 | 0.464454715 | 0.03248 | 0.01279151 |
| 16885 | chromosome segregation 1-like | 121.07 | 97.77 | 145.66 | 350.27 | 345.42 | 378.07 | 298.67 | 387.07 | 410.09 | 0.336008186 | 0.03254 | 2.39E-005 |

TABLE 8B-continued

| Row | Gene | Oct. 4, 2001 | Oct. 4, 2002 | Oct. 4, 2003 | NI.1.1 | NI.1.2 | NI.1.3 | NI.2.1 | NI.2.2 | NI.2.3 | foldchange | fdr | t.pvals |
|---|---|---|---|---|---|---|---|---|---|---|---|---|---|
| 29192 | cleavage and polyadenylation specific factor 6 (*S. cerevisiae*) | 17.6 | 44.66 | 34.12 | 174.3 | 133 | 221.06 | 127.6 | 192.74 | 129.81 | 0.196993388 | 0.03256 | 8.84E-005 |
| 8733 | transmembrane emp24 protein transport domain containing 5 | 207.72 | 120.4 | 223.01 | 611.94 | 436.79 | 466.68 | 476.75 | 506.84 | 551.44 | 0.361344593 | 0.03257 | 0.00015655 |
| 8642 | DB_XREF = gi: 14318706 /FEA = FLmRNA /CNT = 134 /TIER = FL + Stack /STK = 29 /UG = Mm.29500 /DEF = *Mus musculus*, hypothetical protein FLJ10788, clone MGC: 6884 IMAGE: 2651599, mRNA, complete cds. | 180.91 | 186.12 | 138.75 | 443.86 | 379.97 | 493.4 | 573.62 | 451.43 | 424.69 | 0.365584014 | 0.03261 | 5.25E-005 |
| 27736 | RIKEN cDNA C730049O14 gene | 468.55 | 201.7 | 280.69 | 854.88 | 650.64 | 580.29 | 733.69 | 724.56 | 697.53 | 0.448388458 | 0.03263 | 0.00126179 |
| 15165 | glutaredoxin 2 (thioltransferase) | 187.31 | 23.63 | 26.17 | 284.27 | 207.99 | 195.31 | 286.09 | 281.75 | 295.36 | 0.305796475 | 0.03264 | 0.00335924 |
| 34773 | coiled-coil domain containing 66 | 327.65 | 244.56 | 99.43 | 681.69 | 370.27 | 538.09 | 732.89 | 447.88 | 631.69 | 0.394790904 | 0.03268 | 0.00477611 |
| 22170 | hexosaminidase B | 466.76 | 254.86 | 157.95 | 680.55 | 374.26 | 443.5 | 767.08 | 800.87 | 731.5 | 0.463204626 | 0.03271 | 0.01339699 |
| 41702 | PREDICTED: *Mus musculus* similar to aspartoacylase-3 (LOC629627), mRNA | 52.96 | 7.24 | 13.47 | 124.13 | 107.95 | 76.94 | 201.8 | 231.95 | 168.21 | 0.161737909 | 0.03274 | 0.00107041 |
| 8599 | mitochondrial ribosomal protein S6 | 84.99 | 90.76 | 80.52 | 172.16 | 157.7 | 188.73 | 395.52 | 436.4 | 635.42 | 0.258085632 | 0.03279 | 0.00751919 |
| 12768 | zinc finger protein 644 | 15.61 | 32.03 | 46.1 | 366.23 | 40.06 | 93.41 | 192.4 | 133.37 | 321.07 | 0.163518063 | 0.03279 | 0.01131652 |
| 19905 | junction-mediating and regulatory protein | 169.13 | 233.3 | 148.29 | 543.3 | 293 | 427.21 | 657.56 | 428.21 | 656.69 | 0.366417496 | 0.03284 | 0.00158297 |
| 13983 | bolA-like 2 (*E. coli*) | 640.93 | 283.51 | 474.89 | 891.08 | 567.86 | 705.83 | 1189.8 | 1104.23 | 1324 | 0.483961112 | 0.03286 | 0.01507785 |
| 12572 | BCL2-associated transcription factor 1 | 2243.95 | 1513.18 | 2041.07 | 3292.2 | 2694 | 3229.5 | 3913.7 | 3100.47 | 3629.4 | 0.583930579 | 0.03293 | 0.00247576 |
| 13491 | phosphatidylinositol 4-kinase type 2 alpha | 106.26 | 77.85 | 116.88 | 271.2 | 295.15 | 204.29 | 626.53 | 277.93 | 551.44 | 0.270365679 | 0.03294 | 0.00205473 |
| 8482 | nucleolar complex associated 2 homolog (*S. cerevisiae*) | 984.9 | 484.36 | 571.5 | 1289.3 | 1202.7 | 1169.9 | 1470.8 | 1389.35 | 1671.63 | 0.498135738 | 0.03297 | 0.00193977 |
| 18925 | hippocampus abundant gene transcript 1 | 1626.37 | 984.96 | 926.25 | 1800.2 | 1384 | 1711.6 | 2542 | 2468.73 | 3077.91 | 0.544894435 | 0.03302 | 0.02020823 |
| 29821 | general transcription factor III C1 | 649.54 | 697.58 | 431.58 | 1080.6 | 901.53 | 1212.7 | 1452 | 1192.11 | 1707.24 | 0.471422324 | 0.03303 | 0.00235796 |
| 28901 | RIKEN cDNA 4932408B21 gene | 57.42 | 28.78 | 34.91 | 186.88 | 112.52 | 187.44 | 217.22 | 178.97 | 178.07 | 0.228272547 | 0.03307 | 6.72E-005 |
| 27240 | nucleoporin 98 | 708.33 | 558.18 | 484.95 | 1086.1 | 858.65 | 840.28 | 1314.9 | 1255.99 | 1590.24 | 0.504291543 | 0.0331 | 0.00479921 |
| 16347 | DEAD (Asp-Glu-Ala-Asp) box polypeptide 21 | 691.31 | 341.98 | 479.23 | 933.21 | 720.44 | 1161.8 | 1068.9 | 1079.18 | 1463.87 | 0.470644611 | 0.03313 | 0.00388951 |
| 12433 | general transcription factor IIIC, polypeptide 2, beta | 134.75 | 114 | 117.11 | 326.86 | 320.97 | 220.76 | 337.18 | 352.3 | 512.23 | 0.3534367 | 0.03314 | 0.00046942 |
| 16878 | nuclear fragile X mental retardation protein interacting protein 1 | 735.99 | 520.27 | 616.98 | 1152 | 1106.6 | 1108.4 | 1669.9 | 1264.41 | 1709.52 | 0.467676882 | 0.03316 | 0.00109882 |
| 20819 | ubiquitin-conjugating enzyme E2C | 1431.97 | 1109.57 | 1108.32 | 1340.1 | 1457.9 | 1689.9 | 3079.3 | 3096.31 | 3132.89 | 0.529102477 | 0.03318 | 0.04620446 |
| 15367 | adhesion regulating molecule 1 | 2376.07 | 1243.06 | 1825.49 | 2794.9 | 2623 | 3207.4 | 2488.6 | 3090.31 | 3801.22 | 0.604778024 | 0.0332 | 0.00947177 |

TABLE 8B-continued

| Row | Gene | Oct. 4, 2001 | Oct. 4, 2002 | Oct. 4, 2003 | NI1.1 | NI1.2 | NI1.3 | NI2.1 | NI2.2 | NI2.3 | foldchange | fdr | t.pvals |
|---|---|---|---|---|---|---|---|---|---|---|---|---|---|
| 35487 | TatD DNase domain containing 1 | 49.58 | 54.22 | 10.94 | 234.77 | 114.06 | 144.99 | 202.21 | 154.66 | 288.54 | 0.201434302 | 0.03323 | 0.00129083 |
| 26869 | guanine monphosphate synthetase | 122.92 | 142.78 | 107.6 | 432.72 | 251.71 | 382.77 | 333.62 | 321.76 | 588.17 | 0.323098561 | 0.03324 | 0.0004596 |
| 17750 | Zinc finger protein 644 | 18.41 | 38 | 141.75 | 287.13 | 126.78 | 223.87 | 231.07 | 167.08 | 286.89 | 0.299602365 | 0.03327 | 0.00457717 |
| 10563 | ring finger protein 11 | 81.84 | 78.97 | 111.45 | 413.57 | 203.45 | 266.73 | 291.63 | 298.49 | 401.2 | 0.290399825 | 0.03333 | 0.00019063 |
| 22525 | ribosomal protein L23 | 1694.63 | 1408.99 | 1322.27 | 2543.8 | 2122.1 | 2440.6 | 2267.4 | 2629.52 | 3731.63 | 0.562553901 | 0.03333 | 0.00413512 |
| 41190 | methyltransferase like 2 | 201.66 | 120.68 | 113.21 | 444.44 | 370.04 | 370.14 | 371.11 | 445.47 | 374.11 | 0.366731079 | 0.03333 | 9.87E−005 |
| 22167 | CNDP dipeptidase 2 (metallopeptidase M20 family) | 22.88 | 61.95 | 32.07 | 330.23 | 79.86 | 180.33 | 84.76 | 218.18 | 158.8 | 0.22220955 | 0.0334 | 0.00380262 |
| 1037 | craniofacial development protein 1 | 632.43 | 487.38 | 759.93 | 1272.7 | 874.72 | 1051.5 | 1332.9 | 1198.09 | 1629.04 | 0.510874572 | 0.03341 | 0.00315993 |
| 19490 | Rho GTPase activating protein 8 | 561.58 | 232.84 | 159.57 | 755.26 | 534.11 | 863.06 | 783.69 | 493.49 | 842.26 | 0.446638123 | 0.03343 | 0.00744318 |
| 23936 | RIKEN cDNA 2810004A10 gene | 611.4 | 319.12 | 196.57 | 795.57 | 922.98 | 799.63 | 775.73 | 795.6 | 585.57 | 0.482169289 | 0.03346 | 0.00506537 |
| 38670 | fibroblast growth factor receptor-like 1 | 170.84 | 122.93 | 50.89 | 527.58 | 138.93 | 388.29 | 327.68 | 457.46 | 183.49 | 0.340669062 | 0.03349 | 0.01815324 |
| 13982 | bolA-like 2 (E. coli) | 667.26 | 327.26 | 632.69 | 997.91 | 533.2 | 734.58 | 1519.4 | 1322.18 | 1597.39 | 0.485396 | 0.03353 | 0.03999237 |
| 21923 | gene /// RIKEN cDNA 5830484A20 gene /// similar to Sp110 nuclear body protein /// sortilin 1 | 936.03 | 563.58 | 807.33 | 1249.3 | 1254.4 | 1612.3 | 1349.6 | 1971.41 | 2092.11 | 0.48419199 | 0.03354 | 0.00309151 |
| 7522 | sortilin 1 | 47.52 | 42.59 | 83.69 | 467.9 | 79.92 | 299.98 | 346.19 | 142.97 | 127.38 | 0.237376566 | 0.0336 | 0.01339749 |
| 20481 | SDA1 domain containing 1 | 1362.71 | 859.8 | 1118.87 | 2204.8 | 1724.2 | 2050.9 | 2051.9 | 2375.74 | 1968.44 | 0.539978684 | 0.03364 | 0.00101078 |
| 677 | cathepsin C | 620.48 | 261.03 | 388.32 | 1142.3 | 623.95 | 597.3 | 1072.2 | 767.24 | 1113.22 | 0.47772632 | 0.03365 | 0.01077421 |
| 12728 | polymerase (RNA) III (DNA directed) polypeptide E | 1173.78 | 856.85 | 818.59 | 1893.6 | 1486.9 | 1477.6 | 1672.1 | 1702.36 | 2013.3 | 0.556175975 | 0.03366 | 0.00133563 |
| 171 | ribosomal protein S26 | 1005.17 | 525.6 | 798.19 | 1159.7 | 1132.3 | 1291 | 1650.3 | 1768.46 | 3066.94 | 0.462613383 | 0.03373 | 0.01726663 |
| 21453 | ribosomal protein S8 | 2653.11 | 1674.67 | 2415.56 | 3453.2 | 3323.5 | 3368.9 | 3676.3 | 3927.51 | 5180.08 | 0.588181318 | 0.03373 | 0.00586965 |
| 18058 | AF4/FMR2 family, member 4 | 66.6 | 79.82 | 102.25 | 260.49 | 269.44 | 166.59 | 260.12 | 196.38 | 405.8 | 0.319049024 | 0.0338 | 0.00066396 |
| 2114 | torsin family 1, member B | 611.51 | 202.39 | 243.41 | 852.18 | 486.97 | 714.88 | 856.26 | 824.23 | 655.93 | 0.481640834 | 0.03386 | 0.00820538 |
| 7324 | metastasis-associated gene family, member 2 | 808.65 | 595.65 | 569.46 | 1393.2 | 875.73 | 1334.4 | 1064 | 1538.48 | 1479.47 | 0.513642858 | 0.03395 | 0.00325528 |
| 20207 | PHD finger protein 17 | 45.11 | 97.31 | 48.99 | 150.19 | 219.06 | 156.4 | 230.13 | 395.67 | 311.67 | 0.261646345 | 0.03398 | 0.00115284 |
| 22719 | myelin protein zero-like 1 | 26.63 | 58.06 | 86.57 | 211.23 | 241.63 | 192.89 | 146.38 | 553.53 | 185.92 | 0.223638334 | 0.034 | 0.00221299 |
| 13129 | mediator of RNA polymerase II transcription, subunit 8 homolog (yeast) | 88.18 | 61.52 | 35.11 | 199.79 | 152.12 | 177.8 | 282.24 | 471.76 | 209.96 | 0.247457604 | 0.03405 | 0.00141734 |
| 33684 | activating transcription factor 7 interacting protein 2 | 465.25 | 439.02 | 701.39 | 1507.1 | 999.44 | 1317.4 | 817.23 | 803.3 | 1090.48 | 0.491410733 | 0.03407 | 0.00480905 |
| 9652 | bone morphogenetic protein receptor, type 1A | 30.66 | 33.23 | 24.13 | 164.86 | 83.03 | 98.67 | 231.61 | 148.75 | 169.39 | 0.196405262 | 0.03412 | 0.00020267 |
| 20214 | RNA binding motif protein 5 | 571.27 | 767.82 | 724.89 | 970.89 | 1114.4 | 1258.3 | 1664.8 | 1551.93 | 1412.32 | 0.517765759 | 0.03415 | 0.00244522 |
| 16715 | spermatogenesis associated 5 | 137.92 | 102.31 | 61.45 | 459.08 | 274.64 | 228.49 | 327.14 | 221.78 | 356.12 | 0.323127594 | 0.03417 | 0.00093717 |
| 24191 | cancer susceptibility candidate 5 /// similar to cancer susceptibility candidate 5 isoform 2 | 152.1 | 164.87 | 125.69 | 368.06 | 261.62 | 337.15 | 517.57 | 426.13 | 722.68 | 0.336213215 | 0.03421 | 0.00163987 |
| 27633 | vitamin K epoxide reductase complex, subunit 1-like 1 | 158.7 | 49.79 | 76.93 | 398.67 | 216.04 | 284.84 | 293.31 | 284.28 | 381.74 | 0.307088139 | 0.03423 | 0.00085041 |
| 7003 | WD repeat domain 77 | 1094.94 | 580.22 | 464.08 | 1369.7 | 1345 | 1526.4 | 1197.9 | 1576.35 | 1489.59 | 0.503058814 | 0.03427 | 0.00254454 |
| 344 | glycine decarboxylase | 449.54 | 174.14 | 151.67 | 613.06 | 279.64 | 804.84 | 631.24 | 715.88 | 615.34 | 0.423688525 | 0.03431 | 0.01299645 |
| 1917 | solute carrier family 12, member 2 | 500.3 | 207.9 | 501 | 1012.6 | 574.08 | 711.55 | 831.2 | 898.12 | 1082.66 | 0.473252358 | 0.03432 | 0.00723914 |

TABLE 8B-continued

| Row | Gene | Oct. 4, 2001 | Oct. 4, 2002 | Oct. 4, 2003 | NI1.1 | NI1.2 | NI1.3 | NI2.1 | NI2.2 | NI2.3 | foldchange | fdr | t.pvals |
|---|---|---|---|---|---|---|---|---|---|---|---|---|---|
| 15722 | DEAD (Asp-Glu-Ala-Asp) box polypeptide 17 | 385.08 | 297.48 | 284.8 | 475.57 | 561.19 | 524.9 | 865.28 | 1016.7 | 851.49 | 0.450445039 | 0.03434 | 0.00548161 |
| 3811 | DNA segment, human DXS9928E | 157.43 | 142.21 | 194.44 | 493.98 | 482.27 | 475.73 | 458.09 | 304.57 | 395.93 | 0.378522698 | 0.03438 | 0.00016711 |
| 14157 | RIKEN cDNA 2610101J03 gene | 1078.89 | 693.47 | 683.97 | 1413 | 1116.9 | 1409.9 | 2146.7 | 1725.33 | 1648.32 | 0.519305374 | 0.0344 | 0.00470655 |
| 21888 | death inducer-obliterator 1 | 489.88 | 352.87 | 242.07 | 885.74 | 746.18 | 817.23 | 629.22 | 636.1 | 1048.16 | 0.455555019 | 0.0344 | 0.00196002 |
| 6127 | Willi/Angelman syndrome 2 homolog (human) | 146.49 | 115.62 | 62.97 | 277.82 | 180.98 | 205.37 | 423.86 | 504.78 | 426.8 | 0.32192354 | 0.03448 | 0.00497845 |
| 10418 | pantothenate kinase 3 | 571.77 | 464.21 | 419.81 | 1151.2 | 770.81 | 1060.5 | 873.11 | 919.21 | 1010 | 0.503316456 | 0.03455 | 0.00060585 |
| 7942 | torsin family 2, member A | 56.41 | 57.84 | 15.89 | 182.4 | 117.93 | 153.01 | 167.89 | 264.45 | 201.53 | 0.239401772 | 0.03455 | 0.00088711 |
| 6639 | sorting nexin 3 | 120.78 | 103.65 | 110.21 | 326.23 | 216.07 | 202.87 | 341.2 | 336.98 | 604.44 | 0.330053901 | 0.03456 | 0.00250308 |
| 3398 | abhydrolase domain containing 6 | 330.84 | 210.9 | 246.57 | 422.75 | 380.61 | 691.33 | 684.84 | 889.36 | 650.71 | 0.423868158 | 0.03459 | 0.00458787 |
| 640 | translocase of inner mitochondrial membrane 8 homolog a1 (yeast) | 878.17 | 670.48 | 908.3 | 1804.6 | 1319 | 1419.3 | 1722.5 | 1433.31 | 1537.61 | 0.532026734 | 0.03462 | 0.00067228 |
| 7006 | protein kinase C, delta | 411.25 | 383.64 | 115.26 | 712.82 | 315.54 | 733.67 | 910.26 | 661.36 | 733.23 | 0.447591274 | 0.03465 | 0.02184294 |
| 15510 | Williams-Beuren syndrome chromosome region 1 homolog | 387.38 | 65.5 | 224.42 | 655.34 | 402.2 | 299.57 | 683.74 | 452.6 | 930.59 | 0.395614537 | 0.03469 | 0.0206498 |
| 1970 | midasin homolog (yeast) | 72.03 | 19.88 | 33.69 | 203.55 | 127.77 | 190.18 | 139.01 | 179.55 | 201.68 | 0.241135024 | 0.03474 | 0.0003368 |
| 3936 | purine rich element binding protein B | 1414.47 | 939.03 | 992.32 | 1815.5 | 1442.8 | 1699.3 | 2127.5 | 2327.95 | 2198.24 | 0.576307096 | 0.03476 | 0.00541495 |
| 11214 | thioesterase superfamily member 4 | 209.2 | 140.63 | 221.22 | 557.73 | 459.97 | 598.38 | 413.32 | 339.06 | 663.38 | 0.376701937 | 0.03481 | 0.00078993 |
| 20608 | RIKEN cDNA 2610304G08 gene | 85.77 | 64.41 | 24.73 | 216 | 142.41 | 211.13 | 393.72 | 237.84 | 189.99 | 0.251471867 | 0.03483 | 0.00126552 |
| 401 | KTI12 homolog, chromatin associated (S. cerevisiae) | 204.06 | 74 | 121.41 | 306.83 | 197.69 | 220.06 | 546.92 | 436.97 | 511.52 | 0.359884504 | 0.03484 | 0.00978944 |
| 4187 | gb:AV006589 /DB_XREF = gi: 4783576 /DB_XREF = AV006589 /CLONE = 1100006A23 /FEA = EST /CNT = 1 /TID = Mm.198379.1 /TIER = ConsEnd /STK = 0 /UG = Mm.198379 /LL = 99251 /UG_GENE = AV006589 /UG_TITLE = expressed sequence AV006589 | 750.81 | 258.88 | 477.14 | 770.5 | 790.87 | 855.25 | 1131.1 | 1138.45 | 1223.11 | 0.503222073 | 0.03488 | 0.00891259 |
| 20263 | ATP-binding cassette, sub-family F (GCN20), member 1 | 1974.08 | 1512.28 | 1591.36 | 2799.7 | 2379.2 | 2881.9 | 3476.5 | 3087.76 | 3006.5 | 0.575978511 | 0.03492 | 0.00134869 |
| 6063 | nuclear receptor coactivator 6 interacting protein | 96.49 | 66.05 | 71.48 | 230.69 | 170.41 | 262.11 | 380.42 | 250.08 | 337.13 | 0.286993206 | 0.035 | 0.00026083 |
| 7582 | signal recognition particle receptor ('docking protein') associated 3 | 772.56 | 580.96 | 729.21 | 1398.6 | 1166.8 | 1297.1 | 1691.5 | 1392.13 | 1417.23 | 0.498064757 | 0.03503 | 0.00033862 |
| 7829 | | 1178.28 | 396.35 | 506.11 | 1274.3 | 1169.1 | 1329.2 | 1193.6 | 1444.27 | 1684.77 | 0.51406442 | 0.03505 | 0.00684649 |
| 1149 | solute carrier family 34 (sodium phosphate), member 2 | 1671.27 | 1451.17 | 1598.15 | 2771.9 | 2571.2 | 2756.1 | 2423.9 | 2605.98 | 2900.33 | 0.588995153 | 0.03509 | 0.00034828 |
| 23975 | RIKEN cDNA D530033C11 gene | 15.02 | 9.78 | 12.59 | 135.75 | 30.07 | 112.3 | 106.24 | 70.57 | 148.16 | 0.12399476 | 0.03512 | 0.00060996 |
| 3060 | T-cell immunoglobulin and | 695.08 | 248.62 | 328 | 826.75 | 592.21 | 729.65 | 1034 | 1032.95 | 1807.45 | 0.422278451 | 0.03518 | 0.01412352 |

TABLE 8B-continued

| Row | Gene | Oct. 4, 2001 | Oct. 4, 2002 | Oct. 4, 2003 | NI1.1 | NI1.2 | NI1.3 | NI.2.1 | NI.2.2 | NI.2.3 | foldchange | fdr | t.pvals |
|---|---|---|---|---|---|---|---|---|---|---|---|---|---|
| 7965 | mucin domain containing 2 | 108.79 | 143.67 | 117.13 | 263.16 | 266.45 | 284.38 | 553.99 | 382.53 | 444.37 | 0.336774676 | 0.0352 | 0.00079899 |
| 15134 | integrator complex subunit 4 | 2879.67 | 1822.12 | 2555.47 | 3715 | 3487.6 | 3736.8 | 3939 | 4199.88 | 5464.29 | 0.591403484 | 0.03525 | 0.0054164 |
| 10616 | ribosomal protein S8 | 302.65 | 177.5 | 294.36 | 828.01 | 459.32 | 599.96 | 670.2 | 546.64 | 765.82 | 0.400268737 | 0.03526 | 0.00086754 |
| 19022 | sarcolemma associated protein | 295.13 | 157.89 | 124.56 | 512.13 | 492.87 | 451.56 | 490.43 | 421.28 | 529.28 | 0.39866784 | 0.03526 | 0.00048712 |
| 39934 | folate receptor 1 (adult) | 948.04 | 617.96 | 722.82 | 1276.2 | 1461.4 | 1309.1 | 1701.5 | 1341.04 | 1647.3 | 0.523969663 | 0.03527 | 0.00085077 |
| 27541 | RIKEN cDNA 2410019A14 gene | 29.79 | 29.13 | 17.85 | 111.26 | 148.96 | 160.01 | 179.04 | 101.84 | 124.88 | 0.185886028 | 0.03534 | 1.86E-005 |
| 13353 | hypothetical protein 543042I B17 | 366.32 | 286.12 | 242.58 | 661.8 | 568.59 | 569.17 | 785.19 | 691.43 | 896.88 | 0.428951417 | 0.03535 | 0.00044813 |
| 8628 | cyclin L2 | 437.6 | 464.66 | 259.65 | 801.65 | 552.59 | 757.67 | 924.15 | 849.4 | 912.93 | 0.484291606 | 0.03542 | 0.00233476 |
| 15335 | cleavage and polyadenylation specific factor 4 | 74.5 | 32.14 | 51.2 | 212.66 | 134.11 | 162.73 | 340.99 | 117.8 | 348.25 | 0.239780029 | 0.03544 | 0.00207122 |
| 21143 | RIKEN cDNA 2810409H07 gene | 55.86 | 42.84 | 49.42 | 191.63 | 97.34 | 143.81 | 238.34 | 247.68 | 216.44 | 0.260949227 | 0.03544 | 0.00048204 |
| 27810 | RIKEN cDNA 2900097C17 gene | 187.42 | 198.71 | 152.25 | 448.07 | 341.04 | 401.19 | 578.87 | 431.83 | 634.48 | 0.379745228 | 0.03549 | 0.00040675 |
| 21839 | mannosidase 2, alpha 2 | 682.51 | 376.13 | 741.32 | 1355.9 | 913.47 | 1360.2 | 1021.7 | 1106.77 | 1232.25 | 0.514990859 | 0.03564 | 0.00340949 |
| 27178 | B-cell receptor-associated protein 31 | 1161.91 | 964.7 | 1257.96 | 2142.9 | 1761.6 | 1953.7 | 1664.5 | 2350.84 | 2119.38 | 0.564429895 | 0.03571 | 0.00117285 |
| 27596 | spermatogenesis associated 2 | 164.06 | 50.24 | 97.33 | 314.61 | 235.05 | 369.8 | 208.02 | 349.59 | 306.67 | 0.34941191 | 0.03579 | 0.00171003 |
| 8359 | Expressed sequence AI195381 | 34.37 | 35.38 | 21.55 | 153.44 | 52.09 | 164.71 | 185.96 | 151.36 | 190.7 | 0.203281901 | 0.03581 | 0.0010864 |
| 21158 | SEH1-like (S. cerevisiae) | 762.08 | 527.82 | 423.16 | 1268.1 | 1111.2 | 1110.2 | 1163.3 | 1112.98 | 1052.34 | 0.502508789 | 0.03586 | 0.00058213 |
| 20989 | phosphoserine aminotransferase 1 | 265.68 | 159.08 | 539.01 | 502.7 | 517.5 | 685.71 | 1247.6 | 1948.95 | 3246.7 | 0.236531774 | 0.0359 | 0.02475044 |
| 20676 | ribosomal protein L37 | 1574.4 | 894.92 | 1056.14 | 1903.9 | 1775.2 | 1903.2 | 2525.3 | 2161.78 | 2275.69 | 0.562051115 | 0.03594 | 0.0030746 |
| 11523 | reticulon 4 | 1456.62 | 734.62 | 1199.01 | 1588.9 | 1504 | 1639.4 | 2484.2 | 2389.48 | 2308.26 | 0.569109376 | 0.03598 | 0.01491284 |
| 6500 | ornithine decarboxylase, structural 1 /// similar to Ornithine decarboxylase (ODC) | 47.88 | 151.19 | 39.47 | 198.56 | 143.95 | 151.5 | 374.75 | 347.89 | 480.81 | 0.281055224 | 0.03599 | 0.00760032 |
| 7881 | lysophospholipase 3 | 214.62 | 75.2 | 94.84 | 335.84 | 369.33 | 256.77 | 372.81 | 272.48 | 580.32 | 0.351681104 | 0.03602 | 0.00252792 |
| 10737 | transmembrane protein 49 | 273.69 | 269.17 | 162.25 | 547.62 | 550.93 | 515.68 | 525.29 | 571.28 | 535.32 | 0.434432492 | 0.03605 | 0.00015943 |
| 9707 | SNAP-associated protein | 150.44 | 125.82 | 60.94 | 231.93 | 196.75 | 216.83 | 442.18 | 529.47 | 633.71 | 0.299617481 | 0.03608 | 0.00854339 |
| 10862 | leukocyte specific transcript 1 | 189.88 | 169.84 | 165.37 | 414.6 | 338.87 | 451.82 | 646.18 | 343.8 | 583.16 | 0.371951846 | 0.03617 | 0.00088473 |
| 12376 | cyclin G associated kinase | 548.67 | 181.79 | 376.6 | 789.75 | 643.57 | 739.91 | 846.21 | 866 | 924.2 | 0.460350463 | 0.03618 | 0.00344332 |
| 12925 | p53 and DNA damage regulated 1 | 971.59 | 772.44 | 792.75 | 1277.8 | 1052.4 | 1432.2 | 1720.9 | 1915.14 | 1795 | 0.551868619 | 0.03625 | 0.0060476 |
| 980 | enhancer of rudimentary homolog (Drosophila) | 684.31 | 450.34 | 486.4 | 856.32 | 653.88 | 1067.7 | 1220 | 1189.37 | 1652.28 | 0.488299694 | 0.03627 | 0.01051729 |
| 29430 | fibrillarin | 683.71 | 635.1 | 523.7 | 922.49 | 833 | 1035.4 | 1440.4 | 1366.46 | 1588.41 | 0.512799033 | 0.03632 | 0.0059473 |
| 22752 | trans-acting transcription factor 6 | 117.47 | 70.55 | 76.49 | 280.19 | 226.01 | 244.57 | 283.43 | 365.03 | 342.8 | 0.303680189 | 0.03636 | 8.87E-005 |
| 14032 | phosphoglucomutase 3 | 23.56 | 3.91 | 6.09 | 51.61 | 168.7 | 132.62 | 164.68 | 29.4 | 81.1 | 0.106860263 | 0.0364 | 0.0018215 |
| 21869 | seizure related 6 homolog like 2 | 1092.71 | 549.03 | 901.08 | 1326.5 | 1044.1 | 1421.4 | 1855.2 | 1998.4 | 2994.86 | 0.477956614 | 0.03646 | 0.02013608 |
| 15947 | similar to ubiquitin A-52 residue ribosomal protein fusion product 1 | 59.53 | 130.96 | 145.41 | 238.39 | 245.29 | 390.12 | 422.46 | 217.98 | 589.3 | 0.319366401 | 0.03648 | 0.00409729 |
| 360 | expressed sequence AI593864 | 1631.2 | 1255.22 | 1597.8 | 2366.3 | 1976.9 | 2233.4 | 2873.1 | 2724.96 | 2719.92 | 0.602127754 | 0.03656 | 0.00313083 |
| 13232 | ankyrin repeat domain 10 | 249.7 | 149.34 | 101.69 | 500.78 | 396.36 | 411.4 | 449.86 | 312.53 | 480.19 | 0.392556995 | 0.03664 | 0.00094472 |
| 7575 | brix domain containing 5 | 169.06 | 151.5 | 175.74 | 345.56 | 264.16 | 208.33 | 557.93 | 543.22 | 522.86 | 0.40646012 | 0.03665 | 0.01048791 |
| 847 | SWI/SNF related, matrix associated, actin dependent regulator of chromatin, subfamily c, member 1 | 637.03 | 556.11 | 625.16 | 1200.8 | 846.84 | 1332.8 | 1136 | 1117.74 | 2353.11 | 0.455300635 | 0.03672 | 0.00785991 |
| | developmental pluripotency | | | | | | | | | | | | |

TABLE 8B-continued

| Row | Gene | Oct. 4, 2001 | Oct. 4, 2002 | Oct. 4, 2003 | NI1.1 | NI1.2 | NI1.3 | NI2.1 | NI2.2 | NI2.3 | foldchange | fdr | t.pvals |
|---|---|---|---|---|---|---|---|---|---|---|---|---|---|
| 19522 | WW domain containing adaptor with coiled-coil associated 5 | 1020.92 | 699.47 | 883.58 | 1264.2 | 1408.6 | 1531 | 1740.2 | 1592.41 | 1789.74 | 0.558426352 | 0.03672 | 0.0014871 |
| 21628 | uridine monophosphate synthetase | 98.18 | 94.72 | 68.1 | 288.06 | 248.98 | 175.65 | 306.21 | 226.92 | 452.59 | 0.307346283 | 0.0368 | 0.00065722 |
| 15391 | ras responsive element binding protein 1 | 141.53 | 165.74 | 217.71 | 421.99 | 422.79 | 503.87 | 510.83 | 456.58 | 227.76 | 0.41274933 | 0.03686 | 0.00261093 |
| 13913 | Heterogeneous nuclear ribonucleoprotein U | 22.26 | 32.92 | 25.16 | 157.59 | 122.26 | 145.62 | 79.73 | 130.3 | 273.63 | 0.1767404 | 0.03688 | 0.00020361 |
| 28627 | solute carrier family 19 (sodium/hydrogen exchanger), member 3 | 485.43 | 151.49 | 233.17 | 737.26 | 511.1 | 592.5 | 613.8 | 620.42 | 958.53 | 0.431419994 | 0.03694 | 0.00454474 |
| 18771 | elongation factor RNA polymerase II 2 | 604.78 | 436.5 | 353.74 | 1119.5 | 733.54 | 995.87 | 939.53 | 968.34 | 900.94 | 0.493137707 | 0.03696 | 0.00098 |
| 10803 | TBC1 domain family, member 20 | 126.56 | 81.16 | 223.11 | 336.16 | 248.27 | 209.16 | 442.89 | 430.88 | 702.71 | 0.363558882 | 0.037 | 0.01061646 |
| 13848 | expressed sequence AA408556 | 215.08 | 107.35 | 165.18 | 295.85 | 310.39 | 421.99 | 454.92 | 383.23 | 796.93 | 0.366168414 | 0.03707 | 0.00397733 |
| 1685 | XPA binding protein 1 | 410.06 | 452.6 | 766.71 | 1401.7 | 1053.2 | 878.62 | 1090.9 | 995.33 | 1162.31 | 0.495088976 | 0.03712 | 0.00193188 |
| 19044 | ERGIC and golgi 3 | 44.81 | 65.7 | 48.44 | 93.9 | 72.33 | 245.35 | 177.49 | 438.27 | 277.99 | 0.243539948 | 0.03714 | 0.01416792 |
| 27096 | like) 10 | 20.8 | 3.27 | 12.57 | 89.8 | 103.08 | 86.03 | 136.13 | 47.95 | 210.38 | 0.108825757 | 0.03717 | 0.00063987 |
| 727 | 6-phosphofructo-2-kinase/fructose-2,6-biphosphatase 3 | 63.36 | 20.84 | 112.36 | 213.6 | 178.27 | 137.99 | 367.86 | 210.92 | 349.81 | 0.269546436 | 0.03724 | 0.00380938 |
| 2739 | RGS16 | 351.74 | 117.12 | 76.23 | 503.15 | 162.89 | 413.91 | 695.01 | 773.54 | 1692.2 | 0.257075483 | 0.03727 | 0.02968997 |
| 24940 | DNA segment, Chr 8, Brigham & Women's Genetics 1414 expressed | 118.78 | 53.72 | 55.79 | 186.53 | 261.76 | 155.04 | 261.02 | 198.73 | 393.02 | 0.311563629 | 0.0373 | 0.00157746 |
| 10152 | heat shock protein 110 | 1398.12 | 830.88 | 1073.63 | 1668.8 | 1565.5 | 2160 | 2008.3 | 1789.22 | 2316.3 | 0.573965664 | 0.03731 | 0.0040989 |
| 19155 | kinesin family member 22 | 398.22 | 450.27 | 354.46 | 841.6 | 654.47 | 559 | 989.59 | 886.55 | 947.43 | 0.49314973 | 0.03736 | 0.00219119 |
| 7723 | phosphoribosylaminoimidazole carboxylase, phosphoribosylaminoribosylami | 391.13 | 442.83 | 339.16 | 827.89 | 516.64 | 792.43 | 952.32 | 677.57 | 929.92 | 0.499543303 | 0.03737 | 0.002641 |
| 11302 | jumonji, AT rich interactive domain 1B (Rbp2 like) | 1673.42 | 942.45 | 1166.08 | 2053.4 | 1794.3 | 2099.4 | 2527.4 | 2125.87 | 2560.26 | 0.574734303 | 0.03738 | 0.00388238 |
| 13496 | ribosomal protein L38 | 1996.91 | 1375.66 | 2224.12 | 2929.6 | 2359.3 | 2980.6 | 2797.4 | 3517.85 | 4415.85 | 0.58910883 | 0.03741 | 0.01204374 |
| 18935 | eukaryotic translation initiation factor 4E /// hypothetical LOC630527 | 2312.87 | 1828.13 | 2131.71 | 3207.1 | 2800.9 | 3286.2 | 3402.3 | 3230.56 | 3391.04 | 0.649411718 | 0.03742 | 0.00176804 |
| 10415 | translocase of inner mitochondrial membrane 17a | 1200.54 | 871.03 | 958.28 | 1480.2 | 1104.9 | 1390.9 | 2541.1 | 2448.39 | 2310.83 | 0.537385623 | 0.03744 | 0.02830428 |
| 11848 | TNFAIP3 interacting protein 1 | 321.33 | 225.29 | 228.01 | 806.72 | 511.77 | 512.88 | 594.28 | 486.89 | 1024.8 | 0.393478846 | 0.03745 | 0.00199172 |
| 29413 | DCN1, defective in cullin neddylation 1, domain containing 3 (S. cerevisiae) | 208.2 | 181.55 | 129.44 | 483.09 | 350.59 | 483.79 | 304.94 | 421.64 | 437.94 | 0.418365908 | 0.0375 | 0.0005084 |
| 19069 | myc induced nuclear antigen | 198.52 | 93.12 | 89.6 | 515.36 | 223.46 | 260.41 | 415.61 | 176.74 | 570.73 | 0.352622889 | 0.03754 | 0.01215379 |
| 22250 | karyopherin (importin) alpha 1 | 487.51 | 288.58 | 322.38 | 647.95 | 625.2 | 643.16 | 953.35 | 982.64 | 857.55 | 0.466456469 | 0.03755 | 0.00199203 |
| 20912 | ribosomal protein S24 | 1503.87 | 981.91 | 1382.51 | 1903.5 | 1485 | 1825.7 | 2662.4 | 2502.71 | 2852.52 | 0.584700379 | 0.03757 | 0.01797688 |
| 40811 | gem (nuclear organelle) associated protein 5 | 66.66 | 15.96 | 108.86 | 341.52 | 213.42 | 149.85 | 199.83 | 127.31 | 288.52 | 0.290022341 | 0.0376 | 0.00628726 |
| 19408 | RIKEN cDNA 1810020D17 gene | 70.67 | 116.83 | 133.45 | 300.46 | 275.02 | 220.85 | 330.43 | 391.71 | 361.99 | 0.341352648 | 0.03761 | 0.00033814 |

TABLE 8B-continued

| Row | Gene | Oct. 4, 2001 | Oct. 4, 2002 | Oct. 4, 2003 | NI.1.1 | NI.1.2 | NI.1.3 | NI.2.1 | NI.2.2 | NI.2.3 | foldchange | fdr | t.pvals |
|---|---|---|---|---|---|---|---|---|---|---|---|---|---|
| 16317 | GM2 ganglioside activator protein | 1460.32 | 965.39 | 1158.55 | 1585.9 | 1681.4 | 1877.4 | 2813.6 | 2472.1 | 2183.15 | 0.568322595 | 0.03761 | 0.00878651 |
| 15388 | RIKEN cDNA 2610042O14 gene | 385.77 | 161.98 | 351.7 | 704.56 | 394.83 | 574.8 | 563.17 | 1018.26 | 1190.97 | 0.4045572 | 0.03763 | 0.01369527 |
| 18450 | brix domain containing 1 | 368.46 | 490.29 | 890 | 1496.2 | 1126.8 | 1048.1 | 945.53 | 776.39 | 1481.18 | 0.508783516 | 0.03764 | 0.01101669 |
| 721 | oncogene family | 79.2 | 22.75 | 80.1 | 172.14 | 152.77 | 222.72 | 326.45 | 170.57 | 344.7 | 0.262064994 | 0.03765 | 0.00211936 |
| 22384 | DEAD (Asp-Glu-Ala-Asp) box polypeptide 54 | 319.22 | 262.39 | 315.65 | 522.53 | 433.98 | 484.6 | 736.35 | 779.63 | 1015.23 | 0.451756153 | 0.03768 | 0.00631429 |
| 32708 | cDNA sequence BC068171 | 1424.91 | 1570.38 | 1471.39 | 2308.1 | 2391.8 | 2968.3 | 2287.8 | 2852.25 | 2449.75 | 0.585484655 | 0.03768 | 0.00081003 |
| 13654 | ubiquitin-conjugating enzyme E2O | 656.86 | 318.47 | 383.2 | 924.15 | 728.47 | 782.62 | 1092.4 | 932.79 | 1270.08 | 0.474140955 | 0.03769 | 0.00312346 |
| 15701 | proteasome (prosome, macropain) subunit, beta type 4 | 711.54 | 339.67 | 377.73 | 882.09 | 954.28 | 936.36 | 747.49 | 930.36 | 1311.81 | 0.495953936 | 0.0377 | 0.00367955 |
| 43187 | jumonji domain containing 1B | 13.53 | 5.03 | 18.14 | 102.01 | 28.28 | 55.5 | 131.11 | 118.55 | 104.24 | 0.136004002 | 0.0377 | 0.00131957 |
| 44702 | zinc finger protein 407 | 25.36 | 30.71 | 38.29 | 227.66 | 134.41 | 183.53 | 100.04 | 82.93 | 152.65 | 0.214157645 | 0.03772 | 0.00029598 |
| 14551 | ribosomal protein S24 | 1773.15 | 1158.27 | 1610.42 | 2156.3 | 1692.9 | 2124.5 | 2913.4 | 2832.19 | 3114.02 | 0.61238471 | 0.03774 | 0.0206946 |
| 379 | zinc finger, A20 domain containing 2 | 1713.11 | 1445.5 | 1218.63 | 2269.6 | 2150 | 2173.5 | 2659.8 | 2431.14 | 3458.7 | 0.578127838 | 0.03774 | 0.00444974 |
| 20984 | splicing factor, arginine/serine-rich 1 (ASF/SF2) | 2351.06 | 1787.06 | 1796.58 | 3052.8 | 2627.1 | 2864.6 | 3491.7 | 3251.35 | 3629.06 | 0.627461802 | 0.03775 | 0.00349604 |
| 17472 | amine oxidase, copper containing 3 | 69.46 | 19.83 | 7.36 | 85.43 | 273.68 | 193.82 | 107.32 | 107.65 | 335.47 | 0.175190553 | 0.03778 | 0.00363781 |
| 29573 | RIKEN cDNA 4930535B03 gene | 86.18 | 17.31 | 12.72 | 377.01 | 80.79 | 145.39 | 180.67 | 103.3 | 181.19 | 0.217750428 | 0.03778 | 0.00481092 |
| 738 | ubiquitin-like 1 (sentrin) activating enzyme E1A | 239.75 | 189.44 | 212.92 | 490.87 | 339.53 | 437.9 | 482.8 | 633.06 | 755.85 | 0.408985959 | 0.03779 | 0.00153851 |
| 8834 | solute carrier family 39 (metal ion transporter), member 6 | 926.32 | 580.02 | 618.52 | 917.82 | 1152.3 | 1077.5 | 1430.5 | 1479.23 | 1557.51 | 0.558085418 | 0.0378 | 0.00688556 |
| 3709 | guanine nucleotide binding protein 13, gamma | 60.13 | 20.72 | 5.19 | 102.97 | 138.52 | 82.41 | 150.51 | 146.09 | 148.15 | 0.223873024 | 0.0378 | 0.00231997 |
| 36724 | interferon-induced protein 35 | 1116.96 | 271.9 | 305 | 985.49 | 1595.5 | 746.92 | 620.37 | 1621.46 | 1471.57 | 0.48112275 | 0.03782 | 0.03491781 |
| 240 | minichromosome maintenance deficient 5, cell division cycle | 3.51 | 116.93 | 27.29 | 275.96 | 137.29 | 122.81 | 381.1 | 145.29 | 202.31 | 0.233609539 | 0.03783 | 0.00879308 |
| 12377 | p53 and DNA damage regulated 1 | 725.38 | 231.39 | 442.6 | 715.57 | 694.98 | 822.93 | 1022.5 | 1047.48 | 1095.64 | 0.5183687 | 0.03784 | 0.01170324 |
| 12147 | scaffold attachment factor B2 | 121.67 | 55.05 | 141.82 | 202.46 | 205.91 | 445.2 | 256.47 | 382.54 | 338.31 | 0.34796192 | 0.03785 | 0.00328657 |
| 11762 | activating transcription factor 7 interacting protein 2 | 225.98 | 243.54 | 179.98 | 629.85 | 458.47 | 542.77 | 416.46 | 320.25 | 530.93 | 0.448127283 | 0.03785 | 0.00146075 |
| 1985 | protein kinase, AMP-activated, gamma 1 non-catalytic subunit | 41.91 | 31.4 | 14.25 | 149.26 | 132.45 | 140.8 | 117.68 | 165.53 | 217.77 | 0.189628475 | 0.03786 | 9.79E−005 |
| 924 | solute carrier family 1 (neutral amino acid transporter), member 5 | 10.9 | 13.02 | 15.54 | 68.86 | 61.47 | 39.47 | 135.13 | 217.53 | 154.55 | 0.116571395 | 0.03787 | 0.00095526 |
| 12998 | splicing factor, arginine/serine-rich 1 (ASF/SF2) | 665.47 | 668.28 | 445.98 | 808.48 | 849.06 | 987.04 | 1495.4 | 1250.6 | 1317.15 | 0.530647294 | 0.03789 | 0.00796067 |
| 22322 | drebrin-like | 16.85 | 15.82 | 9.22 | 61.28 | 99.35 | 52.2 | 236.1 | 101.96 | 127.64 | 0.123472801 | 0.0379 | 0.00042543 |
| 23370 | RNA binding motif protein 3 | 39.43 | 20.38 | 13.54 | 161.7 | 136.81 | 113.63 | 64.65 | 102.43 | 161.88 | 0.197948995 | 0.03791 | 0.00037432 |
| 15912 | MBD2-interacting zinc finger | 391.59 | 235.52 | 209.12 | 595.63 | 489.39 | 563.7 | 600.44 | 667.79 | 618.68 | 0.473030266 | 0.03793 | 0.0007328 |
| 21512 | makorin, ring finger protein, 1 | 1072.98 | 807.82 | 1014.98 | 1919.8 | 1380 | 1377.3 | 1555.2 | 1824.23 | 2003.22 | 0.575718958 | 0.03793 | 0.00309783 |
| 18256 | cofactor required for Sp1 transcriptional activation, subunit 2 | 478.92 | 496.91 | 461.96 | 789.66 | 829.56 | 748.74 | 1285.9 | 1020.77 | 1061.21 | 0.501333715 | 0.03794 | 0.0015605 |
| 18900 | GTP binding protein 4 | 1225.17 | 664.56 | 760.91 | 1492.5 | 1158.4 | 1447.9 | 2173.7 | 1808.18 | 1582.59 | 0.548608423 | 0.03795 | 0.00801715 |

TABLE 8B-continued

| Row | Gene | Oct. 4, 2001 | Oct. 4, 2002 | Oct. 4, 2003 | NI1.1 | NI1.2 | NI1.3 | NI2.1 | NI2.2 | NI2.3 | foldchange | fdr | t.pvals |
|---|---|---|---|---|---|---|---|---|---|---|---|---|---|
| 29040 | expressed sequence AA673488 | 484.11 | 218.8 | 155.21 | 630.18 | 425.47 | 677.11 | 680.05 | 395.77 | 933.82 | 0.458593416 | 0.03796 | 0.01368159 |
| 5392 | Pbx/knotted 1 homeobox | 136.46 | 110.17 | 38.04 | 161.58 | 245.89 | 197.24 | 309.66 | 326.55 | 315.1 | 0.36589504 | 0.03796 | 0.0048399 |
| 21315 | importin 7 | 1897.13 | 1382.87 | 1447.66 | 2615.2 | 2038 | 2474.9 | 2454.8 | 2754.77 | 2633.6 | 0.631563479 | 0.03798 | 0.00311793 |
| 29563 | cDNA sequence BC068171 | 663.48 | 885.66 | 893.34 | 1434 | 1361.4 | 1572.1 | 1455.6 | 1492.34 | 1452.45 | 0.557143297 | 0.038 | 0.00034246 |
| 15723 | centromere protein E | 638.18 | 667.92 | 635.85 | 1062.6 | 840.39 | 1209.8 | 1570.6 | 1201.87 | 1244.4 | 0.544756305 | 0.03801 | 0.00298774 |
| 14383 | eukaryotic translation initiation factor 5B | 20.96 | 15.05 | 9.7 | 81.27 | 106.34 | 102.48 | 124.36 | 76.5 | 147.21 | 0.14325561 | 0.03802 | 1.95E-005 |
| 10833 | eukaryotic translation initiation factor 3, subunit 9 (eta) | 88.55 | 23.79 | 36.88 | 226.1 | 76.88 | 140.2 | 208.42 | 168.48 | 203.88 | 0.291456698 | 0.03803 | 0.00358346 |
| 657 | FK506 binding protein 4 | 880.01 | 451.63 | 640.66 | 1073.2 | 846.29 | 1012.7 | 1672.7 | 1558.58 | 1505.66 | 0.514345769 | 0.03803 | 0.01132742 |
| 30138 | anti-Mullerian hormone type 2 receptor | 144.16 | 58.14 | 204.59 | 277.7 | 226.3 | 364.45 | 492.22 | 340.87 | 636.14 | 0.34811437 | 0.03803 | 0.00675705 |
| 20815 | phosphatidylinositol transfer protein, cytoplasmic 1 | 80.4 | 58.16 | 113.91 | 393.06 | 254.86 | 712.53 | 266.43 | 91.96 | 256.22 | 0.255658056 | 0.03804 | 0.01559053 |
| 6603 | integrin alpha 6 | 593.83 | 573.74 | 427.75 | 925.3 | 1185.7 | 1056.8 | 971.42 | 1090.26 | 915.58 | 0.519219472 | 0.03807 | 0.0004221 |
| 12382 | EBNA1 binding protein 2 | 939.31 | 650.84 | 646.44 | 1300.7 | 865.58 | 1123.9 | 1609.4 | 1404.18 | 1650.05 | 0.562392505 | 0.0381 | 0.01050595 |
| 5650 | transmembrane protein 49 | 178.72 | 95.35 | 104.83 | 304.43 | 188.62 | 201.94 | 473.19 | 397.83 | 447.36 | 0.376383874 | 0.0381 | 0.00693338 |
| 16338 | proteasome (prosome, macropain) subunit, beta type 2 | 230.23 | 131.35 | 156.94 | 402.72 | 255.26 | 414.95 | 581.61 | 681.86 | 363.66 | 0.384080354 | 0.03814 | 0.00393859 |
| 9656 | PRP4 pre-mRNA processing factor 4 homolog B (yeast) | 299.22 | 298.41 | 149.09 | 561.48 | 546.09 | 598.99 | 669.75 | 360.25 | 512.38 | 0.459669923 | 0.03815 | 0.00313005 |
| 21930 | transcription factor-like 5 (basic helix-loop-helix) | 21.09 | 38.28 | 22.9 | 250.91 | 115.79 | 62.22 | 136.62 | 119.48 | 296.43 | 0.167649906 | 0.03819 | 0.00144596 |
| 21395 | guanine nucleotide binding protein (G protein), beta polypeptide 2 like 1 | 226.37 | 103.26 | 158.36 | 279.05 | 215.92 | 341.37 | 489.8 | 485.86 | 609.01 | 0.403129272 | 0.0382 | 0.01001628 |
| 484 | Sec61 alpha 1 subunit (S. cerevisiae) | 2767.22 | 1784.91 | 2139.43 | 3540.3 | 2633.9 | 3422.7 | 3549.9 | 3286.01 | 3718.63 | 0.664131513 | 0.03822 | 0.00962031 |
| 41081 | RIKEN cDNA 2700023E23 gene | 383.97 | 263.74 | 193.02 | 576.37 | 466.4 | 578.03 | 626.96 | 633.72 | 924.84 | 0.441754766 | 0.03826 | 0.00216237 |
| 22751 | REI-silencing transcription factor | 2083.8 | 1792.43 | 1660.4 | 2301.8 | 2518.9 | 2548.3 | 3491.2 | 3525.95 | 3353.07 | 0.624228963 | 0.03827 | 0.00982946 |
| 6782 | Ribosomal protein L41 | 2170.73 | 1455.5 | 2121.76 | 2890.9 | 2673.8 | 2954.3 | 3287.7 | 3064.33 | 3459.93 | 0.627133956 | 0.03827 | 0.00351568 |
| 23799 | PRP4 pre-mRNA processing factor 4 homolog A (yeast) | 139.76 | 105.45 | 114.11 | 272.96 | 233.13 | 303.29 | 299.62 | 458.97 | 563.81 | 0.337107957 | 0.03828 | 0.00127622 |
| 5220 | guanylate cyclase activator 1a (retina) | 1137.82 | 874.49 | 1002.71 | 1303.4 | 1212.1 | 1554.2 | 2394.2 | 2176.13 | 2314.5 | 0.550467392 | 0.03829 | 0.01816163 |
| 22682 | gb: BB204543 /DB_XREF = gi: 8869496 /DB_XREF = BB204543 /CLONE = A430058H10 /FEA = EST /CNT = 1 /TID = Mm.215042.2 /TIER = ConsEnd /STK = 0 /UG = Mm.215042 /UG_TITLE = ESTs | 101.6 | 39.07 | 67.86 | 262.21 | 64.78 | 123.41 | 308.26 | 237.22 | 438.68 | 0.290723288 | 0.03833 | 0.02815887 |
| 7211 | ADP-ribosylation factor 4 | 228.83 | 119.48 | 108.04 | 327.09 | 279.11 | 307.49 | 457.63 | 425.84 | 551.85 | 0.388546664 | 0.03833 | 0.00201733 |
| 2543 | galactosidase, alpha | 273.94 | 147.47 | 118.3 | 418.22 | 369.57 | 248.33 | 523.01 | 438.32 | 654.08 | 0.407093263 | 0.03834 | 0.00570311 |
| 19658 | cDNA sequence BC021395 | 585.54 | 403.84 | 321.3 | 781.58 | 616.26 | 679.87 | 1012.7 | 951.38 | 1013.92 | 0.518495955 | 0.03834 | 0.00493793 |
| 27841 | BTAF1 RNA polymerase II, B-TFIID transcription factor-associated, (Mot1 homolog, S. cerevisiae) | 28.85 | 6.86 | 11.93 | 42.58 | 39.42 | 232.36 | 46.01 | 239.9 | 187.23 | 0.120990476 | 0.03834 | 0.00833485 |

TABLE 8B-continued

| Row | Gene | Oct. 4, 2001 | Oct. 4, 2002 | Oct. 4, 2003 | NI.1.1 | NI.1.2 | NI.1.3 | NI.2.1 | NI.2.2 | NI.2.3 | foldchange | fdr | t.pvals |
|---|---|---|---|---|---|---|---|---|---|---|---|---|---|
| 30576 | Transcribed locus | 510.18 | 377.24 | 438.04 | 946.62 | 823.44 | 1198.9 | 651.44 | 766.79 | 926.47 | 0.498886833 | 0.0384 | 0.00188992 |
| 29457 | WD repeat domain 46 | 218.17 | 112.46 | 94.73 | 408.68 | 196.3 | 309.16 | 631.99 | 252.45 | 611.74 | 0.352948986 | 0.0384 | 0.01177698 |
| 19166 | solute carrier family 39 (zinc transporter), member 4 | 46.7 | 42.22 | 31.16 | 170.36 | 69.43 | 62.77 | 295.72 | 198.68 | 333.58 | 0.211429458 | 0.03846 | 0.01086785 |
| 43448 | TatD DNase domain containing 1 | 77.05 | 76.25 | 15.42 | 213.53 | 120.79 | 170.2 | 248.59 | 156.85 | 449.66 | 0.248186993 | 0.03846 | 0.00550496 |
| 6729 | YY1 transcription factor | 283.21 | 139.65 | 276.18 | 630.7 | 488.31 | 503.98 | 593.02 | 531.08 | 482.62 | 0.432880971 | 0.03853 | 0.00073673 |
| 3998 | procollagen, type V, alpha 3 | 33.3 | 2.46 | 6.94 | 108.05 | 51.77 | 59.8 | 243.66 | 175.36 | 95.74 | 0.11628857 | 0.03853 | 0.00187396 |
| 14394 | acetyltransferase 2 | 315.87 | 400.24 | 148.72 | 745.68 | 497.68 | 1107.4 | 690.17 | 601.4 | 547.17 | 0.412858906 | 0.03864 | 0.00534374 |
| 4785 | RIKEN cDNA 2410016F19 gene | 2626.86 | 1700.7 | 1801.16 | 2574.1 | 2660.6 | 2995.8 | 4101.9 | 3403.46 | 3437.85 | 0.639284686 | 0.03864 | 0.01416184 |
| 19007 | GTP binding protein 3 | 315.42 | 126.56 | 117.97 | 465.37 | 336.42 | 416.21 | 408.64 | 480.29 | 597.69 | 0.414069259 | 0.03872 | 0.00246244 |
| 7933 | protein regulator of cytokinesis 1 | 717.27 | 432.74 | 439.28 | 852.9 | 910.14 | 799.31 | 1103 | 1075.94 | 1372.07 | 0.519941636 | 0.03905 | 0.0038711 |
| 18762 | RIKEN cDNA 1810003N24 gene | 844.39 | 363.6 | 396.78 | 978.22 | 773.69 | 906.85 | 985.65 | 1181.43 | 1314.69 | 0.522681267 | 0.0394 | 0.00727294 |
| 10372 | IMP4, U3 small nucleolar ribonucleoprotein, homolog (yeast) | 1079.23 | 720.29 | 726.16 | 1229.9 | 1161 | 1507.8 | 1381.4 | 1559.21 | 2228.6 | 0.557065661 | 0.03946 | 0.00884479 |
| 41173 | gb: BB209183 /DB_XREF = gi: 8874136 /DB_XREF = BB209183 /CLONE = A43091G17 /FEA = EST /CNT = 18 /TID = Mm.129698.1 /TIER = Stack /STK = 17 /UG = Mm.129698 /UG_TITLE = ESTs | 496.81 | 534.73 | 672.17 | 964.31 | 1013.3 | 1068.5 | 823.07 | 1042.47 | 1568.62 | 0.525809642 | 0.03951 | 0.00333501 |
| 15338 | RAB20, member RAS oncogene family | 486.8 | 419.24 | 302.02 | 593.19 | 602.78 | 611.39 | 1207 | 970.25 | 1217.61 | 0.46443661 | 0.03951 | 0.0195215 |
| 15902 | Crx opposite strand transcript 1 | 216.2 | 196.78 | 180.31 | 438.71 | 365.54 | 284.58 | 517.72 | 489.36 | 491.25 | 0.458567465 | 0.03955 | 0.00125293 |
| 13638 | ribosomal protein S21 | 2584.81 | 1818.73 | 2032.86 | 3125.7 | 2859.6 | 3137.7 | 3666 | 3359.24 | 5278.12 | 0.600791827 | 0.03957 | 0.0123343 |
| 7634 | cyclin M2 | 191.94 | 160.39 | 185.32 | 529.15 | 281.25 | 348.56 | 414.53 | 418.85 | 581.74 | 0.417741484 | 0.03961 | 0.00131644 |
| 3158 | GATA binding protein 4 | 243.29 | 314.72 | 216.04 | 548.17 | 372.29 | 460.72 | 660.84 | 563.02 | 829.97 | 0.450682822 | 0.03963 | 0.00324729 |
| 14053 | denticleless homolog (Drosophila) | 117.57 | 78.14 | 95.78 | 349.89 | 205.74 | 183.08 | 336.21 | 206.1 | 338.68 | 0.359930851 | 0.03967 | 0.0011816 |
| 21575 | tubulin, beta 5 | 38.96 | 56.74 | 38.01 | 155.85 | 185.38 | 153.18 | 142.88 | 165.48 | 195.42 | 0.267904908 | 0.03967 | 1.01E-005 |
| 1352 | peptidylprolyl isomerase D (cyclophilin D) /// lysosomal-associated membrane protein 3 /// similar to peptidylprolyl isomerase D | 707.11 | 447.21 | 263.78 | 1140.3 | 699.01 | 928.31 | 1030.2 | 754.1 | 902.76 | 0.519960034 | 0.03969 | 0.00795448 |
| 17069 | autophagy-related 3 (yeast) | 314.5 | 241.22 | 433.46 | 642.61 | 635.28 | 677.38 | 1423 | 439.15 | 1211.18 | 0.393420846 | 0.03973 | 0.01356134 |
| 20883 | RIKEN cDNA 2900053A13 gene | 46.21 | 35.31 | 27.79 | 124.96 | 115.95 | 155.72 | 172.07 | 129.07 | 221.68 | 0.237772581 | 0.03978 | 6.40E-005 |
| 12626 | dipeptidase 3 | 414.84 | 426.47 | 469.53 | 773.35 | 660.61 | 710.24 | 1012.5 | 968.29 | 930.73 | 0.518554122 | 0.03979 | 0.00111782 |
| 24211 | zinc finger protein 292 | 14.9 | 34.16 | 12.24 | 99.79 | 76.57 | 80.72 | 137 | 132.44 | 131.78 | 0.186237278 | 0.03985 | 0.00012921 |
| 10640 | kelch-like 22 (Drosophila) | 63.35 | 36.5 | 154.28 | 373.75 | 196.24 | 394.95 | 84.02 | 140.12 | 513.75 | 0.29847959 | 0.03988 | 0.03136841 |
| 5230 | von Hippel-Lindau syndrome homolog | 242.32 | 87.46 | 145.37 | 415.71 | 238.33 | 239.9 | 369.93 | 417.03 | 500.62 | 0.435613701 | 0.03994 | 0.00838939 |
| 12058 | ring finger protein (C3H2C3 type) 6 | 554.18 | 420.14 | 401.07 | 655.12 | 583.25 | 868.77 | 1096.2 | 908.12 | 1006.93 | 0.537426516 | 0.03997 | 0.0070928 |
| 10617 | sarcolemma associated protein | 102.17 | 105.27 | 51.27 | 194.14 | 150.33 | 224.98 | 300.15 | 333.64 | 268.15 | 0.351653878 | 0.04 | 0.00175258 |

TABLE 8B-continued

| Row | Gene | Oct. 4, 2001 | Oct. 4, 2002 | Oct. 4, 2003 | NI.1.1 | NI.1.2 | NI.1.3 | NI.2.1 | NI.2.2 | NI.2.3 | foldchange | fdr | t.pvals |
|---|---|---|---|---|---|---|---|---|---|---|---|---|---|
| 39100 | nucleolar protein 9 | 340.36 | 166.21 | 323.61 | 458.72 | 342.33 | 403.84 | 935.22 | 768.76 | 875.51 | 0.438740296 | 0.04 | 0.02347893 |
| 10978 | homeodomain interacting protein kinase 3 | 11.81 | 29.62 | 9.18 | 120.44 | 57.72 | 112.28 | 96.61 | 68.27 | 152.13 | 0.166630998 | 0.04003 | 0.00030594 |
| 13562 | cDNA sequence BC010304 | 1318.59 | 952.75 | 1281.75 | 1970.4 | 1624.2 | 2021.9 | 1486.9 | 2242.25 | 2206.77 | 0.615126394 | 0.04003 | 0.00682695 |
| 7422 | H3 histone, family 3A | 878.81 | 631.98 | 853.13 | 1174.7 | 1128.4 | 1357.7 | 1349.5 | 1593.59 | 2334.29 | 0.528957723 | 0.04006 | 0.00865031 |
| 16942 | SUMO/sentrin specific peptidase 3 | 2271.54 | 1602.51 | 1721.79 | 2780.1 | 2659.1 | 2911.5 | 2929.1 | 2911.41 | 3250.48 | 0.641664431 | 0.04006 | 0.00238324 |
| 21171 | ribosomal protein L29 /// hypothetical protein LOC669999 /// similar to 60S ribosomal protein L29 | 1696.19 | 634.99 | 1377.16 | 1987.6 | 2266.4 | 1883.6 | 1592.1 | 2337.53 | 4074.9 | 0.524436456 | 0.04009 | 0.02917422 |
| 18445 | Yip1 domain family, member 4 | 782.63 | 357.97 | 422.77 | 943.49 | 888.23 | 831.02 | 1009.3 | 1081.25 | 1031.26 | 0.540531103 | 0.04011 | 0.00347794 |
| 23583 | CXXC finger 6 | 166.09 | 59.38 | 58.14 | 251.54 | 278.86 | 292.88 | 369.76 | 167.47 | 233.69 | 0.355802283 | 0.04012 | 0.00239894 |
| 11104 | RAN binding protein 5 | 1214.6 | 825.31 | 930.44 | 1439.4 | 1397.7 | 1332.6 | 1951.6 | 1977.64 | 2086.45 | 0.583253563 | 0.04015 | 0.00776708 |
| 20617 | placenta specific 9 | 196.43 | 91.79 | 72.6 | 352.41 | 222.51 | 218.3 | 278.58 | 511.3 | 340.48 | 0.37515466 | 0.04017 | 0.00430094 |
| 2867 | tumor necrosis factor receptor superfamily, member 12a | 301.25 | 159.52 | 151.05 | 479.97 | 246.27 | 564 | 471.44 | 369.03 | 575.57 | 0.452148336 | 0.0402 | 0.00844923 |
| 16007 | hypothetical LOC435970 /// similar to gonadotropin inducible ovarian transcription factor 2 | 678.45 | 317.43 | 184.75 | 688.24 | 630.48 | 750.43 | 1021.2 | 760.72 | 1173.03 | 0.469985729 | 0.04022 | 0.01029519 |
| 38800 | Glutamine fructose-6-phosphate transaminase 1 | 154.6 | 86.66 | 72.39 | 201.4 | 144.57 | 299 | 425.52 | 262.91 | 388.13 | 0.364385169 | 0.04027 | 0.00670534 |
| 13746 | deoxyhypusine synthase | 40.12 | 11.88 | 30.86 | 40.89 | 74.65 | 90.18 | 175.94 | 258.31 | 230.11 | 0.190465245 | 0.04028 | 0.00951161 |
| 12807 | peptidyl prolyl isomerase H /// hypothetical protein LOC624822 /// similar to Peptidyl-prolyl cis-trans isomerase H (PPIase H) (Rotamase H) | 48.4 | 49.08 | 49.99 | 166.67 | 194.54 | 121.42 | 198.1 | 204.78 | 97.2 | 0.300129234 | 0.04032 | 0.00035827 |
| 13130 | protein | 102.04 | 67.67 | 139.68 | 333.55 | 151.31 | 287.34 | 230.45 | 274.04 | 374.05 | 0.374850067 | 0.04033 | 0.00283292 |
| 2362 | cofilin 2, muscle | 978.51 | 785.68 | 989.09 | 1233.6 | 1142.6 | 1301.9 | 2052.8 | 1861.5 | 1865.78 | 0.582208806 | 0.04038 | 0.01428345 |
| 6144 | eukaryotic translation initiation factor 4E member 2 | 106.88 | 47.69 | 39.81 | 160 | 100.21 | 135.61 | 343.08 | 263.59 | 456.25 | 0.266503969 | 0.04038 | 0.00981135 |
| 14010 | eukaryotic translation initiation factor 5B | 630.83 | 605.07 | 661.68 | 984.87 | 922.28 | 1001.4 | 1288.8 | 1369.41 | 1283.35 | 0.554029868 | 0.04039 | 0.00170399 |
| 17195 | ariadne homolog 2 (Drosophila) | 1041.91 | 675.07 | 711.19 | 1533 | 934.55 | 1369.8 | 1554.4 | 1033.03 | 1685.49 | 0.598785251 | 0.04042 | 0.01816852 |
| 38383 | mitochondrial ribosomal protein S6 | 1289.27 | 719.43 | 948.29 | 1789.4 | 1403.2 | 1559.5 | 1291.6 | 2038.19 | 1795.1 | 0.598760357 | 0.04043 | 0.00896259 |
| 16985 | mitochondrial ribosomal protein L39 | 192.78 | 74.48 | 65.23 | 382.08 | 203.89 | 182.76 | 355.09 | 320.19 | 281.17 | 0.385455431 | 0.04046 | 0.00469527 |
| 2261 | mitochondrial ribosomal protein L39 | 11.28 | 52.99 | 34.16 | 169.89 | 124.95 | 91.91 | 119.25 | 152.47 | 153.1 | 0.242566877 | 0.04049 | 0.00084464 |
| 39073 | phosphatidylinositol 3-kinase, catalytic, beta polypeptide | 76.55 | 96.39 | 113.73 | 271.48 | 148.58 | 263.12 | 289.7 | 255.76 | 314.46 | 0.371550774 | 0.0405 | 0.00077467 |
| 5910 | proteasome (prosome, macropain) 26S subunit, non-ATPase, 14 | 774.34 | 476.98 | 629.32 | 1287.5 | 896.48 | 1249 | 1056.8 | 933.88 | 1219.72 | 0.566167074 | 0.0405 | 0.00346014 |
| 38875 | RIKEN cDNA 1110008B24 gene | 723.82 | 473.87 | 306.58 | 908.37 | 546.03 | 872.14 | 1023.5 | 1117.82 | 1343 | 0.517740797 | 0.04052 | 0.01875828 |
| 44707 | expressed sequence AF013969 | 143.57 | 109.96 | 108.78 | 314.91 | 203.78 | 285.29 | 503.61 | 242.43 | 417.29 | 0.36833036 | 0.04052 | 0.00212647 |

TABLE 8B-continued

| Row | Gene | Oct. 4, 2001 | Oct. 4, 2002 | Oct. 4, 2003 | NI1.1 | NI1.2 | NI1.3 | NI2.1 | NI2.2 | NI2.3 | foldchange | fdr | t.pvals |
|---|---|---|---|---|---|---|---|---|---|---|---|---|---|
| | /// similar to CG5514-PB, isoform B /// region containing expressed sequence AF013969; RIKEN cDNA A230054D04 gene | | | | | | | | | | | | |
| 8041 | ring finger and WD repeat domain 3 | 1896.6 | 1829.31 | 1380.91 | 2772 | 2658.2 | 3056.2 | 2072.4 | 2195.33 | 2804.08 | 0.656477432 | 0.04054 | 0.01044825 |
| 28154 | methyltransferase like 2 | 51.31 | 48.28 | 45.52 | 144.77 | 183.34 | 169.06 | 101.31 | 165.95 | 286.78 | 0.276081849 | 0.04056 | 0.00042431 |
| 30269 | nucleolar protein 11 | 29.76 | 6.59 | 11.32 | 94.82 | 98.86 | 59.84 | 176.47 | 125.5 | 88.54 | 0.148036582 | 0.04058 | 0.00033177 |
| 7189 | valosin containing protein /// similar to Transitional endoplasmic reticulum ATPase (TER ATPase) (15S Mg(2+)-ATPase p97 subunit) (Valosin-containing protein) (VCP) | 441.58 | 368.14 | 517.63 | 943.18 | 758.44 | 743.25 | 937.83 | 818.51 | 891.57 | 0.521267363 | 0.04058 | 0.0004249 |
| 16306 | ubiquitin specific peptidase 10 | 257.9 | 263.88 | 466.98 | 838.32 | 498.36 | 592.08 | 738.05 | 449.15 | 994.08 | 0.481143736 | 0.04059 | 0.0102128 |
| 24333 | activating transcription factor 7 interacting protein 2 | 998.36 | 673.13 | 860.25 | 1461.8 | 1354.6 | 1323.4 | 1579.9 | 1425.89 | 1629.02 | 0.577057117 | 0.0406 | 0.00102143 |
| 18466 | host cell factor C1 | 217.35 | 291.13 | 173.2 | 369.82 | 317.79 | 306.44 | 711.47 | 663.73 | 675.05 | 0.447840226 | 0.04061 | 0.01723647 |
| 7354 | hippocampus abundant gene transcript 1 | 392.76 | 231.65 | 210.52 | 490.55 | 398.57 | 461.1 | 662.98 | 750.7 | 838.3 | 0.463566709 | 0.04063 | 0.00703408 |
| 11196 | eukaryotic translation initiation factor 4, gamma 1 | 795.82 | 790.01 | 913.29 | 1492.1 | 1297.2 | 1320.6 | 1521.8 | 1501.26 | 1366.38 | 0.588076665 | 0.04065 | 0.00040865 |
| 12088 | pyridoxal (pyridoxine, vitamin B6) kinase | 341.59 | 275.6 | 123.17 | 435.93 | 526.52 | 455.27 | 643.14 | 513.95 | 833.89 | 0.434394344 | 0.04067 | 0.0051941 |
| 955 | eukaryotic translation initiation factor 3, subunit 10 (theta) | 3497.53 | 2343.31 | 2333.08 | 3666.5 | 3233.6 | 3908.4 | 5268.7 | 4157.74 | 4381.74 | 0.664095243 | 0.0407 | 0.01798116 |
| 21792 | Zinc finger protein 444 | 311.39 | 109.74 | 33.14 | 452.64 | 198.57 | 309.81 | 294.53 | 537.31 | 689.29 | 0.36602945 | 0.0407 | 0.01990646 |
| 2633 | WD repeat domain 33 | 130.08 | 90.77 | 188.21 | 291.14 | 355.77 | 593.08 | 234.78 | 271.81 | 596.3 | 0.349194154 | 0.04072 | 0.00518948 |
| 16350 | complement component 1, q subcomponent binding protein | 1157.96 | 830.97 | 657.36 | 1662.1 | 1312.4 | 1366.6 | 1453.8 | 1506.64 | 2023.78 | 0.567554294 | 0.04074 | 0.00450461 |
| 16278 | RIKEN cDNA 2610524G07 gene | 445.79 | 163.3 | 359.19 | 701.15 | 580.47 | 1519.9 | 587.27 | 478.76 | 1412.36 | 0.366776895 | 0.04075 | 0.0187662 |
| 41375 | core-binding factor, runt domain, alpha subunit 2, translocated to, 2 homolog (human) | 362.76 | 159.53 | 39.4 | 549.54 | 295.88 | 488.83 | 219.51 | 745.72 | 448.33 | 0.408827393 | 0.04076 | 0.02903456 |
| 9888 | vitelliform macular dystrophy 2-like protein 1 | 26.77 | 68.92 | 92.66 | 159.89 | 205.9 | 333.32 | 240.53 | 128.6 | 182.61 | 0.301155214 | 0.04079 | 0.0025478 |
| 12466 | ribosomal protein S24 | 1501.15 | 1020.57 | 1349 | 1942.8 | 1498.5 | 1804.5 | 2346.8 | 2369.96 | 2625.8 | 0.614966159 | 0.04082 | 0.01377549 |
| 6758 | zinc finger protein 143 | 70.96 | 68.45 | 69.67 | 183.06 | 92.13 | 284.13 | 176.81 | 250.89 | 303.16 | 0.324109814 | 0.04085 | 0.0039866 |
| 23587 | GTPase activating protein and VPS9 domains 1 | 333.58 | 155.43 | 192.66 | 424.38 | 502.98 | 467.39 | 685.61 | 645.29 | 353.59 | 0.442752108 | 0.04086 | 0.00362749 |
| 12738 | type 2B | 125.53 | 76.26 | 48.2 | 253.24 | 181.84 | 235.81 | 167.98 | 240.57 | 313.04 | 0.359057222 | 0.04087 | 0.00119569 |
| 14480 | Son cell proliferation protein | 352.01 | 285.74 | 318.7 | 532.78 | 480.48 | 448.55 | 821.48 | 910.68 | 792.96 | 0.479792723 | 0.04088 | 0.00694346 |
| 11012 | SET translocation | 915.35 | 704.29 | 595.07 | 1259.9 | 1330.6 | 1160.7 | 1068.8 | 1370.79 | 1550.02 | 0.572220299 | 0.04088 | 0.00220896 |
| 2866 | tumor necrosis factor receptor superfamily, member 12a | 320.47 | 172.16 | 158.2 | 480.91 | 257.13 | 582.58 | 497.84 | 384.37 | 599.54 | 0.464485418 | 0.0409 | 0.00962175 |
| 38041 | sorting nexin 6 | 279.12 | 83.74 | 111.89 | 319.18 | 284.78 | 562.5 | 346.75 | 388.99 | 594.39 | 0.380318755 | 0.0409 | 0.00500672 |
| 13631 | protein tyrosine phosphatase-like A domain containing 1 | 221.52 | 140.45 | 439.19 | 494.52 | 549.29 | 538.97 | 573.99 | 612.57 | 1361.41 | 0.387900502 | 0.04091 | 0.00955865 |

TABLE 8B-continued

| Row | Gene | Oct. 4, 2001 | Oct. 4, 2002 | Oct. 4, 2003 | NI1.1 | NI1.2 | NI1.3 | NI2.1 | NI2.2 | NI2.3 | foldchange | fdr | t.pvals |
|---|---|---|---|---|---|---|---|---|---|---|---|---|---|
| 40666 | bromodomain and PHD finger containing, 3 | 123.25 | 66.62 | 84.15 | 270.72 | 241.5 | 263.39 | 137.62 | 214.11 | 397.32 | 0.359450632 | 0.04092 | 0.00275523 |
| 25023 | cyclin M4 | 81.3 | 61.69 | 90.14 | 148.79 | 264.46 | 223.53 | 165.53 | 233.02 | 314.14 | 0.345513424 | 0.04095 | 0.00066368 |
| 15839 | peroxisome proliferator activated receptor binding protein | 3.63 | 2.38 | 10.41 | 65.58 | 38.61 | 88.28 | 38.4 | 118.58 | 104.52 | 0.072339582 | 0.04096 | 0.00013507 |
| 14494 | DnaJ (Hsp40) homolog, subfamily B, member 12 | 183.48 | 163.99 | 62.66 | 294.14 | 274.02 | 311.49 | 605.82 | 320.93 | 536.74 | 0.350068711 | 0.04097 | 0.00463062 |
| 10865 | xylulokinase homolog (H. influenzae) | 570.91 | 332.39 | 251.87 | 818.91 | 532.81 | 562.41 | 921.59 | 711.51 | 946.94 | 0.514074901 | 0.04101 | 0.00971793 |
| 16446 | Unc-51 like kinase 1 (C. elegans) | 688.42 | 447.89 | 387.79 | 998.96 | 689.04 | 942.76 | 783.34 | 1059.4 | 1087.82 | 0.548107284 | 0.04102 | 0.00483918 |
| 12517 | PRP38 pre-mRNA processing factor 38 (yeast) domain containing B | 453.67 | 395.38 | 239.57 | 654.65 | 564.35 | 746.42 | 1167 | 624.92 | 806.21 | 0.477090355 | 0.04103 | 0.0054774 |
| 12358 | DEAH (Asp-Glu-Ala-His) box polypeptide 40 | 72.27 | 61.52 | 54.09 | 167.12 | 149.31 | 199 | 299.91 | 175.4 | 477.91 | 0.255854016 | 0.04106 | 0.00156953 |
| 13777 | general transcription factor III C 1 | 161.54 | 193.59 | 135.49 | 406.5 | 272.1 | 321.91 | 350.92 | 440.43 | 553.06 | 0.418453508 | 0.04108 | 0.00119698 |
| 1549 | spermatogenesis associated 5 | 119.35 | 125.19 | 136.28 | 318.86 | 254.39 | 257.63 | 387.86 | 321.28 | 353.57 | 0.402220122 | 0.04111 | 0.000123 |
| 7228 | activity-dependent neuroprotective protein | 454.34 | 277.92 | 262.38 | 806.44 | 487.17 | 695.53 | 665.1 | 564.28 | 782.06 | 0.497247899 | 0.04113 | 0.00268655 |
| 17344 | glutamine fructose-6-phosphate transaminase 1 | 374.81 | 257.95 | 316.1 | 699.57 | 464.92 | 769.86 | 656.51 | 363.82 | 746.9 | 0.51267837 | 0.04113 | 0.0111343 |
| 22765 | purine rich element binding protein B | 155.98 | 78.28 | 45.27 | 264.07 | 195.74 | 234.5 | 347.63 | 237.43 | 304.74 | 0.352917411 | 0.04118 | 0.00165563 |
| 2822 | FUS interacting protein (serine-arginine rich) 1 | 2250.39 | 1979.57 | 1833.46 | 2877.6 | 2467.7 | 3105.4 | 3470 | 3149.84 | 3432.49 | 0.65539575 | 0.04119 | 0.00493355 |
| 29854 | ADP-ribosylation factor-like 15 | 102.07 | 159.07 | 161.91 | 336.3 | 397.43 | 326.19 | 521.65 | 339.7 | 306.09 | 0.379866748 | 0.04131 | 0.00035486 |
| 14013 | DEAD (Asp-Glu-Ala-Asp) box polypeptide 52 | 388.08 | 161.92 | 274.42 | 654.08 | 454.68 | 714 | 468.82 | 637.43 | 504.22 | 0.480259115 | 0.0414 | 0.00404719 |
| 44759 | expressed sequence AA763515 | 8.75 | 107.57 | 93.59 | 266.69 | 476.12 | 367.11 | 115.8 | 208.23 | 76.04 | 0.278028331 | 0.04145 | 0.03222834 |
| 25723 | nucleolar protein 9 | 814.25 | 472.11 | 250.05 | 1027.7 | 836.53 | 843.91 | 990.85 | 1023.2 | 913.87 | 0.545203243 | 0.04161 | 0.00953711 |
| 19626 | sestrin 2 | 492.49 | 377.96 | 378.76 | 576.84 | 439.85 | 945.27 | 773.15 | 957.31 | 978.1 | 0.534934012 | 0.04167 | 0.02023325 |
| 17889 | phosphatidylinositol 4-kinase type 2 beta | 199.31 | 230.48 | 234.25 | 466.28 | 327.46 | 508.52 | 589.11 | 402.49 | 715.19 | 0.441361892 | 0.04173 | 0.0022702 |
| 24760 | RIKEN cDNA 4933402C05 gene | 526.44 | 324.33 | 277.42 | 582.5 | 656.43 | 516.22 | 821.01 | 823.62 | 1015 | 0.511096816 | 0.04177 | 0.00786959 |
| 40677 | RIKEN cDNA D530033C11 gene | 62.8 | 31.87 | 92.29 | 229.92 | 169.71 | 276.49 | 176.84 | 152.21 | 205.02 | 0.308976276 | 0.04182 | 0.00070361 |
| 40756 | cDNA sequence BC057371 | 266.3 | 343.51 | 142.19 | 489.41 | 461.09 | 497.84 | 765.56 | 698.43 | 524.25 | 0.437644402 | 0.04183 | 0.00285669 |
| 15702 | ribosomal protein S17 | 3413.68 | 2189.66 | 2823.31 | 4101 | 3483.9 | 3592.5 | 4611.8 | 4168.53 | 4913.62 | 0.677620117 | 0.04188 | 0.01435464 |
| 16556 | nuclear import 7 homolog (S. cerevisiae) | 1117.61 | 701.46 | 924.84 | 1468.6 | 1454.8 | 1208.1 | 1615.1 | 1894.95 | 1641.93 | 0.591138237 | 0.04193 | 0.00457958 |
| 11703 | poly (A) polymerase alpha | 15.3 | 45.46 | 34.26 | 129.02 | 144.67 | 119.25 | 158.08 | 76.86 | 140.95 | 0.247180781 | 0.04198 | 0.0004212 |
| 5457 | homeodomain interacting protein kinase 1 | 982.38 | 849.34 | 1301 | 1736.4 | 1266.8 | 1727.8 | 1609.9 | 1888.44 | 2141.79 | 0.604126672 | 0.04203 | 0.00752055 |
| 21337 | carboxypeptidase D | 52.84 | 88.41 | 40.22 | 258.05 | 184.47 | 187.52 | 155.3 | 168.61 | 253.58 | 0.300563961 | 0.04209 | 0.00026393 |
| 21183 | ubiquitin associated protein 2-like | 704.73 | 268.76 | 278.2 | 1175.1 | 736.68 | 781.12 | 765.49 | 711.76 | 1019.45 | 0.48238121 | 0.04214 | 0.00655066 |
| 16501 | eukaryotic translation initiation factor 3, subunit 10 (theta) | 1962.76 | 1345.41 | 1507.34 | 2379.6 | 1854.1 | 2427.1 | 3453.2 | 2549.07 | 3057.45 | 0.612638481 | 0.04218 | 0.01453233 |
| 791 | Morf4 family associated protein 1 | 1393.96 | 988.45 | 1124.79 | 1873 | 1359.9 | 1748.1 | 1989.4 | 2140.18 | 2023.47 | 0.629994243 | 0.04224 | 0.00786029 |
| 9218 | protein arginine N-methyltransferase 6 | 1192.36 | 520.85 | 617.17 | 1347.3 | 1072.8 | 1130.9 | 1415.4 | 1423.29 | 1354.94 | 0.601806934 | 0.04277 | 0.01108551 |

TABLE 8B-continued

| Row | Gene | Oct. 4, 2001 | Oct. 4, 2002 | Oct. 4, 2003 | NI1.1 | NI1.2 | NI1.3 | NI2.1 | NI2.2 | NI2.3 | foldchange | fdr | t.pvals |
|---|---|---|---|---|---|---|---|---|---|---|---|---|---|
| 39489 | RIKEN cDNA 2610206G21 gene | 385.68 | 426.03 | 475.42 | 734.42 | 556.38 | 887.02 | 879.79 | 778.82 | 850.91 | 0.549194212 | 0.04282 | 0.00202463 |
| 14334 | WD repeats and SOF domain containing 1 | 431.5 | 295.6 | 235.2 | 806.65 | 558.06 | 634.33 | 784.95 | 603.44 | 597.88 | 0.482923537 | 0.04287 | 0.00128243 |
| 24209 | RIKEN cDNA 2610020H08 gene | 32.11 | 23.32 | 52.07 | 145.28 | 75.19 | 165.2 | 243.85 | 127.48 | 115.24 | 0.246491791 | 0.04302 | 0.00099377 |
| 20784 | DEAD (Asp-Glu-Ala-Asp) box polypeptide 10 | 70.39 | 42.43 | 116.81 | 234.66 | 140.44 | 219.65 | 270.65 | 147.92 | 253.11 | 0.362641441 | 0.04305 | 0.00237097 |
| 7934 | protein regulator of cytokinesis 1 | 882.29 | 561.67 | 562.14 | 1130.7 | 990.99 | 915.08 | 1248.9 | 1220.25 | 1392.55 | 0.581610598 | 0.04307 | 0.00476743 |
| 8707 | zinc finger, CCCH-type with G patch domain | 51.69 | 25.13 | 56.62 | 118.43 | 68.27 | 140.57 | 216.62 | 178.11 | 256.1 | 0.272855536 | 0.0431 | 0.00395268 |
| 21424 | ubiquitin specific peptidase 36 | 186.19 | 106.7 | 198.31 | 424.4 | 291.16 | 431.35 | 322.19 | 484.24 | 311.35 | 0.433790055 | 0.04312 | 0.0015881 |
| 7817 | signal peptide peptidase 3 | 87.29 | 42.07 | 37.9 | 188.55 | 124.22 | 96.45 | 188.49 | 216.63 | 182.01 | 0.335745471 | 0.04317 | 0.00179556 |
| 22171 | stathmin-like 3 | 280.8 | 139.85 | 201.65 | 475.25 | 288.43 | 374.17 | 564.11 | 475.36 | 454.23 | 0.472953202 | 0.04321 | 0.00392245 |
| 20309 | cofactor required for Sp 1 transcriptional activation, subunit 7 | 401.97 | 260.33 | 241.18 | 724.75 | 562.78 | 486.97 | 470.51 | 624.15 | 970.19 | 0.470642166 | 0.04322 | 0.00490214 |
| 1349 | RIKEN cDNA 0610009D07 gene | 161.97 | 142.69 | 83.83 | 332.41 | 184.17 | 281.59 | 388.71 | 302.32 | 482.73 | 0.394020072 | 0.04326 | 0.00393886 |
| 10566 | CUG triplet repeat, RNA binding protein 1 | 368.59 | 320.29 | 329.52 | 818.02 | 671.83 | 693.42 | 734.46 | 490.43 | 505.7 | 0.520406964 | 0.04332 | 0.00216732 |
| 8579 | cell cycle progression 1 | 220.05 | 202.83 | 244.27 | 519.44 | 428.94 | 471.56 | 477.1 | 413 | 524.9 | 0.470662518 | 0.04333 | 8.49E−005 |
| 15916 | BTB and CNC homology 1 | 299.52 | 142.08 | 280.99 | 509.03 | 500.69 | 370.86 | 552.06 | 427.69 | 703.89 | 0.47163627 | 0.04338 | 0.00429197 |
| 4645 | nucleolar protein 7 | 551.77 | 243.19 | 360.68 | 894.12 | 728.94 | 555.6 | 772.7 | 534.61 | 874.95 | 0.529998257 | 0.04348 | 0.00928765 |
| 29317 | NIMA (never in mitosis gene a)-related expressed kinase 2 | 692.79 | 642.8 | 418.9 | 917.15 | 746.99 | 927.21 | 1171.3 | 1253.89 | 1243.99 | 0.560496959 | 0.04353 | 0.00770205 |
| 11419 | tropomyosin 3, gamma | 574.31 | 530.72 | 522.22 | 1153.2 | 848.47 | 1058.4 | 816.32 | 879.3 | 1247.36 | 0.542146497 | 0.04358 | 0.0016093 |
| 1594 | NIMA (never in mitosis gene a)-related expressed kinase 2 | 750.07 | 650.55 | 453.52 | 1026.9 | 842.77 | 1001 | 1176.3 | 1304.61 | 1168.12 | 0.568777283 | 0.04363 | 0.00385126 |
| 23285 | RIKEN cDNA 1110004B13 gene | 32.86 | 16.77 | 16.39 | 47.07 | 45.2 | 114.19 | 120.64 | 162.14 | 140.35 | 0.209723788 | 0.04369 | 0.00294454 |
| 8141 | FUS interacting protein (serine-arginine rich) 1 | 657.7 | 606.69 | 401.25 | 1289.5 | 963.26 | 940.8 | 1005.2 | 1015.79 | 962.73 | 0.539283789 | 0.04379 | 0.0014819 |
| 694 | heme oxygenase (decycling) 2 | 228.15 | 127.34 | 175.71 | 429.17 | 306.91 | 318.12 | 522.16 | 364.93 | 537.19 | 0.428649818 | 0.0438 | 0.0018308 |
| 21921 | WD repeat domain 33 | 423.94 | 236.64 | 225.43 | 650.55 | 442.71 | 521.71 | 588.06 | 600.77 | 812.98 | 0.489944094 | 0.04384 | 0.0034789 |
| 23670 | BRF2, subunit of RNA polymerase III transcription initiation factor, BRF1-like | 101.79 | 131.02 | 195.54 | 374.57 | 304.79 | 715.04 | 381.23 | 100.11 | 630.97 | 0.341762709 | 0.04385 | 0.05104204 |
| 29502 | transmembrane protein 39b | 176.13 | 81.2 | 214.01 | 384.29 | 398.39 | 485.44 | 203.27 | 287.14 | 367.76 | 0.443344981 | 0.04389 | 0.00918906 |
| 17866 | caspase 3 | 628.36 | 670.27 | 458.61 | 1113.9 | 883.27 | 1268.1 | 856.19 | 1204.37 | 987.32 | 0.556689339 | 0.0439 | 0.00269251 |
| 21277 | ribosomal protein L23 | 4511.51 | 3680.37 | 3884.36 | 5456.7 | 5071.7 | 5720.7 | 6020.5 | 5596.08 | 6154.6 | 0.709944642 | 0.04396 | 0.00538158 |
| 6830 | N-acetylated alpha-linked acidic dipeptidase 2 | 977.43 | 735.87 | 1119.53 | 1576.5 | 1513.4 | 1599.2 | 1649.9 | 1277.79 | 1688.28 | 0.608881433 | 0.04401 | 0.0026034 |
| 14469 | growth arrest specific 2 | 296.03 | 215.2 | 25.66 | 413.01 | 244.06 | 357.68 | 862.42 | 415.16 | 513.27 | 0.382727402 | 0.0441 | 0.02873344 |
| 12046 | RIKEN cDNA 2610304G08 gene | 258.49 | 114.73 | 87.48 | 371.57 | 264.27 | 368.45 | 247.09 | 401.41 | 444.6 | 0.439307902 | 0.04412 | 0.00518255 |
| 688 | EMG1 nucleolar protein homolog (S. cerevisiae) | 747.94 | 398.7 | 373.77 | 892.83 | 714.84 | 908.61 | 952.79 | 986.65 | 1139.24 | 0.543492715 | 0.04414 | 0.00487152 |
| 12472 | phosphoribosyl pyrophosphate amidotransferase | 1491.3 | 1292.29 | 865.49 | 1886.3 | 1875.6 | 1977.5 | 2339.7 | 2006.58 | 1731.57 | 0.617588445 | 0.04415 | 0.005014 |
| 6656 | solute carrier family 30 (zinc | 297.02 | 228.45 | 223.91 | 509.29 | 464.77 | 462.7 | 542.34 | 536.01 | 601.37 | 0.480914365 | 0.04415 | 0.00017236 |

TABLE 8B-continued

| Row | Gene | Oct. 4, 2001 | Oct. 4, 2002 | Oct. 4, 2003 | NI.1.1 | NI.1.2 | NI.1.3 | NI.2.1 | NI.2.2 | NI.2.3 | foldchange | fdr | t.pvals |
|---|---|---|---|---|---|---|---|---|---|---|---|---|---|
| 20828 | transporter), member 5 survival motor neuron domain containing 1 | 1251.34 | 889.9 | 1044.49 | 1444.9 | 1549 | 1671.9 | 1831.8 | 1993.53 | 1836.28 | 0.616951332 | 0.04419 | 0.00303399 |
| 1798 | replication factor C (activator 1) 2 | 112.63 | 81.23 | 219.08 | 447.59 | 301.17 | 360.79 | 232.07 | 199.2 | 517.32 | 0.401274938 | 0.0442 | 0.00918665 |
| 15103 | polymerase (RNA) III (DNA directed) polypeptide A | 722.68 | 439.95 | 880.64 | 968.12 | 883.9 | 1401.1 | 997.47 | 1601.38 | 1547.52 | 0.552273944 | 0.04421 | 0.01694181 |
| 25102 | Protein phosphatase 2 (formerly 2A), catalytic subunit, beta isoform | 174.77 | 85.22 | 66.46 | 204.94 | 186.65 | 182.56 | 357.01 | 457.2 | 468.36 | 0.351641605 | 0.04424 | 0.00971819 |
| 11003 | programmed cell death 2-like | 554.47 | 517.02 | 316.42 | 881.18 | 628.34 | 852.95 | 854.94 | 1019.81 | 858.95 | 0.544687481 | 0.04425 | 0.00361332 |
| 1176 | myeloid cell leukemia sequence 1 | 967.2 | 721.92 | 533.68 | 1440.5 | 1391.5 | 1486.5 | 898.34 | 715.94 | 1658.09 | 0.585653235 | 0.04426 | 0.04611204 |
| 519 | zinc finger and BTB domain containing 17 | 53.35 | 146.21 | 217.39 | 394.13 | 287.82 | 382.18 | 413.55 | 194.42 | 1009.27 | 0.310997736 | 0.04435 | 0.01661823 |
| 7589 | MYB binding protein (P160) 1a | 627.85 | 220.85 | 196.3 | 619.81 | 559.46 | 543.97 | 759.99 | 756.52 | 1180.53 | 0.472820726 | 0.04436 | 0.01351934 |
| 15255 | hexosaminidase B | 452.07 | 322.98 | 329.02 | 829.4 | 691.76 | 686.04 | 625.54 | 661.85 | 990.61 | 0.492316954 | 0.04441 | 0.00102269 |
| 13783 | 5,10-methylenetetrahydrofolate reductase | 92.68 | 23.2 | 61.28 | 119.07 | 236.68 | 128.56 | 224.28 | 167.49 | 212.1 | 0.325607896 | 0.04442 | 0.0031695 |
| 22165 | ribosomal protein S23 | 1550.31 | 917.07 | 1521.18 | 2053.3 | 1593.8 | 1798.2 | 2341.2 | 2253.28 | 2552.84 | 0.633474792 | 0.04447 | 0.01650885 |
| 1699 | ELOVL family member 6, elongation of long chain fatty acids (yeast) | 123.87 | 55.45 | 27.87 | 238.32 | 107.52 | 110.47 | 373.69 | 190.73 | 287.91 | 0.316649346 | 0.04452 | 0.01238244 |
| 30087 | RIKEN cDNA 4930515G01 gene | 30.95 | 26.16 | 15.9 | 110.2 | 64.69 | 112.74 | 138.13 | 116.5 | 168.78 | 0.205361161 | 0.04458 | 0.00016379 |
| 9641 | ankyrin repeat and MYND domain containing 2 | 67.44 | 57.45 | 75.7 | 180.49 | 149.85 | 218.49 | 301.23 | 86.12 | 363.81 | 0.308602374 | 0.04462 | 0.007918 |
| 12034 | RIKEN cDNA 1100001I22 gene | 632 | 348.59 | 642.76 | 973.51 | 834.59 | 1122.8 | 900.12 | 946.7 | 1813.9 | 0.49254739 | 0.04463 | 0.00948749 |
| 6044 | Son of sevenless homolog 1 (Drosophila) | 230.34 | 128.95 | 112.01 | 438.22 | 273.17 | 373.78 | 444.95 | 294.97 | 346.44 | 0.43407183 | 0.04468 | 0.00166919 |
| 3604 | podoplanin | 129.35 | 118.81 | 88.89 | 294.23 | 216.59 | 222.67 | 344.13 | 264.7 | 548.92 | 0.356432817 | 0.04469 | 0.00216879 |
| 22451 | heterogeneous nuclear ribonucleoprotein K | 1641.05 | 1528.27 | 1311.2 | 2707.7 | 2502.9 | 2859.9 | 1831.5 | 2175.84 | 1879.69 | 0.642018685 | 0.04473 | 0.01239415 |
| 8159 | ribosomal protein S11 | 1905.11 | 755.25 | 1126.75 | 2116.3 | 1573.3 | 1611.4 | 2104.2 | 2067.46 | 2512.79 | 0.631950714 | 0.04489 | 0.02807283 |
| 19749 | SET and MYND domain containing 5 | 83.2 | 60.13 | 96.49 | 253.01 | 152.74 | 155.94 | 279.3 | 195.61 | 293.15 | 0.36069938 | 0.04494 | 0.00109287 |
| 18114 | nucleolar and coiled-body phosphoprotein 1 | 447.22 | 412.6 | 479.77 | 809.13 | 599.42 | 798.12 | 444.95 | 790.66 | 1288.01 | 0.494922719 | 0.04504 | 0.00517173 |
| 21966 | ring finger protein 7 | 978.6 | 679.37 | 530.73 | 1504.8 | 910.25 | 1298.1 | 1164.5 | 1209.11 | 1470.39 | 0.579244127 | 0.04509 | 0.00830564 |
| 33824 | Rap1 interacting factor 1 homolog (yeast) /// similar to Telomere-associated protein RIF1 (Rap1-interacting factor 1 homolog) (mRif1) | 1336.02 | 1290.49 | 1278.51 | 1985.5 | 1726 | 2113.1 | 2351.9 | 1874.39 | 2319.62 | 0.631344433 | 0.04515 | 0.00227917 |
| 14479 | solute carrier family 5 (sodium-dependent vitamin transporter), member 6 | 1025.49 | 706.6 | 869.51 | 1379.5 | 1274.1 | 1219.6 | 1518.8 | 1593.95 | 1642.94 | 0.602996207 | 0.0452 | 0.00271465 |
| 19667 | RIKEN cDNA 1500011J06 gene | 2082.92 | 1586.47 | 1424.05 | 2592.1 | 2138.8 | 2584.9 | 3671.4 | 2264.15 | 2862.89 | 0.632167509 | 0.04561 | 0.01397112 |
| 21211 | protein tyrosine phosphatase-like A domain containing 1 | 488.96 | 206.07 | 471.03 | 602.68 | 571.37 | 650.06 | 818.59 | 878.21 | 1244.5 | 0.489384964 | 0.04566 | 0.01423314 |
| 20126 | expressed sequence AA408296 | 1123.36 | 793.87 | 596.32 | 1599.9 | 1397.9 | 1490.4 | 981.23 | 1241.52 | 1475.94 | 0.614046445 | 0.04591 | 0.0132658 |

TABLE 8B-continued

| Row | Gene | Oct. 4, 2001 | Oct. 4, 2002 | Oct. 4, 2003 | NI.1.1 | NI.1.2 | NI.1.3 | NI.2.1 | NI.2.2 | NI.2.3 | foldchange | fdr | t.pvals |
|---|---|---|---|---|---|---|---|---|---|---|---|---|---|
| 20457 | splicing factor, arginine/serine-rich 1 (ASF/SF2) | 2421.27 | 1796.6 | 1659.9 | 2947.2 | 2521.6 | 2808.5 | 3149 | 2942.53 | 3230.58 | 0.667956494 | 0.04596 | 0.00568803 |
| 5056 | synaptosomal-associated protein 23 | 749.26 | 643.08 | 613.45 | 1161.8 | 1012.4 | 1087.2 | 1424.7 | 1123.3 | 1276.51 | 0.566141158 | 0.04602 | 0.00087345 |
| 23156 | peptidylprolyl isomerase (cyclophilin)-like 1 | 304.9 | 357.27 | 348.55 | 845.83 | 673.8 | 668.59 | 562.18 | 556.37 | 635.42 | 0.51277082 | 0.04607 | 0.00062062 |
| 14444 | AT rich interactive domain 4B (Rbp1 like) | 54.11 | 86.93 | 51.53 | 199.78 | 154.66 | 258.1 | 146.18 | 272.78 | 173.72 | 0.319559914 | 0.04675 | 0.00042303 |
| 979 | fibrillarin | 527.33 | 324.24 | 338.18 | 693.11 | 444.03 | 799.63 | 1106.8 | 681.18 | 990.6 | 0.50462636 | 0.04681 | 0.01468203 |
| 14590 | RIKEN cDNA 4732471D19 gene | 51.05 | 36.62 | 123.36 | 196.47 | 132.63 | 198.82 | 195.08 | 238.56 | 382.09 | 0.314114539 | 0.04688 | 0.0029813 |
| 2168 | PWP1 homolog (S. cerevisiae) | 253.54 | 123.82 | 124.06 | 398.21 | 231.41 | 365.55 | 410.58 | 364.75 | 416.54 | 0.458537567 | 0.04691 | 0.00338099 |
| 11080 | ATP-binding cassette, sub-family F (GCN20), member 1 | 147.69 | 158.88 | 142.97 | 345.18 | 164.53 | 215.87 | 707.42 | 447.31 | 892.23 | 0.324280263 | 0.04693 | 0.03515947 |
| 19751 | ankyrin repeat and MYND domain containing 2 | 3.72 | 28.84 | 6.61 | 112.14 | 69.74 | 61.26 | 111.73 | 38.77 | 117.79 | 0.153178343 | 0.04696 | 0.0011350 |
| 14756 | Kruppel-like factor 9 | 210.02 | 29.37 | 90.94 | 354.82 | 272.53 | 212.2 | 254.78 | 274.03 | 358.42 | 0.382596509 | 0.04698 | 0.00747019 |
| 15073 | YTH domain family 1 | 215.69 | 353.03 | 190.75 | 634.54 | 438.28 | 329.92 | 608.02 | 420.79 | 788.44 | 0.471721962 | 0.04701 | 0.01026759 |
| 27459 | RNA pseudouridylate synthase domain containing 3 | 35.48 | 20.56 | 13.51 | 94.07 | 113.99 | 134.1 | 103.42 | 130.55 | 442.34 | 0.136577415 | 0.04707 | 0.00101169 |
| 182 | Trk-fused gene | 784.41 | 340.53 | 295.58 | 928.5 | 564.98 | 679.38 | 871.81 | 1022.58 | 1079.02 | 0.552058093 | 0.04717 | 0.02052607 |
| 16390 | cell division cycle 2 homolog A (S. pombe) | 1520.87 | 991.88 | 1873.5 | 1922.5 | 2470.7 | 2908.9 | 2019.7 | 2007.39 | 3556.92 | 0.589307355 | 0.0472 | 0.02144756 |
| 2140 | claudin 6 | 377.34 | 362.31 | 248.66 | 836.91 | 293.71 | 421.11 | 822.38 | 709.62 | 736.86 | 0.517359884 | 0.04722 | 0.04780535 |
| 23988 | RIKEN cDNA 2210011C24 gene | 72.37 | 81.79 | 46.68 | 176.2 | 192.27 | 212.67 | 138.15 | 189.52 | 394.55 | 0.308188068 | 0.04725 | 0.00136374 |
| 14006 | La ribonucleoprotein domain family, member 5 | 423.27 | 344.14 | 388.76 | 594.63 | 701.46 | 735.35 | 726.67 | 737.66 | 830.55 | 0.534481962 | 0.04727 | 0.00036524 |
| 8270 | insulin-like growth factor 2 receptor | 434.23 | 266.75 | 433.37 | 781.98 | 500.48 | 705.3 | 745.85 | 596 | 939.69 | 0.53139859 | 0.04738 | 0.0059995 |
| 15878 | zinc finger protein 289 | 81.46 | 122.04 | 76.07 | 252.08 | 206.46 | 182.53 | 595.85 | 231.71 | 743.7 | 0.252738063 | 0.04741 | 0.00831163 |
| 27919 | casein kinase 1, epsilon | 10.44 | 8.6 | 20.89 | 54.93 | 27.16 | 86.67 | 149.6 | 94.28 | 120.88 | 0.14968511 | 0.04752 | 0.00167154 |
| 3281 | ubiquitously expressed transcript | 138.54 | 90.92 | 30.95 | 203.48 | 182.02 | 211.77 | 247.35 | 247.04 | 374.41 | 0.355249067 | 0.04754 | 0.0043143 |
| 16269 | RIKEN cDNA 5730403B10 gene | 77.47 | 94.8 | 164.04 | 275.16 | 166.89 | 142.51 | 330.15 | 361.39 | 315.31 | 0.422656638 | 0.04759 | 0.01185988 |
| 13417 | IBR domain containing 3 | 1392.62 | 1504.44 | 1813.39 | 2414 | 2004.9 | 2264.8 | 2704.7 | 2941.42 | 2367 | 0.641018401 | 0.04762 | 0.00504366 |
| 23624 | protein phosphatase 1A, magnesium dependent, alpha isoform | 690.04 | 292.96 | 486.52 | 859.53 | 850.37 | 1201.6 | 707.21 | 1015.61 | 891.22 | 0.531900954 | 0.04765 | 0.00698808 |
| 10324 | caspase 3 | 74.65 | 40.81 | 90.44 | 109.36 | 153.83 | 190.24 | 284.59 | 203.65 | 344.59 | 0.320153002 | 0.0477 | 0.00417898 |
| 17368 | RB1-inducible coiled-coil 1 | 901.84 | 849.94 | 864.96 | 1457.9 | 1313.9 | 1382.7 | 1641.7 | 1296.45 | 1849.88 | 0.585240717 | 0.04772 | 0.00145884 |
| 40892 | Smg-7 homolog, nonsense mediated mRNA decay factor (C. elegans) | 670.82 | 509.13 | 594.16 | 909.72 | 935.57 | 910.25 | 1666.9 | 1373.11 | 1068.38 | 0.516934078 | 0.04777 | 0.00541515 |
| 14699 | low density lipoprotein receptor-related protein associated protein 1 | 75.98 | 47.15 | 136.94 | 150.37 | 243.04 | 316.66 | 208.78 | 258.74 | 221.87 | 0.371671931 | 0.0478 | 0.00218354 |
| 9696 | protein phosphatase 1A, magnesium dependent, alpha isoform | 281.46 | 111.9 | 158.2 | 565.15 | 304.18 | 544.53 | 369.01 | 388.93 | 396.41 | 0.429528738 | 0.04783 | 0.00343167 |

TABLE 8B-continued

| Row | Gene | Oct. 4, 2001 | Oct. 4, 2002 | Oct. 4, 2003 | NI1.1 | NI1.2 | NI1.3 | NI2.1 | NI2.2 | NI2.3 | foldchange | fdr | t.pvals |
|---|---|---|---|---|---|---|---|---|---|---|---|---|---|
| 12475 | DEAD (Asp-Glu-Ala-Asp) box polypeptide 10 | 278.51 | 119.19 | 117.37 | 431.43 | 222.53 | 267.29 | 496.73 | 357.89 | 488.83 | 0.454868194 | 0.04785 | 0.0119792 |
| 12733 | UTP11-like, U3 small nucleolar ribonucleoprotein, (yeast) | 1652.37 | 1247.73 | 876.11 | 2092.8 | 2024.9 | 1852.2 | 1938.2 | 1738.63 | 2374.91 | 0.628236461 | 0.04788 | 0.00801569 |
| 16773 | ribosomal protein L36a-like | 2127.47 | 1381.86 | 1791.81 | 2318 | 2118.3 | 2209.7 | 3314.3 | 3112.02 | 3538.96 | 0.638255937 | 0.04798 | 0.02608004 |
| 28991 | phospholipase C, delta 4 | 138.83 | 132.49 | 147.63 | 335.85 | 224.94 | 209.08 | 437.46 | 324.88 | 403.75 | 0.432808529 | 0.04808 | 0.0029441 |
| 8894 | solute carrier family 25 (mitochondrial carrier, phosphate carrier), member 25 | 207.47 | 125.99 | 152.31 | 472.41 | 322.97 | 339.68 | 379.28 | 255.45 | 490.21 | 0.429884956 | 0.04813 | 0.00168341 |
| 12544 | small nuclear RNA activating complex, polypeptide 3 | 209.56 | 210.89 | 181.97 | 483.56 | 393.07 | 376.22 | 534.26 | 381.24 | 455.1 | 0.459257847 | 0.0483 | 0.00019626 |
| 21985 | ribosomal protein S24 | 1695.18 | 1059.62 | 1483.47 | 2021.2 | 1554.3 | 1896.5 | 2472.7 | 2477.22 | 2756.87 | 0.643194644 | 0.0484 | 0.02471089 |
| 7941 | MOB1, Mps One Binder kinase activator-like 1B (yeast) | 559.19 | 330.53 | 241.51 | 736.04 | 605.17 | 626.58 | 639.84 | 1041.82 | 1058.44 | 0.480567728 | 0.04846 | 0.00718575 |
| 7576 | SWI/SNF related, matrix associated, actin dependent regulator of chromatin, subfamily c, member 1 | 431.94 | 141.49 | 156.2 | 467.97 | 379.07 | 430.91 | 503.05 | 853.05 | 827.37 | 0.421578427 | 0.04851 | 0.01096394 |
| 3178 | poly A binding protein, cytoplasmic 1 | 1067.51 | 748.21 | 815.73 | 1481.8 | 1078.9 | 1271.7 | 1877 | 1398.42 | 2496.99 | 0.547952194 | 0.04868 | 0.01791445 |
| 535 | proteasome (prosome, macropain) subunit, beta type 7 | 683.88 | 672 | 512.62 | 1128.4 | 1099.8 | 764.78 | 900.56 | 1120.79 | 1147.58 | 0.606465831 | 0.04873 | 0.00532769 |
| 10969 | jumonji domain containing 1A | 120.68 | 130.02 | 130.27 | 359 | 253.12 | 231.81 | 183.78 | 364.53 | 594.57 | 0.383499177 | 0.04874 | 0.00763501 |
| 23568 | BAT2 domain containing 1 | 1319.8 | 1222.06 | 1121.76 | 2051.9 | 1915.5 | 1889.3 | 2016.7 | 1664.87 | 1912.55 | 0.639891151 | 0.04878 | 0.00118966 |
| 20689 | eukaryotic translation initiation factor 2, subunit 1 alpha | 873.2 | 655.24 | 823.56 | 1212.8 | 1067.3 | 1162.7 | 1408.9 | 1473.86 | 1531.6 | 0.598688079 | 0.04879 | 0.00311329 |
| 13607 | expressed sequence AU014645 | 1511.34 | 1084.22 | 1023.43 | 1777.7 | 1571.1 | 1910.8 | 1920.8 | 1977.06 | 2014.19 | 0.647889341 | 0.04882 | 0.00448388 |
| 10857 | heterogeneous nuclear ribonucleoprotein M | 1632.02 | 1042.99 | 1052.83 | 1963.8 | 1558.9 | 1934.4 | 1928.3 | 2260.45 | 2173.42 | 0.630807682 | 0.04884 | 0.00723852 |
| 16722 | WD repeat domain 12 | 55.39 | 143.68 | 73.22 | 227.44 | 175.28 | 219.03 | 230.08 | 395.68 | 302.9 | 0.351249024 | 0.04887 | 0.0019824 |
| 3863 | mitogen activated protein kinase 1 | 192.12 | 80.19 | 241.96 | 690.93 | 358.51 | 359.34 | 325.02 | 315.25 | 558.26 | 0.394483203 | 0.04889 | 0.00710119 |
| 29078 | RIKEN cDNA D330037H05 gene /// similar to La-related protein 4 (La ribonucleoprotein domain family member 4) | 1816.97 | 1506.16 | 1606.86 | 2248.8 | 2319.3 | 2211 | 2969.8 | 2795.29 | 2623.9 | 0.65004971 | 0.04892 | 0.00408689 |
| 10770 | proteasome (prosome, macropain) 26S subunit, ATPase 2 | 97.46 | 73.58 | 87.82 | 238.69 | 150.72 | 194.9 | 269.55 | 209.28 | 386.58 | 0.357117236 | 0.04893 | 0.00134467 |
| 22147 | ERO1-like (S. cerevisiae) /// ribosomal protein L31 | 1617.14 | 815.67 | 1036.5 | 1391.6 | 1541.5 | 2086.7 | 1682.1 | 2068.83 | 2407.9 | 0.62070841 | 0.04895 | 0.02270587 |
| 14175 | Sec61 alpha 1 subunit (S. cerevisiae) | 1726.8 | 1072.28 | 1292.76 | 2085.2 | 1791.8 | 2048.5 | 2261.1 | 2116.35 | 2459.79 | 0.641215536 | 0.04899 | 0.00585437 |
| 22705 | ets variant gene 5 | 505.73 | 222.21 | 367.1 | 690.41 | 565.33 | 752.06 | 668.44 | 1034.4 | 639.83 | 0.503412275 | 0.049 | 0.00575794 |
| 16198 | t-complex protein 1 | 1790.6 | 1179.11 | 1413.64 | 2167.2 | 1848.4 | 2128.3 | 2997.3 | 2246.75 | 2828.77 | 0.61664846 | 0.04902 | 0.01018077 |
| 20029 | cDNA sequence BC024969 | 39.51 | 47.41 | 37.05 | 94.02 | 167.9 | 143.54 | 230.28 | 67.15 | 149.97 | 0.290715944 | 0.04904 | 0.00244613 |
| 6054 | eukaryotic translation initiation factor 2, subunit 3, structural gene X-linked /// similar to eukaryotic translation initiation factor 2, subunit 3, structural gene X-linked | 752.35 | 559.3 | 604.82 | 1247.6 | 942.02 | 997.47 | 1342.5 | 1152.54 | 1009.05 | 0.572833831 | 0.04905 | 0.00183039 |
| 21965 | similar to PRAME family | 2409.02 | 1514.52 | 1777.52 | 2919.6 | 2279.5 | 3009.7 | 2492.5 | 2865.6 | 3135.81 | 0.682651308 | 0.04905 | 0.01414262 |

TABLE 8B-continued

| Row | Gene | Oct. 4, 2001 | Oct. 4, 2002 | Oct. 4, 2003 | NI.1.1 | NI.1.2 | NI.1.3 | NI.2.1 | NI.2.2 | NI.2.3 | foldchange | fdr | t.pvals |
|---|---|---|---|---|---|---|---|---|---|---|---|---|---|
| 7639 | member 8 /// expressed sequence AU018829 | 103.2 | 75.19 | 118.35 | 278.21 | 178.97 | 208.17 | 352.34 | 374.83 | 213.44 | 0.369548432 | 0.04907 | 0.0014996 |
| 14311 | nucleolar protein 11 | 421.11 | 232.74 | 227.15 | 553.16 | 581.34 | 405.68 | 580.26 | 619.3 | 637.51 | 0.521726257 | 0.04909 | 0.003325 |
| 7266 | expressed sequence C78212 ubiquitin-conjugating enzyme E2B, RAD6 homology (S. cerevisiae) | 527.65 | 343.53 | 429.59 | 890.61 | 526.22 | 809.78 | 736.6 | 884.92 | 789.17 | 0.56100317 | 0.0491 | 0.00503997 |
| 11354 | Mus musculus, clone IMAGE: 3983419, mRNA | 72 | 27.43 | 24.72 | 143.74 | 119.31 | 60.58 | 222.57 | 201.82 | 145.95 | 0.277749813 | 0.04912 | 0.00430038 |
| 10003 | RNA guanylyltransferase and 5′-phosphatase | 106.94 | 84.63 | 87.19 | 301.26 | 182.18 | 150.86 | 353.53 | 154.09 | 362.86 | 0.370499342 | 0.04914 | 0.00611854 |
| 1462 | exosome component 5 | 40.73 | 61.74 | 17.43 | 87.19 | 68.73 | 139.55 | 145.69 | 246.81 | 177.61 | 0.277039673 | 0.04916 | 0.00522601 |
| 8293 | ring finger and SPRY domain containing 1 | 633.65 | 573.63 | 579.76 | 1137.8 | 1373.9 | 1161.8 | 843.63 | 923.02 | 883.55 | 0.565188996 | 0.04916 | 0.00324511 |
| 8271 | insulin-like growth factor 2 receptor | 74.29 | 195.52 | 490.69 | 528.54 | 492.61 | 528.94 | 459.73 | 649.21 | 498.88 | 0.481647672 | 0.04917 | 0.01382869 |
| 8020 | pleckstrin homology domain containing, family F (with FYVE domain) member 2 | 625.38 | 324.51 | 341.8 | 1052.9 | 850.6 | 998.02 | 505.77 | 626.89 | 737.95 | 0.54134623 | 0.04918 | 0.01741884 |
| 39491 | zinc finger protein 710 | 727.55 | 440.46 | 524.24 | 900.66 | 784.47 | 1074.7 | 975.36 | 1333.25 | 979.43 | 0.559617585 | 0.04919 | 0.00456617 |
| 1486 | DnaJ (Hsp40) homolog, subfamily B, member 9 | 2390.47 | 1648.72 | 1910.19 | 2935.8 | 2556.3 | 2981.4 | 2867.2 | 2942.9 | 3211.21 | 0.68013085 | 0.0492 | 0.00549139 |
| 15093 | ribosomal protein S17 | 2459.15 | 1443.18 | 2004.58 | 2845.5 | 2447 | 2579.6 | 3506.8 | 2970.35 | 3555.66 | 0.659810063 | 0.0492 | 0.0169152 |
| 2115 | torsin family 1, member B | 256.19 | 89.29 | 93.92 | 278.8 | 251.82 | 363.38 | 456.6 | 304.99 | 408.7 | 0.425715379 | 0.04921 | 0.00453646 |
| 27418 | cDNA sequence BC035295 | 443.69 | 439.27 | 554.8 | 570.76 | 834.16 | 708.51 | 1041.6 | 1097.16 | 911.05 | 0.556925937 | 0.04922 | 0.00861834 |
| 17466 | G patch domain containing 4 | 560.23 | 265.59 | 219.67 | 798.37 | 518.64 | 726.56 | 747.62 | 528.15 | 616.45 | 0.531273264 | 0.04923 | 0.00884928 |
| 2013 | eukaryotic translation initiation factor 3, subunit 4 (delta) | 271.74 | 95.04 | 221.24 | 323.99 | 248.6 | 395.58 | 465.04 | 463.27 | 611.39 | 0.468939778 | 0.04924 | 0.01506929 |
| 27189 | RIKEN cDNA E430025E21 gene | 155.47 | 124.82 | 115.94 | 304.08 | 355.62 | 222.62 | 391.26 | 261.61 | 311.02 | 0.429236111 | 0.04925 | 0.00055666 |
| 7846 | mannosidase, alpha, class 2C, member 1 | 6.08 | 8.03 | 3.61 | 38.99 | 14.56 | 85.09 | 59.15 | 145.44 | 156.62 | 0.07090127 | 0.04928 | 0.00203805 |
| 15948 | ATPase type 13A3 | 1601.83 | 1562.47 | 1794.92 | 2141.2 | 2094.8 | 2038.2 | 3190.7 | 2860.13 | 3084.85 | 0.643639106 | 0.0493 | 0.01688862 |
| 3056 | insulin-like growth factor 2 mRNA binding protein 1 | 23.6 | 23.13 | 59.05 | 86.87 | 175.53 | 124.87 | 113.81 | 134.37 | 168.17 | 0.263258754 | 0.0493 | 0.00046644 |
| 31866 | M-phase phosphoprotein 1 | 584.18 | 393.46 | 472.99 | 807.12 | 805.27 | 884.71 | 916.93 | 822.02 | 1167.48 | 0.536919384 | 0.04933 | 0.00130358 |
| 11154 | growth factor, erv1 (S. cerevisiae)-like (augmenter of liver regeneration) | 390.69 | 114.24 | 604.44 | 777.64 | 571.65 | 1161.3 | 360.32 | 727.15 | 1012.77 | 0.481198735 | 0.04935 | 0.04517723 |
| 4640 | cyclin M3 | 240.03 | 342.07 | 62.47 | 256.37 | 380.42 | 457.8 | 470.6 | 681.96 | 476.52 | 0.473309909 | 0.04937 | 0.02795838 |
| 12184 | phosphatidylinositol transfer protein, cytoplasmic 1 | 70.98 | 70.85 | 77.64 | 242.87 | 150.65 | 236.21 | 204.73 | 89.26 | 219.98 | 0.383789455 | 0.0494 | 0.00477932 |
| 16753 | COX4 neighbor | 595.77 | 603.5 | 354.09 | 995.56 | 953.48 | 706.37 | 894.23 | 725.76 | 1113.09 | 0.576547419 | 0.04941 | 0.00769649 |
| 8770 | TruB pseudouridine (psi) synthase homolog 2 (E. coli) | 1598.35 | 788.01 | 714.92 | 2065.6 | 1575.7 | 1737.5 | 1380 | 1601.91 | 1777.98 | 0.611769533 | 0.04943 | 0.01407303 |
| 35301 | gb: AV268519 /DB_XREF = gi: 16389684 /DB_XREF = AV268519 /CLONE = 493053J16 /FEA = EST /CNT = 4 /TID = Mm.38413.1 /TIER = ConsEnd /STK = 2 | 446.43 | 227.18 | 224.84 | 668.78 | 557.23 | 627.97 | 642.03 | 432.62 | 473.25 | 0.528207932 | 0.04945 | 0.00529613 |

TABLE 8B-continued

| Row | Gene | Oct. 4, 2001 | Oct. 4, 2002 | Oct. 4, 2003 | NI.1.1 | NI.1.2 | NI.1.3 | NI.2.1 | NI.2.2 | NI.2.3 | foldchange | fdr | t.pvals |
|---|---|---|---|---|---|---|---|---|---|---|---|---|---|
| | /UG = Mm.38413 /UG_TITLE = ESTs | | | | | | | | | | | | |
| 11455 | cDNA sequence BC010304 | 237.84 | 308.43 | 345.14 | 374.3 | 548.32 | 431.79 | 1196.5 | 751.72 | 656.51 | 0.450306002 | 0.04951 | 0.02034917 |
| 14840 | ERO1-like (S. cerevisiae) /// ribosomal protein L31 | 1914.61 | 1048.97 | 1332.05 | 1815.1 | 1860.9 | 2459.7 | 2005.3 | 2401.75 | 2725.53 | 0.647509527 | 0.04952 | 0.01837773 |
| 16309 | prion protein | 5.67 | 27.92 | 7.5 | 114.55 | 67.49 | 114.67 | 39.64 | 77.22 | 93.19 | 0.162167495 | 0.04953 | 0.00068104 |
| 7219 | proliferation-associated 2G4 | 3806.66 | 2690.44 | 2523.51 | 4149.4 | 3627.7 | 3863 | 4934.9 | 4376.47 | 4773.38 | 0.701316785 | 0.04956 | 0.01729256 |
| 22327 | proteasome (prosome, macropain) subunit, alpha type 4 | 310.97 | 225.94 | 272.82 | 597.48 | 410.26 | 388.07 | 523.64 | 561.2 | 597.35 | 0.526140351 | 0.04956 | 0.00218884 |
| 17151 | exonuclease 3"-5" domain-like 2 | 69.67 | 29.49 | 42.91 | 151.69 | 68.29 | 135.72 | 157.58 | 233.27 | 169.66 | 0.310125408 | 0.04957 | 0.00330747 |
| 10743 | sorbitol dehydrogenase | 167.8 | 89.01 | 200.21 | 398.11 | 251.14 | 352.86 | 403.04 | 323.86 | 301.79 | 0.450088635 | 0.04957 | 0.00219161 |
| 6064 | nuclear receptor coactivator 6 interacting protein | 1342.43 | 996.25 | 1101.97 | 1935.4 | 1486.3 | 1789.3 | 1894 | 2042.34 | 1527.18 | 0.64464665 | 0.04958 | 0.00539514 |
| 14546 | exocyst complex component 8 | 38.13 | 48.15 | 41.87 | 130.42 | 147.06 | 97.95 | 144.96 | 178.44 | 148.81 | 0.30236893 | 0.04961 | 4.94E-005 |
| 14589 | RIKEN cDNA 4732471D19 gene | 50.72 | 36.59 | 43.82 | 139.69 | 116.02 | 153.6 | 151.77 | 176.54 | 113.67 | 0.308073629 | 0.04963 | 3.73E-005 |
| 17331 | ribosomal protein L15 | 1103.58 | 552.38 | 1197.41 | 1368.2 | 1136.3 | 1371.7 | 1675.9 | 2054.56 | 2318.95 | 0.574953378 | 0.04963 | 0.02851657 |
| 29240 | catenin (cadherin associated protein), delta 1 | 55.32 | 151.05 | 51.37 | 125.57 | 252.74 | 142.05 | 216.39 | 309.83 | 274.46 | 0.390207715 | 0.04966 | 0.00867468 |
| 8570 | expressed sequence AI840826 | 48.97 | 43.58 | 48.65 | 146.36 | 99.71 | 108.05 | 225.48 | 172.99 | 158.23 | 0.310050284 | 0.04967 | 0.00041891 |
| 29169 | RNA binding motif protein 4 | 177.47 | 100.66 | 79.8 | 250.81 | 194.96 | 248.25 | 310.54 | 382.4 | 312.05 | 0.421139486 | 0.04967 | 0.00235887 |
| 40440 | RIKEN cDNA C130032F08 gene | 1581.36 | 805.74 | 827.62 | 1302.8 | 1329.3 | 1510.7 | 2220.7 | 2011.87 | 2336.34 | 0.600228723 | 0.0497 | 0.03109115 |
| 18873 | basic leucine zipper and W2 domains 1 | 1856.21 | 1429.11 | 1724.42 | 2392.9 | 2189.5 | 2377.5 | 2784.2 | 2571.65 | 2854.64 | 0.660457255 | 0.04971 | 0.00401185 |
| 13899 | karyopherin (importin) beta 1 | 30.07 | 36.79 | 45.53 | 113.82 | 67.63 | 72.13 | 158.24 | 180.43 | 197.68 | 0.284556859 | 0.04972 | 0.00325133 |
| 18692 | GA repeat binding protein, alpha | 1521.21 | 896.36 | 993.48 | 1692.9 | 1670.9 | 1806.1 | 2042.8 | 1734.73 | 2022.7 | 0.621877894 | 0.04976 | 0.00459458 |
| 42681 | activating signal cointegrator 1 complex subunit 3 | 300.81 | 273.13 | 256.77 | 436.29 | 426.49 | 352.72 | 661.15 | 697.71 | 694.37 | 0.508276915 | 0.04976 | 0.00901142 |
| 7056 | solute carrier family 22 (organic anion/cation transporter), member 12 | 78 | 127.98 | 90.24 | 109.02 | 174.7 | 301.99 | 259.41 | 365.4 | 248.19 | 0.406139671 | 0.04977 | 0.01328366 |
| 2136 | peroxisomal membrane protein 2 | 28.37 | 71.63 | 15.47 | 123.16 | 112.33 | 103.51 | 137.14 | 245.59 | 211.62 | 0.247431296 | 0.0498 | 0.00176646 |
| 12220 | histone aminotransferase 1 | 95.59 | 63.13 | 63.73 | 206.98 | 126.57 | 201.11 | 258.49 | 221.04 | 202.13 | 0.365757454 | 0.0498 | 0.00050866 |
| 12258 | splicing factor, arginine/serine-rich 1 (ASF/SF2) | 1549.68 | 1176.89 | 1231.71 | 2058.8 | 1861 | 1951.5 | 1990.7 | 2140.9 | 2193.12 | 0.649106926 | 0.04981 | 0.00186597 |
| 12983 | PAK1 interacting protein 1 | 75.66 | 34.9 | 47.76 | 190.93 | 119.37 | 100.33 | 294.26 | 127.72 | 233.41 | 0.297030074 | 0.04981 | 0.00310024 |
| 12327 | ribosomal protein L31 | 1611.89 | 822.91 | 1110.43 | 1525.1 | 1520 | 1916.3 | 1780.2 | 2157.72 | 2472.13 | 0.623354481 | 0.04981 | 0.01946329 |
| 14684 | heterogeneous nuclear ribonucleoprotein A1 | 1389.69 | 888.32 | 1178.26 | 1690.6 | 1425.1 | 1871.4 | 1956.1 | 2275.22 | 1706.98 | 0.632700133 | 0.04981 | 0.00961426 |
| 21465 | translocase of outer mitochondrial membrane 20 homolog (yeast) | 1215 | 813.02 | 1005.8 | 1760.6 | 1492.5 | 1269.6 | 1678.3 | 1498.07 | 2176.74 | 0.614391051 | 0.04982 | 0.00941987 |
| 13601 | guanine nucleotide binding protein-like 3 (nucleolar) | 627.77 | 328.73 | 461.31 | 838.59 | 772.45 | 739.06 | 836.66 | 835.1 | 1505.97 | 0.512971636 | 0.04985 | 0.00920993 |
| 25426 | DNA segment, Chr 5, Wayne State University 178, expressed | 31.53 | 65.26 | 42.32 | 176 | 76.21 | 139.61 | 139.72 | 309.45 | 160.76 | 0.277733966 | 0.04985 | 0.00304201 |
| 22109 | RIKEN cDNA 2700007P21 gene | 563.57 | 337.22 | 396.2 | 764.62 | 661.9 | 636.46 | 1052.8 | 777.27 | 896.81 | 0.541561061 | 0.04986 | 0.00415005 |
| 34705 | uroporphyrinogen | 312.94 | 195.7 | 307.86 | 802.17 | 395.61 | 379.25 | 967.5 | 396.14 | 683.09 | 0.450636908 | 0.04986 | 0.02054484 |

TABLE 8B-continued

| Row | Gene | Oct. 4, 2001 | Oct. 4, 2002 | Oct. 4, 2003 | NI.1.1 | NI.1.2 | NI.1.3 | NI.2.1 | NI.2.2 | NI.2.3 | foldchange | fdr | t.pvals |
|---|---|---|---|---|---|---|---|---|---|---|---|---|---|
| 3486 | decarboxylase homeodomain interacting protein kinase 3 | 514.46 | 276.53 | 265.41 | 530.11 | 301.61 | 663.23 | 1201.7 | 793.58 | 994.76 | 0.471080332 | 0.04986 | 0.05047199 |
| 23671 | polycomb group ring finger 5 | 728.53 | 398.49 | 398.87 | 916.23 | 850.34 | 1205.5 | 787.59 | 737.65 | 933.74 | 0.561910338 | 0.04986 | 0.00662276 |
| 3870 | zinc finger protein 292 | 61.98 | 31.99 | 50.41 | 171.7 | 60.09 | 122.44 | 175.23 | 148.97 | 187.23 | 0.333572072 | 0.0499 | 0.00486358 |
| 1959 | N-myc downstream regulated gene 3 | 19.32 | 37.3 | 32.34 | 163.21 | 83.33 | 51.59 | 232.87 | 162 | 63.09 | 0.255315902 | 0.04991 | 0.00686013 |
| 21127 | coiled-coil domain containing 86 | 132.83 | 55.7 | 44.7 | 210.48 | 136.27 | 157.44 | 194.19 | 308.63 | 357.29 | 0.341904273 | 0.04991 | 0.00496129 |
| 7468 | trans-golgi network protein | 504.95 | 301.85 | 270.73 | 671.72 | 450.68 | 487.94 | 700.65 | 843.07 | 702.27 | 0.558837029 | 0.04991 | 0.01315788 |
| 4093 | component of oligomeric golgi complex 4 | 747.08 | 426.75 | 620.57 | 928.72 | 864.53 | 976.28 | 1190.5 | 1078.38 | 2087.76 | 0.503609237 | 0.04995 | 0.01527683 |
| 19091 | phosphoserine aminotransferase 1 | 962.82 | 668.17 | 307.26 | 1569 | 751.88 | 888.84 | 1338.8 | 947.09 | 1617.53 | 0.544979622 | 0.04995 | 0.03781093 |
| 7812 | ATPase, Na+/K+ transporting, alpha 1 polypeptide | 47.24 | 70.25 | 39.58 | 362.38 | 201.58 | 163.49 | 145.12 | 138.2 | 113.32 | 0.279461609 | 0.04995 | 0.0017652 |

TABLE 9A

| Row | Gene | CycA2.1 | CycA2.2 | CycA2.3 | NI1.1 | NI1.2 | NI1.3 | NI2.1 | NI2.2 | NI2.3 | FoldChange | R | MeanFDR | T |
|---|---|---|---|---|---|---|---|---|---|---|---|---|---|---|
| 8013 | Rasl11b: RAS-like, family 11, member B | 1175.28 | 1162.12 | 866.08 | 67.51 | 155.4 | 83.97 | 28.63 | 67.32 | 76.13 | 13.37793368 | 0 | 0.013333333 | 281.069 |
| 16505 | Gyg: glycogenin | 2774.07 | 3647.22 | 2911.43 | 451.4 | 788.3 | 545 | 633.2 | 808.2 | 736 | 4.71113938 | 0 | 0.036666667 | 146.474 |
| 44280 | Gyg: glycogenin | 2716.28 | 3189.75 | 2680.95 | 587.4 | 955.1 | 642.4 | 640.7 | 735.8 | 665.4 | 4.063169251 | 0 | 0.046666667 | 115.459 |
| 19189 | Hsbp1: heat shock factor binding protein 1 | 2054.28 | 1787.07 | 1312.02 | 326.5 | 423.8 | 376.3 | 415.9 | 610.1 | 588.6 | 3.760019554 | 0 | 0.056666667 | 88.0219 |
| 38879 | 0610008C08Rik /// LOC621156 /// LOC631337: RIKEN cDNA 0610008C08 gene /// hypothetical LOC621156 /// hypothetical protein LOC631337 | 574.74 | 794.44 | 810.38 | 108.3 | 279.7 | 167.9 | 96.73 | 84.66 | 122.9 | 5.068037018 | 0 | 0.044285714 | 82.2657 |
| 21617 | Ywhab: tyrosine 3-monooxygenase/tryptophan 5-monooxygenase activation protein, beta polypeptide | 1175.16 | 1329.81 | 1339.93 | 250.9 | 326.1 | 341.3 | 285.4 | 335.3 | 415.3 | 3.935031906 | 0 | 0.045 | 79.1967 |
| 12776 | Gpsn2: glycoprotein, synaptic 2 | 960.08 | 781.16 | 213.63 | 107.9 | 146.7 | 123.1 | 160.8 | 174.9 | 137.5 | 4.595531107 | 0 | 0.043333333 | 75.6419 |
| 38623 | Rgs2: regulator of G-protein signaling 2 | 963.98 | 951.57 | 378.04 | 252.3 | 232 | 224.9 | 47.94 | 265.8 | 134.4 | 3.963622853 | 0 | 0.041666667 | 72.6641 |
| 14769 | Ywhab: tyrosine 3-monooxygenase/tryptophan 5-monooxygenase activation protein, beta polypeptide | 984.18 | 1329.73 | 1254.81 | 241 | 312 | 348.2 | 323.2 | 330.1 | 398.3 | 3.654921319 | 0 | 0.043333333 | 69.7329 |
| 21642 | Tax1bp3 /// Rpl13: Tax1 (human T-cell leukemia virus type I) binding protein 3 /// ribosomal protein L13 | 1245.68 | 2205.53 | 913.44 | 382.1 | 394.4 | 282.3 | 507.1 | 145.2 | 438.7 | 4.060385047 | 0 | 0.041666667 | 68.3463 |
| 22387 | BC018601: cDNA sequence BC018601 | 871.11 | 1011.02 | 988.69 | 263 | 239.9 | 197.1 | 251.4 | 209.6 | 269.5 | 4.013785582 | 0 | 0.041555556 | 67.9884 |
| 28288 | Zfp291: zinc finger protein 291 | 987.39 | 413.21 | 165.77 | 31.66 | 208.2 | 60.95 | 9.02 | 50.48 | 51.43 | 7.609463431 | 0 | 0.038333333 | 65.2239 |
| 15663 | Ninj1: ninjurin 1 | 768.76 | 910.41 | 1337.77 | 236.5 | 145 | 273.4 | 260.1 | 211.1 | 352.7 | 4.080392223 | 0 | 0.037121212 | 60.0212 |
| 27398 | Zar1: zygote arrest 1 | 196.34 | 550.87 | 430.24 | 96.91 | 62.32 | 61.6 | 36.14 | 73.34 | 105 | 5.409708024 | 0 | 0.0376 | 56.505 |
| 8065 | Hsbp1: heat shock factor binding protein 1 | 1479.03 | 1221.16 | 1148.4 | 399 | 455.2 | 495.6 | 385.2 | 442.7 | 494.5 | 2.880433196 | 0.0222222 | 0.053111111 | 42.8537 |
| 20436 | Gltscr2: glioma tumor suppressor candidate region gene 2 | 229.4 | 345.29 | 561.03 | 117.9 | 44.11 | 14.4 | 87.12 | 56.32 | 106 | 5.334448536 | 0.0227273 | 0.054166667 | 42.8606 |
| 10123 | Hspb1: heat shock protein 1 | 451.26 | 233.48 | 504.65 | 36.78 | 60.45 | 103.9 | 181.6 | 70.72 | 133.1 | 4.055475996 | 0.0232558 | 0.054263566 | 43.1189 |
| 32039 | Myo5b: myosin Vb | 932.01 | 832.86 | 419.75 | 167 | 224 | 201.3 | 246.4 | 398.8 | 209.8 | 3.018911206 | 0.025641 | 0.057435897 | 43.5021 |
| 19373 | Mtap: methylthioadenosine phosphorylase | 430.05 | 544.69 | 232.61 | 76.62 | 179.7 | 135.6 | 24.53 | 69.42 | 68.87 | 4.352771519 | 0.0263158 | 0.058877193 | 43.6173 |
| 15861 | Ptk9l: protein tyrosine kinase 9-like (A6-related protein) | 3879.84 | 515.28 | 668.16 | 278.3 | 548 | 167.5 | 39.25 | 201.2 | 238.1 | 6.87782117 | 0.027027 | 0.053873874 | 45.4725 |
| 5039 | Ywhab: tyrosine 3-monooxygenase/tryptophan 5-monooxygenase activation protein, beta polypeptide | 786.43 | 1401.89 | 1268.98 | 550.3 | 550.1 | 542.5 | 548.9 | 344.8 | 534.8 | 2.251344699 | 0.0275229 | 0.057889908 | 31.9962 |
| 7118 | Zfp313: zinc finger protein 313 | 664.63 | 959.1 | 606.33 | 102.2 | 233.1 | 167.5 | 260.6 | 238.4 | 243.2 | 3.917884751 | 0.0277778 | 0.052314815 | 45.8903 |
| 27301 | Chsy1: carbohydrate (chondroitin) synthase 1 | 3606.66 | 3856.21 | 3309.81 | 1920 | 1952 | 1650 | 1778 | 2224 | 1985 | 1.872169743 | 0.0283019 | 0.058207547 | 32.1594 |
| 23482 | Wdr51b: WD repeat domain 51B | 549.71 | 635.29 | 186.24 | 78.52 | 121.3 | 128.3 | 70.8 | 228.5 | 105.5 | 3.74236511 | 0.0285714 | 0.052857143 | 46.074 |

TABLE 9A-continued

| Row | Gene | CycA2.1 | CycA2.2 | CycA2.3 | NI1.1 | NI1.2 | NI1.3 | NI2.1 | NI2.2 | NI2.3 | FoldChange | R | MeanFDR | T |
|---|---|---|---|---|---|---|---|---|---|---|---|---|---|---|
| 22475 | Sept11: septin 11 | 379.67 | 680.28 | 606.49 | 144.3 | 278.7 | 239.7 | 234.4 | 123.4 | 131 | 2.894758327 | 0.0288462 | 0.05875 | 32.2155 |
| 16314 | 2700060E02Rik: RIKEN cDNA 2700060E02 gene | 1657.64 | 2133.91 | 1718.85 | 759.8 | 1151 | 666.9 | 740.4 | 552.1 | 918.6 | 2.301557302 | 0.0291262 | 0.05776699 | 32.463 |
| 40450 | Pfdn4: prefoldin 4 | 835.74 | 1351.12 | 1275.03 | 465.7 | 482.3 | 379.6 | 367.1 | 416.9 | 417 | 2.738241285 | 0.0294118 | 0.052941176 | 46.429 |
| 3542 | Rgs2: regulator of G-protein signaling 2 | 910.45 | 1375.3 | 511.1 | 289.8 | 380.2 | 277.6 | 309.3 | 389.5 | 287.4 | 2.89283424 | 0.0294118 | 0.05622549 | 37.2147 |
| 38514 | Prkaca: protein kinase, cAMP dependent, catalytic, alpha | 1061.04 | 1151.27 | 898.98 | 699.1 | 230.1 | 414.1 | 446.6 | 245.9 | 459.6 | 2.493540321 | 0.0294118 | 0.058267974 | 32.4698 |
| 9746 | Ptpjj: protein tyrosine phosphatase, receptor type, J | 313.63 | 348.74 | 149.56 | 38.69 | 84.77 | 85.95 | 59.83 | 36.02 | 100.1 | 4.005574741 | 0.029703 | 0.058778878 | 32.499 |
| 21697 | Zfp313: zinc finger protein 313 | 3162.11 | 3960.29 | 3102.1 | 1059 | 1648 | 1223 | 1678 | 2090 | 1793 | 2.154513004 | 0.0298507 | 0.054328358 | 37.9163 |
| 19162 | Gtf2b: general transcription factor IIB | 952.55 | 1437.02 | 1358.53 | 532.4 | 552.3 | 466.5 | 425.1 | 572.2 | 544.4 | 2.423695714 | 0.030303 | 0.05479798 | 37.9814 |
| 5038 | Ywhab: tyrosine 3-monooxygenase/tryptophan 5-monooxygenase activation protein, beta polypeptide | 842.81 | 1251.66 | 740.5 | 218.4 | 255.6 | 347.1 | 475.5 | 409.7 | 250.6 | 2.897586852 | 0.030303 | 0.058754209 | 32.6829 |
| 16058 | Gm428 /// LOC623180 /// LOC623197 /// LOC623210 /// LOC623219: gene model 428, (NCBI) /// hypothetical LOC623180 /// hypothetical LOC623197 /// hypothetical LOC623210 /// hypothetical LOC623219 | 1730.14 | 2814.61 | 2209.92 | 719 | 1302 | 938 | 1086 | 1344 | 986.9 | 2.118852909 | 0.0309278 | 0.059450172 | 32.7088 |
| 1904 | Ube2a: ubiquitin-conjugating enzyme E2A, RAD6 homolog (S. cerevisiae) | 835.58 | 1090.31 | 1082.16 | 322.8 | 424.9 | 331.9 | 208 | 371.1 | 379.5 | 2.9516296 | 0.03125 | 0.053854167 | 46.9047 |
| 1431 | Smpk2: serine/arginine-rich protein specific kinase 2 | 1149.91 | 1761.01 | 1427.58 | 473.3 | 698.9 | 399.7 | 966.1 | 423.3 | 728.8 | 2.351516006 | 0.03125 | 0.06 | 32.7117 |
| 11264 | 2610510J17Rik: RIKEN cDNA 2610510J17 gene | 957.03 | 1024.23 | 729.2 | 175.1 | 254.7 | 235.5 | 303 | 296 | 462.7 | 3.138886637 | 0.0322581 | 0.054086022 | 47.3645 |
| 16336 | Uchl1: ubiquitin carboxy-terminal hydrolase L1 | 1255.01 | 1792.27 | 1364.58 | 299 | 536.1 | 340.2 | 818.6 | 772.9 | 910.7 | 2.399366965 | 0.0325203 | 0.061382114 | 30.5168 |
| 16195 | Bpgm: 2,3-bisphosphoglycerate mutase | 1084.63 | 1316.44 | 933.03 | 223.6 | 542.2 | 298.2 | 441 | 450.4 | 441 | 2.78256733 | 0.0327869 | 0.055846995 | 38.5724 |
| 15069 | 2700060E02Rik: RIKEN cDNA 2700060E02 gene | 1911.39 | 1978.28 | 1849.47 | 866 | 1267 | 698.8 | 686.8 | 853.4 | 876.6 | 2.186763905 | 0.032967 | 0.058608059 | 33.4602 |
| 1378 | Sec61b: Sec61 beta subunit | 629.4 | 1333.69 | 789.37 | 274.4 | 516.3 | 341.2 | 201.2 | 346.8 | 199.6 | 2.929224024 | 0.0330579 | 0.061019284 | 30.716 |
| 277 | Herpud2: HERPUD family member 2 | 1579.89 | 1939.26 | 1921.14 | 868.5 | 883.8 | 596.7 | 827.7 | 1099 | 877.4 | 2.111163511 | 0.0333333 | 0.059185185 | 33.4759 |
| 22096 | Mm.69144.1 | 453.06 | 395.64 | 858.44 | 130.4 | 120.9 | 231.2 | 100.7 | 88.48 | 177.7 | 4.019684715 | 0.0337079 | 0.057453184 | 33.9669 |
| 28335 | Usp27x: ubiquitin specific peptidase 27, X chromosome | 1037.34 | 637.29 | 144.44 | 150.5 | 158.3 | 218 | 119.3 | 163.4 | 242.3 | 3.459491841 | 0.0338983 | 0.056384181 | 39.0302 |
| 1111 | Nek7: NIMA (never in mitosis gene a)-related expressed kinase 7 | 717.12 | 574.95 | 336.93 | 210.7 | 267.8 | 172 | 134 | 130 | 199.5 | 2.924911121 | 0.0338983 | 0.060988701 | 30.8699 |
| 12221 | Cpa1: carboxypeptidase A1 | 1233.98 | 1187.56 | 1071.87 | 304.4 | 410.4 | 369.7 | 630.8 | 505.1 | 743.8 | 2.357067674 | 0.0344828 | 0.061005747 | 30.9745 |
| 10438 | 5830415L20Rik: RIKEN cDNA 5830415L20 gene | 1215.2 | 1852.35 | 1334.99 | 447.1 | 794.1 | 612.1 | 547.1 | 578.6 | 472.5 | 2.550718424 | 0.0348837 | 0.059224806 | 33.9864 |
| 20740 | Mm.27444.1 | 337.59 | 481.47 | 424.2 | 81.2 | 144.9 | 122.1 | 82.14 | 158 | 135.1 | 3.437268455 | 0.0350877 | 0.06 | 31.3576 |
| 6654 | Hmgn1: high mobility group nucleosomal binding domain 1 | 2802.24 | 3952.07 | 3639.58 | 1578 | 1726 | 1428 | 2308 | 2200 | 2526 | 1.766840536 | 0.0357143 | 0.061142857 | 29.2973 |

TABLE 9A-continued

| Row | Gene | CycA2.1 | CycA2.2 | CycA2.3 | NI1.1 | NI1.2 | NI1.3 | NI2.1 | NI2.2 | NI2.3 | FoldChange | R | MeanFDR | T |
|---|---|---|---|---|---|---|---|---|---|---|---|---|---|---|
| 2773 | Lmo1: LIM domain only 1 | 728.82 | 1098.32 | 1034.76 | 305.5 | 364.2 | 304 | 486.9 | 565.8 | 414.4 | 2.345012373 | 0.036 | 0.060986667 | 30.4439 |
| 16848 | Ube2a: ubiquitin-conjugating enzyme E2A, RAD6 homolog (S. cerevisiae) | 986.42 | 1081.65 | 857.17 | 294.9 | 401.6 | 308.1 | 491.7 | 435.7 | 385.5 | 2.524566112 | 0.0363636 | 0.058787879 | 31.7403 |
| 28139 | Mall: mal, T-cell differentiation protein-like | 140.43 | 181.82 | 65.34 | 2.1 | 15.41 | 3.36 | 15.11 | 1 | 10.85 | 16.20698307 | 0.037037 | 0.058436214 | 34.7455 |
| 23084 | 2410127E18Rik: RIKEN cDNA 2410127E18 gene | 526.43 | 815.91 | 633.99 | 308.7 | 278.7 | 283.9 | 152.4 | 171.6 | 168.7 | 2.897993299 | 0.037037 | 0.060518519 | 29.7435 |
| 42427 | Mrg1: myeloid ecotropic viral integration site-related gene 1 | 1187.24 | 1519.64 | 1212.95 | 887.5 | 524.6 | 553.7 | 452.6 | 589.9 | 467.5 | 2.255569398 | 0.037037 | 0.063101852 | 25.4067 |
| 34813 | LOC627488 /// LOC627520 /// LOC667692 /// LOC667695 /// LOC673990: similar to THO complex subunit 4 (Tho4) (RNA and export factor binding protein 1) (REF1-I) (Ally of AML-1 and LEF-1) (Aly/REF) /// similar to THO complex subunit 4 (Tho4) (RNA and export factor binding protein 1) (REF1-I) (Ally of AML-1 and LEF-1) (Aly/REF) /// similar to THO complex subunit 4 (Tho4) (RNA and export factor binding protein 1) (REF1-I) (Ally of AML-1 and LEF-1) (Aly/REF) /// similar to THO complex subunit 4 (Tho4) (RNA and export factor binding protein 1) (REF1-I) (Ally of AML-1 and LEF-1) (Aly/REF) /// similar to THO complex subunit 4 (Tho4) (RNA and export factor binding protein 1) (REF1-I) (Ally of AML-1 and LEF-1) (Aly/REF) | 2997.33 | 4389.29 | 4558.04 | 2547 | 3079 | 2572 | 1852 | 2591 | 2372 | 1.591199861 | 0.0372093 | 0.063224806 | 25.4182 |
| 14324 | 2700060E02Rik: RIKEN cDNA 2700060E02 gene | 1736.22 | 1743.31 | 1787.5 | 771.8 | 1146 | 670 | 697.7 | 850.4 | 807.8 | 2.130990215 | 0.0373134 | 0.060746269 | 29.8051 |
| 5988 | Ak3l1: adenylate kinase 3 alpha-like 1 | 923.36 | 955.8 | 444.05 | 293.2 | 479 | 230.4 | 457.2 | 322.9 | 400.3 | 2.128475753 | 0.0373832 | 0.063317757 | 25.4548 |
| 1245 | Tnfaip8: tumor necrosis factor, alpha-induced protein 8 | 360.72 | 565.75 | 517.2 | 173.1 | 264.6 | 167.2 | 150.3 | 188 | 131 | 2.668048113 | 0.0375587 | 0.063067293 | 25.4969 |
| 29349 | Srm2: serine/arginine repetitive matrix 2 | 422.76 | 520.49 | 235.84 | 276.2 | 142 | 111.1 | 23.71 | 54.04 | 95.17 | 3.358560971 | 0.0378788 | 0.060505051 | 30.0013 |
| 18213 | Gnas: GNAS (guanine nucleotide binding protein, alpha stimulating) complex locus | 749.56 | 1054.77 | 1007.27 | 303.1 | 467.2 | 274.3 | 329.4 | 595 | 414.5 | 2.359288924 | 0.0381679 | 0.060916031 | 30.0133 |
| 12033 | Zfp313: zinc finger protein 313 | 2750.76 | 3476.54 | 2573.42 | 687.5 | 1148 | 821.6 | 1426 | 1577 | 1289 | 2.532599515 | 0.0384615 | 0.048589744 | 51.1083 |
| 27637 | Nr2e1: nuclear receptor subfamily 2, group E, member 1 | 1154.42 | 1358.16 | 898.95 | 372.1 | 477.2 | 439.9 | 220.9 | 478.6 | 491.6 | 2.750834556 | 0.0384615 | 0.055705128 | 40.7351 |
| 2211 | Fxc1: fractured callus expressed transcript 1 | 319.96 | 265.72 | 286.07 | 4.63 | 47.28 | 3.92 | 13.61 | 90.27 | 179.1 | 5.146103896 | 0.0384615 | 0.058162393 | 35.2462 |
| 23218 | 5730405I09Rik: RIKEN cDNA 5730405I09 gene | 1466.98 | 1315.46 | 1000.54 | 584.5 | 638.8 | 679.3 | 643.1 | 491.1 | 601.7 | 2.079343049 | 0.038835 | 0.062718447 | 25.8477 |

TABLE 9A-continued

| Row | Gene | CycA2.1 | CycA2.2 | CycA2.3 | NI1.1 | NI1.2 | NI1.3 | NI2.1 | NI2.2 | NI2.3 | FoldChange | R | MeanFDR | T |
|---|---|---|---|---|---|---|---|---|---|---|---|---|---|---|
| 9918 | Nobox: NOBOX oogenesis homeobox | 557.22 | 579.54 | 288.37 | 129 | 371.4 | 87.59 | 172.8 | 98.82 | 245.1 | 2.580168012 | 0.0390244 | 0.062520325 | 25.9252 |
| 27981 | 1110003E01Rik: RIKEN cDNA 1110003E01 gene | 935.07 | 637 | 979.71 | 438.5 | 639.8 | 244.7 | 270.6 | 373.4 | 222.4 | 2.331073921 | 0.0392157 | 0.060915033 | 28.4683 |
| 23766 | 493043IB09Rik: RIKEN cDNA 493043IB09 gene | 288.09 | 929.85 | 626.58 | 234.9 | 253.4 | 170 | 197.8 | 182.5 | 246.5 | 2.870446163 | 0.0396825 | 0.061349206 | 30.3043 |
| 2222 | Ddx19a: DEAD (Asp-Glu-Ala-Asp) box polypeptide 19a | 1171.65 | 1506.5 | 1210.32 | 497.4 | 638.6 | 587.9 | 581.9 | 501.6 | 556.5 | 2.311923278 | 0.0397727 | 0.062424242 | 27.0664 |
| 9267 | BC004728: cDNA sequence BC004728 | 2914.05 | 3310.43 | 4063.56 | 1785 | 1884 | 1762 | 2063 | 1805 | 2091 | 1.80671016 | 0.039801 | 0.063034826 | 25.9867 |
| 11008 | Sec24b: SEC24 related gene family, member B (S. cerevisiae) | 491.17 | 371.38 | 563.69 | 38.39 | 140.5 | 93.28 | 159.3 | 103.5 | 197.2 | 3.896085448 | 0.04 | 0.056866667 | 41.2419 |
| 20332 | 2610510I17Rik: RIKEN cDNA 2610510I17 gene | 920.34 | 904.56 | 875.79 | 268.6 | 445 | 387.9 | 292.4 | 305.2 | 492.6 | 2.464504236 | 0.04 | 0.061555556 | 28.6135 |
| 1259 | Eefsec: eukaryotic elongation factor, selenocysteine-tRNA-specific | 420.39 | 175.37 | 131.6 | 27.72 | 33.52 | 41.27 | 19.45 | 30.53 | 65.01 | 6.688367816 | 0.04 | 0.062038095 | 27.1963 |
| 17879 | Ehd4: EH-domain containing 4 | 1018.34 | 1327.03 | 1393.04 | 514.7 | 741 | 621.1 | 418.3 | 856.2 | 476.6 | 2.06100183 | 0.04 | 0.062966667 | 26.0088 |
| 7236 | Snx9: sorting nexin 9 | 2034.25 | 2223.65 | 2179.13 | 937.6 | 906.1 | 769.4 | 1117 | 1452 | 1343 | 1.972975541 | 0.0402685 | 0.060939597 | 28.7304 |
| 19870 | Ggta1: glycoprotein galactosyltransferase alpha 1, 3 | 2076.84 | 1911.12 | 1747.57 | 1034 | 1405 | 1131 | 712.7 | 1003 | 500.2 | 1.982372856 | 0.040404 | 0.063013468 | 26.0912 |
| 4975 | Ywhag: 3-monooxygenase/tryptophan 5-monooxygenase activation protein, gamma polypeptide | 1701.12 | 2425.78 | 1962.92 | 1046 | 935.4 | 694.1 | 728.4 | 780.6 | 1140 | 2.287531271 | 0.0405405 | 0.057837838 | 35.922 |
| 3840 | Atp6v1c1: ATPase, H+ transporting, lysosomal V1 subunit C1 | 1562.18 | 1993.36 | 1324.28 | 641.1 | 676.2 | 434.4 | 835.1 | 1096 | 751.8 | 2.200907908 | 0.0405405 | 0.061306306 | 28.7411 |
| 1499 | Kdelr2: KDEL (Lys-Asp-Glu-Leu) endoplasmic reticulum protein retention receptor 2 | 1134.97 | 1840.76 | 1296.63 | 454.7 | 740.1 | 649.3 | 505.6 | 898.4 | 565.5 | 2.240609193 | 0.0405405 | 0.063108108 | 25.1968 |
| 19039 | Csda: cold shock domain protein A | 1886.38 | 2541.08 | 2229.73 | 996.1 | 1299 | 937.6 | 1283 | 1407 | 1167 | 1.877663438 | 0.040724 | 0.06321267 | 25.2231 |
| 9095 | Dnahc8: dynein, axonemal, heavy chain 8 | 275.09 | 424.82 | 466.62 | 57.34 | 144.7 | 48.48 | 81.76 | 152.8 | 74.6 | 4.169007541 | 0.0408163 | 0.054013605 | 41.8892 |
| 4403 | Gadd45b: Growth arrest and DNA-damage-inducible 45 beta | 325.8 | 1088.25 | 1693.72 | 59.09 | 210.2 | 129.8 | 401.4 | 453.8 | 881.7 | 2.91008774 | 0.0408163 | 0.061360544 | 28.7836 |
| 23361 | Fbxo28: F-box protein 28 | 728.16 | 665.63 | 382.02 | 171.4 | 132.3 | 122.3 | 209.7 | 213.5 | 344.9 | 2.974406646 | 0.0410959 | 0.056164384 | 36.4751 |
| 6486 | Gopd2 /// G6pdx: glucose-6-phosphate dehydrogenase 2 /// glucose-6-phosphate dehydrogenase X-linked | 919.61 | 1851.91 | 1150.83 | 309.7 | 590.7 | 402 | 725.6 | 646.1 | 587.9 | 2.404866938 | 0.0412371 | 0.063487973 | 26.2283 |
| 22429 | Gorasp2: golgi reassembly stacking protein 2 | 1053.97 | 1211.58 | 759.04 | 341.9 | 459 | 419.6 | 583.3 | 420.2 | 553.7 | 2.177773618 | 0.0414747 | 0.063195084 | 25.3481 |
| 6921 | Kif17: kinesin family member 17 | 1050.79 | 1040.1 | 651.51 | 576.5 | 561.7 | 248.7 | 435.1 | 356.1 | 394 | 2.132420979 | 0.0416667 | 0.063368056 | 26.3333 |
| 13584 | Dcp1a: decapping enzyme | 1250.95 | 1233.21 | 734.43 | 514.4 | 536.9 | 508.7 | 712.4 | 438.6 | 473.5 | 2.021454389 | 0.0418848 | 0.063560209 | 26.3363 |
| 4967 | Ncoa4 /// LOC627557: nuclear receptor coactivator 4 /// similar to nuclear receptor coactivator 4 | 819.67 | 1349.74 | 597.1 | 225.4 | 376.8 | 254.5 | 372.8 | 517.1 | 318.5 | 2.679817891 | 0.0419162 | 0.06257485 | 27.4886 |
| 14382 | Pcid2: PCI domain containing 2 | 208.21 | 208.84 | 103.64 | 13.83 | 77.97 | 8.25 | 39.19 | 18.14 | 57.28 | 4.85129973 | 0.0424242 | 0.063030303 | 27.5603 |
| 9970 | Csrp1: cysteine and glycine-rich protein 1 | 707.37 | 1081.76 | 451.86 | 402.1 | 254.6 | 515.3 | 117.8 | 186.2 | 282.4 | 2.54908518 | 0.042471 | 0.065933076 | 23.6583 |

TABLE 9A-continued

| Row | Gene | CycA2.1 | CycA2.2 | CycA2.3 | NI1.1 | NI1.2 | NI1.3 | NI2.1 | NI2.2 | NI2.3 | FoldChange | R | MeanFDR | T |
|---|---|---|---|---|---|---|---|---|---|---|---|---|---|---|
| 9611 | Ptprj /// AW125753: protein tyrosine phosphatase, receptor type, J /// expressed sequence AW125753 | 276.18 | 258.57 | 380.78 | 49.33 | 87.25 | 38.19 | 50.96 | 146.2 | 102.3 | 3.861366512 | 0.0425532 | 0.064255319 | 24.6082 |
| 12280 | 2610528K11Rik: RIKEN cDNA 2610528K11 gene | 847.62 | 350.15 | 887.05 | 191.3 | 286.5 | 257.4 | 379.5 | 362.4 | 372.6 | 2.254139704 | 0.0426829 | 0.063130081 | 27.6 |
| 14887 | Tmem109: transmembrane protein 109 | 1049.13 | 1100.4 | 693.15 | 487.8 | 701.2 | 347.9 | 350.2 | 365 | 381.9 | 2.158401859 | 0.0427807 | 0.064171123 | 26.423 |
| 8101 | Camk2g: calcium/calmodulin-dependent protein kinase II gamma | 283.06 | 354.25 | 367.2 | 116.7 | 94.65 | 136.1 | 97.12 | 109.2 | 105.9 | 3.04563095 | 0.0428016 | 0.065823606 | 23.7561 |
| 22457 | Sepw1: selenoprotein W, muscle 1 | 2758.54 | 3164.45 | 4104.83 | 1518 | 1644 | 1398 | 1870 | 1618 | 3062 | 1.805050019 | 0.0429688 | 0.065950521 | 23.7661 |
| 15377 | Tm2d2: TM2 domain containing 2 | 761.31 | 348.95 | 1367.84 | 465.4 | 283.5 | 356.7 | 295.1 | 314.2 | 225.9 | 2.553662885 | 0.0431373 | 0.066183007 | 23.7726 |
| 13610 | Pnrc1: proline-rich nuclear receptor coactivator 1 | 1875.98 | 2497.69 | 2218.37 | 912.7 | 1173 | 1023 | 1143 | 1267 | 1272 | 1.9415163 | 0.0432099 | 0.063333333 | 27.6831 |
| 22912 | Calcoco1: calcium binding and coiled coil domain 1 | 645.5 | 564.97 | 318.61 | 259.5 | 280.1 | 113.5 | 190.8 | 154.3 | 163.4 | 2.632509534 | 0.0432432 | 0.063972973 | 26.5901 |
| 7409 | Tgfb2: transforming growth factor, beta 2 | 793.78 | 1590.37 | 1213.53 | 412.2 | 635.7 | 521.1 | 714.9 | 491.8 | 663.4 | 2.09223397 | 0.0433071 | 0.065721785 | 23.8689 |
| 38991 | Tll11: tubulin tyrosine ligase-like family, member 11 | 629.88 | 997.15 | 450.48 | 230.8 | 216.8 | 257.8 | 240 | 375.5 | 152.5 | 2.819887748 | 0.0434783 | 0.063967391 | 26.5994 |
| 21361 | Slc25a4: solute carrier family 25 (mitochondrial carrier, adenine nucleotide translocator), member 4 | 609.28 | 302.35 | 741.44 | 237 | 343.3 | 259.4 | 201.2 | 188.6 | 100.2 | 2.486193413 | 0.0434783 | 0.065144928 | 24.6327 |
| 21528 | Cnn3: calponin 3, acidic | 842.6 | 930.24 | 788.12 | 354.8 | 542.4 | 337.9 | 180.8 | 351.3 | 267 | 2.518163806 | 0.04375 | 0.062583333 | 27.9931 |
| 15242 | Pofut2: protein O-fucosyltransferase 2 | 1778.35 | 1399.41 | 2187.94 | 882.1 | 1202 | 822.3 | 491.1 | 875.2 | 1214 | 1.955775711 | 0.0438247 | 0.064940239 | 24.0113 |
| 23699 | Cd164l2: D164 sialomucin-like 2 | 294.25 | 488.64 | 324.23 | 53.73 | 65.52 | 83.92 | 138.4 | 143.4 | 130 | 3.600624431 | 0.0438596 | 0.064809942 | 24.7437 |
| 37480 | 4930562C15Rik: RIKEN cDNA 4930562C15 gene | 266.99 | 324.53 | 138.98 | 37.48 | 48.81 | 45.36 | 87.04 | 111.8 | 47.11 | 3.868968805 | 0.043956 | 0.063791209 | 26.6715 |
| 16487 | Wfs1: Wolfram syndrome 1 homolog (human) | 539 | 852.8 | 431.85 | 108 | 256.6 | 262.6 | 278.2 | 201 | 172.7 | 2.851658705 | 0.044 | 0.065093333 | 24.0215 |
| 20014 | Arrb2: arrestin, beta 2 | 261.8 | 442.51 | 421.66 | 79.45 | 122.9 | 130.7 | 191.7 | 126.2 | 149.4 | 2.813975283 | 0.0440529 | 0.064375918 | 24.8594 |
| 33055 | 2700050L05Rik: RIKEN cDNA 2700050L05 gene | 504.87 | 984.48 | 426.53 | 189 | 221.1 | 184 | 321.7 | 177.9 | 178.4 | 3.012176811 | 0.0443686 | 0.067963595 | 22.5402 |
| 408 | Fkbp8: FK506 binding protein 8 | 590.14 | 427.04 | 302.19 | 164.6 | 241.9 | 117.1 | 99.71 | 136.4 | 185.6 | 2.791638014 | 0.0444444 | 0.069534392 | 21.8165 |
| 39254 | 8430429K09Rik: RIKEN cDNA 8430429K09 gene | 483.61 | 603.3 | 382.14 | 140.5 | 172.4 | 143.3 | 254.2 | 103.1 | 239.1 | 2.791278738 | 0.0445344 | 0.06560054 | 24.0684 |
| 159 | Bpgm: 2,3-bisphosphoglycerate mutase | 4125.5 | 4888.39 | 3943.66 | 2337 | 3162 | 2111 | 2186 | 2053 | 2563 | 1.798272305 | 0.044586 | 0.063078556 | 28.0958 |
| 1105 | Mea1: male enhanced antigen 1 | 641.79 | 1052.56 | 800.16 | 373.2 | 443.3 | 291.3 | 373 | 331.2 | 365 | 2.291779211 | 0.044586 | 0.069522293 | 21.8514 |
| 38903 | 2600010E01Rik: RIKEN cDNA 2600010E01 gene | 247.28 | 200.25 | 369.05 | 57.76 | 100.1 | 37.76 | 33.32 | 102.2 | 59.89 | 4.175811813 | 0.0446429 | 0.064449405 | 24.9266 |
| 15195 | Tm2d2: TM2 domain containing 2 | 807.85 | 315.89 | 1436.51 | 527.6 | 320.7 | 388.1 | 290.4 | 286.3 | 252.4 | 2.479036756 | 0.0446735 | 0.068373425 | 22.5493 |
| 21185 | D10Wsu102e: DNA segment, Chr 10, Wayne State University 102, expressed | 2625.46 | 3167.45 | 2893.72 | 1716 | 1847 | 1338 | 1962 | 1712 | 1577 | 1.711233117 | 0.0447284 | 0.069158679 | 21.9226 |
| 4343 | 2410022L05Rik: RIKEN cDNA 2410022L05 gene | 1605.23 | 1541.87 | 1099.08 | 1006 | 799.1 | 735.3 | 264.5 | 1067 | 383.1 | 1.995685441 | 0.044898 | 0.0637415 | 24.1286 |
| 12245 | Dnm1l: dynamin 1-like | 714.07 | 890.45 | 642.35 | 203.1 | 404.7 | 362.8 | 383.8 | 214.8 | 288 | 2.419788054 | 0.0449827 | 0.068373702 | 22.606 |
| 109 | Atp6v1b2: ATPase, H+ | 1155.57 | 1164.53 | 728.39 | 468.3 | 602.1 | 390.5 | 479.6 | 654.4 | 600.1 | 1.908347679 | 0.0450161 | 0.069464094 | 21.9365 |

TABLE 9A-continued

| Row | Gene | CycA2.1 | CycA2.2 | CycA2.3 | NI1.1 | NI1.2 | NI1.3 | NI2.1 | NI2.2 | NI2.3 | FoldChange | R | MeanFDR | T |
|---|---|---|---|---|---|---|---|---|---|---|---|---|---|---|
| | transporting, lysosomal V1 subunit B2 | | | | | | | | | | | | | |
| 41382 | 9230115E21Rik: RIKEN cDNA 9230115E21 gene | 1049.24 | 1705.49 | 1742 | 671.1 | 1012 | 681.8 | 714.7 | 866.2 | 989.2 | 1.822353437 | 0.045082 | 0.065560109 | 24.1432 |
| 1430 | Srpk2: serine/arginine-rich protein specific kinase 2 | 1999.89 | 2326.25 | 2092.34 | 1043 | 1218 | 1110 | 1149 | 875.2 | 960.9 | 2.019612501 | 0.0451613 | 0.06172043 | 28.271 |
| 16430 | G6pdx: glucose-6-phosphate dehydrogenase X-linked | 1912.61 | 2849.68 | 1863.38 | 787.9 | 1752 | 1060 | 912.4 | 963.3 | 1065 | 2.025944759 | 0.0451613 | 0.068913978 | 22.0228 |
| 2300 | Sdhb: succinate dehydrogenase complex, subunit B, iron sulfur (Ip) | 538.02 | 229.97 | 832.03 | 138.8 | 236.8 | 218.7 | 38.77 | 316.8 | 160 | 2.883334535 | 0.0452675 | 0.065775034 | 24.1473 |
| 6223 | Zbtb20: zinc finger and BTB domain containing 20 | 134.97 | 146.13 | 16 | 4.9 | 11.08 | 4.9 | 9.14 | 2.83 | 47.12 | 7.430286357 | 0.0452962 | 0.068222997 | 22.6625 |
| 13279 | Dcp1a: decapping enzyme | 370.06 | 844.47 | 493.12 | 102.2 | 141.4 | 115.2 | 321.2 | 207.5 | 303.8 | 2.866964391 | 0.0453074 | 0.068727077 | 22.0548 |
| 9363 | Ddx19a /// Ddx19b: DEAD (Asp-Glu-Ala-Asp) box polypeptide 19a /// DEAD (Asp-Glu-Ala-Asp) box polypeptide 19b | 1900.93 | 2603.49 | 1537.03 | 1167 | 1153 | 885.9 | 897.4 | 1007 | 1065 | 1.956903393 | 0.0454545 | 0.06739899 | 23.3704 |
| 10998 | Pold3: polymerase (DNA-directed), delta 3, accessory subunit | 1214.68 | 1819.91 | 1832.16 | 850.3 | 830.5 | 871 | 1004 | 1059 | 901.8 | 1.764581113 | 0.045614 | 0.068175439 | 22.7446 |
| 18210 | Lnk: linker of T-cell receptor pathways | 473.25 | 331.54 | 156.1 | 95.8 | 81.69 | 130.4 | 71.84 | 51.82 | 156.5 | 3.267666463 | 0.0456432 | 0.065172891 | 24.3452 |
| 21746 | Tmem109: transmembrane protein 109 | 786.47 | 847.01 | 508.13 | 367.6 | 528.2 | 245.5 | 273.8 | 272.9 | 273.3 | 2.183845573 | 0.0457746 | 0.068004695 | 22.7842 |
| 16900 | Ube2j1: ubiquitin-conjugating enzyme E2, J1 | 1048.14 | 731.11 | 425.79 | 189.2 | 297.8 | 190.2 | 412.6 | 359 | 345.7 | 2.457827565 | 0.0458333 | 0.065013889 | 24.4002 |
| 14774 | Surf4: surfeit gene 4 | 2026.91 | 2349.99 | 1707.51 | 1143 | 1323 | 1046 | 1020 | 1066 | 1054 | 1.82922382 | 0.0462046 | 0.069229923 | 22.1641 |
| 6591 | Dbi: diazepam binding inhibitor | 748.16 | 1411.18 | 1571.45 | 551.5 | 796.2 | 566.5 | 644.3 | 687.8 | 749.4 | 1.867435173 | 0.0462633 | 0.067793594 | 22.8636 |
| 916 | Llgl1: lethal giant larvae homolog 1 (Drosophila) | 1430.08 | 1103.73 | 1765.18 | 919.1 | 927.7 | 845 | 526.8 | 632.3 | 506.2 | 1.97334894 | 0.0463576 | 0.069392936 | 22.1803 |
| 14725 | Aldh9a1: aldehyde dehydrogenase 9, subfamily A1 | 2464.65 | 2087.14 | 1545.48 | 936.9 | 1225 | 1018 | 1310 | 1014 | 1062 | 1.857250556 | 0.0464135 | 0.065316456 | 24.4636 |
| 22776 | Abhd13: abhydrolase domain containing 13 | 1448.41 | 1446.62 | 1230.77 | 644.7 | 823 | 682.5 | 642.8 | 658.9 | 939.6 | 1.879049135 | 0.0464396 | 0.070846233 | 21.5641 |
| 8799 | Arl8a: ADP-ribosylation factor-like 8A | 450.63 | 484.52 | 240.82 | 185.2 | 144.7 | 165.6 | 126.1 | 202.3 | 138.2 | 2.444844075 | 0.0465116 | 0.071792636 | 20.9911 |
| 4729 | Tcl1b3: T-cell leukemia/lymphoma 1B, 3 | 3067.43 | 4225.86 | 3944.03 | 1750 | 2137 | 2048 | 2719 | 3084 | 2462 | 1.582715554 | 0.0465839 | 0.070662526 | 21.5931 |
| 8719 | Pstpip1: proline-serine-threonine phosphatase-interacting protein 1 | 133 | 150.18 | 47.71 | 10.97 | 19.4 | 25.08 | 18.91 | 12.49 | 10.27 | 6.814044481 | 0.0466667 | 0.069311111 | 22.2252 |
| 5059 | Rab18: RAB18, member RAS oncogene family | 1682.03 | 1655.73 | 1019.13 | 929.2 | 817.7 | 742.1 | 723.3 | 1044 | 764.4 | 1.735622591 | 0.0467836 | 0.072017544 | 21.015 |
| 11799 | Runxlt1: runt-related transcription factor 1; translocated to, 1 (cyclin D-related) | 720.19 | 672.38 | 443.2 | 238.1 | 239.4 | 221.5 | 336.5 | 333.9 | 281.5 | 2.224016573 | 0.046875 | 0.0708125 | 21.6373 |
| 3543 | Rgs2: regulator of G-protein signaling 2 | 871.75 | 1343.48 | 839.92 | 552.5 | 601.3 | 456.3 | 215.4 | 392.9 | 290.8 | 2.435178026 | 0.0469799 | 0.069519016 | 22.2513 |
| 11937 | Defb8: defensin beta 8 | 322.3 | 225.13 | 147.33 | 19.16 | 51.47 | 86.7 | 48.97 | 79.85 | 82 | 3.774331115 | 0.0470588 | 0.072215686 | 21.0551 |
| 22002 | Anapc5: anaphase-promoting complex subunit 5 | 2197.5 | 1065.37 | 1661.25 | 652.3 | 960.9 | 647.2 | 1135 | 645.4 | 1044 | 1.936841774 | 0.0471014 | 0.067777778 | 22.9611 |

TABLE 9A-continued

| Row | Gene | CycA2.1 | CycA2.2 | CycA2.3 | NI1.1 | NI1.2 | NI1.3 | NI2.1 | NI2.2 | NI2.3 | FoldChange | R | MeanFDR | T |
|---|---|---|---|---|---|---|---|---|---|---|---|---|---|---|
| 270 | Carhsp1: calcium regulated heat stable protein 1 | 695.96 | 1334.14 | 836.29 | 323.6 | 378.2 | 367.8 | 428.5 | 461.3 | 410.2 | 2.419384517 | 0.047138 | 0.06959596 | 22.2624 |
| 11459 | Lhx8: LIM homeobox protein 8 | 915.65 | 1329.12 | 940.38 | 474.1 | 516.8 | 519 | 579.1 | 373.5 | 302.8 | 2.303731001 | 0.0471698 | 0.070597484 | 21.6799 |
| 34771 | 2700050L05Rik: RIKEN cDNA 2700050L05 gene | 83.83 | 110.47 | 358.76 | 26.54 | 30.56 | 15.02 | 19.41 | 28.26 | 5.59 | 8.822140692 | 0.0472441 | 0.074041995 | 20.0479 |
| 412 | Orc3l: origin recognition complex, subunit 3-like (*S. cerevisiae*) | 512.79 | 479.04 | 423.31 | 81.65 | 207.6 | 115.3 | 178 | 144.3 | 323.5 | 2.694683525 | 0.0472727 | 0.067612121 | 22.9795 |
| 8298 | Rap1a: RAS-related protein-1a | 1038.15 | 1345.27 | 1417.09 | 535.1 | 752.6 | 615 | 727.4 | 726.5 | 676.4 | 1.884757581 | 0.0473373 | 0.071577909 | 21.187 |
| 18549 | H1f0: H1 histone family, member 0 | 1417.73 | 1021.56 | 619.53 | 522.4 | 740.5 | 456.5 | 358.3 | 405.5 | 425.7 | 2.103018928 | 0.0479042 | 0.070588822 | 21.3322 |
| 29960 | LOC433810: similar to transmembrane protein SHREW1 | 689.22 | 717.53 | 441.92 | 260.5 | 343.3 | 371.8 | 226.1 | 240.7 | 301.5 | 2.120070873 | 0.048 | 0.072835556 | 20.2788 |
| 2778 | Ggta1: glycoprotein galactosyltransferase alpha 1, 3 | 615.11 | 636.67 | 665.46 | 268.8 | 335 | 231.9 | 263.9 | 175.6 | 342.7 | 2.369976637 | 0.048048 | 0.070640641 | 21.3411 |
| 23726 | 1700010D01Rik /// MGC118250: RIKEN cDNA 1700010D01 gene /// similar to hypothetical protein LOC76386 | 514.54 | 738.88 | 626.14 | 342.7 | 278.7 | 196.3 | 235.7 | 321 | 246.24 | 2.319556713 | 0.0482574 | 0.073038427 | 20.3038 |
| 12425 | Zcchc3: zinc finger, CCHC domain containing 3 | 601.6 | 494.73 | 290.75 | 165 | 163.9 | 195.7 | 202.5 | 148.4 | 244.5 | 2.476795886 | 0.0483384 | 0.070956697 | 21.3504 |
| 10133 | Trim25: tripartite motif protein 25 | 616.96 | 638.71 | 337.03 | 143.7 | 248.1 | 271 | 339.9 | 229.3 | 207.6 | 2.21282094 | 0.0484848 | 0.071151515 | 21.3508 |
| 8706 | Car10: carbonic anhydrase 10 | 126.12 | 168.15 | 16.02 | 9.61 | 16.81 | 12.12 | 1.76 | 21.12 | 7.68 | 8.98089725 | 0.0485075 | 0.067524876 | 23.2315 |
| 7747 | Arpc4: actin related protein 2/3 complex, subunit 4 | 1172.92 | 1818.6 | 1389.88 | 803.2 | 994.5 | 747.6 | 842.5 | 574.3 | 530.5 | 1.950496372 | 0.0485934 | 0.075302643 | 19.7699 |
| 39091 | Ches1: checkpoint suppressor 1 | 691.62 | 717.97 | 330.8 | 186.5 | 461.5 | 200.6 | 209.6 | 288.8 | 218.2 | 2.223671686 | 0.0486891 | 0.067752809 | 23.2316 |
| 1396 | Hspa2: heat shock protein 1 | 1165.3 | 1847.21 | 1706.76 | 768.3 | 1326 | 888 | 653 | 1010 | 758.9 | 1.746794118 | 0.0487179 | 0.0752564 | 19.7915 |
| 43852 | LOC545637 /// LOC623272 /// LOC623281 /// LOC636750 /// LOC667780: hypothetical LOC545637 /// hypothetical LOC623272 /// hypothetical LOC623281 /// hypothetical protein LOC636750 /// hypothetical protein LOC667780 | 3154.18 | 5046.7 | 4038.1 | 1862 | 3004 | 2393 | 2912 | 2908 | 2108 | 1.611845948 | 0.0487805 | 0.073486902 | 20.3393 |
| 1723 | Gng3: guanine nucleotide binding protein (G protein), gamma 3 subunit | 939.26 | 1673.4 | 1032.44 | 377 | 611.2 | 390.9 | 606.5 | 482.2 | 588.5 | 2.385349318 | 0.0488722 | 0.067531328 | 23.2874 |
| 8545 | Reep2: receptor accessory protein 2 | 1276.5 | 951.38 | 773.57 | 228.1 | 348.3 | 268 | 801 | 510.5 | 544.4 | 2.223139853 | 0.0489297 | 0.07108053 | 21.4329 |
| 26935 | Bahd1: bromo adjacent homology domain containing 1 | 496.5 | 645.98 | 493.5 | 200.3 | 217.8 | 255.2 | 202.4 | 244.1 | 139.5 | 2.598567276 | 0.0489691 | 0.075197595 | 19.8532 |
| 927 | Mod1 /// LOC624892 /// LOC677317: malic enzyme, supernatant /// similar to NADP-dependent malic enzyme (NADP-ME) (Malic enzyme 1) /// similar to NADP-dependent malic enzyme (NADP-ME) (Malic enzyme 1) | 998.06 | 922.67 | 686.51 | 467.8 | 580.6 | 523.9 | 272.3 | 372.6 | 349.5 | 2.031565455 | 0.0491803 | 0.072905282 | 20.4366 |

TABLE 9A-continued

| Row | Gene | CycA2.1 | CycA2.2 | CycA2.3 | NI1.1 | NI1.2 | NI1.3 | NI2.1 | NI2.2 | NI2.3 | FoldChange | R | MeanFDR | T |
|---|---|---|---|---|---|---|---|---|---|---|---|---|---|---|
| 38626 | Mfap2: microfibrillar-associated protein 2 | 509.37 | 115.67 | 349.24 | 27.37 | 198.3 | 120.4 | 76.61 | 70.93 | 137 | 3.089568568 | 0.0492308 | 0.071117949 | 21.4898 |
| 33836 | Transcribed locus | 22.68 | 284.45 | 137.88 | 67.18 | 11.32 | 10.03 | 13.47 | 8.36 | 30.26 | 6.329256151 | 0.0494792 | 0.0740625 | 20.0011 |
| 13825 | Plekhc1: pleckstrin homology domain containing, family C (with FERM domain) member 1 | 433.88 | 1351.76 | 1329.49 | 686.8 | 581.8 | 481.9 | 519 | 457 | 620.7 | 1.861357091 | 0.0495868 | 0.072901745 | 20.4943 |
| 20764 | Txn2: thioredoxin 2 | 417.2 | 626.98 | 484.3 | 144.4 | 244.2 | 113.1 | 228.5 | 145.6 | 295.8 | 2.609329521 | 0.0498615 | 0.072816251 | 20.5416 |

TABLE 9B

| Row | Gene | CycA2.1 | CycA2.2 | CycA2.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 3646 | 0610007P06Rik: RIKEN cDNA 0610007P06 gene | 53.21 | 84.8 | 297.2 | 251.3 | 275.76 | 304.24 | 515.25 | 489.89 | 705.1 | 0.342476048 | 0.04973822 | 0.0741274 | 20.028 |
| 4498 | 0610016J10Rik: RIKEN cDNA 0610016J10 gene | 4.86 | 1.17 | 7.33 | 143.31 | 63.22 | 200.98 | 78.49 | 177.41 | 3.9 | 0.04004136 | 0.042105263 | 0.06375439 | 26.372 |
| 21983 | LOC625193 /// LOC636633: RIKEN cDNA 1110005A23 gene /// similar to cytokine induced protein 29 kDa /// similar to cytokine induced protein 29 kDa | 278.64 | 96.47 | 238.75 | 422.57 | 521.22 | 543.58 | 778.62 | 488.14 | 494.2 | 0.377955374 | 0.048632219 | 0.07113475 | 21.376 |
| 38875 | 1110008B24Rik: RIKEN cDNA 1110008B24 gene | 377.94 | 192.85 | 622.98 | 908.37 | 546.03 | 872.14 | 1023.5 | 1117.8 | 1343 | 0.41087267 | 0.044303797 | 0.06272152 | 28.081 |
| 14747 | 1110014K08Rik /// LOC664786 /// LOC664849 /// LOC669054 /// LOC672175: RIKEN cDNA 1110014K08 gene /// hypothetical protein LOC664786 /// hypothetical protein LOC664849 /// hypothetical protein LOC669054 /// hypothetical protein LOC672175 | 181.23 | 248.59 | 247.67 | 383.41 | 393.19 | 537.89 | 753.56 | 769.32 | 870.7 | 0.365414799 | 0.041666667 | 0.06175926 | 28.886 |
| 40498 | 1110034A24Rik: RIKEN cDNA 1110034A24 gene | 43.95 | 64.41 | 50.95 | 319.84 | 238.19 | 282.21 | 220.54 | 188.83 | 248.3 | 0.212711129 | 0.034965035 | 0.06109557 | 29.101 |
| 23309 | 1600002K03Rik: RIKEN cDNA 1600002K03 gene | 107 | 59.9 | 245.28 | 683.77 | 429.59 | 346.82 | 750.02 | 281.7 | 595.3 | 0.267023406 | 0.033333333 | 0.05611111 | 38.745 |
| 41245 | 2010107H07Rik: RIKEN cDNA 2010107H07 gene | 194.12 | 113.48 | 300.45 | 660.66 | 354.66 | 360.51 | 650.65 | 483.92 | 1044 | 0.342111408 | 0.040816327 | 0.06326531 | 26.148 |
| 12325 | 2310036O22Rik: RIKEN cDNA 2310036O22 gene | 355.44 | 333.42 | 817.17 | 1346.9 | 1033.9 | 1084.7 | 1228.3 | 1278.2 | 1731 | 0.391021738 | 0.039473684 | 0.05811404 | 35.678 |
| 16489 | 2410016O06Rik: RIKEN cDNA 2410016O06 gene | 569.29 | 93.03 | 367.09 | 890.36 | 502.25 | 860.54 | 1000.8 | 906.94 | 1398 | 0.370354647 | 0.035714286 | 0.0597619 | 31.466 |
| 15550 | 2510039O18Rik: RIKEN cDNA 2510039O18 gene | 530.8 | 99.11 | 420.85 | 1242.7 | 731.24 | 1077.5 | 660.72 | 895.16 | 784.1 | 0.389791149 | 0.044198895 | 0.06355433 | 26.759 |
| 19105 | 2510039O18Rik: RIKEN cDNA 2510039O18 gene | 89.8 | 83.01 | 199.83 | 321.54 | 214.67 | 216.65 | 401.71 | 481.55 | 470.2 | 0.353830377 | 0.049450549 | 0.07271978 | 20.494 |
| 35340 | 2600011C06Rik: RIKEN cDNA 2600011C06 gene | 1515.45 | 1353.66 | 1480.64 | 2833.1 | 2791.7 | 2941 | 2356.4 | 2682.9 | 2361 | 0.544860232 | 0.041176471 | 0.06201961 | 27.458 |
| 2216 | 2610029G23Rik: RIKEN cDNA 2610029G23 gene | 572.06 | 520.64 | 750.01 | 1471 | 1141.3 | 1096.6 | 1730.3 | 1327.7 | 1092 | 0.46894679 | 0.046931408 | 0.06761733 | 22.954 |
| 12846 | 2810409H07Rik: RIKEN cDNA 2810409H07 gene | 86.52 | 29.18 | 100.39 | 480.67 | 269.97 | 281.71 | 245.18 | 142.85 | 326.2 | 0.247440742 | 0.042553191 | 0.0643617 | 26.376 |
| 8238 | 2900073H19Rik: RIKEN cDNA 2900073H19 gene | 211.83 | 95.11 | 192.63 | 574.46 | 220.64 | 424.2 | 345.06 | 612.16 | 561.1 | 0.36496265 | 0.044444444 | 0.06426667 | 24.924 |

TABLE 9B-continued

| Row | Gene | CycA2.1 | CycA2.2 | CycA2.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 13588 | cDNA, RIKEN full-length enriched library, clone: A630012F14 product: unclassifiable, full insert sequence | 573.65 | 184.37 | 288.58 | 996.46 | 770.78 | 953.56 | 685.85 | 734.41 | 780.1 | 0.425345141 | 0.045751634 | 0.06929194 | 22.066 |
| 36328 | 3110050K21Rik: RIKEN cDNA 3110050K21 gene | 311.28 | 401.01 | 530.93 | 1030.8 | 761.38 | 1078.3 | 1332.5 | 1029.5 | 1510 | 0.368745523 | 0.036144578 | 0.05738956 | 34.695 |
| 24498 | 3110050K21Rik: RIKEN cDNA 3110050K21 gene | 451.12 | 293.97 | 202.68 | 849.56 | 599.42 | 547.68 | 1108.3 | 684.07 | 839.1 | 0.409568423 | 0.043103448 | 0.06469828 | 24.629 |
| 23071 | 3300001M20Rik: RIKEN cDNA 3300001M20 gene | 108.79 | 169.76 | 262.21 | 708.72 | 562.73 | 499.17 | 858.23 | 902.18 | 429.2 | 0.27309456 | 0.02173913 | 0.05210145 | 42.838 |
| 32215 | 4833426J09Rik: RIKEN cDNA 4833426J09 gene | 101.24 | 83.15 | 123.05 | 403.04 | 266.83 | 290.65 | 664.64 | 325.8 | 820.3 | 0.221874211 | 0.03 | 0.05903333 | 32.544 |
| 41050 | 4930427A07Rik: RIKEN cDNA 4930427A07 gene | 154.04 | 258.9 | 438 | 462.21 | 493.17 | 756.34 | 822.19 | 1212.3 | 977.7 | 0.36026859 | 0.036036036 | 0.05921922 | 31.601 |
| 24760 | 4933402C05Rik: RIKEN cDNA 4933402C05 gene | 184.74 | 248.77 | 343.55 | 582.5 | 656.43 | 516.22 | 821.01 | 823.62 | 1015 | 0.352026602 | 0.031578947 | 0.06042105 | 32.742 |
| 23146 | 4933417E01Rik: RIKEN cDNA 4933417E01 gene | 1233.06 | 595.65 | 1580.61 | 2342.5 | 1725.8 | 1965.4 | 2559.7 | 2606.8 | 2682 | 0.491168017 | 0.035714286 | 0.05678571 | 34.675 |
| 23294 | 4933440H19Rik: RIKEN cDNA 4933440H19 gene | 222.08 | 110.71 | 164.48 | 490.16 | 293.12 | 477.16 | 332.22 | 512.35 | 433.1 | 0.391838118 | 0.049079755 | 0.07127812 | 21.435 |
| 23653 | 5730406M06Rik: RIKEN cDNA 5730406M06 gene | 175.07 | 173.9 | 279.19 | 681.23 | 606.53 | 632.71 | 617.02 | 514.97 | 512.6 | 0.352402939 | 0.037593985 | 0.06057644 | 29.915 |
| 39158 | 5730406M06Rik: RIKEN cDNA 5730406M06 gene | 475.1 | 352.64 | 504.28 | 956.32 | 865.18 | 1125.5 | 938.04 | 1078.7 | 754.1 | 0.46591231 | 0.047318612 | 0.07053628 | 21.709 |
| 27731 | 5730406M06Rik: RIKEN cDNA 5730406M06 gene | 984.39 | 305.06 | 745.9 | 1521.6 | 1377 | 1419.4 | 1034.7 | 1357.1 | 1056 | 0.524172156 | 0.048192771 | 0.07079317 | 21.344 |
| 27732 | 5730406M06Rik: RIKEN cDNA 5730406M06 gene | 964.44 | 283.46 | 700.66 | 1444 | 1271 | 1384.7 | 996.72 | 1324 | 1015 | 0.5241432 | 0.049315068 | 0.07291324 | 20.452 |
| 40394 | A230097K15Rik: RIKEN cDNA A230097K15 gene | 739.64 | 322.54 | 497.24 | 1135.4 | 943.8 | 714.8 | 1147.6 | 1095.1 | 1136 | 0.5052463 | 0.044871795 | 0.06926282 | 21.935 |
| 40844 | A530082C11Rik: RIKEN cDNA A530082C11 gene | 132.33 | 27.77 | 268.5 | 459.34 | 222.66 | 476.49 | 456.67 | 365.07 | 541.5 | 0.339926717 | 0.044444444 | 0.06285185 | 26.878 |
| 13848 | AA408556: expressed sequence AA408556 | 171.39 | 60.02 | 172.24 | 295.85 | 310.39 | 421.99 | 454.92 | 383.23 | 796.9 | 0.303119051 | 0.044843049 | 0.06391629 | 25.047 |
| 44961 | AA591059: Expressed sequence AA591059 | 56.29 | 33.55 | 46.52 | 130.59 | 70.28 | 207.6 | 293.95 | 193.18 | 298.1 | 0.228462286 | 0.044067797 | 0.06924294 | 22.352 |
| 20263 | Abcf1: ATP-binding cassette, sub-family F (GCN20), member 1 | 1565.6 | 1512.55 | 1825.57 | 2799.7 | 2379.2 | 2881.9 | 3476.5 | 3087.8 | 3007 | 0.556241255 | 0.038461538 | 0.06267628 | 25.741 |
| 3399 | Abhd6: abhydrolase domain containing 6 | 74 | 36.87 | 87.35 | 553.9 | 326.89 | 296.3 | 593.6 | 167.18 | 618.8 | 0.15505865 | 0 | 0.04020833 | 66.025 |
| 3398 | Abhd6: abhydrolase domain containing 6 | 209.56 | 278.43 | 237.36 | 422.75 | 380.61 | 691.33 | 684.84 | 889.36 | 650.7 | 0.390015055 | 0.040229885 | 0.06212644 | 27.231 |
| 7228 | Adnp: activity-dependent neuroprotective protein | 290.38 | 98.62 | 340.91 | 806.44 | 487.17 | 695.53 | 665.1 | 564.28 | 782.1 | 0.364902089 | 0.036764706 | 0.06019608 | 29.716 |
| 28853 | AI449441: expressed sequence AI449441 | 152.43 | 274.6 | 83.3 | 549.74 | 575.03 | 368.81 | 540.27 | 415.64 | 365.1 | 0.362629281 | 0.044176707 | 0.06532798 | 24.024 |
| 43126 | AI553587: expressed sequence AI553587 | 45.94 | 59.16 | 164.25 | 440.23 | 390.53 | 659.33 | 420.52 | 199.69 | 203.5 | 0.232819462 | 0.035087719 | 0.05421053 | 39.797 |
| 27478 | Alkbh1: alkB, alkylation | 367.13 | 252.58 | 364.88 | 684.73 | 472.21 | 782.39 | 1187.3 | 1539.4 | 783.2 | 0.361366497 | 0.039408867 | 0.06277504 | 25.948 |

TABLE 9B-continued

| Row | Gene | CycA2.1 | CycA2.2 | CycA2.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 41185 | repair homolog 1 (*E. coli*) Ankrd11: ankyrin repeat domain 11 | 194.44 | 140.3 | 145.55 | 605.72 | 556.5 | 490.08 | 635.77 | 558.13 | 541.3 | 0.283567726 | 0.030769231 | 0.05533333 | 38.133 |
| 17472 | Aoc3: amine oxidase, copper containing 3 | 14.01 | 4.63 | 37.83 | 85.43 | 273.68 | 193.82 | 107.32 | 107.65 | 335.5 | 0.102359136 | 0.0390625 | 0.06083333 | 30.258 |
| 20486 | Aspm: asp (abnormal spindle)-like, microcephaly associated (*Drosophila*) | 199.52 | 137.22 | 144.24 | 521.87 | 545.05 | 411.51 | 527.32 | 557.97 | 437 | 0.3205796 | 0.027777778 | 0.0583642 | 32.011 |
| 43330 | Aspm: asp (abnormal spindle)-like, microcephaly associated (*Drosophila*) | 158.72 | 62.35 | 100.75 | 406.86 | 421 | 369.44 | 451.38 | 451.4 | 444 | 0.252998172 | 0.031746032 | 0.0562963 | 38.255 |
| 32443 | Aspm: asp (abnormal spindle)-like, microcephaly associated (*Drosophila*) | 292.51 | 187.37 | 247.14 | 625.22 | 519.02 | 571.3 | 712.94 | 561.32 | 557.8 | 0.409864669 | 0.04787234 | 0.07400709 | 20.159 |
| 30016 | Atrx: Alpha thalassemia/mental retardation syndrome X-linked homolog (human) | 120.99 | 183.34 | 102.72 | 558.59 | 325.41 | 576.41 | 338.6 | 384.09 | 383.9 | 0.317145573 | 0.048148148 | 0.06746914 | 23.163 |
| 15284 | AU040096: expressed sequence AU040096 | 1327.17 | 938.18 | 1971.18 | 2586.3 | 2194.2 | 3019.8 | 2743.2 | 2441.9 | 2608 | 0.543384867 | 0.037914692 | 0.06336493 | 25.536 |
| 8675 | B230354K17Rik: RIKEN cDNA B230354K17 gene | 814.67 | 430.9 | 611.56 | 2576.3 | 1355.6 | 1878.6 | 1425.7 | 1638.7 | 1475 | 0.358860153 | 0.025 | 0.05741667 | 43.36 |
| 15916 | Bach1: BTB and CNC homology 1 | 214.4 | 51.49 | 267.98 | 509.03 | 500.69 | 370.86 | 552.06 | 427.69 | 703.9 | 0.348454093 | 0.038647343 | 0.06276973 | 25.755 |
| 8637 | Bbs2: Bardet-Biedl syndrome 2 homolog (human) | 118.85 | 61.19 | 192.91 | 337.79 | 236.48 | 247.56 | 500.41 | 586.34 | 389.9 | 0.324523048 | 0.045602606 | 0.06908795 | 22.06 |
| 8704 | BC003965: cDNA sequence BC003965 | 318.96 | 314.61 | 589.74 | 1242.2 | 913.8 | 906.78 | 1067.1 | 675.98 | 1004 | 0.421130361 | 0.044692737 | 0.06277467 | 26.933 |
| 31179 | BF642829: expressed sequence BF642829 | 55.1 | 17.77 | 90.7 | 564.5 | 291.99 | 569.64 | 719.96 | 231.69 | 348.6 | 0.11998973 | 0 | 0.04888889 | 85.429 |
| 1110 | Bub3: budding uninhibited by benzimidazoles 3 homolog (*S. cerevisiae*) | 163.69 | 146.39 | 195.19 | 499.57 | 444.31 | 468.08 | 309.06 | 361.39 | 554.5 | 0.383223042 | 0.046728972 | 0.07061267 | 21.629 |
| 18450 | Bxdc1: brix domain containing 1 | 521.77 | 121.43 | 552.63 | 1496.2 | 1126.8 | 1048.1 | 945.53 | 776.39 | 1481 | 0.347916279 | 0.034482759 | 0.05551724 | 39.356 |
| 10968 | C430004E15Rik: RIKEN cDNA C430004E15 gene | 125.61 | 72.26 | 122.92 | 346.64 | 170.85 | 293.11 | 500.16 | 350.92 | 598.3 | 0.283891237 | 0.038277512 | 0.06291866 | 25.625 |
| 27736 | C730049O14Rik: RIKEN cDNA C730049O14 gene | 279.36 | 161.54 | 258.16 | 854.88 | 650.64 | 580.29 | 733.69 | 724.56 | 697.5 | 0.329621675 | 0.04 | 0.05737778 | 35.895 |
| 34773 | Ccdc66: coiled-coil domain containing 66 | 152.66 | 109.96 | 220.57 | 681.69 | 370.27 | 538.09 | 732.89 | 447.88 | 631.7 | 0.284019738 | 0.036363636 | 0.05381818 | 40.471 |
| 29123 | Cdca2: cell division cycle associated 2 | 209.02 | 187.77 | 269.92 | 719 | 518.46 | 652.95 | 696.51 | 623.21 | 618 | 0.348322414 | 0.032258065 | 0.06094086 | 30.502 |
| 41131 | Cdca2: cell division cycle associated 2 | 160.58 | 179.33 | 233.01 | 408.1 | 505.8 | 456.62 | 590.37 | 765.51 | 518.8 | 0.353086549 | 0.042918455 | 0.06473534 | 24.623 |
| 8311 | CDNA clone IMAGE: 30031514 | 1064.61 | 532.91 | 1115.12 | 1802.7 | 1683.2 | 1977.4 | 2026.2 | 1949.5 | 2208 | 0.465796823 | 0.031914894 | 0.05836879 | 33.071 |
| 4656 | Cebpz: CCAAT/enhancer binding protein zeta | 801.7 | 466.96 | 1043.21 | 2020.2 | 1604.2 | 1858.7 | 1691.2 | 1501.9 | 1690 | 0.446033561 | 0.028571429 | 0.05825397 | 32.212 |
| 15723 | Cenpe: centromere protein E | 595.49 | 593.11 | 496.28 | 1062.6 | 840.39 | 1209.8 | 1570.6 | 1201.9 | 1244 | 0.472642964 | 0.043390043 | 0.06494949 | 24.63 |

TABLE 9B-continued

| Row | Gene | CycA2.1 | CycA2.2 | CycA2.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 39617 | Ckap21: cytoskeleton associated protein 2-like | 98.96 | 178.8 | 150.55 | 296.31 | 387.77 | 321.94 | 430.71 | 480.09 | 416.2 | 0.367180032 | 0.047761194 | 0.07039801 | 21.332 |
| 16339 | Cndp2: CNDP dipeptidase 2 (metallopeptidase M20 family) | 95.72 | 12.15 | 118.99 | 542.76 | 229.08 | 165.59 | 150.97 | 419.23 | 414.1 | 0.23609485 | 0.032786885 | 0.06057377 | 30.714 |
| 13932 | Cox17: cytochrome c oxidase, subunit XVII assembly protein homolog (yeast) | 609.8 | 99.15 | 883.83 | 1560.4 | 816.01 | 1231.3 | 757.93 | 1492.8 | 1260 | 0.447513191 | 0.04494382 | 0.06275281 | 26.972 |
| 1878 | Crlz1: charged amino acid rich leucine zipper 1 | 547.14 | 492.43 | 937.54 | 1867.1 | 1324.2 | 1689.6 | 1664.4 | 1073.1 | 1696 | 0.424524879 | 0.035714286 | 0.05494048 | 39.916 |
| 677 | Ctsc: cathepsin C | 560.59 | 170.75 | 535.58 | 1142.3 | 623.95 | 597.3 | 1072.2 | 767.24 | 1113 | 0.476631541 | 0.047619048 | 0.07378307 | 20.134 |
| 10567 | Cugbp1: CUG triplet repeat, RNA binding protein 1 | 144.44 | 139.03 | 182.01 | 475.93 | 188.63 | 348.36 | 686.59 | 538.56 | 396.3 | 0.353388653 | 0.046822742 | 0.0693534 | 22.241 |
| 10566 | Cugbp1: CUG triplet repeat, RNA binding protein 1 | 454.48 | 148.16 | 264.74 | 818.02 | 671.83 | 693.42 | 734.46 | 490.43 | 505.7 | 0.443235067 | 0.04719764 | 0.07229105 | 21.077 |
| 41846 | D14Abb1e: DNA segment, Chr 14, Abbott 1 expressed | 166.7 | 221.03 | 266.86 | 493.13 | 316.45 | 653.17 | 637.61 | 639.35 | 503.7 | 0.40364059 | 0.047445255 | 0.06781022 | 22.983 |
| 18143 | D3Erd300e: DNA segment, Chr 3, ERATO Doi 300, expressed | 651.01 | 741.63 | 789.6 | 1222.2 | 863.98 | 1291 | 1855.7 | 1684.9 | 1720 | 0.50282071 | 0.042635659 | 0.06616279 | 23.66 |
| 38498 | D530033C11Rik: RIKEN cDNA D530033C11 gene | 890.62 | 74.97 | 669.69 | 1354.2 | 1034.7 | 1547.4 | 1172.7 | 959.68 | 1176 | 0.45145483 | 0.043650794 | 0.06470899 | 24.01 |
| 29413 | Dcun1d3: DCN1, defective in cullin neddylation 1, domain containing 3 (S. cerevisiae) | 112.69 | 125.06 | 198.24 | 483.09 | 350.59 | 483.79 | 304.94 | 421.64 | 437.9 | 0.35132293 | 0.044715447 | 0.06539295 | 24.096 |
| 15722 | Ddx17: DEAD (Asp-Glu-Ala-Asp) box polypeptide 17 | 190.78 | 456.61 | 194.03 | 475.57 | 561.19 | 524.9 | 865.28 | 1016.7 | 851.5 | 0.391801878 | 0.04109589 | 0.06312024 | 25.292 |
| 16347 | Ddx21: DEAD (Asp-Glu-Ala-Asp) box polypeptide 21 | 496.86 | 124.45 | 757.01 | 933.21 | 720.44 | 1161.8 | 1068.9 | 1079.2 | 1464 | 0.428886151 | 0.040462428 | 0.06244701 | 27.25 |
| 27562 | Depdc1b: DEP domain containing 1B | 18.58 | 56.46 | 148.7 | 299.93 | 171.91 | 324.22 | 316.42 | 295.91 | 377.9 | 0.250513646 | 0.038461538 | 0.06087179 | 30.132 |
| 14683 | Dgke: diacylglycerol kinase, epsilon | 343.02 | 114.18 | 420.65 | 1081.8 | 777.24 | 733.1 | 1097.9 | 905.2 | 997.7 | 0.313911367 | 0.03030303 | 0.0530303 | 46.768 |
| 7310 | Dnajb11: DnaJ (Hsp40) homolog, subfamily B, member 11 | 556.18 | 649.73 | 756.84 | 1341.8 | 1134.7 | 1077.5 | 1277.8 | 1479.7 | 1532 | 0.5005132 | 0.046511628 | 0.06949059 | 22.185 |
| 14950 | Eif2c5: eukaryotic translation initiation factor 2C, 5 | 73.43 | 7.99 | 58.25 | 207.56 | 115.15 | 151.62 | 314.47 | 175.57 | 291.9 | 0.222360199 | 0.046296296 | 0.07078189 | 21.539 |
| 22419 | Eif3s6: eukaryotic translation initiation factor 3, subunit 6 | 381.28 | 298.29 | 530.64 | 867.23 | 627.04 | 653.69 | 1252.5 | 944.86 | 908.5 | 0.460694538 | 0.047021944 | 0.07048067 | 21.669 |
| 395 | Eif3s7: eukaryotic translation initiation factor 3, subunit 7 (zeta) | 29.43 | 61.47 | 88.84 | 294.07 | 351.69 | 339.68 | 230.39 | 167.87 | 157.3 | 0.233274065 | 0.038961039 | 0.06056277 | 28.457 |
| 153 | Eif3s8: eukaryotic | 647.41 | 374.43 | 471.72 | 1108.7 | 888.34 | 784.61 | 1267.7 | 1026.1 | 1313 | 0.467559382 | 0.048327138 | 0.06748451 | 23.186 |

TABLE 9B-continued

| Row | Gene | CycA2.1 | CycA2.2 | CycA2.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 18771 | translation initiation factor 3, subunit 8 | 298.51 | 184.57 | 392.63 | 1119.5 | 733.54 | 995.87 | 939.53 | 968.34 | 900.9 | 0.309562316 | 0.033333333 | 0.05511111 | 47.605 |
| 17713 | Ell2: elongation factor RNA polymerase II 2 | 159.03 | 73.22 | 93.44 | 636.72 | 598.27 | 683.95 | 479.48 | 375.04 | 558.7 | 0.195485743 | 0 | 0.03666667 | 65.023 |
| 42522 | Etnk1: Ethanolamine kinase 1 | 235.24 | 234.96 | 201.67 | 561.14 | 449.79 | 487.17 | 710.1 | 690.61 | 645.7 | 0.379109935 | 0.039215686 | 0.0625 | 25.944 |
| 33019 | Fancm: Fanconi anemia, complementation group M | 324.67 | 275.04 | 276.12 | 624.04 | 629.44 | 728.5 | 955.82 | 882.68 | 793 | 0.379684662 | 0.04137931 | 0.06165517 | 28.839 |
| 16073 | Fancm: Fanconi anemia, complementation group M | 372.48 | 232.77 | 365.4 | 583.78 | 592.92 | 710.05 | 789.6 | 732.26 | 922.8 | 0.448189166 | 0.048648649 | 0.07340541 | 20.319 |
| 14660 | Fen1: flap structure specific endonuclease 1 | 461.57 | 282.56 | 398.88 | 1199.4 | 1125.7 | 829.3 | 821.82 | 831.08 | 814 | 0.406671055 | 0.049056604 | 0.0674717 | 23.342 |
| 6438 | Fv1: Friend virus susceptibility 1 | 38.2 | 81.88 | 76.52 | 241.25 | 95.92 | 244.58 | 302.26 | 159.26 | 316 | 0.289264406 | 0.048991354 | 0.07193084 | 20.911 |
| 18071 | Fzd7: frizzled homolog 7 (Drosophila) | 340.48 | 178.18 | 288.66 | 840.79 | 815.36 | 819.63 | 1126.2 | 951.13 | 832.4 | 0.299813573 | 0.023809524 | 0.05539683 | 43.152 |
| 23587 | Gapvd1: GTPase activating protein and VPS9 domains 1 | 129.82 | 259.4 | 193.47 | 424.38 | 502.98 | 467.39 | 685.61 | 645.29 | 353.6 | 0.378463517 | 0.048710602 | 0.07160458 | 20.899 |
| 22636 | Gfpt1: glutamine fructose-6-phosphate transaminase 1 | 38.52 | 89.06 | 120.23 | 335.73 | 165.1 | 314.89 | 566.93 | 599.99 | 90.41 | 0.239077687 | 0.04232804 | 0.06405644 | 26.375 |
| 28204 | Glb1: galactosidase, beta 1 | 1082.26 | 154.29 | 824.12 | 1713.4 | 1707.9 | 1919 | 2551.5 | 2521.8 | 2748 | 0.31313842 | 0 | 0.041 | 74.678 |
| 33270 | Gm104: gene model 104, (NCBI) | 270.98 | 111.96 | 218.82 | 623.96 | 423.95 | 354.11 | 625.11 | 416.17 | 774.7 | 0.373997433 | 0.04676259 | 0.06773381 | 22.928 |
| 29375 | Gm1564: gene model 1564, (NCBI) | 200.31 | 157.46 | 220.69 | 547.93 | 543.11 | 730.67 | 543.28 | 424.1 | 561.8 | 0.345259589 | 0.041420118 | 0.06234714 | 27.459 |
| 3500 | Gpatc4: G patch domain containing 4 | 440.58 | 205.69 | 292.42 | 950.82 | 529.03 | 789.31 | 962.71 | 725.77 | 902.3 | 0.386293771 | 0.034782609 | 0.05953623 | 31.334 |
| 9979 | Gpatc4: G patch domain containing 4 | 1300.71 | 154.78 | 656.61 | 2341.4 | 1228.2 | 1953.3 | 2071.8 | 1558.3 | 1585 | 0.393399692 | 0.042553191 | 0.05496454 | 42.186 |
| 29821 | Gtf3c1: general transcription factor III C 1 | 1082.02 | 314.5 | 452.3 | 1080.6 | 901.53 | 1212.7 | 1452 | 1192.1 | 1707 | 0.490006758 | 0.049608355 | 0.07422106 | 20.008 |
| 13878 | Gtf3c4: general transcription factor IIIC, polypeptide 4 | 249.77 | 12.55 | 161.14 | 474.48 | 220.1 | 217.44 | 516.42 | 384.03 | 566.5 | 0.355996822 | 0.045454545 | 0.06888528 | 22.058 |
| 7302 | Gtpbp4: GTP binding protein 4 | 505.74 | 834.95 | 1152 | 1902.8 | 1140.8 | 1610.7 | 1950.4 | 1522.4 | 1944 | 0.495037098 | 0.044025157 | 0.06255765 | 28.043 |
| 20122 | H47: histocompatibility 47 | 624.17 | 411.69 | 853.39 | 1601.4 | 1273.8 | 1337.6 | 1610.6 | 1602.3 | 1546 | 0.421159518 | 0.03125 | 0.05572917 | 38.172 |
| 16780 | H47: histocompatibility 47 | 1553.67 | 678.07 | 1382.64 | 2610 | 1889.2 | 2344.4 | 2583.7 | 2481.4 | 2674 | 0.495709628 | 0.034482759 | 0.05862069 | 33.984 |
| 14429 | H47: histocompatibility 47 | 1937.91 | 764.71 | 1187.44 | 2611 | 1869.7 | 2265.5 | 2327.5 | 2522.8 | 2347 | 0.557987889 | 0.044217687 | 0.06821995 | 22.482 |
| 29582 | Hectd1: HECT domain containing 1 | 886.78 | 469.71 | 529.57 | 1198 | 860.21 | 1101.7 | 1757.5 | 1238.8 | 1402 | 0.499059992 | 0.049350649 | 0.07448485 | 19.948 |
| 8699 | Hipk1: homeodomain interacting protein kinase 1 | 992.48 | 402.72 | 711.08 | 1281.1 | 954.65 | 1185.9 | 1575.7 | 1648.7 | 1862 | 0.495129872 | 0.045627376 | 0.06700887 | 23.415 |
| 8270 | Igf2r: insulin-like growth factor 2 receptor | 327.8 | 119.68 | 339.68 | 781.98 | 500.48 | 705.3 | 745.85 | 596 | 939.7 | 0.36875366 | 0.039370079 | 0.06091864 | 30.301 |
| 8271 | Igf2r: insulin-like growth factor 2 receptor | 169.96 | 242.38 | 158.23 | 528.54 | 492.61 | 528.94 | 459.73 | 649.21 | 498.9 | 0.361359253 | 0.046218487 | 0.06540616 | 24.44 |
| 22514 | Ilf3: interleukin enhancer binding factor 3 | 170.07 | 35.32 | 121.1 | 560.62 | 295.08 | 376.34 | 300.48 | 289.94 | 360.2 | 0.299171183 | 0.046594982 | 0.06761051 | 22.913 |

TABLE 9B-continued

| Row | Gene | CycA2.1 | CycA2.2 | CycA2.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 7251 | Incenp: inner centromere protein | 393.46 | 237.19 | 218.41 | 663.52 | 579.94 | 476.28 | 892.65 | 816.19 | 920.6 | 0.390447811 | 0.042944785 | 0.06310838 | 27.646 |
| 21315 | Ipo7: importin 7 | 1777.24 | 743.47 | 1888.27 | 2615.2 | 2038 | 2474.9 | 2454.8 | 2754.8 | 2634 | 0.588991329 | 0.048128342 | 0.07298574 | 20.287 |
| 27085 | Isg2012: interferon stimulated exonuclease gene 20-like 2 | 416.94 | 227.53 | 402 | 1147.7 | 772.85 | 990.8 | 770.46 | 676.05 | 841.5 | 0.402541876 | 0.044247788 | 0.06415929 | 24.912 |
| 4798 | Jmy: junction-mediating and regulatory protein | 165.05 | 95.76 | 208.4 | 547.49 | 231.34 | 463.45 | 532.88 | 603.44 | 674.5 | 0.30736729 | 0.036685366 | 0.05780488 | 34.745 |
| 4799 | Jmy: junction-mediating and regulatory protein | 886.39 | 251.37 | 566.34 | 1194 | 1060.9 | 1111.5 | 1676.9 | 1290.8 | 1588 | 0.43020715 | 0.043478261 | 0.06289855 | 27.762 |
| 19905 | Jmy: junction-mediating and regulatory protein | 187.78 | 141.18 | 219.35 | 543.3 | 293 | 427.2 | 657.56 | 428.21 | 656.7 | 0.36481402 | 0.046099291 | 0.06806147 | 22.831 |
| 2694 | Kctd9: potassium channel tetramerisation domain containing 9 | 171.19 | 85.46 | 175.44 | 439.95 | 379.75 | 353.67 | 485.57 | 295.15 | 503.3 | 0.351672947 | 0.044520548 | 0.0681621 | 22.544 |
| 20342 | Kif11: kinesin family member 11 | 351.66 | 218.63 | 237.15 | 802.55 | 400.74 | 666.11 | 896.31 | 538.17 | 967.6 | 0.37806277 | 0.035460993 | 0.06096927 | 29.228 |
| 19155 | Kif22: kinesin family member 22 | 291.5 | 250.11 | 329.46 | 841.6 | 654.47 | 559 | 989.59 | 886.55 | 947.4 | 0.35709542 | 0.028985507 | 0.05560386 | 37.101 |
| 7972 | Kif22: kinesin family member 22 | 202.55 | 190.1 | 260.35 | 873.55 | 734.19 | 599.86 | 722.03 | 806.28 | 1047 | 0.273030408 | 0.034482759 | 0.05172414 | 48.72 |
| 15135 | Kif2c: kinesin family member 2C | 167.17 | 158.49 | 331.1 | 532.54 | 543.91 | 578.45 | 476.24 | 472.46 | 1022 | 0.362287382 | 0.047297297 | 0.069651577 | 22.301 |
| 21863 | Klf9: Kruppel-like factor 9 | 1075.11 | 184.91 | 618.97 | 1413.6 | 1073.9 | 1024.2 | 1693.1 | 992.37 | 1695 | 0.476142088 | 0.046242775 | 0.07190751 | 20.929 |
| 9017 | L2hgdh: L-2-hydroxyglutarate dehydrogenase | 356.73 | 197.34 | 475.3 | 1034.2 | 590.33 | 965.17 | 1621.2 | 1345.6 | 1418 | 0.295197523 | 0 | 0.03680556 | 58.335 |
| 12344 | Larp1 /// LOC631268: La ribonucleoprotein domain family, member 1 /// similar to la related protein isoform 1 | 347.33 | 50.62 | 240.65 | 510.75 | 581.65 | 447.49 | 684.6 | 681.6 | 1010 | 0.326124981 | 0.028037383 | 0.05772586 | 32.144 |
| 27871 | Lemd3: LEM domain containing 3 | 355.22 | 46.19 | 248.38 | 639.18 | 502.36 | 726.84 | 660.72 | 542.9 | 577.8 | 0.356070777 | 0.044871795 | 0.06168803 | 28.233 |
| 21965 | /// LOC546201 /// LOC619753 /// LOC621019 /// LOC622792 /// LOC664993 /// LOC665003 /// LOC665558 /// LOC665616 /// LOC665711 /// LOC665718 /// LOC665723 /// LOC665802 /// LOC666058 /// LOC666140: similar to PRAME family member 8 /// expressed sequence AU018829 /// similar to PRAME family member 8 /// | 1318.37 | 1146.56 | 2240.92 | 2919.6 | 2279.5 | 3009.7 | 2492.5 | 2865.6 | 3136 | 0.563483748 | 0.03960396 | 0.06283828 | 25.972 |

TABLE 9B-continued

| Row | Gene | CycA2.1 | CycA2.2 | CycA2.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| | similar to PRAME family member 8 /// similar to PRAME family member 8 /// similar to PRAME family member 8 /// similar to PRAME family member 8 /// similar to PRAME family member 8 /// similar to PRAME family member 8 /// similar to PRAME family member 8 /// similar to PRAME family member 8 /// similar to PRAME family member 8 /// similar to PRAME family member 8 /// similar to PRAME family member 8 /// similar | | | | | | | | | | | | | |
| 10972 | Ltv1: LTV1 homolog (S. cerevisiae) | 174.72 | 230.6 | 499.42 | 754.54 | 608.63 | 673.92 | 720.95 | 681.5 | 835.4 | 0.423275126 | 0.046052632 | 0.069375 | 22.107 |
| 27592 | Mdc1: mediator of DNA damage checkpoint 1 | 262.4 | 166.34 | 518.6 | 980.38 | 695.34 | 702.31 | 682.3 | 773.12 | 895.3 | 0.400671635 | 0.043478261 | 0.06484848 | 23.974 |
| 20064 | Mgat2: mannoside acetylglucosaminyltransferase 2 | 469.73 | 304.14 | 823.62 | 1323.3 | 860.58 | 1140.1 | 1038.6 | 1107.9 | 1146 | 0.482879947 | 0.045138889 | 0.06842593 | 22.62 |
| 19069 | Mina: myc induced nuclear antigen | 78.98 | 36.19 | 157.22 | 515.36 | 223.46 | 260.41 | 415.61 | 176.74 | 570.7 | 0.251943523 | 0.035211268 | 0.06105634 | 29.175 |
| 21512 | Mkrn1: makorin, ring finger protein, 1 | 648.36 | 512.8 | 1294.71 | 1919.8 | 1380 | 1377.3 | 1555.2 | 1824.2 | 2003 | 0.488259093 | 0.04519774 | 0.06293785 | 26.996 |
| 6466 | Mm.218588.1 | 254.43 | 33.9 | 245.82 | 906 | 787.64 | 785.29 | 730.81 | 656.42 | 846.7 | 0.226678125 | 0 | 0.04019608 | 65.243 |
| 12365 | Mm.29909.1 | 281.86 | 28.14 | 399.88 | 829.02 | 524.34 | 892.94 | 1101.1 | 1108.6 | 1026 | 0.2901034 | 0 | 0.03666667 | 63.212 |
| 29718 | Mnab: membrane associated DNA binding protein | 118.68 | 46.27 | 176.41 | 283.79 | 408.91 | 313.29 | 413.11 | 248.67 | 694.3 | 0.289035842 | 0.040909091 | 0.06340909 | 25.243 |
| 8643 | Mobk1b: MOB1, Mps One Binder kinase activator-like 1B (yeast) | 331.14 | 291.72 | 770.54 | 1112.7 | 863.99 | 1204.8 | 1306.9 | 1049 | 1226 | 0.412053466 | 0.030612245 | 0.05911565 | 32.694 |
| 7941 | Mobk1b: MOB1, Mps One Binder kinase activator-like 1B (yeast) | 254.91 | 242.34 | 466.56 | 736.04 | 605.17 | 626.58 | 639.84 | 1041.8 | 1058 | 0.409444571 | 0.047745358 | 0.07390805 | 20.138 |
| 791 | Mrfap1: Morf4 family associated protein 1 | 768.71 | 852.78 | 1066.33 | 1873 | 1359.9 | 1748.1 | 1989.4 | 2140.2 | 2023 | 0.48280997 | 0.03539823 | 0.0600295 | 31.382 |
| 2811 | Mtf2: metal response element binding transcription factor 2 | 1035.21 | 1134.68 | 1619.57 | 2148.1 | 1573.3 | 2029 | 2913.6 | 2368.9 | 2633 | 0.554570812 | 0.044303797 | 0.06973629 | 21.775 |
| 16360 | Ndufc1: NADH dehydrogenase (ubiquinone) 1, subcomplex unknown, 1 | 305.64 | 283.11 | 391.61 | 1442.1 | 822.36 | 1025.9 | 1048.3 | 788.41 | 1349 | 0.302783972 | 0.035714286 | 0.0497619 | 49.45 |
| 14278 | Nme1: expressed in non-metastatic cells 1, protein | 58.62 | 18.15 | 143.92 | 450.69 | 102.76 | 119.29 | 425.45 | 295.56 | 236.6 | 0.270720502 | 0.048387097 | 0.07321685 | 20.305 |
| 23157 | Osbpl7: oxysterol binding protein-like 7 | 208.36 | 123.05 | 167.34 | 291.45 | 385.78 | 284.54 | 615.7 | 485.5 | 504.2 | 0.38856622 | 0.048843188 | 0.07529563 | 19.82 |
| 10534 | Oxnad1: oxidoreductase NAD-binding domain containing 1 | 230.13 | 169.82 | 311.6 | 693.65 | 782.99 | 681.59 | 465.88 | 438.48 | 324.6 | 0.42014425 | 0.047368421 | 0.0742193 | 20.048 |
| 10418 | Pank3: pantothenate kinase 3 | 425.65 | 241.73 | 280.88 | 1151.2 | 770.81 | 1060.5 | 873.11 | 919.21 | 1010 | 0.327845955 | 0.024390244 | 0.05658537 | 43.275 |

TABLE 9B-continued

| Row | Gene | CycA2.1 | CycA2.2 | CycA2.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 3006 | Pdgfa: platelet derived growth factor, alpha | 301.5 | 109.27 | 223.39 | 769.44 | 1041 | 424.85 | 654.37 | 303.32 | 583.3 | 0.335864925 | 0.03649635 | 0.06034063 | 29.635 |
| 12377 | Pdrg1: p53 and DNA damage regulated 1 | 372.77 | 252.95 | 540.97 | 715.57 | 694.98 | 822.93 | 1022.5 | 1047.5 | 1096 | 0.432177036 | 0.040201005 | 0.06324958 | 26.01 |
| 12376 | Pdrg1: p53 and DNA damage regulated 1 | 285.31 | 282.96 | 545.59 | 789.75 | 643.57 | 739.91 | 846.21 | 866 | 924.2 | 0.463178117 | 0.048850575 | 0.0717433 | 20.906 |
| 727 | Pfkfb3: 6-phosphofructo-2-kinase/fructose-2,6-biphosphatase 3 | 39.57 | 6.24 | 92.23 | 213.6 | 178.27 | 137.99 | 367.86 | 210.92 | 349.8 | 0.189296856 | 0.040935673 | 0.06185185 | 27.429 |
| 14762 | Pgd: phosphogluconate dehydrogenase | 929.25 | 508.03 | 877.51 | 1851.3 | 1253.4 | 1745.2 | 1403.8 | 1529.3 | 1992 | 0.473598818 | 0.039473684 | 0.06089912 | 28.571 |
| 15044 | Pgd: phosphogluconate dehydrogenase | 864.91 | 479.01 | 841.06 | 1775 | 1198.1 | 1646 | 1302.6 | 1437.5 | 1852 | 0.474396469 | 0.042168675 | 0.06273092 | 27.53 |
| 15538 | Pgd: phosphogluconate dehydrogenase | 641.54 | 351.22 | 569.81 | 1194 | 750.15 | 1094.5 | 1037.2 | 1017.5 | 1354 | 0.48475081 | 0.046376812 | 0.07173913 | 20.978 |
| 28991 | Plcd4: phospholipase C, delta 4 | 85.67 | 50.61 | 173.34 | 335.85 | 224.94 | 209.08 | 437.46 | 324.88 | 403.8 | 0.319861981 | 0.045454545 | 0.06839161 | 22.702 |
| 16204 | Ppgb: protective protein for beta-galactosidase | 440.09 | 225.35 | 350.75 | 1117.8 | 569.65 | 1350.3 | 1365.1 | 642.54 | 1357 | 0.317445293 | 0 | 0.03811594 | 58.402 |
| 1352 | Ppid /// Lamp3 /// LOC671770: peptidylprolyl isomerase D (cyclophilin D) /// lysosomal-associated membrane protein 3 /// similar to peptidylprolyl isomerase D | 177.09 | 265.27 | 578.82 | 1140.3 | 699.01 | 928.31 | 1030.2 | 754.1 | 902.8 | 0.37442549 | 0.032608696 | 0.05804348 | 33.459 |
| 39148 | Ppm1a: protein phosphatase 1A, magnesium dependent, alpha isoform | 678.05 | 348.48 | 381.66 | 1276.6 | 1065.7 | 1257 | 1597.5 | 1131.1 | 1120 | 0.378124375 | 0.027777778 | 0.05555556 | 36.552 |
| 9696 | Ppm1a: protein phosphatase 1A, magnesium dependent, alpha isoform | 132.05 | 88.38 | 124.3 | 565.15 | 304.18 | 544.53 | 369.01 | 388.93 | 396.4 | 0.268459355 | 0.033333333 | 0.06136111 | 30.736 |
| 32940 | Ppp1r3e: Protein phosphatase 1, regulatory (inhibitor) subunit 3E | 5.81 | 13.38 | 13.14 | 172.3 | 123.7 | 36.66 | 111.76 | 102.91 | 75.79 | 0.103768135 | 0.049723757 | 0.07308471 | 20.499 |
| 15897 | Pramel7: preferentially expressed antigen in melanoma like 7 | 228.49 | 144.58 | 867.63 | 970.28 | 608.23 | 1186 | 963.95 | 982.9 | 977.8 | 0.436162808 | 0.038095238 | 0.06279365 | 25.608 |
| 15898 | Pramel7: preferentially expressed antigen in melanoma like 7 | 883.77 | 273.04 | 670.2 | 1610.9 | 1098.7 | 1406.8 | 1266 | 1347.1 | 1587 | 0.439380494 | 0.03875969 | 0.06098191 | 30.2 |
| 7006 | Prkcd: protein kinase C, delta | 235.8 | 93.35 | 81.71 | 712.82 | 315.54 | 733.67 | 910.26 | 661.36 | 733.2 | 0.202051696 | 0 | 0.03909091 | 73.85 |
| 9218 | Prmt6: protein arginine N-methyltransferase 6 | 738.14 | 448.83 | 800.51 | 1347.3 | 1072.8 | 1130.9 | 1415.4 | 1423.3 | 1355 | 0.513255025 | 0.044827586 | 0.06847126 | 22.56 |
| 41444 | Prpf19: PRP19/PSO4 pre-mRNA processing factor 19 homolog (S. cerevisiae) | 3993.02 | 2736.93 | 2277.87 | 4887.6 | 4659.6 | 4958.5 | 4053.2 | 4990.6 | 4177 | 0.64976133 | 0.04664723 | 0.07188533 | 21.001 |
| 33047 | Prr11: proline rich 11 | 401.64 | 173.26 | 234.39 | 568.15 | 688.18 | 606.56 | 817.5 | 1134 | 740.9 | 0.355318761 | 0.036231884 | 0.06014493 | 29.566 |
| 35103 | Prr11: proline rich 11 | 265.25 | 149.08 | 442.11 | 729.69 | 571.34 | 733.59 | 873.03 | 564.31 | 1014 | 0.381823653 | 0.040697674 | 0.06170543 | 27.381 |

TABLE 9B-continued

| Row | Gene | CycA2.1 | CycA2.2 | CycA2.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 21158 | Psat1: phosphoserine aminotransferase 1 | 608.23 | 383.49 | 505.63 | 1268.1 | 1111.2 | 1110.2 | 1163.3 | 1113 | 1052 | 0.439232447 | 0.043010753 | 0.06390681 | 26.531 |
| 14945 | Psma6: proteasome (prosome, macropain) subunit, alpha type 6 | 297.18 | 193.17 | 579.11 | 823.99 | 814.83 | 842.51 | 1149.9 | 1450.2 | 1654 | 0.31757146 | 0.039215686 | 0.05627451 | 41.002 |
| 14001 | Ptdss2: phosphatidylserine synthase 2 | 286.3 | 79.67 | 434.04 | 847.59 | 360.31 | 528.7 | 764.33 | 553.32 | 802 | 0.414917121 | 0.045901639 | 0.06926776 | 22.092 |
| 3935 | Purb: purine rich element binding protein B | 255.68 | 124.63 | 215.26 | 618.23 | 457.69 | 488.12 | 438.8 | 529.05 | 494.2 | 0.393626056 | 0.04851752 | 0.07339623 | 20.306 |
| 16286 | Rab1: RAB1, member RAS oncogene family | 24.78 | 29.32 | 63.21 | 200.41 | 213.31 | 158.37 | 260.27 | 168.49 | 186.4 | 0.197609683 | 0.037735849 | 0.06314465 | 25.528 |
| 15338 | Rab20: RAB20, member RAS oncogene family | 448.47 | 171.13 | 416.25 | 593.19 | 602.78 | 611.39 | 1207 | 970.25 | 1218 | 0.398230769 | 0.045977011 | 0.06689655 | 23.518 |
| 4228 | Rbm35b: RNA binding motif protein 35b | 187.48 | 63.54 | 221.76 | 590.29 | 628.16 | 453.65 | 363.16 | 321 | 412.3 | 0.34153495 | 0.047619048 | 0.06794872 | 22.995 |
| 12058 | Rnf6: ring finger protein (C3H2C3 type) 6 | 508.38 | 239.28 | 418.61 | 655.12 | 583.25 | 868.77 | 1096.2 | 908.12 | 1007 | 0.455713959 | 0.047794118 | 0.06800245 | 23.019 |
| 12057 | Rnf6: ring finger protein (C3H2C3 type) 6 | 861.12 | 396.56 | 614.69 | 1246.8 | 778.27 | 939.73 | 1510 | 1251.2 | 1413 | 0.524537304 | 0.049095607 | 0.07514212 | 19.872 |
| 1293 | Rrs1: RRS1 ribosome biogenesis regulator homolog (*S. cerevisiae*) | 618.8 | 397.87 | 439.42 | 1053.2 | 649.43 | 1070.2 | 1408.1 | 1440.1 | 939.1 | 0.443918374 | 0.042372881 | 0.06426554 | 24.588 |
| 8403 | Rwdd4a: RWD domain containing 4A | 120.1 | 127.06 | 198.13 | 517.17 | 347.78 | 401.78 | 607.87 | 348.3 | 679.5 | 0.30684367 | 0.04109589 | 0.06171233 | 28.805 |
| 20481 | Sdad1: SDA1 domain containing 1 | 850.27 | 363.33 | 872.76 | 2204.8 | 1724.2 | 2050.9 | 2051.9 | 2375.7 | 1968 | 0.337163067 | 0 | 0.03539683 | 62.679 |
| 15545 | Sf3b2: splicing factor 3b, subunit 2 | 805.59 | 473.95 | 826.78 | 1604.5 | 2014.8 | 1868.8 | 1091.8 | 1101.2 | 1830 | 0.442914549 | 0.028169014 | 0.05497653 | 36.878 |
| 12258 | Sfrs1: splicing factor, arginine/serine-rich 1 (ASF/SF2) | 1313.28 | 772.48 | 1279.84 | 2058.8 | 1861 | 1951.5 | 1990.7 | 2140.9 | 2193 | 0.551915042 | 0.048780488 | 0.07106707 | 21.424 |
| 4980 | Sgpp1: sphingosine-1-phosphate phosphatase 1 | 171.97 | 94.46 | 279.34 | 1215.3 | 589.36 | 577.14 | 509.63 | 536.21 | 763.9 | 0.260417512 | 0.032258065 | 0.05677419 | 38.387 |
| 4981 | Sgpp1: sphingosine-1-phosphate phosphatase 1 | 1314.88 | 188.41 | 379.99 | 1556.5 | 1386.4 | 1522.7 | 1138.2 | 1603.8 | 1205 | 0.447708184 | 0.033613445 | 0.06098039 | 30.851 |
| 18042 | Sgpp1: sphingosine-1-phosphate phosphatase 1 | 31.01 | 17.03 | 39.22 | 176.04 | 188.98 | 215.43 | 109.27 | 132.56 | 153.3 | 0.178895791 | 0.044354839 | 0.06548387 | 24.039 |
| 1917 | Slc12a2: solute carrier family 12, member 2 | 437.13 | 331.4 | 303.71 | 1012.6 | 574.08 | 711.55 | 831.2 | 898.12 | 1083 | 0.419649444 | 0.041450777 | 0.06310881 | 26.299 |
| 16856 | Slc12a2: solute carrier family 12, member 2 | 153.39 | 179.89 | 175.06 | 527.45 | 337.21 | 487.48 | 447.9 | 572.27 | 515.6 | 0.352051858 | 0.043715847 | 0.06347905 | 26.669 |
| 21716 | Slc1a4: solute carrier family 1 (glutamate/neutral amino acid transporter), member 4 | 60.95 | 35.65 | 114.42 | 292.45 | 192.95 | 238.64 | 177.44 | 338.73 | 362.2 | 0.263384861 | 0.043668122 | 0.06537118 | 24.64 |
| 28457 | Slc30a1: solute carrier family 30 (zinc transporter), member 1 | 317.74 | 103.14 | 73.18 | 315.4 | 343.75 | 619.79 | 393.91 | 491.5 | 503.8 | 0.370338999 | 0.04761904 | 0.07036706 | 21.319 |
| 23716 | Sltm: SAFB-like, transcription modulator | 370.13 | 284.47 | 502.78 | 1011.1 | 760.09 | 1052 | 1179.5 | 795.6 | 946 | 0.402964314 | 0.034188034 | 0.06111111 | 30.894 |
| 7575 | Smarcc1: SWI/SNF related, | 97.38 | 219.78 | 155.82 | 345.56 | 264.16 | 208.33 | 557.93 | 543.22 | 522.9 | 0.38736149 | 0.049222798 | 0.0747323 | 19.915 |

TABLE 9B-continued

| Row | Gene | CycA2.1 | CycA2.2 | CycA2.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| | matrix associated, actin dependent regulator of chromatin, subfamily c, member 1 | | | | | | | | | | | | | |
| 6834 | Smarce1: SWI/SNF related, matrix associated, actin dependent regulator of chromatin, subfamily e, member 1 | 873.62 | 915.47 | 718.44 | 1533.2 | 1416.9 | 1757.6 | 1787.9 | 1926.5 | 1710 | 0.49496406 | 0.041666667 | 0.06248016 | 27.473 |
| 6044 | Sos1: Son of sevenless homolog 1 (*Drosophila*) | 134.91 | 61.07 | 109.98 | 438.22 | 273.17 | 373.78 | 444.95 | 294.97 | 346.4 | 0.281792101 | 0.039735099 | 0.06119205 | 28.59 |
| 6045 | Sos1: Son of sevenless homolog 1 (*Drosophila*) | 391.93 | 223.27 | 270.95 | 684.56 | 368.73 | 779.87 | 937.33 | 493.55 | 698.7 | 0.447245565 | 0.048913043 | 0.07344203 | 20.356 |
| 27178 | Spata2: spermatogenesis associated 2 | 1669.65 | 719.38 | 963.1 | 2142.9 | 1761.6 | 1953.7 | 1664.5 | 2350.8 | 2119 | 0.559020019 | 0.047477745 | 0.07050445 | 21.273 |
| 15690 | Spint2: serine protease inhibitor, Kunitz type 2 | 120.15 | 171.41 | 256.46 | 612.14 | 318.08 | 490.9 | 552.94 | 367.02 | 613.8 | 0.370927895 | 0.041284404 | 0.06328746 | 25.297 |
| 21622 | Stt3a: STT3, subunit of the oligosaccharyltransferase complex, homolog A (*S. cerevisiae*) | 295.43 | 563.39 | 363.82 | 1099.3 | 829.32 | 1154.4 | 987.79 | 752.3 | 707.2 | 0.442161261 | 0.045801527 | 0.06703562 | 23.437 |
| 6577 | suppressor of Ty 4 homolog 1 (*S. cerevisiae*) /// suppressor of Ty 4 homolog 2 (*S. cerevisiae*) | 782.52 | 691.08 | 832.99 | 1708.4 | 1408.4 | 1683.3 | 1689.4 | 2017.7 | 2325 | 0.425897785 | 0.034090909 | 0.0580303 | 33.971 |
| 1745 | Tacc3: transforming, acidic coiled-coil containing protein 3 | 738.85 | 414.57 | 618.79 | 1661.2 | 1187.9 | 1268.8 | 1516.9 | 1282.6 | 1702 | 0.411215669 | 0.035294118 | 0.05729412 | 34.361 |
| 13841 | Tbl2: transducin (beta)-like 2 | 293.54 | 36.54 | 247.36 | 684.47 | 780.75 | 476.82 | 685.89 | 393.26 | 569.1 | 0.321667609 | 0.0375 | 0.057375 | 35.143 |
| 41362 | Ter2Ip: telomeric repeat binding factor 2, interacting protein | 127.85 | 108.83 | 96.14 | 286.88 | 330.88 | 351.36 | 345.81 | 519.43 | 330.2 | 0.307523146 | 0.04797048 | 0.06747847 | 23.114 |
| 182 | Tfg: Trk-fused gene | 388.74 | 156.37 | 629.82 | 928.5 | 564.98 | 679.38 | 871.81 | 1022.6 | 1079 | 0.456614208 | 0.046428571 | 0.0677619 | 22.889 |
| 7468 | Tgoln1: trans-golgi network protein | 305.53 | 236.42 | 345.51 | 671.72 | 450.68 | 487.94 | 700.65 | 843.07 | 702.3 | 0.46026144 | 0.047493404 | 0.0739314 | 20.081 |
| 3061 | Timd2: T-cell immunoglobulin and mucin domain containing 2 | 608.39 | 151.76 | 231.44 | 1866.9 | 1351.1 | 1401.1 | 1475.4 | 1242.5 | 1993 | 0.212552423 | 0 | 0.06166667 | 97.488 |
| 1794 | Timm10: translocase of inner mitochondrial membrane 10 homolog (yeast) | 207.76 | 55.6 | 617.54 | 1237.7 | 550.92 | 497.86 | 560.37 | 1173.8 | 1446 | 0.322267911 | 0.038961039 | 0.05835498 | 35.358 |
| 785 | Tmed6: transmembrane emp24 protein transport domain containing 6 | 254.44 | 20.44 | 279.48 | 508.83 | 418.62 | 577.06 | 745.64 | 731.85 | 729.6 | 0.298720754 | 0.037037037 | 0.05450617 | 40.498 |
| 23223 | Impo: thymopoietin | 372.55 | 239.05 | 785 | 1127.4 | 1035.5 | 974.18 | 1028.2 | 951.54 | 1085 | 0.450399171 | 0.042735043 | 0.06450142 | 24.609 |
| 13926 | Tomm22: translocase of outer mitochondrial membrane 22 homolog (yeast) | 1013.62 | 632.86 | 904.75 | 2273.2 | 1748.6 | 1962.2 | 1195.2 | 1371.2 | 1705 | 0.497524304 | 0.040609137 | 0.06323181 | 26.103 |
| 16924 | Tor1b: torsin family 1, member B | 272.73 | 156.58 | 572.98 | 1028.7 | 649.17 | 887.96 | 740.56 | 964.62 | 1195 | 0.36670801 | 0.037974684 | 0.05776371 | 35.2 |

TABLE 9B-continued

| Row | Gene | CycA2.1 | CycA2.2 | CycA2.3 | NI1.1 | NI1.2 | NI1.3 | NI2.1 | NI2.2 | NI2.3 | FoldChange | MedianFDR | MeanFDR | T |
|---|---|---|---|---|---|---|---|---|---|---|---|---|---|---|
| 21932 | Transcribed locus | 332.77 | 106.56 | 140.03 | 583.75 | 309.89 | 572.13 | 653.87 | 636.22 | 766.5 | 0.328962199 | 0.032258065 | 0.0578853 | 33.372 |
| 43944 | Transcribed locus | 53.89 | 21.65 | 39.31 | 224.22 | 170.32 | 140.35 | 49.01 | 235.17 | 219.2 | 0.221231267 | 0.046153846 | 0.06666667 | 23.586 |
| 24471 | Isc22d2: TSC22 domain family 2 | 936.98 | 613.69 | 879.83 | 1530.6 | 1318.9 | 1453.7 | 2101.3 | 2010.4 | 1899 | 0.47129429 | 0.035971223 | 0.06131894 | 29.34 |
| 10769 | Ttf1: transcription termination factor 1 | 42.37 | 81.67 | 164.99 | 294.59 | 226.16 | 368.82 | 336.41 | 367.68 | 251.5 | 0.313279391 | 0.045936396 | 0.067791519 | 22.809 |
| 14944 | Txndc1: thioredoxin domain containing 1 | 424.55 | 133.69 | 462.39 | 960.94 | 645.2 | 984.25 | 612.43 | 1057.4 | 631.1 | 0.417324638 | 0.045454545 | 0.06567493 | 24.209 |
| 22950 | Unkl: unkempt-like (Drosophila) | 270.84 | 139.44 | 154.65 | 747.39 | 286.66 | 573.67 | 677.07 | 831.48 | 565.6 | 0.306874571 | 0.028571429 | 0.05490476 | 37.096 |
| 16306 | Usp10: ubiquitin specific peptidase 10 | 173.21 | 255.12 | 344.42 | 838.32 | 498.36 | 592.08 | 738.05 | 449.15 | 994.1 | 0.376030404 | 0.041025641 | 0.06345299 | 26.165 |
| 12733 | Utp11l: UTP11-like, U3 small nucleolar ribonucleoprotein, (yeast) | 955.84 | 514.61 | 1811.24 | 2092.8 | 2024.9 | 1852.2 | 1938.2 | 1738.6 | 2375 | 0.545964687 | 0.046920821 | 0.07209189 | 21.037 |
| 27185 | Utp15: UTP15, U3 small nucleolar ribonucleoprotein, homolog (yeast) | 222.46 | 131.63 | 302.63 | 1588.6 | 802.68 | 700.69 | 623.36 | 1475.8 | 538 | 0.22925845 | 0.037037037 | 0.0491358 | 50.551 |
| 15510 | Wbscr1: Williams-Beuren syndrome chromosome region 1 homolog (human) | 117.48 | 136.2 | 356.85 | 655.34 | 402.2 | 299.57 | 683.74 | 452.6 | 930.6 | 0.356613825 | 0.046025105 | 0.06517434 | 24.432 |
| 26959 | Wdr3: WD repeat domain 3 | 772.19 | 388.92 | 483.21 | 1122.9 | 1121.4 | 1247.2 | 1065.7 | 962.84 | 1081 | 0.498168587 | 0.049046322 | 0.07336966 | 20.372 |
| 21792 | Zfp444: Zinc finger protein 444 | 75.01 | 31.45 | 145.74 | 452.64 | 198.57 | 309.81 | 294.53 | 537.31 | 689.3 | 0.203210926 | 0.041666667 | 0.055 | 41.9 |
| 39491 | Zfp710: zinc finger protein 710 | 371.26 | 333.7 | 313.27 | 900.66 | 784.47 | 1074.7 | 975.36 | 1333.3 | 979.4 | 0.336722951 | 0.037735849 | 0.05540881 | 40.5 |

That which is claimed is:

1. A system comprising:
   (a) a computing environment;
   (b) an input device in communication with the computing environment, wherein the input device comprises a platform for entry of a fertility profile for a female subject and for entry of data sets, the data sets comprising,
      (i) a first data set comprising fertility profiles of a group of female individuals, wherein successful and unsuccessful IVF treatments from the fertility profiles are identified within the data set,
      (ii) a second data set comprising clinical variables known to be associated with or influence a female individual's probability of having a live birth event, and
      (iii) a third data set comprising variables related to in vitro fertilization (IVF) treatment protocols;
   (c) a non-transitory computer readable storage medium in communication with the computing environment comprising at least one algorithm that,
      (i) analyzes the data sets of (b) to identify variables from the data sets that are predictive of a probability of a live birth event in a female individual undergoing an IVF treatment,
      generates a prediction model for a likelihood of a female individual having a live birth event from an IVF treatment based upon the identified variables of (c)(i), validates the prediction model by testing the prediction model on at least one independent data set comprising fertility profiles of a group of female individuals, wherein the fertility profiles of the group of female individuals have variables that are correlated to the variables of (c)(i) that were found to be predictive of the probability of the live birth and applies the validated prediction model to the at least one independent data set to generate prognostic stratification of the independent data set, wherein the prognostic stratification is represented by percentile assignments representing a likelihood of the female individuals of the at least one independent data set to experience a live birth event from an IVF treatment, and
      (iii) applies the validated prediction model and prognostic stratification of (c)(ii) to the fertility profile of the female subject of (b) to obtain the female subject's predictive probability of having a live birth event from an IVF treatment and the percentile assignment of the female subject's probability of having a live birth event from an IVF treatment relative to the female individuals of the at least one independent data set;
   (d) an output device in communication with the computing environment for providing results generated by the at least one prediction model for the female subject, wherein the results are deliverable to a user of the system as a fertility management protocol for the female subject based upon the predicted probability and percentile assignment of (c)(iii).

2. The system of claim 1, wherein a successful IVF treatment comprises data on a live birth outcome.

3. The system of claim 1, wherein the variables known to be associated with or influence a female individual's probability of having a live birth event are selected from the group consisting of age, previous infertility history, number of previous pregnancies, number of previous term deliveries, number of spontaneous miscarriages, number of previous unsuccessful IVF treatments, body mass index, day 3 follicle stimulating hormone (FSH) level or other estimates of ovarian reserve, contraceptive use, number of motile sperm before wash, number of motile sperm after wash, number of total motile sperm after wash, number of total motile sperm before wash, sperm collection, sperm from donor, age of sperm donor or male partner, methods and origin of sperm collection, endometrial thickness, ultrasound monitoring results, clinical diagnosis of infertility, and combinations thereof.

4. The system of claim 3, wherein the variable related to clinical diagnosis of infertility is selected from the group consisting of diminished ovarian reserve, endometriosis, hydrosalpinx, polycystic ovarian disease, tubal disease, tubal ligation, male infertility, male infertility causes, unexplained female infertility, uterine fibroids, other causes of female infertility, and combinations thereof.

5. The system of claim 1, wherein the variables related to IVF treatment protocols are selected from the group consisting of oral contraceptive use, downregulation by gonadotropin-releasing hormone agonists (GnRHa), dosage of GnRHa, number of times GnRHa injected per day, use of GnRH antagonist, clinical criteria for starting GnRH antagonists, type of gonadotropins administered, total dosage of gonadotropins, use of human chorionic gonadotropin, dosage of human chorionic gonadotropin, clinical criteria for administering human chorionic gonadotropin, time interval between human chorionic gonadotropin administration and oocyte retrieval, downregulation initiated in menstrual cycle luteal phase, frequency of ultrasound monitoring, type of progesterone supplementation, performance of intracytoplasmic sperm injection (ICSI), assisted hatching, medications used, number of days of stimulation, and combinations thereof.

6. The system of claim 1, wherein the input device is configured to receive a fourth data set (iv) comprising oocyte and/or embryo parameters for a group of female individuals.

7. The system of claim 6, wherein the oocyte and/or embryo parameters are cohort-specific oocyte and embryo parameters.

8. The system of claim 6, wherein the oocyte and/or embryo parameters are selected from the group consisting of number of oocytes, number or percent of normal and mature oocytes, number or percent of normally fertilized eggs, number or percent of unfertilized eggs, number or percent of abnormally fertilized eggs, time for appearance of 2 pronuclei morula and blastocyst to be observed after insemination, time for appearance of 2 cell morula and blastocyst to be observed after insemination, time for appearance of 4 cell morula and blastocyst to be observed after insemination, time for appearance of 8 cell morula and blastocyst to be observed after insemination, total number of embryos on day 3 of embryo culture, total number of embryos on day 5 of embryo culture, assisted hatching, average grade of embryos, average number of cells per embryo, blastocyst development rate, compaction on day 3 of embryo culture, rate of cleavage arrest, number or percent of embryos arrested at the 4-cell stage, day of embryo transfer, number or percentage of 8-cell embryos, number or percentage of 8-cell embryos transferred, number or percentage of blastocysts, number or percentage of cryopreserved embryos, number or percentage of cryopreserved oocytes, season of procedure, year of procedure, sufficient quality for cryopreservation, and pre-implantation genetic testing positive for genetic disease or aneuploidy.

9. The system of claim 6, wherein the oocyte and/or embryo parameters comprise data from one or more single cell embryos.

10. The system of claim 6, wherein the oocyte and/or embryo parameters comprise data from one or more embryos with at least two cells.

11. The system of claim 6, wherein the oocyte and/or embryo parameters comprise data from one or more embryos at a morula or blastocyst stage.

12. The system of claim 6 wherein the oocyte and embryo parameters comprise data from one or more oocytes or embryos in arrested development.

13. The system of claim 6, wherein the oocyte and embryo parameters comprise data from one or more cryopreserved embryos.

14. The system of claim 6, wherein the oocyte and/or embryo parameters comprise data for normalized gene expression levels for one or more infertility indicator genes.

15. The system of claim 14, wherein the data for the normalized gene expression levels for the one or more infertility indicator genes are measured from samples selected from the group consisting of one or more embryos, one or more oocytes, a fertilized egg, dissociated cells, one or more dissociated embryos, one or more dissociated oocytes, and combinations thereof.

16. The system of claim 15, wherein the one or more embryos are single cell embryos.

17. The system of claim 15, wherein the one or more embryos are embryos with at least two cells.

18. The system of claim 15, wherein the one or more embryos are embryos at a morula or blastocyst stage.

19. The system of claim 15, wherein the one or more embryos are cryopreserved embryo.

20. The system of claim 15, wherein the one or more dissociated embryos are dissociated blastomeres.

21. The system of claim 14, wherein the data for the normalized gene expression levels for the one or more infertility indicator genes is output from a procedure selected from the group consisting of a gene chip, a BioMark® Dynamic Array, RT-PCR, gene sequencing, and combinations thereof.

22. The system of claim 14, wherein the one or more infertility indicator genes are selected from the group consisting of ADM, β-ACTIN, BCLAF1, BMPR1A, BRF2, BTAF1, BTBD14A, CBX4, CCNA1, CCNA2, CDC2, CDH1, CDH2, CDT1, CENPE, CITED2, CPSF4, CPSF6, CRB3, CSE11, CS1L, CTSB, DIDOI, DNMT3A, DNMT3B, DPPA5, E112, ECSIT, EIF2C5, EIF2S1, EIF3B, EIF3C, EIF3E, EIF3G, EIF3H, EIF3S, EIF3S10, EIF4E, EIF4E2, EIF4G1, EIF5B, EIF6, ETF1, ETV1, EZH2, FGF4, FGFRI, FGFRL1, GATA4, GATA6, GAPDH, GENS, GJA1, GTF3C1, GTF3C2, GTF3C4, GTF3C5, H3F3A, HAT1, HBEGF, HIPK1, HIPK3, HNRPA1, HNRPAB, HRNPK, HNRPM, I117RD, IGF2R, IMP1, INTS4, INTS7, JMJD2A, JMY, KDM3A, KDM3B, KDM5B, KDM5C, KFF9, KIF11, KIF22, KITLG, KLF9, KRTI6, LIN26, M113, MAPK1, MCM3, MCM5, MED8, MEDI4, METT12, MKRN1, MRIF1, MTA2, NANOG, NES, NRF1, OCT4, ORC41, PA2G4, PAPOLA, PARD3, PELP1, PIWIL2, PKNOX1, POLR2H, POLR3A, POLR3E, POLR3K, POU5F1, PPM1A, PPM1G, PPP2CB, PRKAG1, PRKCA, PRKCD, PRPF4, PRPF38B, PURB, RARS, RBM3, RBM4, RMB5, REST1, RFC2, RFC3, RSC8, SALL4, SESN1, SFRS15, SGPP1, SIRT1, SMARCA4, SMARCC1, SNUPN, SOX2, TAF9, TCEB3, TEFL5, TSTT1, UBTF, UGDH, and YY1.

23. The system of claim 14, wherein the one or more infertility indicator genes are selected from a molecular fingerprint of normal human embryos.

24. The system of claim 23, wherein the normal human embryos are selected from single-cell samples, multi-cell samples, or pooled embryo samples.

25. The system of claim 23, wherein the molecular fingerprint comprises data obtained from analysis of genes that are differentially expressed between normal and abnormal embryo samples.

26. The system of claim 25, wherein the normal and abnormal embryo samples are human or animal embryo samples.

27. The method of claim 25, wherein abnormal embryo status is based upon characteristics selected from the group consisting of lack of responsiveness to IVF treatment, arrested embryo development, failure to produce a pregnancy, biochemical pregnancy, spontaneous abortion, and combinations thereof.

28. The method of claim 25, wherein the analysis of genes that are differentially expressed between normal and abnormal embryo samples comprises removing one gene from a normal embryo through a gene targeting procedure.

29. The method of claim 28, wherein the gene targeting procedure is selected from the group consisting of homologous recombination, transgenesis, injection of anti-sense morpholino oligonucleotides, and combinations thereof.

30. The system of claim 1, wherein the input device is configured to receive a fifth data set (v) comprising information relating to oocyte culture, embryo culture, and fertilization.

31. The system of claim 30, wherein the information relating to oocyte culture, embryo culture, and fertilization are selected from the group consisting of culture group, number of oocytes per culture group, number of embryos per culture group, volume of culture media droplet used, brand of culture media, manufacturer of culture media, lot of culture media, whether ICSI is performed, time interval between oocyte retrieval and oocyte insemination, temperature of culture environment, gas composition of culture environment, brand and manufacturer of equipment used in culture environment, brand and manufacturer of equipment used for embryo procedures, and combinations thereof.

32. The system of claim 31, wherein the information relating to oocyte culture, embryo culture, and fertilization is gas composition of the culture environment, wherein the gas composition of the culture environment is selected from the group consisting of percentage of $O_2$, percentage of $CO_2$, percentage of $N_2$, and combinations thereof.

33. The system of claim 31, wherein the information relating to oocyte culture, embryo culture, and fertilization is brand and manufacturer of equipment used for embryo procedures, wherein the embryo procedures are selected from the group consisting of assisted hatching and embryo transfer.

34. The system of claim 1, wherein the computing environment (a) comprises at least one local computer local to the user and at least one remote computer at a site remote to the user, wherein the at least one local computer and the at least one remote computer are in communication through a network.

35. The system of claim 34, wherein the communication between the at least one local computer and the at least one remote computer is selected from the group consisting of an intranet network, an internet network, a wired connection, a wireless connection, a cellular phone connection protocol, code derived multiple access, and a global system for mobile communication.

36. The system of claim 1, wherein the input device (b) is selected from the group consisting of a personal computing device, a mobile device, a portable computer, a mainframe, a minicomputer, and a Smartphone device.

37. The system of claim 1, wherein the computer readable storage medium (c) is provided on a computer remote to the input device.

38. The system of claim 1, wherein the system transmits part or all of the input from the user entered into the input device (b) and/or the results of from the output device (d) electronically or telephonically to the user.

39. The system of claim 1, wherein the system electronically transmits part or all of the input from the user entered into the input device (b) and/or the results from the output device (d) directly to an electronic medical record for the female subject.

40. The system of claim 1, wherein the algorithm of the computer readable storage medium (c) provides relative weighting of the variables.

41. The system of claim 1, wherein the algorithm of the computer readable storage medium (c) uses a decision rule, a classification tree, a multiple additive regression tree, gradient boosting, logistic regression, nonparametric techniques, or combinations thereof.

42. The system of claim 1, wherein the algorithm of the computer readable storage medium (c) detects differences in a distribution of feature values.

* * * * *

SEQUENCE LISTING

<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 1
tcgaggtgcc cggcatcgcg gctcc                                25

<210> SEQ ID NO 2
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 2
ctgtcggcgg cagagcgttc acagc                                25

<210> SEQ ID NO 3
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 3
tccaggtccc ccgcatcccg gatcc                                25

<210> SEQ ID NO 4
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 4
agtctgaagc caggtgtcca gccat                                25

<210> SEQ ID NO 5
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 5
actctcaagc cacgtgtgca gcgat                                25

<210> SEQ ID NO 6
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 6
ctccgatttg catatctggg caggg                                25

<210> SEQ ID NO 7
<211> LENGTH: 25
<212> TYPE: DNA
<213> ORGANISM: Artificial Sequence

```
<220> FEATURE:
<223> OTHER INFORMATION: Synthetic Oligonucleotide

<400> SEQUENCE: 7
ctgcgatttc catatgtgcg cacgg                                          25

<210> SEQ ID NO 8
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 8
tccaggtccc ccgcatcccg gatcc                                          25
```